US012766158B2

(12) United States Patent
Crabtree et al.

(10) Patent No.: US 12,766,158 B2
(45) Date of Patent: Oct. 20, 2026

(54) METHODS OF TREATMENTS BASED UPON ANTHRACYCLINE RESPONSIVENESS

(71) Applicant: The Board of Trustees of the Leland Stanford Junior University, Stanford, CA (US)

(72) Inventors: Gerald R. Crabtree, Woodside, CA (US); Christina Curtis, Stanford, CA (US); Jose A. Seoane Fernandez, L'Hospitalet de Llobregat (ES); Jacob G. Kirkland, Oklahoma City, OK (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1008 days.

(21) Appl. No.: 17/600,004

(22) PCT Filed: Mar. 30, 2020

(86) PCT No.: PCT/US2020/025842

§ 371 (c)(1),
(2) Date: Sep. 29, 2021

(87) PCT Pub. No.: WO2020/205807

PCT Pub. Date: Oct. 8, 2020

(65) Prior Publication Data

US 2022/0233563 A1 Jul. 28, 2022

Related U.S. Application Data

(60) Provisional application No. 62/826,775, filed on Mar. 29, 2019.

(51) Int. Cl.

| | |
|---|---|
| ***C12Q 1/6886*** | (2018.01) |
| ***A61K 31/136*** | (2006.01) |
| ***A61K 31/138*** | (2006.01) |
| ***A61K 31/337*** | (2006.01) |
| ***A61K 31/395*** | (2006.01) |
| ***A61K 31/4745*** | (2006.01) |
| ***A61K 31/513*** | (2006.01) |
| ***A61K 31/519*** | (2006.01) |
| ***A61K 31/565*** | (2006.01) |
| ***A61K 31/675*** | (2006.01) |
| ***A61K 31/704*** | (2006.01) |
| ***A61K 31/7068*** | (2006.01) |
| ***A61K 33/243*** | (2019.01) |
| ***A61P 35/00*** | (2006.01) |

(52) U.S. Cl.
CPC .......... *A61K 31/704* (2013.01); *A61K 31/136* (2013.01); *A61K 31/138* (2013.01); *A61K 31/337* (2013.01); *A61K 31/4745* (2013.01); *A61K 31/513* (2013.01); *A61K 31/519* (2013.01); *A61K 31/5545* (2017.08); *A61K 31/565* (2013.01); *A61K 31/675* (2013.01); *A61K 31/7068* (2013.01); *A61K 33/243* (2019.01); *A61P 35/00* (2018.01); *C12Q 1/6886* (2013.01); *C12Q 2600/106* (2013.01); *C12Q 2600/158* (2013.01)

(58) Field of Classification Search
CPC .................................................... C12Q 1/6886
See application file for complete search history.

(56) References Cited

U.S. PATENT DOCUMENTS

| | | | |
|---|---|---|---|
| 2013/0287772 | A1 | 10/2013 | Halbert et al. |
| 2017/0091937 | A1 | 3/2017 | Barnes et al. |
| 2017/0160171 | A1 | 6/2017 | Tsujikawa et al. |
| 2018/0250397 | A1 | 9/2018 | Benyunes et al. |
| 2019/0040464 | A1 | 2/2019 | Giresi et al. |
| 2019/0219580 | A1 | 7/2019 | Michel et al. |
| 2023/0047712 | A1 | 2/2023 | Curtis et al. |

FOREIGN PATENT DOCUMENTS

| | | | |
|---|---|---|---|
| CN | 107502671 | A | 12/2017 |
| CN | 114787374 | A | 7/2022 |
| EP | 3947719 | A1 | 2/2022 |
| EP | 4051805 | A1 | 9/2022 |
| JP | 2009515148 | A | 4/2009 |
| JP | 2015506678 | A | 3/2015 |
| JP | 2016531097 | A | 10/2016 |
| JP | 2018084568 | A | 5/2018 |
| JP | 2019519772 | A | 7/2019 |
| JP | 2023500460 | A | 1/2023 |
| WO | 2010076322 | A1 | 7/2010 |
| WO | 2010119133 | A1 | 10/2010 |
| WO | 2012125828 | A2 | 9/2012 |
| WO | 2015114146 | A1 | 8/2015 |
| WO | 2015169857 | A1 | 11/2015 |
| WO | 2016008048 | A1 | 1/2016 |
| WO | 2017096458 | A1 | 6/2017 |
| WO | 2018132287 | A1 | 7/2018 |

(Continued)

OTHER PUBLICATIONS

Allantaz et al. PLoS One. 2012. 7(1):e29979. (Year: 2012).*

(Continued)

*Primary Examiner* — Joseph G. Dauner
(74) *Attorney, Agent, or Firm* — KPPB LLP

(57) ABSTRACT

Methods of treatment based on a neoplasm's responsiveness to anthracycline are provided. Chromatin accessibility or expression levels of chromatin regulatory genes are used in some instances to determine whether a neoplasm will respond to anthracycline treatment. Anthracyclines are utilized to treat various individuals' neoplasms and cancers, as determined by their anthracycline responsiveness.

13 Claims, 36 Drawing Sheets

Specification includes a Sequence Listing.

(56) References Cited

FOREIGN PATENT DOCUMENTS

WO 2020205807 A1 10/2020
WO 2021087167 A1 5/2021

OTHER PUBLICATIONS

Whitehead et al. Genome Biology. 2005. 6: R13. (Year: 2005).*
Min et al. BMC Genomics. 2010. 11:96. (Year: 2010).*
Palmer et al. BMC Genomics. 2006. 7:115. (Year: 2006).*
Kumar et al. Nature Communications. 2015. 6:7971. (Year: 2015).*
Saito-Hisaminato et al. DNA Research. 2002. 9:35-45. (Year: 2002).*
Maier et al. FEBS Letter. 2009. 583:3966-3973. (Year: 2009).*
Kendrick. A gene's mRNA level does not usually predict its protein level. Sep. 25, 2014. (Year: 2014).*
Chan et al. G&P magazine. 2006. 6(3):20-26. (Year: 2006).*
Chen et al. Molecular & Cellular Proteomics 1.4. 2002. 1:304-313. (Year: 2002).*
Greenbaum et al. Genome Biology. 2003. 4:117. (Year: 2003).*
Brase et al. Clin Cancer Res. 2010. 16(8):2391-2401 and Supplementary Data. (Year: 2010).*
Seoane et al. Nat Med. 2019. 25(11):1721-1727. (Year: 2019).*
Extended European Search Report received for European Application No. 20783578.6, Search completed Nov. 29, 2022, Mailed Dec. 7, 2022, 6 pgs.
Extended European Search Report received for European Application No. 20881886.4, Search completed Sep. 25, 2023, Mailed Oct. 4, 2023, 14 pgs.
International Preliminary Report on Patentability received for International Application No. PCT/US2020/025842, issued Sep. 28, 2021, Mailed Oct. 14, 2021, 10 pgs.
International Preliminary Report on Patentability received for International Application No. PCT/US2020/058050, Report issued May 3, 2022, Mailed May 12, 2022, 10 pgs.
International Search Report and Written Opinion received for International Application No. PCT/US2020/025842, Search completed Jul. 7, 2020, Mailed Aug. 26, 2020, 20 pgs.
International Search Report and Written Opinion received for International Application No. PCT/US2020/058050, Search completed Dec. 30, 2020, Mailed Feb. 5, 2021, 12 pgs.
Aas et al., "Specific P53 mutations are associated with de novo resistance to doxorubicin in breast cancer patients", Nature Medicine, vol. 2, No. 7, Jul. 1, 1996, pp. 811-814, doi: 10.1038/nm0796-811.
Aittokallio et al., "Graph-based methods for analysing networks in cell biology", Briefings in Bioinformatics, vol. 7, No. 3, Sep. 1, 2006, pp. 243-255, doi: 10.1093/bib/bbl022.
Almeida et al., "Topoisomerase II-alfa gene as a predictive marker of response to anthracyclines in breast cancer", Pathology—Research and Practice, vol. 210, No. 10, Oct. 2014, pp. 675-679, doi: 10.1016/J.PRP.2014.06.017.
Alvarez et al., "Functional characterization of somatic mutations in cancer using network-based inference of protein activity", Nature Genetics, vol. 48, No. 8, Aug. 2016, pp. 838-847, doi: 10.1038/ng.3593.
Amaria et al., "Neoadjuvant immune checkpoint blockade in high-risk resectable melanoma", Nature Medicine, vol. 24, No. 11, Oct. 8, 2018, pp. 1649-1654, doi: 10.1038/s41591-018-0197-1.
Aydin et al., "ISWI chromatin remodeling complexes in the DNA damage response", Cell Cycle, vol. 13, No. 19, Oct. 30, 2014, pp. 3016-3025, doi: 10.4161/15384101.2014.956551.
Balko et al., "Molecular Profiling of the Residual Disease of Triple-Negative Breast Cancers after Neoadjuvant Chemotherapy Identifies Actionable Therapeutic Targets", Cancer Discovery, vol. 4, No. 2, Feb. 2014, pp. 232-245, doi: 10.1158/2159-8290.CD-13-0286.
Banito et al., "The SS18-SSX Oncoprotein Hijacks KDM2B-PRC1.1 to Drive Synovial Sarcoma", Cancer Cell, vol. 33, No. 3, Mar. 12, 2018, pp. 527-541.e8, doi: 10.1016/j.ccell.2018.01.018.
Barak et al., "Clinical utility of cytokeratins as tumor markers", Clinical Biochemistry, vol. 37, No. 7, Jul. 2004, pp. 529-540, doi: 10.1016/j.clinbiochem.2004.05.009.
Barretina et al., "The Cancer Cell Line Encyclopedia enables predictive modelling of anticancer drug sensitivity", Nature, vol. 483, No. 7391, Mar. 29, 2012, pp. 603-607, doi: 10.1038/nature11003.
Bates et al., "Fitting Linear Mixed-Effects Models Using Ime4", Journal of Statistical Software, vol. 67, No. 1, Oct. 2015, 48 pgs., doi: 10.18637/jss.v067.i01.
Benjamini et al., "Controlling the False Discovery Rate: a Practical and Powerful Approach to Multiple Testing", Journal of the Royal Statistical Society, vol. 57, No. 1, 1995, pp. 289-300, doi: 10.1111/j.2517-6161.1995.tb02031.x.
Bianchini et al., "Biomarker analysis of the NeoSphere study: pertuzumab, trastuzumab, and docetaxel versus trastuzumab plus docetaxel, pertuzumab plus trastuzumab, or pertuzumab plus docetaxel for the neoadjuvant treatment of HER2-positive breast cancer", Breast Cancer Research, vol. 19, No. 1, Article 16, Feb. 2017, 12 pgs., doi: 10.1186/s13058-017-0806-9.
Binnewies et al., "Understanding the tumor immune microenvironment (TIME) for effective therapy", Nature Medicine, vol. 24, No. 5, May 2018, pp. 541-550, doi: 10.1038/s41591-018-0014-x.
Blum et al., "Anthracyclines in Early Breast Cancer: The ABC Trials—USOR 06-090, NSABP B-46-I/USOR 07132, and NSABP B-49 (NRG Oncology)", Journal of Clinical Oncology, vol. 35, No. 23, Aug. 10, 2017, pp. 2647-2655, doi: 10.1200/JCO.2016.71.4147.
Bodor et al., "EZH2 mutations are frequent and represent an early event in follicular lymphoma", Blood, vol. 122. No. 18, Oct. 31, 2013, pp. 3165-3168, doi: 10.1182/blood-2013-04-496893.
Bownes et al., "On-Treatment Biomarkers Can Improve Prediction of Response to Neoadjuvant Chemotherapy in Breast Cancer", Breast Cancer Research, vol. 21, No. 1, Article 73, Jun. 14, 2019, 12 pgs., doi: 10.1186/s13058-019-1159-3.
Broglio et al., "Association of Pathologic Complete Response to Neoadjuvant Therapy in HER2-Positive Breast Cancer With Long-Term Outcomes A Meta-Analysis", Journal of the American Medical Association Oncology, vol. 2, No. 6, 2016, pp. 751-760, doi: 10.1001/jamaoncol.2015.6113.
Burger et al., "RNA Expression of Breast Cancer Resistance Protein, Lung Resistance-related Protein, Multidrug Resistance-associated Proteins 1 and 2, and Multidrug Resistance Gene 1 in Breast Cancer: Correlation with Chemotherapeutic Response", Clinical Cancer Research, vol. 9, No. 2, Feb. 2003, pp. 827-836.
Cancer Genome Atlas Network, "Comprehensive molecular portraits of human breast tumours", Nature, vol. 490, Oct. 4, 2012, pp. 61-70, doi: 10.1038/nature11412.
Cardoso et al., "70-Gene Signature as an Aid to Treatment Decisions in Early-Stage Breast Cancer", New England Journal of Medicine, vol. 375, No. 8, Aug. 25, 2016, pp. 717-729, doi: 10.1056/NEJMoa1602253.
Caswell-Jin et al., "Clonal replacement and heterogeneity in breast tumors treated with neoadjuvant HER2-targeted therapy", Nature Communications, vol. 10, No. 1, Article 657, Feb. 8, 2019, 12 pgs., doi: 10.1038/s41467-019-08593-4.
Ciriello et al., "Emerging landscape of oncogenic signatures across human cancers", Nature Genetics, vol. 45, No. 10, Oct. 2013, pp. 1127-1133, doi: 10.1038/ng.2762.
Cirillo et al., "Opening of Compacted Chromatin by Early Developmental Transcription Factors HNF3 (FoxA) and GATA-4", Molecular Cell, vol. 9, No. 2, Feb. 2002, pp. 279-289, doi: 10.1016/S1097-2765(02)00459-8.
Cortazar et al., "Pathological complete response and long-term clinical benefit in breast cancer: the CTNeoBC pooled analysis", The Lancet, vol. 384, No. 9938, Jul. 12, 2014, pp. 164-172, doi: 10.1016/S0140-6736(13)62422-8.
Costello et al., "A community effort to assess and improve drug sensitivity prediction algorithms", Nature Biotechnology, vol. 32, No. 12, Dec. 2014, pp. 1202-1212, published online Jun. 1, 2014, doi: 10.1038/nbt.2877.
Curtis et al., "The genomic and transcriptomic architecture of 2,000 breast tumours reveals novel subgroups", Nature, vol. 486, No. 7403, Jun. 21, 2012, pp. 346-352, doi: 10.1038/nature10983.

(56) References Cited

OTHER PUBLICATIONS

De Ronde et al., "SERPINA6, BEX1, AGTR1, SLC26A3, and LAPTM4B are markers of resistance to neoadjuvant chemotherapy in HER2-negative breast cancer", Breast Cancer Research and Treatment, vol. 137, No. 1, Jan. 2013, pp. 213-223, doi: 10.1007/s10549-012-2340-x.
Denkert et al., "Standardized evaluation of tumor-infiltrating lymphocytes in breast cancer: results of the ring studies of the international immuno-oncology biomarker working group", Modern Pathology, vol. 29, No. 10, Oct. 2016, pp. 1155-1164, doi: 10.1038/modpathol.2016.109.
Denkert et al., "Tumor-Associated Lymphocytes as an Independent Predictor of Response to Neoadjuvant Chemotherapy in Breast Cancer", Journal of Clinical Oncology, vol. 28, No. 1, Jan. 1, 2010, pp. 105-113, doi: 10.1200/jco.2009.23.7370.
Dereli et al., "Path2Surv: Pathway/gene set-based survival analysis using multiple kernel learning", Bioinformatics, vol. 35, No. 24, May 30, 2019, pp. 5137-5145, doi: 10.1093/bioinformatics/btz446.
Di Leo et al., "HER2 and TOP2A as predictive markers for anthracycline-containing chemotherapy regimens as adjuvant treatment of breast cancer: a meta-analysis of individual patient data", The Lancet Oncology, vol. 12, No. 12, Nov. 2011, pp. 1134-1142, doi: 10.1016/S1470-2045(11)70231-5.
Di Modica et al., "Predicting the Efficacy of HER2-Targeted Therapies: A Look at the Host", Disease Markers, vol. 2017, Article 7849108, Dec. 18, 2017, 14 pgs., doi: 10.1155/2017/7849108.
Dykhuizen et al., "BAF complexes facilitate decatenation of DNA by topoisomerase IIα", Nature, vol. 497, No. 7451, May 30, 2013, pp. 624-627, doi: 10.1038/nature12146.
EBCTCG, "Comparisons between different polychemotherapy regimens for early breast cancer: meta-analyses of long-term outcome among 100,000 women in 123 randomised trials", Lancet, vol. 379, No. 9814, Feb. 4, 2012, pp. 432-444, doi: 10.1016/S0140-6736(11)61625-5.
Elloumi et al., "Systematic Bias in Genomic Classification Due to Contaminating Non-neoplastic Tissue in Breast Tumor Samples", BMC Medical Genomics, vol. 4, Article 54, 2011, 12 pgs., doi: 10.1186/1755-8794-4-54.
Evers et al., "Sparse kernel methods for high-dimensional survival data", Bioinformatics, vol. 24, No. 14, May 30, 2008, pp. 1632-1638, doi: 10.1093/bioinformatics/btn253.
Farmer et al., "A stroma-related gene signature predicts resistance to neoadjuvant chemotherapy in breast cancer", Nature Medicine, vol. 15, No. 1, Jan. 4, 2009, pp. 68-74, doi: 10.1038/nm.1908.
Fillmore et al., "EZH2 inhibition sensitizes BRG1 and EGFR mutant lung tumors to TopoII inhibitors", Nature, vol. 520, No. 7546, Apr. 9, 2015, pp. 239-242, doi: 10.1038/nature 14122.
Finak et al., "Stromal gene expression predicts clinical outcome in breast cancer", Nature Medicine, vol. 14, No. 5, May 2008, pp. 518-527, doi: 10.1038/nm1764.
Fodor et al., "Jmjd2b antagonizes H3K9 trimethylation at pericentric heterochromatin in mammalian cells", Genes & Development, vol. 20, No. 12, 2006, pp. 1557-1562, doi: 10.1101/gad.388206.
Gasparini et al., "Predicting pathological complete response (pCR) to neoadjuvant trastuzumab in patients with breast cancer using HER2 mass spectrometry", Journal of Clinical Oncology, vol. 36, No. 15, e12643, 2018, 2 pgs., doi: 10.1200/JCO.2018.36.15_suppl.e12643. (Abstract only).
Gautier et al., "affy—analysis of Affymetrix GeneChip data at the probe level", Bioinformatics, vol. 20, No. 3, Feb. 12, 2004, pp. 307-315, doi: 10. 1093/bioinformatics/btg405.
George et al., "A Single-Nucleotide Polymorphism in the MDR1 Gene as a Predictor of Response to Neoadjuvant Chemotherapy in Breast Cancer", Clinical Breast Cancer, vol. 9, No. 3, Aug. 1, 2009, pp. 161-165, doi: 10.3816/cbc.2009.n.026.
Gonzalez-Perez et al., "The mutational landscape of chromatin regulatory factors across 4,623 tumor samples", Genome Biology, vol. 14, No. 9, Article r106, Sep. 24, 2013, 15 pgs., doi: 10.1186/GB-2013-14-9-r106.
Gujam et al., "The relationship between the tumour stroma percentage, clinicopathological characteristics and outcome in patients with operable ductal breast cancer", British Journal of Cancer, vol. 111, No. 1, May 29, 2014, pp. 157-165, doi: 10.1038/bjc.2014.279.
Gurard-Levin et al., "Chromatin Regulators as a Guide for Cancer Treatment Choice", Molecular Cancer Therapeutics, vol. 15, No. 7, Jul. 2016, pp. 1768-1777, doi: 10.1158/1535-7163.MCT-15-1008.
Hafner et al., "Data Descriptor: Quantification of sensitivity and resistance of breast cancer cell lines to anti-cancer drugs using GR metrics", Scientific Data, vol. 4, No. 170166, Nov. 17, 2017, 9 pgs., doi: 10.1038/sdata.2017.166.
Hauri et al., "A High-Density Map for Navigating the Human Polycomb Complexome", Cell Reports, vol. 17, No. 2, Oct. 4, 2016, pp. 583-595, doi: 10.1016/j.celrep.2016.08.096.
Hirano, "Condensins: universal organizers of chromosomes with diverse functions", Genes & Development, vol. 26, No. 15, Aug. 1, 2012, pp. 1659-1678, doi: 10.1101/gad.194746.112.
Hodges et al., "Dominant-negative SMARCA4 mutants alter the accessibility landscape of tissue-unrestricted enhancers", Nature Structural & Molecular Biology, vol. 25, 2018, pp. 61-72, doi: 10.1038/s41594-017-0007-3.
Hodges et al., "The Many Roles of BAF (mSWI/SNF) and PBAF Complexes in Cancer", Cold Spring Harbor Perspectives in Medicine, vol. 6, No. 8, Article a026930, Aug. 2016, 24 pgs., doi: 10.1101/cshperspect.a026930.
Hothorn et al., "Generalized Maximally Selected Statistics", Biometrics, vol. 64, No. 4, Nov. 24, 2008, pp. 1263-1269, doi: 10.1111/j.1541-0420.2008.00995.x.
Huober et al., "Survival outcomes of the NeoALTTO study (BIG 1-06): updated results of a randomised multicenter phase III neoadjuvant clinical trial in patients with HER2-positive primary breast cancer", European Journal of Cancer, vol. 118, Sep. 2019, pp. 169-177, doi: 10.1016/j.ejca.2019.04.038.
Ibrahim et al., "Bayesian Survival Analysis", Springer, 2001, 494 pgs.
Iorio et al., "A Landscape of Pharmacogenomic Interactions in Cancer", Cell, vol. 166, No. 3, Jul. 28, 2016, pp. 740-754, doi: 10.1016/j.cell.2016.06.017.
Ishwaran et al., "Random survival forests", Annals of Applied Statistics, vol. 2, No. 3, Sep. 2008, pp. 841-860, doi: 10.1214/08-AOAS169.
Johansson et al., "Breast cancer quantitative proteome and proteogenomic landscape", Nature Communications, vol. 10, No. 1, Article 1600, Apr. 8, 2019, 14 pgs., doi: 10.1038/s41467-019-09018-y.
Johnson et al., "Adjusting batch effects in microarray expression data using empirical Bayes methods", Biostatistics, vol. 8, No. 1, Apr. 21, 2006, pp. 118-127, doi: 10.1093/biostatistics/kxj037.
Jones et al., "Docetaxel With Cyclophosphamide is Associated With an Overall Survival Benefit Compared With Doxorubicin and Cyclophosphamide: 7-Year Follow-Up of US Oncology Research Trial 9735", Journal of Clinical Oncology, vol. 27, No. 8, Mar. 10, 2009, pp. 1177-1183, doi: 10.1200/JCO.2008.18.4028.
Jones et al., "Phase III Trial Comparing Doxorubicin Plus Cyclophosphamide With Docetaxel Plus Cyclophosphamide as Adjuvant Therapy for Operable Breast Cancer", Journal of Clinical Oncology, vol. 24, No. 34, Dec. 1, 2006, pp. 5381-5387, doi: 10.1200/JCO.2006.06.5391.
Kadoch et al., "Mammalian SWI/SNF chromatin remodeling complexes and cancer: Mechanistic insights gained from human genomics", Science Advances, vol. 1, No. 5, Jun. 12, 2015, 17 pgs., doi: 10.1126/sciadv.1500447.
Kadoch et al., "Reversible Disruption of mSWI/SNF (BAF) Complexes by the SS18-SSX Oncogenic Fusion in Synovial Sarcoma", Cell, vol. 153, No. 1, Mar. 28, 2013, pp. 71-85, doi: 10.1016/j.cell.2013.02.036.
Kallioniemi et al., "Detection and mapping of amplified DNA sequences in breast cancer by comparative genomic hybridization", Proceedings of the National Academy of Sciences, vol. 91, No. 6, Mar. 15, 1994, pp. 2156-2160, doi: 10.1073/pnas.91.6.2156.
Kao et al., "Correlation of microarray-based breast cancer molecular subtypes and clinical outcomes: implications for treatment

(56) References Cited

OTHER PUBLICATIONS optimization", BMC Cancer, vol. 11, No. 143, Apr. 18, 2011, 15 pgs., doi: 10.1186/1471-2407-11-143.
Katzman et al., "DeepSurv: personalized treatment recommender system using a Cox proportional hazards deep neural network", BMC Medical Research Methodology, vol. 18, No. 1, Article 24, Feb. 26, 2018, 12 pgs., doi: 10.1186/s12874-018-0482-1.
Keren et al., "A Structured Tumor-Immune Microenvironment in Triple Negative Breast Cancer Revealed by Multiplexed Ion Beam Imaging", Cell, vol. 174, No. 6, Sep. 6, 2018, pp. 1373-1387.e19, doi: 10.1016/j.cell.2018.08.039.
King et al., "Polycomb repressive complex 1 shapes the nucleosome landscape but not accessibility at target genes", Genome Research, vol. 28, 2018, pp. 1494-1507, doi: 10.1101/gr.237180.118.
Lachmann et al., "ARACNe-AP: gene network reverse engineering through adaptive partitioning inference of mutual information", Bioinformatics, vol. 32, No. 14, Jul. 15, 2016, pp. 2233-2235, doi: 10.1093/bioinformatics/btw216.
Lai et al., "Cancer biology and NuRD: a multifaceted chromatin remodelling complex", Nature Review Cancer, vol. 11, No. 8, Jul. 7, 2011, pp. 588-596, doi: 10.1038/nrc3091.
Lesurf et al., "Genomic characterization of HER2-positive breast cancer and response to neoadjuvant trastuzumab and chemotherapy—results from the ACOSOG Z1041 (Alliance) trial", Annals of Oncology, vol. 28, No. 5, Feb. 21, 2017, pp. 1070-1077, doi: 10.1093/annonc/mdx048.
Li et al., "Amplification of LAPTM4B and YWHAZ contributes to chemotherapy resistance and recurrence of breast cancer", Nature Medicine, vol. 16, No. 2, Feb. 2010, pp. 214-218, doi: 10.1038/nm.2090.
Li et al., "Kernel Cox Regression Models for Linking Gene Expression Profiles to Censored Survival Data", Pacific Symposium on Biocomputing, 2003, pp. 65-76, doi: 10.1142/9789812776303_0007.
Llombart-Cussac et al., "HER2-enriched subtype as a predictor of pathological complete response following trastuzumab and lapatinib without chemotherapy in early-stage HER2-positive breast cancer (PAMELA): an open- label, single-group, multicentre, phase 2 trial", The Lancet Oncology, vol. 18, No. 4, pp. 545-554, Feb. 23, 2017, doi: 10.1016/S1470-2045(17)30021-9.
Loi et al., "Tumor infiltrating lymphocytes are prognostic in triple negative breast cancer and predictive for trastuzumab benefit in early breast cancer: results from the FinHER trial", Annals of Oncology, vol. 25, No. 8, Mar. 7, 2014, pp. 1544-1550, doi: 10.1093/annonc/mdu112.
Love et al., "Moderated estimation of fold change and dispersion for RNA-seq data with DESeq2", Genome Biology, vol. 15, Article 550, Dec. 5, 2014, 21 pgs., doi: 10.1186/s13059-014-0550-8.
Luen et al., "Tumour-infiltrating lymphocytes in advanced HER2-positive breast cancer treated with pertuzumab or placebo in addition to trastuzumab and docetaxel: a retrospective analysis of the CLEOPATRA study", Lancet Oncology, vol. 18, No. 1, Dec. 7, 2016, pp. 52-62, doi: 10.1016/S1470-2045(16)30631-3.
Maire et al., "Polo-like Kinase 1: A Potential Therapeutic Option in Combination with Conventional Chemotherapy for the Management of Patients with Triple-Negative Breast Cancer", Cancer Research, vol. 73, No. 2, Jan. 15, 2013, pp. 813-823, doi: 10.1158/0008-5472.CAN-12-2633.
Malkov et al., "Multiplexed measurements of gene signatures in different analytes using the Nanostring nCounter™ Assay System", BMC Research Notes, vol. 2, No. 80, May 9, 2009, 9 pgs., doi: 10.1186/1756-0500-2-80.
Mao et al., "The Value of Tumor Infiltrating Lymphocytes (TILs) for Predicting Response to Neoadjuvant Chemotherapy in Breast Cancer: A Systematic Review and Meta-Analysis", PLoS One, vol. 9, No. 12, Article e115103, Dec. 12, 2014, 21 pgs., doi: 10.1371/journal.pone.0115103.
Margolin et al., "ARACNE: An Algorithm for the Reconstruction of Gene Regulatory Networks in a Mammalian Cellular Context", BMC Bioinformatics, vol. 7 (Supp. 1), No. S7, Mar. 20, 2006, 15 pgs., doi: 10.1186/1471-2105-7-s1-s7.
McBride et al., "The SS18-SSX Fusion Oncoprotein Hijacks BAF Complex Targeting and Function to Drive Synovial Sarcoma", Cancer Cell, vol. 33, No. 6, Jun. 11, 2018, pp. 1128-1141.e7, doi: 10.1016/j.ccell.2018.05.002.
McNamara et al., "Abstract P4-10-12: Characterizing the tumor and immune microenvironment through treatment to predict response to neoadjuvant HER2-targeted therapy using the Digital Spatial Profiler", Cancer Research, vol. 80, No. 4_Supplement, Feb. 15, 2020, 2 pgs., doi: 10.1158/1538-7445.SABCS19-P4-10-12.
Melino, "p63 is a suppressor of tumorigenesis and metastasis interacting with mutant p53", Cell Death and Differentiation, vol. 18, No. 9, Sep. 2011, pp. 1487-1499, doi: 10.1038/cdd.2011.81.
Merritt et al., "High multiplex, digital spatial profiling of proteins and RNA in fixed tissue using genomic detection methods", Biorxiv, Feb. 22, 2019, 50 pgs., doi: 10.1101/559021.
Miller et al., "An expression signature for p53 status in human breast cancer predicts mutation status, transcriptional effects, and patient survival", Proceedings of the National Academy of Sciences, vol. 102, No. 38, Sep. 20, 2005, pp. 13550-13555, doi: 10.1073/pnas.0506230102.
Miller et al., "TOP2 synergizes with BAF chromatin remodeling for both resolution and formation of facultative heterochromatin", Nature Structural & Molecular Biology, vol. 24, No. 4, Apr. 24, 2017, pp. 344-352, doi: 10.1038/nsmb.3384.
Morin et al., "Somatic mutations altering EZH2 (Tyr641) in follicular and diffuse large B-cell lymphomas of germinal-center origin", Nature Genetics, vol. 42, No. 2, Feb. 2010, pp. 181-185, doi: 10.1038/ng.518.
Morrison et al., "Chromatin remodelling beyond transcription: the INO80 and SWR1 complexes", Nature Reviews Molecular Cell Biology, vol. 10, No. 6, Jun. 2009, pp. 373-384, doi: 10.1038/nrm2693.
Mueller et al., "Protein biomarkers for subtyping breast cancer and implications for future research", Expert Review of Proteomics, vol. 15, No. 2, Nov. 3, 2024, 44 pgs., doi: 10.1080/14789450.2024.2423625.
Mulligan et al., "Identification and Validation of an Anthracycline/Cyclophosphamide-Based Chemotherapy Response Assay in Breast Cancer", JNCI: Journal of the National Cancer Institute, vol. 106, No. 1, djt335, Jan. 2014, 10 pgs., doi: 10.1093/jnci/djt335.
Nagalla et al., "Interactions between immunity, proliferation and molecular subtype in breast cancer prognosis", Genome Biology, vol. 14, No. 4, Article R34, Apr. 29, 2013, 18 pgs., doi: 10.1186/GB-2013-14-4-r34.
Nakayama et al., "SMARCB1 is required for widespread BAF complex-mediated activation of enhancers and bivalent promoters", Nature Genetics, vol. 49, No. 11, Nov. 2017, pp. 1613-1623, doi: 10.1038/ng.3958.
Newman et al., "Robust enumeration of cell subsets from tissue expression profiles", Nature Methods, vol. 12, No. 5, Mar. 30, 2015, pp. 453-457, doi: 10.1038/nmeth.3337.
Ng et al., "Genetic Heterogeneity in Therapy-Naïve Synchronous Primary Breast Cancers and Their Metastases", Clinical Cancer Research, vol. 23, No. 15, Aug. 1, 2017, pp. 4402-4415, doi: 10.1158/1078-0432.CCR-16-3115.
Nuciforo et al., "A predictive model of pathologic response based on tumor cellularity and tumor-infiltrating lymphocytes (CelTIL) in HER2-positive breast cancer treated with chemo-free dual HER2 blockade", Annals of Oncology, vol. 29, No. 1, Jan. 1, 2018, pp. 170-177, doi: 10.1093/annonc/mdx647.
Okosun et al., "Integrated genomic analysis identifies recurrent mutations and evolution patterns driving the initiation and progression of follicular lymphoma", Nature Genetics, vol. 46, No. 2, Feb. 2014, pp. 176-181, doi: 10.1038/ng.2856.
Oppikofer et al., "Expansion of the ISWI chromatin remodeler family with new active complexes", EMBO Reports, vol. 18, No. 10, 2017, pp. 1697-1706, doi: 10.15252/embr.201744011.
Paik et al., "Gene Expression and Benefit of Chemotherapy in Women With Node-Negative, Estrogen Receptor-Positive Breast Cancer", Journal of Clinical Oncology, vol. 24, No. 23, Aug. 10, 2006, pp. 3726-3734, doi: 10.1200/JCO.2005.04.7985.

(56) References Cited

OTHER PUBLICATIONS

Pang et al., "Drug-induced histone eviction from open chromatin contributes to the chemotherapeutic effects of doxorubicin", Nature Communications, vol. 4, No. 1908, May 28, 2013, 13 pgs., doi: 10.1038/ncomms2921.

Paquet et al., "Detecting gene signature activation in breast cancer in an absolute, single-patient manner", Breast Cancer Research, vol. 19, No. 1, Article 32, Mar. 21, 2017, 15 pgs., doi: 10.1186/s13058-017-0824-7.

Parra, "Novel Platforms of Multiplexed Immunofluorescence for Study of Paraffin Tumor Tissues", Journal of Cancer Treatment and Diagnosis, vol. 2, No. 1, Feb. 1, 2018, pp. 43-53, doi: 10.29245/2578-2967/2018/1.1122.

Parra et al., "State-of-the-Art of Profiling Immune Contexture in the Era of Multiplexed Staining and Digital Analysis to Study Paraffin Tumor Tissues", Cancers (Basel), vol. 11, No. 2, Article 247, Feb. 20, 2019, 23 pgs., doi: 10.3390/cancers11020247.

Pawitan et al., "Gene expression profiling spares early breast cancer patients from adjuvant therapy: derived and validated in two population-based cohorts", Breast Cancer Research, vol. 7, No. 6, 2005, pp. R953-R964, doi: 10.1186/bcr1325.

Pedregosa et al., "Scikit-learn: Machine Learning in Python", Journal of Machine Learning Research, vol. 12, Nov. 1, 2011, pp. 2825-2830, doi: 10.5555/1953048.2078195.

Perreard et al., "Classification and risk stratification of invasive breast carcinomas using a real-time quantitative RT-PCR assay", Breast Cancer Research, vol. 8, No. 2, Apr. 20, 2006, 11 pgs., doi: 10.1186/bcr1399.

Pogrebniak et al., "Harnessing Tumor Evolution to Circumvent Resistance", Trends Genetics, vol. 34, No. 8, Jun. 11, 2018, pp. 639-651, doi: 10.1016/j.tig.2018.05.007.

Praga et al., "Risk of Acute Myeloid Leukemia and Myelodysplastic Syndrome in Trials of Adjuvant Epirubicin for Early Breast Cancer: Correlation with Doses of Epirubicin and Cyclophosphamide", Journal of Clinical Oncology, vol. 23, No. 18, Jun. 20, 2005, pp. 4179-4191, doi: 10.1200/JCO.2005.05.029.

Prat et al., "Research-Based PAM50 Subtype Predictor Identifies higher responses and Improved Survival Outcomes in HER2-Positive Breast Cancer in the NOAH Study", Clinical Cancer Research, vol. 20, No. 2, Jan. 15, 2014, pp. 511-521, doi: 10.1158/1078-0432.CCR-13-0239.

Putter et al., "Tutorial in biostatistics: Competing risks and multi-state models", Statistics in Medicine, vol. 26, No. 11, May 20, 2007, pp. 2389-2430, doi: 10.1002/sim.2712.

Rahko et al., "A mutant TP53 gene status is associated with a poor prognosis and anthracycline-resistance in breast cancer patients", European Journal of Cancer, vol. 39, No. 4, Mar. 2003, pp. 447-453, doi: 10.1016/s0959-8049(02)00499-9.

Rajan et al., "Change in Tumor Cellularity of Breast Carcinoma After Neoadjuvant Chemotherapy as a Variable in the Pathologic Assessment of Response", Cancer, vol. 100, No. 7, Apr. 1, 2004, pp. 1365-1373, doi: 10.1002/cncr.20134.

Rimawi et al., "Multicenter Phase II Study of Neoadjuvant Lapatinib and Trastuzumab with Hormonal Therapy and Without Chemotherapy in Patients with Human Epidermal Growth Factor Receptor 2-Overexpressing Breast Cancer: TBCRC 006", Journal of Clinical Oncology, vol. 31, No. 14, Apr. 8, 2013, pp. 1726-1731, doi: 10.1200/JCO.2012.44.8027.

Ritchie et al., "A comparison of background correction methods for two-colour microarrays", Bioinformatics, vol. 23, No. 20, Aug. 25, 2007, pp. 2700-2707, doi: 10.1093/bioinformatics/btm412.

Ritchie et al., "Iimma powers differential expression analyses for RNA-sequencing and microarray studies", Nucleic Acids Research, vol. 43, No. 7, Article e47, 2015, 13 pgs., doi: 10.1093/nar/gkv007.

Rothwell, "Subgroup analysis in randomised controlled trials: importance, indications, and interpretation", Lancet, vol. 365, No. 9454, Jan. 8, 2005, pp. 176-186, doi: 10.1016/S0140-6736(05)17709-5.

Rueda et al., "Dynamics of breast-cancer relapse reveal late-recurring ER-positive genomic subgroups", Nature, vol. 567, No. 7748, Mar. 21, 2019, pp. 399-404, doi: 10.1038/S41586-019-1007-8.

Salgado et al., "The evaluation of tumor-infiltrating lymphocytes (TILs) in breast cancer: recommendations by an International TILs Working Group 2014", Annals of Oncology, vol. 26, No. 2, Feb. 2015, pp. 259-271, doi: 10.1093/annonc/mdu450.

Schindelin et al., "Fiji—an open-source platform for biological-image analysis", Nature Methods, vol. 9, No. 7, Jul. 2012, pp. 676-682, doi: 10.1038/nmeth.2019.

Schuettengruber et al., "Genome Regulation by Polycomb and Trithorax: 70 Years and Counting", Cell, vol. 171, Sep. 21, 2017, pp. 34-57, doi: 10.1016/j.cell.2017.08.002.

Seashore-Ludlow et al., "Harnessing Connectivity in a Large-Scale Small-Molecule Sensitivity Dataset", Cancer Discovery, vol. 5, No. 11, Nov. 2015, pp. 1210-1223, doi: 10.1158/2159-8290.CD-15-0235.

Sever et al., "Signal Transduction in Cancer", Cold Spring Harbor Perspectives in Medicine, vol. 5, No. 4, 2015, 21 pgs., doi: 10.1101/cshperspect.a006098.

Shen et al., "Interplay between the cancer genome and epigenome", Cell, vol. 153, No. 1, Mar. 28, 2013, pp. 38-55, doi: 10.1016/j.cell.2013.03.008.

Slamon et al., "Human Breast Cancer: Correlation of Relapse and Survival with Amplification of the HER-2/neu Oncogene", Science, vol. 235, No. 4785, Jan. 9, 1987, pp. 177-182, doi: 10.1126/science.3798106.

Sparano et al., "Adjuvant Chemotherapy Guided by a 21-Gene Expression Assay in Breast Cancer", New England Journal of Medicine, vol. 379, No. 2, Jul. 12, 2018, pp. 111-121, doi: 10.1056/NEJMoa1804710.

Sparano et al., "Prospective Validation of a 21-Gene Expression Assay in Breast Cancer", New England Journal of Medicine, vol. 373, No. 21, Nov. 19, 2015, pp. 2005-2014, doi: 10.1056/NEJMoa1510764.

St Pierre et al., "Mammalian SWI/SNF complexes in cancer: emerging therapeutic opportunities", Current Opinion in Genetics & Development, vol. 42, Feb. 2017, pp. 56-67, doi: 10.1016/j.gde.2017.02.004.

Talbert et al., "A unified phylogeny-based nomenclature for histone variants", Epigenetics & Chromatin, vol. 5, No. 7, 2012, 19 pgs., doi: 10.1186/1756-8935-5-7.

Tibshirani, "The Lasso Method for Variable Selection in the Cox Model", Statistics in Medicine, vol. 16, No. 4, Feb. 28, 1997, pp. 385-395, doi: 10.1002/(sici)1097-0258(19970228)16:4<385::aid-sim380>3.0.co;2-3.

Tibshirani et al., "Diagnosis of multiple cancer types by shrunken centroids of gene expression", Proceedings of the National Academy of Sciences, vol. 99, No. 10, May 14, 2002, pp. 6567-6572, doi: 10.1073/pnas.082099299.

Toki et al., "Validation of novel high-plex protein spatial profiling quantitation based on NanoString's Digital Spatial Profiling (DSP) technology with quantitative fluorescence (QIF)", Cancer Research, vol. 77, No. 13_Supplement, Article 3810, 2017, 1 pg., doi: 10.1158/1538-7445.AM2017-3810.

Treszezamsky et al., "BRCA1- and BRCA2-Deficient Cells are Sensitive to Etoposide-Induced DNA Double-Strand Breaks via Topoisomerase II", Cancer Research, vol. 67, No. 15, Aug. 1, 2007, pp. 7078-7081, doi: 10.1158/0008-5472.can-07-0601.

Truitt et al., "New frontiers in translational control of the cancer genome", Nature Reviews Cancer, vol. 16, No. 5, Apr. 26, 2016, pp. 288-304, doi: 10.1038/nrc.2016.27.

Untch et al., "Neoadjuvant Treatment with Trastuzumab in HER2-Positive Breast Cancer: Results From the GeparQuattro Study", Journal of Clinical Oncology, vol. 28, No. 12, Apr. 20, 2010, pp. 2024-2031, doi: 10.1200/JCO.2009.23.8451.

Van et al., "A user's perspective on GeoMx™ digital spatial profiling", Immuno-Oncology Technology, vol. 1, May 29, 2019, pp. 11-18, doi: 10.1016/j.iotech.2019.05.001.

Veeraraghavan et al., "A combinatorial biomarker predicts pathologic complete response to neoadjuvant lapatinib and trastuzumab with-

(56) References Cited

OTHER PUBLICATIONS out chemotherapy in patients with HER2+ breast cancer", Annals of Oncology, vol. 30, No. 6, Jun. 1, 2019, pp. 927-933, doi: 10.1093/annonc/mdz076.
Von Ahlfen et al., "Determinants of RNA Quality from FFPE Samples", PLoS One, vol. 2, No. 12, Dec. 5, 2007, 7 pgs., doi: 10.1371/journal.pone.0001261.
Wang et al., "SMARCB1-mediated SWI/SNF complex function is essential for enhancer regulation", Nature Genetics, vol. 49, No. 2, Feb. 2017, pp. 289-295, doi: 10.1038/ng.3746.
Watson, "Perimetric Complexity of Binary Digital Images Notes on Calculation and Relation to Visual Complexity", The Mathematica Journal, vol. 14, 2012, 40 pgs., doi: 10.3888/tmj.14-5.
West et al., "New and emerging HDAC inhibitors for cancer treatment", Journal of Clinical Investigation, vol. 124, No. 1, Jan. 2, 2014, pp. 30-39, doi: 10.1172/JCI69738.
West et al., "Tumor-infiltrating lymphocytes predict response to anthracycline-based chemotherapy in estrogen receptor-negative breast cancer", Breast Cancer Research, vol. 13, No. 6, Article R126, Dec. 8, 2011, 13 pgs., doi: 10.1186/bcr3072.
Williamson et al., "ATR inhibitors as a synthetic lethal therapy for tumours deficient in ARID1A", Nature Communications, vol. 7, No. 13837, Dec. 13, 2016, 13 pgs., doi: 10.1038/ncomms13837.
Wilson et al., "Epigenetic Antagonism between Polycomb and SWI/SNF Complexes during Oncogenic Transformation", Cancer Cell, vol. 18, Oct. 19, 2010, pp. 316-328, doi: 10.1016/j.ccr.2010.09.006.
Witten et al., "Testing Significance of Features by Lassoed Principal Components", The Annals of Applied Statistics, vol. 2, No. 3, Sep. 2008, pp. 986-1012, doi: 10.2307/30245117.
Xin et al., "Effects of lapatinib or trastuzumab, alone and in combination, in human epidermal growth factor receptor 2-positive breast cancer: a meta- analysis of randomized controlled trials", Cancer Medicine, vol. 5, No. 12, Nov. 23, 2016, pp. 3454-3463, doi: 10.1002/cam4.963.
Yang et al., "Anthracyclines induce double-strand DNA breaks at active gene promoters", Mutation Research/Fundamental and Molecular Mechanisms of Mutagenesis, vol. 773, Mar. 2015, pp. 9-15, doi: 10.1016/j.mrfmmm.2015.01.007.
Yates et al., "Subclonal diversification of primary breast cancer revealed by multiregion sequencing", Nature Medicine, vol. 21, No. 7, Jun. 22, 2015, pp. 751-759, doi: 10.1038/nm.3886.
You et al., "Cancer Genetics and Epigenetics: Two Sides of the Same Coin?", Cancer Cell, vol. 22, No. 1, Jul. 10, 2012, pp. 9-20, doi: 10.1016/j.ccr.2012.06.008.
Yousefi et al., "Predicting clinical outcomes from large scale cancer genomic profiles with deep survival models", Scientific Reports, vol. 7, No. 1, Article 11707, Sep. 15, 2017, 11 pgs., doi: 10.1038/s41598-017-11817-6.
Yu et al., "The Importance of Bottlenecks in Protein Networks: Correlation with Gene Essentiality and Expression Dynamics", PLoS Computational Biology, vol. 3, No. 4, Apr. 20, 2007, pp. 0713-0720, doi: 10.1371/journal.pcbi.0030059.
Zardavas et al., "Clinical management of breast cancer heterogeneity", Nature Reviews, Clinical Oncology, vol. 12, No. 7, Apr. 21, 2015, pp. 381-394, doi: 10.1038/nrclinonc.2015.73.
Zhao et al., "Identifying Abundant Immunotherapy and Other Targets in Solid Tumors: Integrating RNA-seq and Mass Spectrometry Proteomics Data Sets", The Cancer Journal, vol. 23, No. 2, Mar./Apr. 2017, pp. 108-114, doi: 10.1097/PPO.0000000000000258.
Zhou et al., "Random rotation survival forest for high dimensional censored data", SpringerPlus, vol. 5, Article 425, Aug. 26, 2016, 10 pgs., doi: 10.1186/s40064-016-3113-5.
Zingoni et al., "Natural Killer Cell Response to Chemotherapy-Stressed Cancer Cells: Role in Tumor Immunosurveillance", Frontiers in Immunology, vol. 8, No. 1194, Sep. 25, 2017, 10 pgs., doi: 10.3389/fimmu.2017.01194.

* cited by examiner

Process 400

Chromatin Regulatory Network

| Chromatin Regulator | p-value |
| --- | --- |
| SMARCD3 | 0.00267 |
| HDAC5 | 0.00516 |
| HDAC7 | 0.0159 |
| KDM4B | 0.0222 |
| KMT2C | 0.0257 |
| CECR2 | 0.0289 |
| HIST4H4 | 0.0295 |
| HDAC6 | 0.0406 |
| SMARCC2 | 0.056 |
| KAT14 | 0.057 |
| PPM1D | 0.0576 |
| INO80E | 0.0599 |
| KAT6B | 0.0727 |
| RSF1 | 0.0785 |
| BCL11A | 0.0886 |
| SMC3 | 0.0823 |
| TAF12 | 0.0816 |
| CDK1 | 0.081 |
| UCHL5 | 0.0757 |
| SMARCC1 | 0.0633 |
| CBX2 | 0.0628 |
| H2AFV | 0.0535 |
| HDAC9 | 0.0349 |
| ATM | 0.0241 |

SEQUENCE LISTING

```
<160> NUMBER OF SEQ ID NOS: 38

<210> SEQ ID NO 1
<211> LENGTH: 1854
<212> TYPE: DNA
<213> ORGANISM: Homo sapiens

<400> SEQUENCE: 1

aagtgtggct gagctccggg gtgtgtggac gccgctttgt tgcctgaggt gggtggcggt      60

ggaagttaag ggagtcaggg gctatcgctc ctcgagactc gcagtcgcgg ccactgcagt     120

cacttcgcca gttagccctt agggtaggag tcgcgccggc agcagccatg agcggcggcg     180

tgtacggggg agatgaagtt ggagcccttg tttttgacat tggatcctat actgtgagag     240

ctggttatgc tggtgaggac tgccccaagg tggattttcc tacagctatt ggtatggtgg     300

tagaaagaga tgacggaagc acattaatgg aaatagatgg cgataaaggc aaacaaggcg     360

gtcccaccta ctacatagat actaatgctc tgcgtgttcc gagggagaat atggaggcca     420

tttcacctct aaaaaatggg atggttgaag actgggatag tttccaagct attttggatc     480

atacctacaa aatgcatgtc aaatcagaag ccagtctcca tcctgttctc atgtcagagg     540

caccgtggaa tactagagca aagagagaga aactgacaga gttaatgttt gaacactaca     600

acatccctgc cttcttcctt tgcaaaactg cagttttgac agcatttgct aatggtcgtt     660

ctactgggct gattttggac agtggagcca ctcataccac tgcaattcca gtccacgatg     720

gctatgtcct tcaacaaggc attgtgaaat cccctcttgc tggagacttt attactatgc     780

agtgcagaga actcttccaa gaaatgaata ttgaattggt tcctccatat atgattgcat     840

caaaagaagc tgttcgtgaa ggatctccag caaactggaa aagaaaagag aagttgcctc     900
```

```
aggttacgag gtcttggcac aattatatgt gtaattgtgt tatccaggat tttcaagctt    960
cggtacttca agtgtcagat tcaacttatg atgaacaagt ggctgcacag atgccaactg   1020
ttcattatga attccccaat ggctacaatt gtgattttgg tgcagagcgg ctaaagattc   1080
cagaaggatt atttgaccct tccaatgtaa aggggttatc aggaaacaca atgttaggag   1140
tcagtcatgt tgtcaccaca agtgttggga tgtgtgatat tgacatcaga ccaggtctct   1200
atggcagtgt aatagtggca ggaggaaaca cactaataca gagttttact gacaggttga   1260
atagagagct gtctcagaaa actcctccaa gtatgcggtt gaaattgatt gcaaataata   1320
caacagtgga acggaggttt agctcatgga ttggcggctc cattctagcc tctttgggta   1380
cctttcaaca gatgtggatt tccaagcaag aatatgaaga aggagggaag cagtgtgtag   1440
aaagaaaatg cccttgagaa agagttccca agcttctacc ttccttttgt caccttacgt   1500
ttcatagctt tagtatactc aggaaaagaa tgaccatctt ttgtagaatg tttatacatt   1560
tttgcatatt tcaatttcca cttaaatttt ttaaagcttt aactggctct ataaattaag   1620
tttgtgcttt ccttgaaatg cacttattct tattacaagc attttataat tttgtataaa   1680
tgtctatttt ctctaaatat tttgctttca gtaaaatgct ttccaactct gtttagtgta   1740
ttaattacca gtggattggt agaactgctt tttattgact agtaaaagtt actgcctatg   1800
ctttttacct taggcttaca gaattaaata aaaattagcc attccagaaa tata         1854
```

<210> SEQ ID NO 2
<211> LENGTH: 5830
<212> TYPE: DNA
<213> ORGANISM: Homo sapiens

<400> SEQUENCE: 2

```
agtctccgtg tgagtgcgcg tagtcgcgcg cctgtccccg cgcgggctcc gtagcgcgtg     60
tgcaggctga cgcagctcgc gggccctcct cctgctctgc agcggcgtcg gcggagtttt    120
gggcgtttgg gagggggcg agggagagag agtcgagaga gggaggcggc ggtggggagg    180
aggaggagga ggaggagcag gcgccgccat ggccgccgct atcaccgaca tggccgacct    240
ggaggagctc tcccgcctga gccctctgcc ccccggcagc ccgggttcgg cggcgcgggg    300
ccgggctgag ccccccgagg aggaggagga agaggaggag gaggaagagg aggcggaggc    360
cgaggcggtg gcggcgctgc tgctgaacgg cggcagcggt gggggcggcg gaggcggcgg    420
cggaggagtg gggggcggcg aggcagagac gatgtcggag ccgagccccg agagcgccag    480
ccaggccggg gaggacgaag acgaggagga ggacgacgag gaggaggaag atgagagcag    540
cagcagcggc gggggtgagg aggagagtag cgccgagagc ctggtgggca gcagcggcgg    600
gagcagcagc gacgagaccc gctcgttgag ccccggcgcc gccagcagca gcagcgggga    660
tggggacggc aaggagggcc tggaggagcc caagggaccg cggggcagcc agggcggcgg    720
cgggggcggc agcagtagca gcagcgtagt ctccagcggc ggcgacgagg gctacgggac    780
tgggggaggc ggaagcagcg cgacctccgg gggccggcgg ggcagcttgg agatgtcgtc    840
ggatggggaa cccctgagcc gcatggactc ggaggacagc ataagcagta ctataatgga    900
tgtagacagc acaatttcca gtgggcgttc aactccagca atgatgaatg gacaaggaag    960
cactacttct tcaagcaaaa atattgccta taattgttgt tgggaccagt gccaggcttg   1020
cttcaactct agcccagatc tggcagatca catccgttcc atacatgtag atggtcagcg   1080
aggaggggta tttgtttgct tatggaaagg ttgtaaagta tataacactc catctaccag   1140
```

-continued

```
tcaaagttgg ttacaaaggc atatgctgac acacagtgga gacaaacctt tcaagtgtgt   1200

tgttggtggc tgcaatgcca gctttgcttc tcagggaggg ctagctcgtc atgtacccac   1260

acacttcagt cagcagaact cctcaaaagt ttctagccag ccaaaggcca aagaagaatc   1320

tccttctaaa gctggaatga acaaaaggag gaaattaaag aacaaaagac gacgctcatt   1380

accacggcca catgatttct tcgatgcaca aacactggat gcgataagac atcgagccat   1440

atgctttaac ctctcagctc atatagaaag tttagggaag ggacacagtg ttgtttttca   1500

tagtactgta atagctaaga gaaaagaaga ttctgggaag atcaaacttt tgcttcattg   1560

gatgcctgaa gacattctgc ctgatgtgtg ggtgaatgaa agtgaacgac atcagttaaa   1620

aactaaagta gttcatttat caaagctacc caaagatact gccttgcttt tggacccaaa   1680

catatacaga acaatgccgc agaagaggtt gaagaggtaa aaaataaata aatacataaa   1740

aagcaaacaa gcggggacac ctgcagtctt agtcactgac aatgggttta gggaaagttg   1800

cacattagag tcaacccctt cttttttttt tttttttttt taaatccagt atttaggata   1860

atatttatgc ttagtgtaaa cattctgtga atgaagtaga ctcttcggtg gaatatatta   1920

atatattact gtatatccac attttcatgg aatggtactg tgggagactg agcaaacact   1980

cttttggcaa cttagtagaa cagcttctta aaggctttgc atgcttgctg ctttaagctg   2040

cttttttttt tcttttcttc cctttagtga tttcagtagt ttatattgga aagaaaaaca   2100

attacaacat gtgcccttac aaataccaaa agcactgtaa ggatatttgt cttgacagtg   2160

tttattgatt tgaagtcata ttaggaaata tttagacaat gaaaattatc aagagataat   2220

ttacctttca attatgataa atagatgtga ttggttgcca tttgtgttct tttgcagaac   2280

tctgataaga aaagtgttca atttgtattt aagcaaacag tgaacgacgt ttgcaatcaa   2340

ctaaaaattc gtctatcgaa ttagggctga aaattactgt taaagagtgt tgcagtatgt   2400

ctggtggctc ccttttcagg actagggctt tctcatggag tacagtatgt taatatttac   2460

ctatataact aatctgttaa cggtttttga aaaacctttc aaattatttg aataatcttc   2520

atattttcat ttaacctata tgactctaat ttttttctg aggaaatcat ttggtttttg   2580

agttgttttt tcttaatgta agaaaaattg tatttttttt acaagtatct tcaaactgaa   2640

tcttttatgc accaaagttg gtcttgaaaa ggaaaataaa atcactttct tgcttggtaa   2700

gcaagaagcc atatcgattt tttttaactt acagaaatgg aaatatgtgt aacttgttag   2760

tattgtatta aacaaatgtt gcatagagat aatagaacat tgcttgtaaa taattcagca   2820

gatttgtaat atatttttat attttgaaat gtactgtaga tgttttctag aggcatgaaa   2880

gttaaatgta tatattatgg tagaaataat attgaaggat attgtacttc actagtgctg   2940

ccagaggaat tgttaataaa agcaccttct ttaacaataa atgtctttca cagacttaag   3000

ggactatgta ctactgttaa tatctctaag aacaaaacac attgaacatc cttccagaaa   3060

gtctttgagg gaggacctat acccataata gaattatggc actcatttct gacagtgatc   3120

aagaaatcag ttatttcctt actgttggaa ggacattgta aagtatgtgg ttatatgcag   3180

tgaaactgca gaaaatactc ctggttgagg agttttcact ttactacagt gatataaaaa   3240

ccagcagttt ttacactaaa ttttttaaag aaatattaga caaaaatata gaattaaaac   3300

ctttggttcc aaaatgggaa aggttccacg atacataaat catttctcat ttgctttaaa   3360

aaatttaaaa gtgtaaaaat tatgagagac tttattcgtt aacaatgggg gtaaagagct   3420

atatacatga aaatgagtct tataaaatta agtgaagtgc aaataaaagc actgctacta   3480

taagacattc tggaatggtt gtttaataag ggtattatcc atttgatcta tagcaatgtg   3540
```

```
attttatttt taaaaagaaa agcagtgtgt tttctttttt tgttgttttc ttttgcttaa   3600
gcacttcatc aattgcttta ttctgtatct gcgaagtaat ctgcaatctc ttttgttctt   3660
tttaaaattt gatttgttat aaaattgcca aatagaagtg tttcagatac atagtttgta   3720
cctgtatttt tattttattg cctcatgttc ttgtaagtca ttcttaattg accaatgatt   3780
gtagaccttg cttgagtatt ttttctaata aaacaaagca aatcacattt agcttcaaat   3840
tgtaacaatt caattgaatt ttaaaatgac acctgaaaag atacatctga tattttctat   3900
atagagcaca gtaaataagt tttttcattg tgtagaaata cttagatgtc aaaaccagat   3960
ttcgtgatcc ttgattaact tctgagtact caatcaatca taatcctttt gctgcttatc   4020
tgatgttggt ttgatactgt taacacacca aaaagaatat ggaattgaaa tgagctagct   4080
ttataacttg tatgtataca tatatacaca taacatccaa ttatgactgg gtaataagtg   4140
tgaaaatttt aatttgtggt tttcatttat taatgtctgc ccatctgtat tgttgctcct   4200
accttcaaat atgacacctg aaataataag tctgttgtcc agaatttatg tattgttcag   4260
catcaagcaa actacagctc acaagcatac ccatttatat gttgtctatg cctgctttct   4320
cctgcagtgg cagaattgag tggtgagacc ttaggtcctg caagccccca atttttacta   4380
caggttggca atccctaatc caaaaatctg acataaaaaa tgctccaaag ttcaaaactt   4440
tctgagtgct gacatcatgc tgcaagtgga aaattccacg cctgacctca tgtgactggt   4500
catagtcaaa acaattaaga ctttgtttca tgcacaaaat tattaaaact gttgtataaa   4560
attaccttca gtctatgtgt ataaggtgtt tgtgagatat aaatgaactt tatgtttagt   4620
cttggatcgc atttctgagt ctcattatgt atatgcagat actcaaaaat ctgaaaaaaa   4680
tcaaaaatct gaaatacttc tggtcccaag catttcggat aagggatact cagcctgtct   4740
ctggtccttt aagaaaaagt tttcgattcc tttgtctagt tgacaaaaag tttggaaaca   4800
taaacttaga ccacacaact tgcattttaa tatgacaatg ttgatcttgg taataagcca   4860
gtacattaaa ttttagtgaa agctgtttca tgtattttac agtaaatact gccatattag   4920
gtacctacaa caaatggtgg tttttggaaa cttttacggt gggtttttaa agttattaat   4980
agtccatcat ttcatcattt gtgtttctgt atttattttg ctaagaacta aataagattt   5040
tgtacatcag attgtgtttg aaccgtaagg cacatctgct ttatctaaaa gaatcttaag   5100
gtggaaatag tgtaaaattt aaaatttttt atatttctaa taaacttttt atatataaat   5160
gttacctaaa gtggacacat gttacttctg aatttcacat gaaaggaaat taaagatgga   5220
caataattat ctctcaatat tttaagattt gttttactaa ttgaaaacag tatgtcagta   5280
aatctttggc cttagtgctt ttttccccct tttacacatt aataaaatgt tttaaatatg   5340
gtaatactct taaaacggta gaatttgcca cagttgttta aagcattttt atttttttctt  5400
tgaattctta attcatggtg aacagatgtt gggttcttaa aatataaaaa tgagaaaata   5460
tgtattaaaa atacttgata gagggttttc tctttaatca caacttaaaa aaagaaacct   5520
ttaatacctc tgcataagtt ctctgaaaga acttaaattc ttagtttata tgaaaactga   5580
tatgtatgtc tgtgtaacaa agcctgttgg gtacaggtct acaaggagat actttgtttc   5640
taaaaaagga gttaaatcgt gtcacctgaa tttttttttt ttgagataag tggacatttt   5700
ggggattttg gttaaaacat atttctctat tctaaaaatt acagaatatg tattcataaa   5760
agggaagaaa ttgttagaaa atttcctgtg tacgtagttt gtttttaaat taaagaatct   5820
tgtgacctgg                                                          5830
```

<210> SEQ ID NO 3
<211> LENGTH: 894
<212> TYPE: DNA
<213> ORGANISM: Homo sapiens

<400> SEQUENCE: 3
atgactccag aggaggaagt ccagagacag agcaccatga cttctgagaa aggtccttca 60
accggtgacc ccactctgag gagaagaatc gaaccctggg agtttgacgt cttctatgac 120
cccagagaac ttcgtaaaga ggcctgtctg ctctacgaaa tcaagtgggg catgagccgg 180
aagatctggc gaagctcagg caaaaacacc accaatcacg tggaagttaa ttttataaaa 240
aaatttacgt cagaaagaga ttttcaccca tccatgagct gctccatcac ctggttcttg 300
tcctggagtc cctgctggga atgctcccag gctattagag agtttctgag tcggcaccct 360
ggtgtgactc tagtgatcta cgtagctcgg ctttttttggc acatggatca acaaaatcgg 420
caaggtctca gggaccttgt taacagtgga gtaactattc agattatgag agcatcagag 480
tattatcact gctggaggaa ttttgtcaac tacccacctg ggatgaagc tcactggcca 540 caatacccac ctctgtggat gatgttgtac gcactggagc tgcactgcat aattctaagt 600
cttccaccct gtttaaagat ttcaagaaga tggcaaaatc atcttacatt tttcagactt 660
catcttcaaa actgccatta ccaaacgatt ccgccacaca tcctttttagc tacagggctg 720 atacatcctt ctgtggcttg gagatgaata ggatgattcc gtgtgtgtac tgattcaaga 780
acaagcaatg atgacccact aaagagtgaa tgccatttag aatctagaaa tgttcacaag 840
gtaccccaaa actctgtagc ttaaaccaac aataaatatg tattacctct ggca 894

<210> SEQ ID NO 4
<211> LENGTH: 7492
<212> TYPE: DNA
<213> ORGANISM: Homo sapiens

<400> SEQUENCE: 4
agaacgtcga gatggagccc aactcactcc agtgggtcgg ctcaccgtgt ggcttgcacg 60
gaccttacat tttctacaag gcttttcaat tccaccttga aggcaaacca agaattttgt 120
cccttggcga ctttttcttt gtaagatgta cgccaaagga tccgatttgc atagcggagc 180
tccagctgtt gtgggaagag aggaccagcc ggcaactttt atccagctct aaactttatt 240
tcctcccaga agacactccc cagggcagaa atagcgacca tggcgaggat gaagtcattg 300
ctgtttccga aaaggtgatt gtgaagcttg aagacctggt caagtgggta cattctgatt 360
tctccaagtg gagatgtggc ttccacgctg gaccagtgaa aactgaggcc ttgggaagga 420
atggacagaa ggaagctctg ctgaagtaca ggcagtcaac cctaaacagt ggactcaact 480
tcaaagacgt tctcaaggag aaggcagacc tgggggagga cgaggaagaa acgaacgtga 540
tagttctcag ctacccccag tactgccggt accgctcgat gctgaaacgc atccaggata 600
agccatcttc cattctaacg gaccagtttg cattggccct ggggggcatt gcagtggtca 660
gcaggaaccc tcagatcctg tactgtcggg acacctttga ccacccgact ctcatagaaa 720
acgagagtat atgcgatgag tttgcgccaa atcttaaagg cagaccacgc aaaaagaaac 780
catgcccaca aagaagagat tcattcagtg gtgttaagga ttccaacaac aattccgatg 840
gcaaagccgt tgccaaggtg aaatgtgagg ccaggtcagc cttgaccaag ccgaagaata 900
accataactg taaaaaagtc tcaaatgaag aaaaaccaaa ggttgccatt ggtgaagagt 960
gcagggcaga tgaacaagcc ttcttggtgg cactttataa atacatgaaa gaaaggaaaa 1020

```
cgccgataga acgaataccc tatttaggtt ttaaacagat taacctttgg actatgtttc   1080
aagctgctca aaaactggga ggatatgaaa caataacagc ccgccgtcag tggaaacata   1140
tttatgatga attaggcggt aatcctggga gcaccagcgc tgccacttgt acccgcagac   1200
attatgaaag attaatccta ccatatgaaa gatttattaa aggagaagaa gataagcccc   1260
tgcctccaat caaacctcgg aaacaggaga acagttcaca ggaaaatgag aacaaaacaa   1320
aagtatctgg aaccaaacgc atcaaacatg aaatacctaa aagcaagaaa gaaaaagaaa   1380
atgccccaaa gccccaggat gcagcagagg tttcatcaga gcaagaaaaa gaacaagaga   1440
ctttaataag ccagaaaagc atccctgagc ctctcccagc agcagacatg aagaaaaaaa   1500
tagaagggta tcaggaattt tcagcgaagc ccctggcatc cagagtagac ccagagaagg   1560
acaacgaaac agaccaaggt tccaacagtg agaaggtggc agaggaggcg ggagagaagg   1620
ggcccacacc tccactccca agtgctcctc tggccccaga aaaagattca gccttggtcc   1680
ctggggccag caaacagcca ctcacctctc ctagtgccct ggtggactca aaacaagaat   1740
ccaaactgtg ctgttttaca gagagccctg aaagtgaacc ccaagaagca tccttcccca   1800
gcttccccac cacacagcca ccgctggcaa accagaatga gacggaggat gacaaactgc   1860
ccgccatggc agattacatt gccaactgca ccgtgaaggt ggaccagctg ggcagtgacg   1920
acatccacaa tgcgctcaag cagaccccaa aggtccttgt ggtccagtcg tttgacatgt   1980
tcaaagacaa agacctgact gggcccatga acgagaacca tggacttaat tacacgcccc   2040
tgctctactc taggggcaac ccaggcatca tgtccccact ggccaagaaa aagcttttgt   2100
cccaagtgag tggggccagc ctctccagca gctaccctta tggctcccca cccctttga    2160
tcagcaaaaa gaaactgatt gctagggatg acttgtgttc cagtttgtcc cagacccacc   2220
atggccaaag cactgaccat atggcggtca gccggccatc agtgattcag cacgtccaga   2280
gtttcagaag caagccctcg gaagagagaa agaccatcaa tgacatcttt aagcatgaga   2340
aactgagtcg atcagatccc caccgctgca gcttctccaa gcatcacctt aacccccttg   2400
ctgactccta cgtcctgaag caagaaattc aggagggcaa ggataaactc ttagagaaaa   2460
gggccctccc ccattcccac atgcctagct tcctggctga cttctactcg tcccctcatc   2520
tccatagcct ctacagacac accgagcacc atcttcataa tgaacagaca tccaaatacc   2580
cttccaggga catgtacagg gaatcggaaa acagttcttt tccttcccac agacaccaag   2640
aaaagctcca tgtaaattat ctcacgtccc tgcacctgca agacaaaaag tcggcggcag   2700
cagaagcccc tacggatgat cagcctacag atctgagcct tcccaagaac ccgcacaaac   2760
ctaccggcaa ggtcctgggc ctggctcatt ccaccacagg gccccaggag agcaaaggca   2820
tctcccagtt ccaggtctta ggcagccaga gtcgagactg tcaccccaaa gcctgtcggg   2880
tatcacccat gaccatgtca ggccctaaaa aataccctga atcgctttca agatcaggaa   2940
aacctcacca tgtgagactg gagaatttca ggaagatgga aggcatggtc cacccaatcc   3000
tgcaccggaa aatgagcccg cagaacattg gggcggcgcg gccgatcaag cgcagcctgg   3060
aggatttgga ccttgtgatt gcagggaaaa aggcccgggc agtgtctccc ttagacccat   3120
ccaaggaggt ctctgggaag gagaaggcct ctgagcagga gagtgaaggc agcaaagcag   3180
cgcacggtgg gcattccggg ggcggatcag aaggccacaa gcttcccctc tcctccccta   3240
tcttcccagg tctgtattcc gggagcctgt gtaactcggg cctcaactcc aggctcccgg   3300
ctgggtattc tcattctctg cagtacttga aaaaccagac tgtgctttct ccactcatgc   3360
```

-continued

```
agcccctggc tttccactcg cttgtgatgc aaagaggaat ttttacatca ccgacaaatt   3420
ctcagcagct gtacagacac ttggctgcgg ctacacctgt aggaagttca tatggggacc   3480
ttttgcataa cagcatttac cctttagctg ctataaatcc tcaagctgcc tttccatctt   3540
cccagctgtc atccgtgcac cccagtacaa aactgtaggc tcagctctgc ccagcagtcc   3600
aaagcggcat ggccaacaga gcttcactcc ttacccagga gtgctggctt atagagttag   3660
aagtcagtat ttcttctaat ctgaggctat gatcagtccc agctgtaggg gcccagaggg   3720
gaggtgaaca tgcctgattt ttgtgggaca actctagccc acaaactgac tggctggtga   3780
gtcttgactc ccttccaaca cagatgccca ggcacctcca gatcattcac ttcgcacgtg   3840
ggccttgtga agggatttgt gaatatccag gaagaactta gaggacccca tctgagttcg   3900
gatggtcagg aaacaatctg ggcaaaaaag aggcaggcat ttcaaaggaa ggggcaagga   3960
agactggcaa acagatggca agggatgccc ctctttttca taaaactctc caaggttcaa   4020
tcaatgcaat gtatagtgaa acttcaatag atctttcatt ttgacactat taaacaatcc   4080
agagaagtaa acactgttaa attgactgta tatatttgct tcttaaaact acctgtatca   4140
ctgtttgctc acctaattta tatacaggta gttccatttt ctcccagttc cttctcgtct   4200
tttttttttt tttttttttt tttttatta aatggtattg cttttgtttg caggtctttt   4260
tgtttttgtt ttgtttttga ggctgactga ctgtcctagt tgttgtgtgt ttgtaatttt   4320
tccacatctt attttgagca gctttgggtg gtaaagttat tgtttacaaa ttgaagcaac   4380
tgattctagt ggaacaaatg aaaaagaaac agtcaagcac acaatagtgc aaagaacgtt   4440
cctttgtaga tccgcaactt aaggattttg ttcctcataa atggcatagt tgaaagagct   4500
tatacactgc ttacccagcc aaatgctttg ctttgaagta ttgggttctg tgaaaatatt   4560
gagcattgta cttaccttat ctaggctgtg aaactgtcct acataccaga gaatcataaa   4620
aacaaaaacc tcactggcag caagctgccg aataacaaca gagtctagag gacatatttg   4680
tgggctgcac agatatttta ggaatttcag aaattagaac aggagccaaa atgatttaca   4740
ttggcgttgg cactgattcc tttaaatggt ctgggaaagg gggttgggaa gaggatggag   4800
ctcaactggc cagaagagga gcagctgcag tcctgatagc ttctctagcc tcggtctttt   4860
gagtgataag tagtcatgtt gttttcatcc agttggtttc ttgtcattcc caagaagaat   4920
ctcccaggcc acatctttgg ggataactga catactggat tagccttttc aaaagaaaag   4980
tcatcctatt tggttttatg ggtgtgagt tttgtgtgta cacacacaga aacatgtaag   5040
gtggtttggg tcatgttttt aaccacctgg caatacagtc cactttctgg tttcttttat   5100
tgtgggaagt aaatggtcaa gctgctcagg cagtgaaaag atgtggagaa tgtccgttgt   5160
cattcttgcc actgtattcc atttgctacc gagatataac attaaggtgg acacattttc   5220
taactgtatt aattaaaagt caatggatac agagagtgga ttttctcccc aagtcccatc   5280
cctgctgaag accgcttgga tgaactcccc aacccactgt gcccctcccg caacactacc   5340
agtagacttt agaaccatag ttaactaagt cttttacctc tgagatactt aattctggga   5400
aaattggtga caattttcaa cttctaaata ggtaactcga ctgcaaaata atcaaaactg   5460
ataacaatga aactgcggct cttaaacaaa gccatgcatg ccgtgcattt gtattgaaat   5520
gtctccatga tatgaagcca aatattcaat gtaacatact taatatccaa aggtggaaac   5580
aaaagaatgt agagatccag tgttaagagt tccatttgct tcaattaatt atttaccttc   5640
ctgtggaata atatatatat atatatttaa tagaaccata gatagactag tagaatttag   5700
attataaatg tgtgagtgca gattatcctg ctattgcaca agctagaggg gggaaaaatc   5760
```

tcaattccag ctggcaagat gctagccagg acacatataa gaaagttgca ctagattgaa 5820
tggtcacaga atcggaggac atggaagaaa aaggaaactt cggtggttct gcagcagaca 5880
tgggctaggt catatgtggt ttctatgagt tcgtgtctca aaaaaaaaag gaggggggc 5940 atctgtcccc ggtggagctc acctatttgg aatatggggc atttgttttt tccactgcaa 6000
tgatttcagt ctggtttcat catgttggaa ttcgatcaca ccattttcaa acaatgttaa 6060
catagtccag cttttgtttt tctcatctct tctgagagga gactcactgt ttctgtctga 6120
ggaagctcat accctcggca aaacatcagg acaaataaag agaaatgggg gtacgcattc 6180
ccaacagaag cagtgtgtta tttgttttaa aactctgaac agagatcttg gaaatctttc 6240
aaaaagacca ttgaattctt cattggctga gaacgacgtt ttaaaatgtc ttaaataagg 6300
ctttgtttgc attgtttgag ttcaaggggc cttattattg aatggaattg cacaagcctt 6360
tctttgtgca atcaaaccat tgttattggt agttctgtaa aggaaactgt ggaatcgaat 6420
tggcagtgga gtcataaatc tatttactga gtgtggcttc caagaaatgt tgcaattcaa 6480
aatgcactaa gtctgtgatt tattggagat ttggagattc taaataatat ttttaaaaaa 6540
cttccatgca acttctggtt taatgtttgg caactccaca tgataaaaaa ataaaaacag 6600
cccaaccgag tttcggaatt aagtattctt ctagtaagtg attcaaactt gtaatatttg 6660
ccacaggact gacttattta tttactagct agaagctctt aagttcactt gtttatcagg 6720
gcatatacag aagggtttgt taaaactcga tgttaacttt acaactttct gacctggtgc 6780
atgaattctc aagtactgta tttcactgtg ttggtgtgtc tgatggaaat ttcgaggtgg 6840
tcccacaaaa atattttatg tagtgtgcct tcaaagagaa ccatttattt ctcttcactt 6900
atcgtcccac aaagtcacat ttggtggtgg tcagccaagt cgcatctggt ctagttttac 6960
tcttgtccca attttaaaga gaaatgggaa tgagtttgcc ctggtgagac ccataccatt 7020
gcaatgatta tcttgagcac ttaaagtcca gtgttggctg ttagtgtatt tgatattctg 7080
cctgtctcct catggttgaa atatgtctga agaatagcag cataatctct tggctgttta 7140 tacttttta aactttcctg tgttgtaaat attgtatact tttggtgatt ccagctatgt 7200
aacctctatg ctctgtaagg tgattatttg tatatagcaa catggcccag tgatattata 7260
tagtttccca atggagaggt tattgagtaa cctttgcatt agtttaaaca ctaccagaag 7320
aatgctgagc caactataaa cactcaattt tgtatgtttt ccaaattgta cttattactg 7380
cttttgatac tgtattacgt gccaatagtt tcccaatcac atagcaggca agagatattt 7440 tgtactttt gatccactgt aatatttaat aaaaaatgtt actatctgtt tc 7492

<210> SEQ ID NO 5
<211> LENGTH: 13147
<212> TYPE: DNA
<213> ORGANISM: Homo sapiens

<400> SEQUENCE: 5
ccggagcccg agccgaaggg cgagccgcaa acgctaagtc gctggccatt ggtggacatg 60
gcgcaggcgc gtttgctccg acgggccgaa tgttttgggg cagtgttttg agcgcggaga 120
ccgcgtgata ctggatgcgc atgggcatac cgtgctctgc ggctgcttgg cgttgcttct 180
tcctccagaa gtgggcgctg ggcagtcacg cagggtttga accggaagcg ggagtaggta 240
gctgcgtggc taacggagaa aagaagccgt ggccgcggga ggaggcgaga ggagtcggga 300
tctgcgctgc agccaccgcc gcggttgata ctactttgac cttccgagtg cagtgacagt 360

```
gatgtgtgtt ctgaaattgt gaaccatgag tctagtactt aatgatctgc ttatctgctg    420
ccgtcaacta gaacatgata gagctacaga acgaaagaaa gaagttgaga aatttaagcg    480
cctgattcga gatcctgaaa caattaaaca tctagatcgg cattcagatt ccaaacaagg    540
aaaatatttg aattgggatg ctgtttttag atttttacag aaatatattc agaaagaaac    600
agaatgtctg agaatagcaa aaccaaatgt atcagcctca acacaagcct ccaggcagaa    660
aaagatgcag gaaatcagta gtttggtcaa atacttcatc aaatgtgcaa acagaagagc    720
acctaggcta aaatgtcaag aactcttaaa ttatatcatg gatacagtga aagattcatc    780
taatggtgct atttacggag ctgattgtag caacatacta ctcaaagaca ttctttctgt    840
gagaaaatac tggtgtgaaa tatctcagca acagtggtta gaattgttct ctgtgtactt    900
caggctctat ctgaaacctt cacaagatgt tcatagagtt ttagtggcta gaataattca    960
tgctgttacc aaaggatgct gttctcagac tgacggatta aattccaaat tttggactt    1020
tttttccaag gctattcagt gtgcgagaca agaaaagagc tcttcaggtc taaatcatat    1080
cttagcagct cttactatct tcctcaagac tttggctgtc aactttcgaa ttcgagtgtg    1140
tgaattagga gatgaaattc ttcccacttt gctttatatt tggactcaac ataggcttaa    1200
tgattcttta aaagaagtca ttattgaatt atttcaactg caaatttata tccatcatcc    1260
gaaaggagcc aaaacccaag aaaaaggtgc ttatgaatca acaaaatgga gaagtatttt    1320
atacaactta tatgatctgc tagtgaatga gataagtcat ataggaagta gaggaaagta    1380
ttcttcagga tttcgtaata ttgccgtcaa agaaaatttg attgaattga tggcagatat    1440
ctgtcaccag gtttttaatg aagataccag atccttggag atttctcaat cttacactac    1500
tacacaaaga gaatctagtg attacagtgt cccttgcaaa aggaagaaaa tagaactagg    1560
ctgggaagta ataaaagatc accttcagaa gtcacagaat gattttgatc ttgtgccttg    1620
gctacagatt gcaacccaat taatatcaaa gtatcctgca agtttaccta actgtgagct    1680
gtctccatta ctgatgatac tatctcagct tctaccccaa cagcgacatg gggaacgtac    1740
accatatgtg ttacgatgcc ttacggaagt tgcattgtgt caagacaaga ggtcaaacct    1800
agaaagctca caaaagtcag atttattaaa actctggaat aaaatttggt gtattacctt    1860
tcgtggtata agttctgagc aaatacaagc tgaaaacttt ggcttacttg gagccataat    1920
tcagggtagt ttagttgagg ttgacagaga attctggaag ttatttactg ggtcagcctg    1980
cagaccttca tgtcctgcag tatgctgttt gactttggca ctgaccacca gtatagttcc    2040
aggaacggta aaaatgggaa tagagcaaaa tatgtgtgaa gtaaatagaa gcttttcttt    2100
aaaggaatca ataatgaaat ggctcttatt ctatcagtta gagggtgact tagaaaatag    2160
cacagaagtg cctccaattc ttcacagtaa ttttcctcat cttgtactgg agaaaattct    2220
tgtgagtctc actatgaaaa actgtaaagc tgcaatgaat tttttccaaa gcgtgccaga    2280
atgtgaacac caccaaaaag ataaagaaga actttcattc tcagaagtag aagaactatt    2340
tcttcagaca acttttgaca agatggactt tttaaccatt gtgagagaat gtggtataga    2400
aaagcaccag tccagtattg gcttctctgt ccaccagaat ctcaaggaat cactggatcg    2460
ctgtcttctg ggattatcag aacagcttct gaataattac tcatctgaga ttacaaattc    2520
agaaactctt gtccggtgtt cacgtctttt ggtgggtgtc cttggctgct actgttacat    2580
gggtgtaata gctgaagagg aagcatataa gtcagaatta ttccagaaag ccaagtctct    2640
aatgcaatgt gcaggagaaa gtatcactct gtttaaaaat aagacaaatg aggaattcag    2700
aattggttcc ttgagaaata tgatgcagct atgtacacgt tgcttgagca actgtaccaa    2760
```

```
gaagagtcca aataagattg catctggctt tttcctgcga ttgttaacat caaagctaat   2820
gaatgacatt gcagatattt gtaaaagttt agcatccttc atcaaaaagc catttgaccg   2880
tggagaagta gaatcaatgg aagatgatac taatggaaat ctaatggagg tggaggatca   2940
gtcatccatg aatctattta acgattaccc tgatagtagt gttagtgatg caaacgaacc   3000
tggagagagc caaagtacca taggtgccat taatccttta gctgaagaat atctgtcaaa   3060
gcaagatcta cttttcttag acatgctcaa gttcttgtgt ttgtgtgtaa ctactgctca   3120
gaccaatact gtgtccttta gggcagctga tattcggagg aaattgttaa tgttaattga   3180
ttctagcacg ctagaaccta ccaaatccct ccacctgcat atgtatctaa tgcttttaaa   3240
ggagcttcct ggagaagagt acccccttgcc aatggaagat gttcttgaac ttctgaaacc   3300
actatccaat gtgtgttctt tgtatcgtcg tgaccaagat gtttgtaaaa ctattttaaa   3360
ccatgtcctt catgtagtga aaaacctagg tcaaagcaat atggactctg agaacacaag   3420
ggatgctcaa ggacagtttc ttacagtaat tggagcattt tggcatctaa caaaggagag   3480
gaaatatata ttctctgtaa gaatggccct agtaaattgc cttaaaactt tgcttgaggc   3540
tgatccttat tcaaaatggg ccattcttaa tgtaatggga aaagactttc ctgtaaatga   3600
agtatttaca caatttcttg ctgacaatca tcaccaagtt cgcatgttgg ctgcagagtc   3660
aatcaataga ttgttccagg acacgaaggg agattcttcc aggttactga aagcacttcc   3720
tttgaagctt cagcaaacag cttttgaaaa tgcatacttg aaagctcagg aaggaatgag   3780
agaaatgtcc catagtgctg agaaccctga aactttggat gaaatttata atagaaaatc   3840
tgttttactg acgttgatag ctgtggtttt atcctgtagc cctatctgcg aaaaacaggc   3900
tttgtttgcc ctgtgtaaat ctgtgaaaga gaatggatta gaacctcacc ttgtgaaaaa   3960
ggttttagag aaagtttctg aaacttttgg atatagacgt ttagaagact ttatggcatc   4020
tcatttagat tatctggttt tggaatggct aaatcttcaa gatactgaat acaacttatc   4080
ttcttttcct tttattttat taaactacac aaatattgag gatttctata gatcttgtta   4140
taaggttttg attccacatc tggtgattag aagtcatttt gatgaggtga agtccattgc   4200
taatcagatt caagaggact ggaaaagtct tctaacagac tgctttccaa agattcttgt   4260
aaatattctt ccttattttg cctatgaggg taccagagac agtgggatgg cacagcaaag   4320
agagactgct accaaggtct atgatatgct taaaagtgaa aacttattgg gaaaacagat   4380
tgatcactta ttcattagta atttaccaga gattgtggtg gagttattga tgacgttaca   4440
tgagccagca aattctagtg ccagtcagag cactgacctc tgtgactttt caggggattt   4500
ggatcctgct cctaatccac ctcattttcc atcgcatgtg attaaagcaa catttgccta   4560
tatcagcaat tgtcataaaa ccaagttaaa aagcatttta gaaattcttt ccaaaagccc   4620
tgattcctat cagaaaattc ttcttgccat atgtgagcaa gcagctgaaa caaataatgt   4680
ttataagaag cacagaattc ttaaaatata tcacctgttt gttagtttat tactgaaaga   4740
tataaaaagt ggcttaggag gagcttgggc ctttgttctt cgagacgtta tttatacttt   4800
gattcactat atcaaccaaa ggccttcttg tatcatggat gtgtcattac gtagcttctc   4860
cctttgttgt gacttattaa gtcaggtttg ccagacagcc gtgacttact gtaaggatgc   4920
tctagaaaac catcttcatg ttattgttgg tacacttata ccccttgtgt atgagcaggt   4980
ggaggttcag aaacaggtat tggacttgtt gaaatactta gtgatagata acaaggataa   5040
tgaaaacctc tatatcacga ttaagctttt agatcctttt cctgaccatg ttgtttttaa   5100
```

ggatttgcgt attactcagc aaaaaatcaa atacagtaga ggacccttttt cactcttgga 5160
ggaaattaac cattttctct cagtaagtgt ttatgatgca cttccattga caagacttga 5220
aggactaaag gatcttcgaa gacaactgga actacataaa gatcagatgg tggacattat 5280
gagagcttct caggataatc cgcaagatgg gattatggtg aaactagttg tcaatttgtt 5340
gcagttatcc aagatggcaa taaaccacac tggtgaaaaa gaagttctag aggctgttgg 5400
aagctgcttg ggagaagtgg gtcctataga tttctctacc atagctatac aacatagtaa 5460
agatgcatct tataccaagg cccttaagtt atttgaagat aaagaacttc agtggacctt 5520
cataatgctg acctacctga ataacacact ggtagaagat tgtgtcaaag ttcgatcagc 5580
agctgttacc tgtttgaaaa acattttagc cacaaagact ggacatagtt tctgggagat 5640
ttataagatg acaacagatc caatgctggc ctatctacag ccttttagaa catcaagaaa 5700
aaagttttta gaagtaccca gatttgacaa agaaaaccct tttgaaggcc tggatgatat 5760
aaatctgtgg attcctctaa gtgaaaatca tgacatttgg ataaagacac tgacttgtgc 5820
ttttttggac agtggaggca caaaatgtga aattcttcaa ttattaaagc caatgtgtga 5880
agtgaaaact gacttttgtc agactgtact tccatacttg attcatgata ttttactcca 5940
agatacaaat gaatcatgga gaaatctgct ttctacacat gttcagggat ttttcaccag 6000
ctgtcttcga cacttctcgc aaacgagccg atccacaacc cctgcaaact tggattcaga 6060
gtcagagcac tttttccgat gctgtttgga taaaaaatca caaagaacaa tgcttgctgt 6120
tgtggactac atgagaagac aaaagagacc ttcttcagga acaattttta atgatgcttt 6180
ctggctggat ttaaattatc tagaagttgc caaggtagct cagtcttgtg ctgctcactt 6240
tacagcttta ctctatgcag aaatctatgc agataagaaa agtatggatg atcaagagaa 6300
aagaagtctt gcatttgaag aaggaagcca gagtacaact atttctagct tgagtgaaaa 6360
aagtaaagaa gaaactggaa taagtttaca ggatcttctc ttagaaatct acagaagtat 6420
aggggagcca gatagtttgt atggctgtgg tggagggaag atgttacaac ccattactag 6480
actacgaaca tatgaacacg aagcaatgtg ggcaaagcc ctagtaacat atgacctcga 6540
aacagcaatc ccctcatcaa cacgccaggc aggaatcatt caggccttgc agaatttggg 6600
actctgccat attctttccg tctatttaaa aggattggat tatgaaaata aagactggtg 6660
tcctgaacta gaagaacttc attaccaagc agcatggagg aatatgcagt gggaccattg 6720
cacttccgtc agcaaagaag tagaaggaac cagttaccat gaatcattgt acaatgctct 6780
acaatctcta agagacagag aattctctac attttatgaa agtctcaaat atgccagagt 6840
aaaagaagtg gaagagatgt gtaagcgcag ccttgagtct gtgtattcgc tctatcccac 6900
acttagcagg ttgcaggcca ttggagagct ggaaagcatt ggggagcttt tctcaagatc 6960
agtcacacat agacaactct ctgaagtata tattaagtgg cagaaacact cccagcttct 7020
caaggacagt gattttagtt ttcaggagcc tatcatggct ctacgcacag tcattttgga 7080
gatcctgatg gaaaaggaaa tggacaactc acaaagagaa tgtattaagg acattctcac 7140
caaacacctt gtagaactct ctatactggc cagaactttc aagaacactc agctccctga 7200
aagggcaata tttcaaatta aacagtacaa ttcagttagc tgtggagtct ctgagtggca 7260
gctggaagaa gcacaagtat tctgggcaaa aaaggagcag agtcttgccc tgagtattct 7320
caagcaaatg atcaagaagt tggatgccag ctgtgcagcg aacaatccca gcctaaaact 7380
tacatacaca gaatgtctga gggtttgtgg caactggtta gcagaaacgt gcttagaaaa 7440
tcctgcggtc atcatgcaga cctatctaga aaaggcagta gaagttgctg gaaattatga 7500

```
tggagaaagt agtgatgagc taagaaatgg aaaaatgaag gcatttctct cattagcccg   7560
gttttcagat actcaatacc aaagaattga aaactacatg aaatcatcgg aatttgaaaa   7620
caagcaagct ctcctgaaaa gagccaaaga ggaagtaggt ctccttaggg aacataaaat   7680
tcagacaaac agatacacag taaaggttca gcgagagctg gagttggatg aattagccct   7740
gcgtgcactg aaagaggatc gtaaacgctt cttatgtaaa gcagttgaaa attatatcaa   7800
ctgcttatta agtggagaag aacatgatat gtgggtattc cgactttgtt ccctctggct   7860
tgaaaattct ggagtttctg aagtcaatgg catgatgaag agagacggaa tgaagattcc   7920
aacatataaa tttttgcctc ttatgtacca attggctgct agaatgggga ccaagatgat   7980
gggaggccta ggatttcatg aagtcctcaa taatctaatc tctagaattt caatggatca   8040
cccccatcac actttgttta ttatactggc cttagcaaat gcaaacagag atgaatttct   8100
gactaaacca gaggtagcca gaagaagcag aataactaaa aatgtgccta aacaaagctc   8160
tcagcttgat gaggatcgaa cagaggctgc aaatagaata atatgtacta tcagaagtag   8220
gagacctcag atggtcagaa gtgttgaggc actttgtgat gcttatatta tattagcaaa   8280
cttagatgcc actcagtgga agactcagag aaaaggcata aatattccag cagaccagcc   8340
aattactaaa cttaagaatt tagaagatgt tgttgtccct actatggaaa ttaaggtgga   8400
ccacacagga gaatatggaa atctggtgac tatacagtca tttaaagcag aatttcgctt   8460
agcaggaggt gtaaatttac caaaaataat agattgtgta ggttccgatg gcaaggagag   8520
gagacagctt gttaagggcc gtgatgacct gagacaagat gctgtcatgc aacaggtctt   8580
ccagatgtgt aatacattac tgcagagaaa cacggaaact aggaagagga aattaactat   8640
ctgtacttat aaggtggttc ccctctctca gcgaagtggt gttcttgaat ggtgcacagg   8700
aactgtcccc attggtgaat ttcttgttaa caatgaagat ggtgctcata aaagatacag   8760
gccaaatgat ttcagtgcct ttcagtgcca aaagaaaatg atggaggtgc aaaaaaagtc   8820
ttttgaagag aaatatgaag tcttcatgga tgtttgccaa aattttcaac cagttttccg   8880
ttacttctgc atggaaaaat tcttggatcc agctatttgg tttgagaagc gattggctta   8940
tacgcgcagt gtagctactt cttctattgt tggttacata cttggacttg gtgatagaca   9000
tgtacagaat atcttgataa atgagcagtc agcagaactt gtacatatag atctaggtgt   9060
tgcttttgaa cagggcaaaa tccttcctac tcctgagaca gttcctttta gactcaccag   9120
agatattgtg gatggcatgg gcattacggg tgttgaaggt gtcttcagaa gatgctgtga   9180
gaaaaccatg gaagtgatga gaaactctca ggaaactctg ttaaccattg tagaggtcct   9240
tctatatgat ccactctttg actggaccat gaatcctttg aaagctttgt atttacagca   9300
gaggccggaa gatgaaactg agcttcaccc tactctgaat gcagatgacc aagaatgcaa   9360
acgaaatctc agtgatattg accagagttt caacaaagta gctgaacgtg tcttaatgag   9420
actacaagag aaactgaaag gagtggaaga aggcactgtg ctcagtgttg gtggacaagt   9480
gaatttgctc atacagcagg ccatagaccc caaaaatctc agccgacttt tcccaggatg   9540
gaaagcttgg gtgtgatctt cagtatatga attacccttt cattcagcct ttagaaatta   9600
tattttagcc tttattttta acctgccaac atactttaag tagggattaa tatttaagtg   9660
aactattgtg ggtttttttg aatgttggtt ttaatacttg atttaatcac cactcaaaaa   9720
tgttttgatg gtcttaagga acatctctgc tttcactctt tagaaataat ggtcattcgg   9780
gctgggcgca gcggctcacg cctgtaatcc cagcactttg ggaggccgag gtgagcggat   9840
```

```
cacaaggtca ggagttcgag accagcctgg ccaagagacc agcctggcca gtatggtgaa   9900
accctgtctc tactaaaaat acaaaaatta gccgagcatg gtggcgggca cctgtaatcc   9960
cagctactcg agaggctgag gcaggagaat ctcttgaacc tgggaggtga aggttgctgt  10020
gggccaaaat catgccattg cactccagcc tgggtgacaa gagcgaaact ccatctcaaa  10080
aaaaaaaaaa aaaaaacaga aacgtatttg gatttttcct agtaagatca ctcagtgtta  10140
ctaaataatg aagttgttat ggagaacaaa tttcaaagac acagttagtg tagttactat  10200
tttttaagt gtgtattaaa acttctcatt ctattctctt tatcttttaa gcccttctgt  10260
actgtccatg tatgttatct ttctgtgata acttcataga ttgccttcta gttcatgaat  10320
tctcttgtca gatgtatata atctctttta ccctatccat tgggcttctt ctttcagaaa  10380
ttgtttttca tttctaatta tgcatcattt ttcagatctc tgtttcttga tgtcattttt  10440
aatgtttttt taatgttttt tatgtcacta attattttaa atgtctgtac ttgatagaca  10500
ctgtaatagt tctattaaat ttagttcctg ctgtttatat ctgttgattt ttgtatttga  10560
taggctgttc atccagtttt gtctttttga aaagtgagtt tattttcagc aaggctttat  10620
ctatgggaat cttgagtgtc tgtttatgtc atattcccag ggctgttgct gcacacaagc  10680
ccattcttat tttaatttct tggctttagg gtttccatac ctgaagtgta gcataaatac  10740
tgataggaga tttcccaggc caaggcaaac acacttcctc ctcatctcct tgtgctagtg  10800
ggcagaatat ttgattgatg ccttttttcac tgagagtata agcttccatg tgtcccacct  10860
ttatggcagg ggtggaagga ggtacattta attcccactg cctgcctttg gcaagccctg  10920
ggttctttgc tccccatata gatgtctaag ctaaaagccg tgggttaatg agactggcaa  10980
attgttccag gacagctaca gcatcagctc acatattcac ctctctggtt tttcattccc  11040
ctcatttttt tctgagacag agtcttgctc tgtcacccag gctggagtgc agtggcatga  11100
tctcagctca ctgaaacctc tgcctcctgg gttcaagcaa ttctcctgcc tcagcctccc  11160
gagtagctgg gactacaggc gtgtgccaac acgcccggct aattttttgt atttttatta  11220
gagacggagt ttcaccgtgt tagccaggat ggtctcgatc gcttgacctc gtgatccacc  11280
ctcctcggcc tcccaaagtg ctgggattac aggtgtgagc caccgcgccc ggcctcattc  11340
ccctcatttt tgaccgtaag gatttcccct ttcttgtaag ttctgctatg tatttaaaag  11400
aatgttttct acattttatc cagcatttct ctgtgttctg ttggaaggga agggcttagg  11460
tatctagttt gatacatagg tagaagtgga acatttctct gtccccccagc tgtcatcata  11520
taagataaac atcagataaa aagccacctg aaagtaaaac tactgactcg tgtattagtg  11580
agtataatct cttctccatc cttaggaaaa tgttcatccc agctgcggag attaacaaat  11640
gggtgattga gctttctcct cgtatttgga ccttgaaggt tatataaatt tttttcttat  11700
gaagagttgg catttctttt tattgccaat ggcaggcact cattcatatt tgatctcctc  11760
accttcccct cccctaaaac caatctccag aactttttgg actataaatt tcttggtttg  11820
acttctggag aactgttcag aatattactt tgcatttcaa attacaaact taccttggtg  11880
tatctttttc ttacaagctg cctaaatgaa tatttggtat atattggtag ttttattact  11940
atagtaaatc aaggaaatgc agtaaactta aaatgtcttt aagaaagccc tgaaatcttc  12000
atgggtgaaa ttagaaatta tcaactagat aatagtatag ataaatgaat ttgtagctaa  12060
ttcttgctag ttgttgcatc cagagagctt tgaataacat cattaatcta ctctttagcc  12120
ttgcatggta tgctatgagg ctcctgttct gttcaagtat tctaatcaat ggctttgaaa  12180
agtttatcaa atttacatac agatcacaag cctaggagaa ataactaatt cacagatgac  12240
```

```
agaattaaga ttataaaaga ttttttttt gtaattttag tagagacagg gttgccattg  12300

tattccagcc ttggcgacag agcaagactc tgcctcaaaa aaaaaaaaaa aaaggttttg  12360

gcaagctgga actctttctg caaatgacta agatagaaaa ctgccaagga caaatgagga  12420

gtagttagat tttgaaaata ttaatcatag aatagttgtt gtatgctaag tcactgaccc  12480

atattatgta cagcatttct gatctttact ttgcaagatt agtgatacta tcccaataca  12540

ctgctggaga aatcagaatt tggagaaata agttgtccaa ggcaagaaga tagtaaatta  12600

taagtacaag tgtaatatgg acagtatcta acttgaaaag atttcaggcg aaaagaatct  12660

ggggtttgcc agtcagttgc tcaaaaggtc aatgaaaacc aaatagtgaa gctatcagag  12720

aagctaataa attatagact gcttgaacag ttgtgtccag attaagggag ataatagctt  12780

tcccacccta ctttgtgcag gtcatacctc cccaaagtgt ttacctaatc agtaggttca  12840

caaactcttg gtcattatag tatatgccta aaatgtatgc acttaggaat gctaaaaatt  12900

taaatatggt ctaaagcaaa taaaagcaaa gaggaaaaac tttggacagc gtaaagacta  12960

gaatagtctt ttaaaaagaa agccagtata ttggtttgaa atatagagat gtgtcccaat  13020

ttcaagtatt ttaattgcac cttaatgaaa ttatctattt tctatagatt ttagtactat  13080

tgaatgtatt actttactgt tacctgaatt tattataaag tgtttttgaa taaataattc  13140

taaaagc                                                            13147
```

<210> SEQ ID NO 6
<211> LENGTH: 6102
<212> TYPE: DNA
<213> ORGANISM: Homo sapiens

<400> SEQUENCE: 6

```
gtctctgtcc atccagactc ctgacgttca agttcgcagg gacgtcacgt ccgcacttga     60

acttgcagct caggggggct tttgccattt ttttcatctc tctctctctc tctccctcta    120

tctctcttct ctctctctcc ctcttttttt ttttttttt ttttttttt ttgcttaaaa    180

aaaagccatg acggctctcc cacaattcat cttccctgcg ccatctttgt attatttcta    240

atttattttg gatgtcaaaa ggcactgatg aagatatttt ctctggagtc tccttctttc    300

taacccggct ctcccgatgt gaaccgagcc gtcgtccgcc cgccgccgcc gccgccgccg    360

ccgccgcccg ccccgcagcc caccatgtct cgccgcaagc aaggcaaacc ccagcactta    420

agcaaacggg aattctcgcc cgagcctctt gaagccattc ttacagatga tgaaccagac    480

cacggcccgt tgggagctcc agaaggggat catgacctcc tcacctgtgg gcagtgccag    540

atgaacttcc cattggggga cattcttatt tttatcgagc acaaacggaa acaatgcaat    600

ggcagcctct gcttagaaaa agctgtggat aagccacctt ccccttcacc aatcgagatg    660

aaaaaagcat ccaatcccgt ggaggttggc atccaggtca cgccagagga tgacgattgt    720

ttatcaacgt catctagagg aatttgcccc aaacaggaac acatagcaga taaacttctg    780

cactggaggg gcctctcctc ccctcgttct gcacatggag ctctaatccc cacgcctggg    840

atgagtgcag aatatgcccc gcagggtatt tgtaaagatg agcccagcag ctacacatgt    900

acaacttgca aacagccatt caccagtgca tggtttctct tgcaacacgc acagaacact    960

catggattaa gaatctactt agaaagcgaa cacggaagtc ccctgacccc gcgggttggt   1020

atcccttcag gactaggtgc agaatgtcct tcccagccac ctctccatgg gattcatatt   1080

gcagacaata accccttaa cctgctaaga ataccaggat cagtatcgag agaggcttcc   1140
```

-continued

```
ggcctggcag aagggcgctt tccacccact ccccccctgt ttagtccacc accgagacat   1200
cacttggacc cccaccgcat agagcgcctg gggggcggaag agatggccct ggccacccat   1260
cacccgagtg cctttgacag ggtgctgcgg ttgaatccaa tggctatgga gcctcccgcc   1320
atggatttct ctaggagact tagagagctg gcagggaaca cgtctagccc accgctgtcc   1380
ccaggccggc ccagccctat gcaaaggtta ctgcaaccat tccagccagg tagcaagccg   1440
cccttcctgg cgacgccccc cctccctcct ctgcaatccg cccctcctcc ctcccagccc   1500
ccggtcaagt ccaagtcatg cgagttctgc ggcaagacgt tcaaatttca gagcaacctg   1560
gtggtgcacc ggcgcagcca cacgggcgag aagccctaca agtgcaacct gtgcgaccac   1620
gcgtgcaccc aggccagcaa gctgaagcgc cacatgaaga cgcacatgca caaatcgtcc   1680
cccatgacgg tcaagtccga cgacggtctc tccaccgcca gctccccgga acccggcacc   1740
agcgacttgg tgggcagcgc cagcagcgcg ctcaagtccg tggtggccaa gttcaagagc   1800
gagaacgacc ccaacctgat cccggagaac ggggacgagg aggaagagga ggacgacgag   1860
gaagaggaag aagaggagga agaggaggag gaggagctga cggagagcga gagggtggac   1920
tacggcttcg ggctgagcct ggaggcggcg cgccaccacg agaacagctc gcggggcgcg   1980
gtcgtgggcg tgggcgacga gagccgcgcc ctgcccgacg tcatgcaggg catggtgctc   2040
agctccatgc agcacttcag cgaggccttc caccaggtcc tgggcgagaa gcataagcgc   2100
ggccacctgg ccgaggccga gggccacagg gacacttgcg acgaagactc ggtggccggc   2160
gagtcggacc gcatagacga tggcactgtt aatggccgcg gctgctcccc gggcgagtcg   2220
gcctcggggg gcctgtccaa aaagctgctg ctgggcagcc ccagctcgct gagccccttc   2280
tctaagcgca tcaagctcga gaaggagttc gacctgcccc cggccgcgat gcccaacacg   2340
gagaacgtgt actcgcagtg gctcgccggc tacgcggcct ccaggcagct caaagatccc   2400
ttccttagct tcggagactc cagacaatcg ccttttgcct cctcgtcgga gcactcctcg   2460
gagaacggga gtttgcgctt ctccacaccg cccggggagc tggacggagg gatctcgggg   2520
cgcagcggca cgggaagtgg agggagcacg ccccatatta gtggtccggg cccgggcagg   2580
cccagctcaa aagagggcag acgcagcgac acttgtgagt actgtgggaa agtcttcaag   2640
aactgtagca atctcactgt ccacaggaga agccacacgg gcgaaaggcc ttataaatgc   2700
gagctgtgca actatgcctg tgcccagagt agcaagctca ccaggcacat gaaaacgcat   2760
ggccaggtgg ggaaggacgt ttacaaatgt gaaatttgta agatgccttt tagcgtgtac   2820
agtaccctgg agaaacacat gaaaaaatgg cacagtgatc gagtgttgaa taatgatata   2880
aaaactgaat agaggtatat taatacccct ccctcactcc cacctgacac cccctttttc   2940
accactcccc ttccccatcg ccctccagcc ccactccctg taggattttt ttctagtccc   3000
atgtgattta aacaaacaaa caaacaaaca gaagtaacga agctaagaat atgagagtgc   3060
ttgtcaccag cacacctgtt ttttttcttt ttcttttttct tttttctttt tcctttttttt   3120
tttttttcct ttatgttctc accgtttgaa tgcatgatct gtatggggca atactattgc   3180
attttacgca aactttgagc ctttctcttg tgcaataatt tacatgttgt gtatgttttt   3240
ttttaaactt agacagcatg tatggtatgt tatggctatt ttaaattgtc cctaattcgt   3300
tgctgagcaa acatgttgct gtttccagtt ccgttctgag agaaaaagag agagagagag   3360
aaaaagacca tgctgcatac attctgtaat acatatcatg tacagtttta ttttataacg   3420
tgaggaggaa aaacagtctt tggattaacc ctctatagac agaatagata gcactgaaaa   3480
aaaatctcta tgagctaaat gtctgtctct aaagggttaa atgtatcaat tggaaaggaa   3540
```

```
gaaaaaaggc cttgaattga caaattaaca gaaaaacaga acaagtttat tctatcattt   3600
ggttttaaaa tatgagtgcc ttggatctat taaaaccaca tcgatggttc tttctacttg   3660
ttataaactt gtagcttaat tcagcattgg gtgaggtaat aaaccttagg aactagcata   3720
taattctata ttgtatttct cacaacaatg gctacctaaa aagatgaccc attatgtcct   3780
agttaatcat catttttcct ttagtttaat tttataaaca aaactgatta taccagtata   3840
aaagctactt tgctcctggt gagagcttaa aagaaatggg ctgttttgcc caaagtttta   3900
tttttttaa acaatgatta aattgaatgt gtaatgtgca aaagccctgg aacgcaatta   3960
aatacactag taaggagttc attttatgaa gatatttgct ttaataatgt ctttttaaaa   4020
atactggcac caaaagaaat agatccagat ctacttggtt gtcaagtgga caatcaaatg   4080
ataaacttta agaccttgta taccatattg aaaggaagag gctgacaata aggtttgaca   4140
gaggggaaca gaagaaaata atatgattta ttagcacaac gtggtactat ttgccattta   4200
aaactagaac aggtatataa gctaatattg atacaatgat gattaactat gaattcttaa   4260
gacttgcatt taaatgtgac attcttaaaa aaagaagaga aagaatttta agagtagcag   4320
tatatatgtc tgtgctccct aaaagttgta cttcatttct tttccataca ctgtgtgcta   4380
tttgtgttaa catggaagag gattcattgt ttttattttt attttttaa tttttcttt   4440
tttattaagc tagcatctgc cccagttggt gttcaaatag cacttgactc tgcctgtgat   4500
atctgtatct tttctctaat cagagataca gaggttgagt ataaaataaa cctgctcaga   4560
taggacaatt aagtgcactg tacaattttc ccagtttaca ggtctatact taagggaaaa   4620
gttgcaagaa tgctgaaaaa aaattgaaca caatctcatt gaggagcatt ttttaaaaac   4680
taaaaaaaaa aaaactttgc cagccattta cttgactatt gagcttactt acttggacgc   4740
aacattgcaa gcgctgtgaa tggaaacaga atacacttaa catagaaatg aatgattgct   4800
ttcgcttcta cagtgcaagg atttttttgt acaaaacttt tttaaatata aatgttaaga   4860
aaaatttttt ttaaaaaaca cttcattatg tttagggggg aactgcattt tagggttcca   4920
ttgtcttggt ggtgttacaa gacttgttat ccatttaaaa atggtagtgg aaattctatg   4980
ccttggatac acaccgctct tcaggttgta aaaaaaaaaa acatacattg gggaaaggtt   5040
taagattata tagtacttaa atataggaaa atgcacactc atgttgattc ctatgctaaa   5100
atacatttat ggtctttttt ctgtatttct agaatggtat ttgaattaaa tgttcatcta   5160
gtgttaggca ctatagtatt tatattgaag cttgtatttt taactgttgc ttgttctctt   5220
aaaaggtatc aatgtacctt ttttggtagt ggaaaaaaaa aagacaggct gccacagtat   5280
attttttttaa tttggcagga taatatagtg caaattattt gtatgcttca aaaaaaaaaa   5340
aaagagagaa acaaaaaagt gtgacattac agatgagaag ccatataatg gcggtttggg   5400
ggagcctgct agaatgtcac atggatggct gtcatagggg ttgtacatat cctttttgt   5460
tcctttttcc tgctgccata ctgtatgcag tactgcaagc taataacgtt ggtttgttat   5520
gtagtgtgct ttttgtccct ttccttctat caccctacat tccagcatct taccttcata   5580
tgcagtaaaa gaaagaaaga aaaaaaaagg aaaaaaaaaa aaaaaccaat gttttgcagt   5640
ttttttcatt gccaaaaact aaatggtgct ttatatttag attggaaaga atttcatatg   5700
caaagcatat taaagagaaa gcccgcttta gtcaatactt ttttgtaaat ggcaatgcag   5760
aatattttgt tattggcctt ttctattcct gtaatgaaag ctgtttgtcg taacttgaaa   5820
ttttatcttt tactatggga gtcactattt attattgctt atgtgccctg ttcaaaacag   5880
```

aggcacttaa tttgatcttt tatttttctt tgtttttatt ttttttttta tttagatgac 5940
caaaggtcat tacaacctgg ctttttattg tatttgtttc tggtctttgt taagttctat 6000
tggaaaaacc actgtctgtg ttttttggc agttgtctgc attaacctgt tcatacaccc 6060
attttgtccc tttattgaaa aaataaaaaa aattaaagta ca 6102

<210> SEQ ID NO 7
<211> LENGTH: 4628
<212> TYPE: DNA
<213> ORGANISM: Homo sapiens

<400> SEQUENCE: 7
ggtgctttgt gtgctgccgg cggggcgcgc ggcggtccgg gcgggtgact ggcggcgggc 60
gccgcggtcg ggctggctgc cgggcagcat ggaggagctg agcagcgtgg gcgagcaggt 120
cttcgccgcc gagtgcatcc tgagcaagcg gctccgcaag ggcaagctgg agtacctggt 180
caagtggcgc ggctggtcct ccaaacataa cagctgggag ccggaggaga acatcctgga 240
cccgaggctg ctcctggcct tccagaagaa ggaacatgag aaggaggtgc agaaccggaa 300
gagaggcaag aggccgagag gccggccaag gaagctcact gccatgtcct cctgcagccg 360
gcgctccaag ctcaaggaac ccgatgctcc ctccaaatcc aagtccagca gttcctcctc 420
ttcctccacg tcatcctcct cttcctcaga tgaagaggat gacagtgact tagatgctaa 480
gaggggtccc cggggccgcg agacccaccc agtgccgcag aagaaggccc agatcctggt 540
ggccaaaccc gagctgaagg atcccatccg gaagaagcgg ggacgaaagc ccctgccccc 600
agagcaaaag gcaacccgaa gacccgtgag cctggccaag gtgctgaaga ccgcccggaa 660
ggatctgggg gccccggcca gcaagctgcc ccctccactc agcgcccccg ttgcaggcct 720
ggcagctctg aaggcccacg ccaaggaggc ctgtggcggc cccagtgcca tggccacccc 780
agagaacctg gccagcctaa tgaagggcat ggccagtagc cccggccggg gtggcatcag 840
ctggcagagc tccatcgtgc actacatgaa ccggatgacc cagagccagg cccaggctgc 900
cagcaggttg gcgctgaagg cccaggccac caacaagtgc ggcctcgggc tggacctgaa 960
ggtgaggacg cagaaagggg agctgggaat gagccctcca ggaagcaaaa tcccgaaggc 1020
ccccagcggt ggggctgtgg agcagaaagt ggggaacaca gggggccccc cgcacaccca 1080
tggtgccagc agggtgcctg ctgggtgccc aggcccccag ccagcaccca cccaggagct 1140
gagcctccag gtcttggact tgcagagtgt caagaatggc atgcccgggg tgggtctcct 1200
tgcccgccac gccaccgcca ccaagggtgt cccggccacc aacccagccc ctgggaaggg 1260
cactgggagt ggcctcattg gggccagcgg ggccaccatg cccaccgaca caagcaaaag 1320
tgagaagctg gcttccagag cagtggcgcc acccacccct gccagcaaga gggactgtgt 1380
caagggcagt gctaccccca gtgggcagga gagccgcaca gcccccggag aagcccgcaa 1440
ggcggccaca ctgccagaga tgagcgcagg tgaggagagt agcagctcgg actccgaccc 1500
cgactccgcc tcgccgccca gcactggaca gaacccgtca gtgtccgttc agaccagcca 1560
ggactggaag cccacccgca gcctcatcga gcacgtattt gtcaccgacg tcactgccaa 1620
cctcatcacc gtcacagtga aggagtctcc caccagcgtg ggcttcttca acctgaggca 1680
ttactgaagc cccggcgcca ccagctgcgc ggtcttactc cccttccctg cctatggtgt 1740
cgcttggcta agtgactccc agcccaagcc ccctcaagag tctgggtcgg gggaggagga 1800
gtgggtggcc tccttgatgg gcaggcttgg aagggacttc tcccgcaccc cactctgtcc 1860
caggacatag ggcagggggc ctcactgcct tgttggtctc caccttgttc ctacctctgc 1920

```
aggcctcttt gctctcccct cttgcctcag gaaacccggt ggcacctgtg gctccaggtg   1980
actgtcttga acagagcggg cttcttcatg gctgcgttgt tgctgagttt gaactgctcc   2040
tccctggcct gcgtgactga atcacagctt tggtccctgt cttgcagggg ctgaggtgtc   2100
aggaggggac ttctggccca ccttgccttc agccctggag tgggcagaga gtattgtggg   2160
gaggcatggc cagtgggact agtgttccct ccatctggcc acagcttttg ggagatgggg   2220
tgggcagggg tggtcctggc tggcattgcc tgagccggca gtgatgaagt ggggagcttg   2280
cccttgacag gtgggggctg gctggggcct taatgtgaaa agacagtggc aggcagctgg   2340
agtagagcga gcccagcagc cctaaaaggc tgccttcatg gccatctagc cccagttcag   2400
ggcagcatcc atagcccaca agccagcgtg ggtggggcgg gggtggtccc acagctgggt   2460
tccacctgaa gagcctccgt gcctcggagc aggagaggca ggctatggct gccaccctcc   2520
ctcctgcctg tgtcccagtg agaactgacc tgagtcccct tccaaaccca gacccacctc   2580
ctgccccagg cccactgaag catgttccat ttctaaaaag cccagagttc agtgtgtccc   2640
aaggaaaacc caaagtggag gtgctcaggt ccaggggagt ccagtgggca ggacccttgg   2700
caggcaagcc cctcccttca ctcccaggac ctaccttctg ctagtaaagg actggcttca   2760
ttctaattat ggcccacaga ctgccccgga gacctggagg acagcagtgc tggcacttgg   2820
gtgtccatgg gcccgtctgc cggctctgcc tgtgctgcaa gtgttggccg tgggtccagc   2880
caacaactcc ctacgtcctg tgtggggccc tgcccaagtg gatgaggcat tccttgagga   2940
gtatcatttt ccctgacaat ccccatcacc tttaggggtt ccctgcttgg ctcctttcca   3000
gctgaaaaac tagacctgtg ccattgggga agctggacaa agtctagggg gcccgcctgg   3060
tagagggtcc cgggaagctg gatctgtcag cctcggccct gaggcccctg ttaactcaag   3120
actgtgagct gcctctaggt ggtcacgtct gggagctagc ttgtatggct tctgaccagt   3180
atcaggattt ctgttctgag agcagcgtgg gcagcaaggc agggcagccc agaggtggca   3240
gcggcaggca atctggtcac taggtctttg tgatgccaaa aataaaagag ggtggggtgg   3300
gtgctttctg ttcctctgat tggatggagt ccgccagcag gcatggggct acattccagt   3360
gcctgactat agggaggcac tcctgattcc atggagcagc ccggactttg agaatgggct   3420
ctggtttgcg gggggcaggc gtaccagact gcaagacccc ccagtacctc accgtgccaa   3480
ataggaagag gtggccttgg tgtagccaaa tggatctttt taacagtgtg cctttgggga   3540
gggacccatg tccatggctt cgttgagggc catccatatg ccagctgggg gccagcccac   3600
agtggccata ttggctgcag caggaatggt gcccacctcg gcgaattgaa gggctaagag   3660
tcccagatag ctaggccaga gctggaagca gacagtaagg ggaagagctg ctcccacagg   3720
agagggagag attccagctc actgcgcagc ctgggaggag gcgtggatcc tggcacgctg   3780
agcctcaggc accagcctcc ctgtgctcga cagcaaagtc ttgactcctt cctgctgagc   3840
actgtgctac cttcactgct ccaaagccag actaacagct ctccaagccc ttggggtgac   3900
tcggcttcca ggagctgttg gagaaatgag gatgtctgtc cctgtctgcc tgggcaggcc   3960
agattcctcc ccagcagccg ggtctctcca gaccctgatt cggtgccttt ctgtttacca   4020
gctacttcaa tcccaaagtt tgaatctgca gataccttac tcccagccac tttgccttct   4080
tactgtgttg tgtgttttc ctggtgcttc aagagcgtgt gcagggcaag tgccgtcact   4140
gggaactgca ccagatgctc agacttggtt gtcttatgtt taccaataaa taaaagtaga   4200
ctttttctat ttttatttgc tgctatttgt gtgtgtgttt gtgtttgtgt agctaggtat   4260
```

ctggcacttc tgacgatgca ttgttgcttt tttcccgaag gtcccgcagg aactgtggca 4320
atggtgtgtg tgtgaaatgg tgtgttaacc gcgttttgtt tgctcctgta ttgaatagga 4380
agcagtggcc agtctgtctt ccttagagat gttagcatat ttttatatgt atatattttg 4440
taccaaaaaa gagtgttcct tgttttggtt acactcgaaa ttctgaccta gctggagagg 4500
gctctgggcc gagagctttc actaagggga gacttcaggg gaggatcaag ctttgaacca 4560
aagccaatca ctggcttgat ttgtgttttt taattaaaaa aaaaatcatt catgtatgcc 4620
acttctaa 4628

<210> SEQ ID NO 8
<211> LENGTH: 2748
<212> TYPE: DNA
<213> ORGANISM: Homo sapiens

<400> SEQUENCE: 8
ggcgggctgc tcgctgcatc tctgggcgtc tttggctcgc cacgctgggc agtgcctgcc 60
tgcgcctttc gcaacctcct cggccctgcg tggtctcgag ctgggtgagc gagcgggcgg 120
gctggtaggc tggcctgggc tgcgaccggc ggctacgact attctttggc cgggtcggtg 180
cgagtggtcg gctgggcaga gtgcacgctg cttggcgccg caggctgatc ccgccgtcca 240
ctcccgggag cagtgatgtt gggcaactct gcgccggggc ctgcgacccg cgaggcgggc 300
tcggcgctgc tagcattgca gcagacggcg ctccaagagg accaggagaa tatcaacccg 360
gaaaaggcag cgcccgtcca acaaccgcgg acccgggccg cgctggcggt actgaagtcc 420
gggaacccgc ggggtctagc gcagcagcag aggccgaaga cgagacgggt tgcacccctt 480
aaggatcttc ctgtaaatga tgagcatgtc accgttcctc cttggaaagc aaacagtaaa 540
cagcctgcgt tcaccattca tgtggatgaa gcagaaaaag aagctcagaa gaagccagct 600
gaatctcaaa aaatagagcg tgaagatgcc ctggctttta attcagccat tagtttacct 660
ggacccagaa aaccattggt ccctcttgat tatccaatgg atggtagttt tgagtcacca 720
catactatgg acatgtcaat tatattagaa gatgaaaagc cagtgagtgt taatgaagta 780
ccagactacc atgaggatat tcacacatac cttagggaaa tggaggttaa atgtaaacct 840
aaagtgggtt acatgaagaa acagccagac atcactaaca gtatgagagc tatcctcgtg 900
gactggttag ttgaagtagg agaagaatat aaactacaga atgagaccct gcatttggct 960
gtgaactaca ttgataggtt cctgtcttcc atgtcagtgc tgagaggaaa acttcagctt 1020
gtgggcactg ctgctatgct gttagcctca aagtttgaag aaatataccc cccagaagta 1080
gcagagtttg tgtacattac agatgatacc tacaccaaga aacaagttct gagaatggag 1140
catctagttt tgaaagtcct tacttttgac ttagctgctc caacagtaaa tcagtttctt 1200
acccaatact ttctgcatca gcagcctgca aactgcaaag ttgaaagttt agcaatgttt 1260
ttgggagaat taagtttgat agatgctgac ccatacctca agtatttgcc atcagttatt 1320
gctggagctg cctttcattt agcactctac acagtcacgg gacaaagctg gcctgaatca 1380
ttaatacgaa agactggata taccctggaa agtcttaagc cttgtctcat ggaccttcac 1440
cagacctacc tcaaagcacc acagcatgca caacagtcaa taagagaaaa gtacaaaaat 1500
tcaaagtatc atggtgtttc tctcctcaac ccaccagaga cactaaatct gtaacaatga 1560
aagactgcct ttgttttcta agatgtaaat cactcaaagt atatggtgta cagtttttaa 1620
cttaggtttt aattttacaa tcatttctga atacagaagt tgtggccaag tacaaattat 1680
ggtatctatt actttttaaa tggttttaat ttgtatatct tttgtatatg tatctgtctt 1740
agatatttgg ctaattttaa gtggttttgt taaagtatta atgatgccag ctgtcaggat 1800
aataaattga tttggaaaac tttgcaagtc aaatttaact tcttcaggat tttgcttagt 1860
aaagaagttt acttggttta ctatataatg ggaagtgaaa agccttcctc taaaattaaa 1920
gtaggtttag gaaaacagac cctcaaattc tgacattcat tttcctaagc aactggatca 1980
atttgctgac ttgggcataa tctaatctaa gcatatctga atacagtatt cagagataga 2040
tacagtagag attccccaga ctttttcgct ctttgtaaaa cctgtttgtt taggttttgc 2100
gaggtaaact caacagaggt tgggagtgga agagggtggg aagcttatat gcaaattaac 2160
agacgagaaa tgctccagaa ggtttattat tttaaagcac attaaaaaca aaaaactatt 2220
tttaaaatcc tgctagattt tataatggat ttgtgaataa aaaataccca gggttctcag 2280
aatggaataa atatcccttt taatagttat atatacagat atacaactgt tagctttaat 2340
tggcagctct cttctttttt cttcttttca ctggcttttt acttggtgct ttttcttgtt 2400
ttgcactggt ggtctgtgtt ctgtgaataa agcaaagtaa gaatttacta agagtatgtt 2460
aagttttgga ttattgaaat aagaggcatt tcttagtttt ccagtaggat ctaaaatgtg 2520
tcagctatga gtaagactgg catccaagaa gtttatatta tagatttagg tcctaatttt 2580
tataaatcac aaggtaaaaa aatcacagaa cagatggatc tctaatgaaa aagggatgtc 2640
tttttgttta tagtcatgtg gcaagatgag agtaaaacca gagagcaaac ctctataagt 2700
gttgagtata tgtatacatt tgaaataaac cagaaatttg ttacctta 2748

<210> SEQ ID NO 9
<211> LENGTH: 1889
<212> TYPE: DNA
<213> ORGANISM: Homo sapiens

<400> SEQUENCE: 9
gcacttggct tcaaagctgg ctcttggaaa ttgagcggag agcgacgcgg ttgttgtagc 60
tgccgctgcg gccgccgcgg aataataagc cgggatctac catacccatt gactaactat 120
ggaagattat accaaaatag agaaaattgg agaaggtacc tatggagttg tgtataaggg 180
tagacacaaa actacaggtc aagtggtagc catgaaaaaa atcagactag aaagtgaaga 240
ggaaggggtt cctagtactg caattcggga aatttctcta ttaaaggaac ttcgtcatcc 300
aaatatagtc agtcttcagg atgtgcttat gcaggattcc aggttatatc tcatctttga 360
gtttctttcc atggatctga agaaatactt ggattctatc cctcctggtc agtacatgga 420
ttcttcactt gttaagagtt atttatacca aatcctacag ggattgtgt tttgtcactc 480 tagaagagtt cttcacagag acttaaaacc tcaaaatctc ttgattgatg acaaaggaac 540
aattaaactg gctgattttg gccttgccag agcttttgga atacctatca gagtatatac 600
acatgaggta gtaacactct ggtacagatc tccagaagta ttgctggggt cagctcgtta 660
ctcaactcca gttgacattt ggagtatagg caccatattt gctgaactag caactaagaa 720
accacttttc catggggatt cagaaattga tcaactcttc aggattttca gagctttggg 780
cactcccaat aatgaagtgt ggccagaagt ggaatcttta caggactata agaatacatt 840
tcccaaatgg aaaccaggaa gcctagcatc ccatgtcaaa aacttggatg aaaatggctt 900
ggatttgctc tcgaaaatgt taatctatga tccagccaaa cgaatttctg gcaaaatggc 960
actgaatcat ccatatttta atgatttgga caatcagatt aagaagatgt agctttctga 1020
caaaaagttt ccatatgtta tatcaacaga tagttgtgtt tttattgtta actcttgtct 1080

```
atttttgtct tatatatatt tctttgttat caaacttcag ctgtacttcg tcttctaatt   1140

tcaaaaatat aacttaaaaa tgtaaatatt ctatatgaat ttaaatataa ttctgtaaat   1200

gtgtgtaggt ctcactgtaa caactatttg ttactataat aaaactataa tattgatgtc   1260

aggaatcagg aaaaaatttg agttggctta aatcatctca gtccttatgg cagttttatt   1320

ttcctgtagt tggaactact aaaatttagg aaaatgctaa gttcaagttt cgtaatgctt   1380

tgaagtattt ttatgctctg aatgtttaaa tgttctcatc agtttcttgc catgttgtta   1440

actatacaac ctggctaaag atgaatattt ttctactggt attttaattt ttgacctaaa   1500

tgtttaagca ttcggaatga gaaaactata cagatttgag aaatgatgct aaatttatag   1560

gagttttcag taacttaaaa agctaacatg agagcatgcc aaaatttgct aagtcttaca   1620

aagatcaagg gctgtccgca acagggaaga acagttttga aaatttatga actatcttat   1680

ttttaggtag gttttgaaag ctttttgtct aagtgaattc ttatgccttg gtcagagtaa   1740

taactgaagg agttgcttat cttggctttc gagtctgagt ttaaaactac acattttgac   1800

atagtgttta ttagcagcca tctaaaaagg ctctaatgta tatttaacta aaattactag   1860

ctttgggaat taaactgttt aacaaataa                                     1889
```

<210> SEQ ID NO 10
<211> LENGTH: 10030
<212> TYPE: DNA
<213> ORGANISM: Homo sapiens

<400> SEQUENCE: 10

```
atctgtttct ccggcgggga ctcgattata ttgtagggga ctgggggcgg ccgccgccgc     60

agccgcggga tggggcgagc gcgcggaccc cgcgggcagc cgcagccgca gccgcctcag    120

tagttcgggc ccccgcgccg ccgccccccg cccggcgccc gccctcggct cctgcactcg    180

ccgagcggcg gcagcagcgg gaggagcgcc ccgccgcccc cgccgaggac cgcgcggagg    240

ctgcggcgct gccgcggcgg gagtcccagg tcggcgggca gagcgcgggc agcgaggggc    300

cgccgcctgt gccgcagcgg ggagatgtgc ccagaggagg gcggcgcggc cgggctgggc    360

gagctccgct cctggtggga ggtcccggcc atcgcgcact tctgctcgct ctttcgcacc    420

gcgttccgcc tgcccgactt cgagatcgag gagttagaag ccgctcttca cagagatgac    480

gtggagttta tcagtgacct gattgcctgc ctgcttcagg gctgctatca acgaagagat    540

atcacgcctc agacattcca cagctaccta gaggacatca tcaactaccg ctgggagctc    600

gaagaaggga agcccaaccc tctgagggaa gccagtttcc aggacctgcc tcttcgcaca    660

cgggtggaga tcctgcaccg actctgtgat taccggctgg atgcagacga tgtcttcgat    720

cttctaaagg gcctggatgc agacagtctc cgtgtggagc cattgggtga agacaattct    780

ggggcactat attggtattt ctatggaaca cgaatgtaca aagaggaccc ggtgcaagga    840

aaatccaatg gagaactctc tttgagcagg gaaagtgaag gacaaaaaaa tgtctcaagt    900

attcctggaa aaacgggaaa aagaagagga agacccccaa aacggaagaa actgcaggag    960

gagattctgt tgagtgaaaa gcaggaagaa aattccttgg catccgagcc acagacaaga   1020

catgggtccc aagggccagg ccaaggtact tggtggctcc tgtgccagac agaagaggaa   1080

tggagacagg tcaccgagag ttttcgcgag aggacctccc ttcgagaacg gcagctctac   1140

aagctcctca gtgaggactt cctgcctgag atctgcaaca tgatcgccca gaagggaaaa   1200

cgtccacagc gcacaaaggc agagttgcat cctaggtgga tgtctgacca cctgtccatc   1260

aaacccgtca agcaagagga gactcctgtg ctgaccagaa tagaaaaaca aaagcgcaaa   1320
```

gaggaggaag aagagcgtca gattcttcta gcagtgcaga agaaggagca ggagcagatg 1380
ctaaaggaag agaggaaacg cgagttggag gagaaggtca aggcagtgga agatcgagcg 1440
aagaggagaa agctcaggga agaaagggca tggctgctgg ctcaaggaaa ggagctccct 1500
ccagaacttt cccatctgga ccccaattcc cccatgagag aggaaaaaaa gactaaagac 1560
ctctttgagt tggatgatga tttcactgct atgtataaag ttctagacgt ggtaaaggct 1620
cacaaggatt cctggccctt cttggaacct gtggatgaat cttatgcccc taactattat 1680
cagattatta aggcccccat ggatatttcc agcatggaga agaaactgaa tggaggttta 1740
tactgtacca aggaggaatt tgtaaatgac atgaagacca tgttcaggaa ttgtcgaaag 1800
tataatgggg aaagtagtga gtataccaag atgtctgata atttagagag gtgtttccat 1860
cgggcaatga tgaaacattt tcctggagaa gatggagaca cagatgaaga attttggatt 1920
cgagaggatg aaaagcggga gaaaagacgg agtcgggctg ggcgaagtgg tgggagccat 1980
gtttggaccc gctccaggga cccagaaggg tccagcagga aacagcagcc catggagaat 2040
ggaggaaagt cgttgccccc cacacgccga gcgccctctt ctggggacga tcagagcagc 2100
agctccacac agcccccgcg ggaggtgggc acttccaatg gccgaggttt ttctcatccc 2160
ctgcattgtg gtgggacacc cagccaggca cccttttaa accagatgag gccagcagta 2220
ccaggaacat ttggccctct gcgaggatca gatcctgcca ccttgtatgg ctcctctgga 2280
gtcccggagc cacaccccgg ggagcctgtg cagcagcgtc agcctttcac catgcagcct 2340
ccagttggaa ttaacagcct ccgaggaccc aggctaggca caccagagga gaagcaaatg 2400
tgcgggggc tgacacacct ttctaacatg ggcccacacc ctggatcctt gcagcttggg 2460
cagataagtg gcccaagtca ggatggaagc atgtatgctc cagctcagtt ccagccagga 2520
ttcattcctc cccggcatgg gggggctcca gcccggccac cagactttcc tgaaagctca 2580
gaaattcctc ccagccatat gtatcgatcg tacaagtacc tgaatcgagt acactctgcc 2640
gtctggaatg ggaaccatgg tgctacgaac caaggaccct tgggcccaga tgagaagccc 2700
cacctggggc caggaccctc tcaccagcct cgcactctcg gtcacgtgat ggattcccga 2760
gtcatgagac cacctgtccc ccccaaccag tggactgaac aatcaggctt cctacctcat 2820
ggagttcctt cctcagggta catgcgaccg ccctgcaagt ctgccggaca tcggttacag 2880
ccacctccag tgccagcacc cagttctttg tttggagcac ctgcccaggc tcttcggggg 2940
gtgcagggag gggactccat gatggacagc ccagagatga ttgcgatgca gcagctctcc 3000
tcccgcgtct gccccccagg tgtgccttac caccccccacc agcctgcaca cccccgttta 3060
cctggccctt ttccgcaggt agctcaccca atgtcagtca ctgtgtcagc ccccaagcct 3120
gccctgggca accctgggag ggcaccggag aacagtgaag cacaagagcc tgagaatgac 3180
caagcagagc cgttgcctgg ccttgaagag aaaccaccag gtgttggtac ttcagagggg 3240
gtctacctca cacaactacc tcaccccaca cctcccctgc agactgactg caccaggcag 3300
agctcaccac aagaaaggga aacagtgggc ccggagctca aaagcagctc ctccgaatct 3360
gcggacaact gtaaagcaat gaagggcaag aatccctggc cctcggatag cagctacccc 3420
ggcccagccg cccaagggtg cgtgagagac ctctccacgg tggcagacag gggcgctcta 3480
tccgagaacg gagtcattgg ggaagcatct ccttgtggat cggaggggaa gggccttggt 3540
agcagtggtt ccgaaaagct gctctgcccc agaggcagaa cgttgcagga aaccatgcca 3600
tgcacgggac agaacgcagc gacaccgccc agcacagacc ccggtttgac gggaggcact 3660

-continued gtgagccagt ttcccccgct gtatatgcct ggcctagagt acccgaattc agctgcccat 3720
taccacatca gtccaggcct gcagggtgtg ggccctgtga tgggagggaa gtccccagca 3780
tcccatcccc agcattttcc cccaaggggc tttcagtcta accacccaca ttctggaggc 3840
tttccccggt atcgcccccc acaaggaatg aggtattcct accacccacc gccacagcct 3900
tcctaccacc actatcagcg aactccttac tatgcctgtc cacagagctt ttctgactgg 3960
cagagacctc tccatcccca gggaagccca agcggacccc cagccagtca gcctccccca 4020
ccaaggtccc tcttctcaga taagaatgcc atggccagtc tgcaaggctg tgagacactg 4080
aatgctgcct taacttctcc aacccgtatg gatgcagtgg ctgctaaagt cccaaatgac 4140
gggcagaatc ctggtccaga ggaagagaag ctggatgaat ctatggagag gccagagagt 4200
cccaaagaat ttttagacct ggacaaccat aacgcagcta ccaagcggca gagctcgttg 4260
tcagccagcg agtatctcta tggaactcct ccgcctctga gttcaggaat gggatttggt 4320
tcatctgcat ttccacccca cagtgtgatg ctgcagacgg ggcctcccta taccccctcag 4380 cggccggcca gtcactttca gcccagggct tactcttccc ctgtggctgc cctcccacct 4440
caccacccag gggccaccca gcccaacggc ctctctcagg agggtcccat ctatcgctgc 4500
caggaagaag gcctgggtca ctttcaagct gtgatgatgg aacaaattgg cactagaagt 4560
ggaataagag gacctttcca ggaaatgtac agaccatcag gaatgcagat gcacccggtc 4620
cagtcgcagg cctcgttccc aaagaccccc acagcagcaa catcacagga ggaggtgccg 4680
cctcataagc ctccaacact tcccctggat cagagctagt ccaaggagga aatgagcccc 4740
aagcaatgga aagctgcaca cgaagactgg aatgtggaga actggggagt gccctgtcag 4800
ctctattccc atcacctgct ccaccccttc acggcgaccc actcgtgcca tacttgagct 4860
ggagccagtc acgggcccta aaaggacact ccttagatga ctgacacaca gattgcaaag 4920
gtcctcggcc agggatctct tgcacagctg atgtagacag tcaggcaaaa ctaatgaacg 4980
tggagttaat gatgactttt ccaaatcctg agacactttt cagggaaaat cactttaaac 5040
ttgggggagg gggtatactc aagaatggag tggtgctttt aaactttgat gagcagctaa 5100
actcaggtat atatttgggg aagggactac tcttagtatt aatggttttg gagctgggtc 5160
cagtttacag aattttcatg ttgcctttta aaataatttt tgttggtggt gaatgtattg 5220
tacataaagt gggaagggtg ggtggggatg cggaagaaat gggggtccta actggtgggc 5280
acacagcact ggagtgattt ttatctgttt acaatcatgt cacactgaat acttatggga 5340
gccggagatg agggtaggaa aggtttgatc ttgtaatatg tcactgtgtt tccttagtgg 5400
ccagccagcc ttcagaatag ctaaaggcct tccttccttc cagtcagcct gagagagaac 5460
acctgtcccc taagcacctg gtgtctccat tggaggcaga ctgctctcag gagactacta 5520
gaagcttcag cccggaagac aggctgctct ctcatgctgg tggcccaaat tgagaaagtg 5580
gtgtcccttc ctgattttgc caccagccct accgaatagt tgtaaaccag tatcaggaat 5640
tgggatcgct agagtgtttc acgtattaga agatgaatcg tcctcatcac agacctccct 5700
gtcaggactg tgatctagaa ggcatcacac acagctttct ggcacgaatc acattttgtg 5760
gaagtgacta ctcaggtttg tatattttag tatcaataaa gaattgcaca ggtttgaata 5820
ggaaaaatgt attctataga tttacagttt gaatttagga atatttcagt atatatagtt 5880
tttattcgtt ttaagtgaat catagtaaaa tcagtcatgg tgatttaaaa tagctatcaa 5940
gaacaagttc ttggaattat ctgttgtatc tgtgatagga aaccatttta cagtattaaa 6000
ttactttatt acagttgtag agttgaatta cactggattc tccctcgtta gcattctgta 6060

```
tttgatttta gctgaaaggt caccaaagtt aggacccatg ttttaaactt ttgaatattc   6120
cacaaaagaa aaaactaagg aaaatactga aattacaggt ctttgtaaag aatagcatat   6180
ttttaagcat gcttttggga tagtagaaga gtctctatga aatattaatc tgccctagtt   6240
tcttataaat tcagctgtgg gaggggccag tagagtgttt ccctccaatt ccaggattcc   6300
tagtgaagca tggaactgtc gtgtttacag tttgctaaac atatgctgtc cgtggaaaag   6360
gaagctaatc ggaagcatcc atgatacaga gaaatgaaag ccaagacacc agttccagga   6420
tgatggaagt tcatatccgt acgcaaatgc tgaacctggt gctgctgcct agggctcagg   6480
cagatttgag agttgagtag ggaacacagg tgcctctaag gtataatgca caaaaataca   6540
gattttctct cagagaggtt ttaattttaa atttgatgta tttgcaagtg gattgagttt   6600
tgagcctgtg ttctcactgg atcctaattc ttgttagaaa cctatcactg gcataacctg   6660
gtttagaaga gtgaagagga cagaaggatt gtggatgggt ctgcccttta gctagtatcc   6720
gctaacatgg ggcattacta cttcagtttc tgtgtttgtg cagaagcagg gaggaggtaa   6780
aaagctagtt tggagctggt tagacctggt ctaggcccag agaatttggc cactgacagc   6840
ctttctcttt tcctggtaat gctggtttga atcagaggcc tctcacttct ccttaacagg   6900
agcactgaca ctgtgggcct ctccccatga ctaccccagg ggcctgggtg ggagtggctg   6960
taagcagcag ttgggccatt gcccccttc cttctgccct cgtggtcctt gagcagttgt   7020
gtgcacactc ttccaggtaa tcctgtctcc tctctctccc agtgaccgcc ccaatcagct   7080
gttgctagag cgatgctgtg aacgatacag gaaaagtcag taaatccctt tatccttaat   7140
ctcccttctt ggttttcgac agaaaatatt aaggaagagc aataggaaat agaactactg   7200
tattataaca ctgtgaacaa gaacatcagc agcagcagaa ttgtcagcct tcctgcgtcc   7260
tgtgtgggaa tgtgtccatg ccttataggt actagtgctt cgtccattgt ccagggagtg   7320
tcctgagctt tcactggtct ttgaagtgca gatctgctat aagctgtctg gagctgcaag   7380
gttgcaggaa tccacaggag cgtgagctgc tgtgaacccc tagcccaccc atccccaagc   7440
aggatcttct tctcaccttt tcttcctcct ctagcacttc tctttccaag tgtcttaagc   7500
agatgcaatg tcttaaagca gatgcaaatg catttgccat cttctccatt aggaaaatga   7560
tggttatgtg atatgttata tttaggaagt agtgtgtaag gtatcctgaa aaggtttgct   7620
ctcaagctag aaggacattt caccctgtgg gtcactgtca ccttgtcagc gtgccggctc   7680
tcagtggtcc ccaggaggat ggggatagct gagatcgtgg agaatgggaa ataccattgc   7740
atctctttga tttaacactc atggctcacc tttagtagag ttgttaataa gttagaaact   7800
tgtgtcccta aggcccaaga gaaaagatga gcttcttggg aggattctgg gtttgttttc   7860
ccctcagaat taaaaaatag tttttaattc agctactttt tcccctcagt taaaaggtag   7920
caggagctat tggctgaaat ttgttacagt gaatgaatgt ggagaataaa taagaacaaa   7980
ccctgtagga ttcttgttga cgtaactttc catcccacct ctccgcctct ccttcatcac   8040
cagccttcat caggttggtt tagtttacct ggccgtacac acgagctgct catcaacagt   8100
tcgtatcttc tcactgagcc cgggccagat gctctcagaa ggccttctca tgctcctctt   8160
cgttaggctt agtgaaaacc ttaagacctg cagtttgtgc ccctcagttc agtcagacct   8220
cagctttaaa tgtcgattta ctctgtcttg ttccctgaaa gtgtttcttg tgactaagca   8280
tttggtgtca ttatcccatg ccatttatct gctgtatagt tactatatta tttttgctga   8340
ttcctactgc tggcagatgc catcccaggc ccacaaaatc ccagtgttgc agtcaccaca   8400
```

gctgtcagaa acaagtttgc aatccatact tcttggttca attttttttt ttaatggaca 8460
ttcaaatctg taaatactac actgctctta agacctgatt tgaaatttca caggaaggcc 8520
taatcctata gtcacaaggt aaggacagtt gagtagtgta agaaccccaa cctgcttgca 8580
gagaaccttg gttttcatag aaaggaaagg ctgaaggttt tctagcattg ttgcccttct 8640
ttgtctgtca gtcagttcac cctctgtgat tctccatgga cccgcattgc agaaaatcag 8700
tcccatatat tagtgagcca tgtactgccc aatccggggg ctcctggggt gtggtgtgtc 8760
caccagtgac tctccggaca ctagcttcag taaggatact tcttatttcg gttgagaatg 8820
cagaggcttt tattcgtgga ctcacatcac tgcatagcac aaagaatgtg attgccattt 8880
gctgcgtgag aaaaagctgg gctccctatt tctttttgg gttggactct gccgtgcagc 8940
cataggacac caagcctcac gcactttccc cttgggacag tagtgtttgg gtgaatgtta 9000
ctgcatcccg tttttttct tttcttttt tttttttt ttttgagacg aaatcttgct 9060
cttgtccccc agactggagt gcaatggcac gatctcggct cactgcaacc tccacctccc 9120
aggttcaagg gattcgtctg cctcggcctc ccaagtagct gggactacaa gcgcgcacca 9180
ccactcccag ctaatttttg tatttttagt agaggcgggg tttcaccatg ttggccaggc 9240
tggtctcaaa ctcctgacct caggtgatcc acccgccttg gcctcccaac atgctgggat 9300
tacaggcgtg agccaacaca ccggaccttc attttttaaa ttaagctggg acacaagttt 9360
tgcctccagg ctggatgttg atcctgctct gtgctagaca gatgtgcgga gggactgttc 9420
cgggctcggc ttgacctttt cctacctagt ttctccctct tgtcctgcac aagaggacta 9480
actgaactct aacgtcagaa cggctgacga gcagttgatt gtccttgctt gtgttgttga 9540
caggggtggg tggggtggga gcaggggtat ggatattgca taagttattg aaatgctgac 9600
ccccgttcag gaaaccatgc agccccttcc cttcccttcc cttcccttcc tttcccttcc 9660
ctagccaggg ctcaggtacc tcactctcct gccttgtgcg tagctcctgg ggccccggtc 9720
agtccccagc agccttggca cacagtgtct ggagcctctg ctcctgctgc aaaagcagaa 9780
accatgtgaa ccttctggcc agtactggaa aggggaatgc tatttatttt tatattgtgt 9840
atattttgtc gtggtctgct gattccctgt ttcactgaga gcgacactta cctcaatagt 9900
tagttcaata ttgtgtgttg gataattttt taaaagaact ttttaaaaag ctttttgatc 9960
cttggaggtc tgtagattta tttccatatg aactggttat tttgtataaa gtacatgctt 10020
aaaatagcaa 10030

<210> SEQ ID NO 11
<211> LENGTH: 2481
<212> TYPE: DNA
<213> ORGANISM: Homo sapiens

<400> SEQUENCE: 11
ctcacggagc tcgtagtttc ccggacgggc cgctcccggc ctcgcggcct cgcctcccca 60
cactacaact cccacggggc agcgggcgcg gctccccgta cccaccagct ggccgggcag 120
ggcagccact tcgcggtcgg gcccgccggc tgcgggcacc cgcgcgacgg gcgggaagat 180
ggcggacgtg gtcgtgggta aagacaaggg cggggagcag cggctcatct cgctgcctct 240
atcccgcatc cgggtcatca tgaagagctc ccccgaggtg tccagcatca accaggaggc 300
gttggtgctc acggccaagg ccacggagct ctttgttcaa tgcctagcca cctattccta 360
cagacacggc agtggaaagg aaaagaaagt actgacttac agtgatttag caaacactgc 420
acagcaatca gaaacttttc agtttcttgc agatatatta ccaaagaaga ttttagctag 480

```
taaatacctg aaaatgctta aagaggaaaa gagggaagaa gatgaggaga atgacaatga    540

taatgaaagt gaccatgatg aagctgactc ctaaaccaaa agtgctttaa aaaccagcct    600

ggcgaggaca gccctggacc cactccactg tctctaagta aacacagcac tgcccgcttt    660

tagcgtcttc acttcttcac agagttccag tgtgtggtat tctttcgagg tattctttcc    720

aggccgagat tgagcacctc atgtacctac gccacagaca gccagaggga aagcgaccca    780

gacagcagcc cctcctcgac aggcccaccc tgcagctcag gcaccaagaa aacagccgat    840

actggcagcc attgcagctc caaactgcag aggcaaggcc aattttaact tttcaattta    900

cagtcgattt tgaagagctt ctacatatcg gttatgtaaa ttcatatatg tatattttgg    960

aatcagttct tataaacagc tcgattcagt tttagctaaa tttatagttt aggtagtatg   1020

ttacatttga atttttgtct taagaaaagt tgactgttca gatatttttc tactgtaaag   1080

aaatatactt ttctattaaa gatctgtaca tatttttaca gtaaaatgct ttatggaact   1140

agttttagag ccctctatgg ctttaaggcc ttgcttactg cctgcaaatt ttgagaaatt   1200

taaaaataag cattctaaca cttttattcc cacagaaaaa ttccaagtca aattatcaaa   1260

tcaaatacaa aaataagtct tacctcttgt ataagcatgt tgtactaaaa aaaaattttg   1320

aaacattttg tatattggag atctctctca tcttactgtt ctttgcttta aattcctggc   1380

acttcttttt actgtctata agagaaaacc tatcataagc ccaatttttt ttttccactt   1440

agggtaaatg tttggctcct ctcatttcat tatctttttt tttttttttt taaagacaga   1500

ttctcactca gttgcccagg ctggattgcg gtggcgctgt ctcagctcac tgcaacctcc   1560

gcctcccagg ttcaagtgat tctcctgcct catcctcctg agtagctggg attacaggcg   1620

tgtgccacca tgcccaacct atttttgtat tttttagtag agacggggtt caccatgttg   1680

gccaggcttg tctcaaactc ctaacctcaa ctgatccacc tgcctcagcc tcccaaagtg   1740

ccgccgggat tacaggcgtg agccaccatg cctggccttc attatctctt ttttaaaaat   1800

gaaaaagttt ataatttaca ttcagtaaaa tcaccctttt tagtgtctag tctgtgaatt   1860

ttgacaaatg catggttttg taaccaatcg ataggacagt tctgccaccc aggacattcc   1920

cctctgttcc tctgttcctc tcttctcctg ccccctagca accactggtg ttttctgtcc   1980

ctcttgttca ttgacattta ttttaaaata aaatatttta aaatctactt tttggtgtac   2040

agttctgagt tttggcaaat gcagtcaagt cactaccacc accacaatta acagctatat   2100

caccctccag taaattccct gtggtcagct ccttccccac cttttaccgt ggcaaccgtc   2160

aagctattct ctgtccctat accaggtgtc atcaaatttt tttctggaaa gggccatgca   2220

gtaaatagtt caagctttgt gggcttttat agtctctgtt gctgctgctg aactcagctg   2280

ttgtagcacg aaagcagcca ggtaattact agatgaagga atgcaggtgg ctgtgtttca   2340

atagagcttt atttctgcaa actgaaactt gagttttgtg taattttcat gtgtcatgaa   2400

atactgtttt ctccaaccat ttaataatgt aaatacttgc tagcttatgt gccattaaaa   2460

aatgacttga tttggcttac a                                             2481
```

```
<210> SEQ ID NO 12
<211> LENGTH: 2088
<212> TYPE: DNA
<213> ORGANISM: Homo sapiens

<400> SEQUENCE: 12

attccacaga ctttcgctcc ctagcagcgg gtcggagatc gaaggaacgg gccaattgcg     60
```

gctgaaacgt ctttggaagg aggaaggggg tgagggagca tccctttgag tttcgcctct 120
tctcgaggcg gtggtgggaa gggagacata cttaatactg ccctcttaat ccaacggacc 180
ttacatcgtg tagactgccg ggagggcggc gggaaaaggg caagacggga gttggggaag 240
ggaaggagcc aggaagccgc gcgggagggc gcgcgcgcgc gcccctttt cagcagtgtg 300 gcggggtcgc acgcacgccc gcctcggcgg ctgggcgcga tttgcgacag tgggggggc 360 ggtggaggtg gcggcggcag cggcaacttt gcggcaagct cgggccgggc ttgcttgacg 420
gcggtgtggc ggaggccccg ccccaggcgg caggaacctg gagggaggcg gaggaatatg 480
tccgagaggg aagtgtcgac tgcgccggcg ggaacagaca tgcctgcggc caagaagcag 540
aagctgagca gtgacgagaa cagcaatcca gacctctctg gagacgagaa tgatgacgct 600
gtcagtatag aaagtggtac aaacactgaa cgccctgata cacctacaaa cacgccaaat 660
gcacctggaa ggaaaagttg gggaaaggga aaatggaagt caaagaaatg caaatattct 720
ttcaaatgtg taaatagtct caaggaagat cataaccaac cattgtttgg agttcagttt 780
aactggcaca gtaaagaagg agatccatta gtgtttgcaa ctgtaggaag caacagagtt 840
accttgtatg aatgtcattc acaaggagaa atccggttgt tgcaatctta cgtggatgct 900
gatgctgatg aaaactttta cacttgtgca tggacctatg atagcaatac gagccatcct 960
ctgctggctg tagctggatc tagaggcata attaggataa taaatcctat aacaatgcag 1020
tgtataaagc actatgttgg ccatggaaat gctatcaatg agctgaaatt ccatccaaga 1080
gatccaaatc ttctcctgtc agtaagtaaa gatcatgctt tacgattatg gaatatccag 1140
acggacactc tggtggcaat atttggaggc gtagaagggc acagagatga agttctaagt 1200
gctgattatg atcttttggg tgaaaaaata atgtcctgtg gtatggatca ttctcttaaa 1260
ctttggagga tcaattcaaa gagaatgatg aatgcaatta aggaatctta tgattataat 1320
ccaaataaaa ctaacaggcc atttatttct cagaaaatcc attttcctga tttttctacc 1380
agagacatac ataggaatta tgttgattgt gtgcgatggt taggcgattt gatactttct 1440
aagtcttgtg aaaatgccat tgtgtgctgg aaacctggca agatggaaga tgatatagat 1500
aaaattaaac ccagtgaatc taatgtgact attcttgggc gatttgatta cagccagtgt 1560
gacatttggt acatgaggtt ttctatggat ttctggcaaa agatgcttgc attgggcaat 1620
caagttggca aactttatgt ttgggattta gaagtagaag atcctcataa agccaaatgt 1680
acaacactga ctcatcataa atgtggtgct gctattcgac aaaccagttt tagcagggat 1740
agcagcattc ttatagctgt ttgtgatgat gccagtattt ggcgctggga tcgacttcga 1800
taaaatactt ttgcctaatc aaaattagag tgtgtttgtt gtctgtgtaa aatagaatta 1860
atgtatcttg ctagtaaggg cacgtagagc atttagagtt gtctttcagc attcaatcag 1920
gctgagctga atgtagtgat gtttacattg tttacattct ttgtactgtc ttcctgctca 1980
gactctactg cttttaataa aaatttattt ttgtaaagct gtgtgtttag ttactttcat 2040
tgtggtgaaa aaaagttaaa agtaataaaa ttatgcctta tcttttta 2088

<210> SEQ ID NO 13
<211> LENGTH: 5095
<212> TYPE: DNA
<213> ORGANISM: Homo sapiens

<400> SEQUENCE: 13
ggggccacgc tgcgggcccg ggccatggcc gccgccgatg ccgaggcagt tccggcgagg 60
ggggagcctc agcaggattg ctgtgtgaaa accgagctgc tgggagaaga gacacctatg 120

```
gctgccgatg aaggctcagc agagaaacag gcaggagagg cccacatggc tgcggacggt    180
gagaccaatg ggtcttgtga aaacagcgat gccagcagtc atgcaaatgc tgcaaagcac    240
actcaggaca gcgcaagggt caaccccag gatggcacca acacactaac tcggatagcg    300
gaaaatgggg tttcagaaag agactcagaa gcggcgaagc aaaaccacgt cactgccgac    360
gactttgtgc agacttctgt catcggcagc aacggataca tcttaaataa gccggcccta    420
caggcacagc ccttgaggac taccagcact ctggcctctt cgctgcctgg ccatgctgca    480
aaaacccttc ctggaggggc tggcaaaggc aggactccaa gcgcttttcc ccagacgcca    540
gccgccccac cagccaccct tggggagggg agtgctgaca cagaggacag gaagctcccg    600
gcccctggcg ccgacgtcaa ggtccacagg gcacgcaaga ccatgccgaa gtccgtcgtg    660
ggcctgcatg cagccagtaa agatcccaga gaagttcgag aagctagaga tcataaggaa    720
ccaaaagagg agatcaacaa aaacatttct gactttggac gacagcagct tttacccccc    780
ttcccatccc ttcatcagtc gctacctcag aaccagtgct acatggccac cacaaaatca    840
cagacagctt gcttgccttt tgttttagca gctgcagtat ctcggaagaa aaaacgaaga    900
atgggaacct atagcctggt tcctaagaaa aagaccaaag tattaaaaca gaggacggtg    960
attgagatgt ttaagagcat aactcattcc actgtgggtt ccaaggggga gaaggacctg   1020
ggcgccagca gcctgcacgt gaatggggag agcctggaga tggactcgga tgaggacgac   1080
tcagaggagc tcgaggagga cgacggccat ggtgcagagc aggcggccgc gttccccaca   1140
gaggacagca ggacttccaa ggagagcatg tcggaggctg atcgcgccca gaagatggac   1200
ggggagtccg aggaggagca ggagtccgtg gacaccgggg aggaggagga aggcggtgac   1260
gagtctgacc tgagttcgga atccagcatt aagaagaaat ttctcaagag gaaaggaaag   1320
accgacagtc cctggatcaa gccagccagg aaaaggaggc ggagaagtag aaagaagccc   1380
agcggtgccc tcggttctga gtcgtataag tcatctgcag gaagcgctga gcagacggca   1440
ccaggagaca gcacagggta catggaagtt tctctggact ccctggatct ccgagtcaaa   1500
ggaattctgt cttcacaagc agaagggttg gccaacggtc cagatgtgct ggagacagac   1560
ggcctccagg aagtgcctct ctgcagctgc cggatggaaa caccgaagag tcgagagatc   1620
accacactgg ccaacaacca gtgcatggct acagagagcg tggaccatga attgggccgg   1680
tgcacaaaca gcgtggtcaa gtatgagctg atgcgcccct ccaacaaggc cccgctcctc   1740
gtgctgtgtg aagaccaccg gggccgcatg gtgaagcacc agtgctgtcc tggctgtggc   1800
tacttctgca cagcgggtaa ttttatggag tgtcagcccg agagcagcat ctctcaccgt   1860
ttccacaaag actgtgcctc tcgagtcaat aacgccagct attgtcccca ctgtggggag   1920
gagagctcca aggccaaaga ggtgacgata gctaaagcag acaccacctc gaccgtgaca   1980
ccagtccccg ggcaggagaa gggctcggcc ctggagggca gggccgacac cacaacgggc   2040
agtgctgccg ggccaccact ctcggaggac gacaagctgc agggtgcagc ctcccacgtg   2100
cccgagggct ttgatccaac gggacctgct gggcttggga ggccaactcc cggcctttcc   2160
cagggaccag ggaaggaaac cttggagagc gctctcatcg ccctcgactc ggaaaaaccc   2220
aagaagcttc gcttccaccc aaagcagctg tacttctccg ccaggcaagg ggagcttcag   2280
aaggtgctcc tcatgctggt ggacggaatt gaccccaact tcaaaatgga gcaccagaat   2340
aagcgctctc cactgcacgc cgcggcagag gctggacacg tggacatctg ccacatgctg   2400
gttcaggcgg gcgctaatat tgacacctgc tcagaagacc agaggacccc gttgatggaa   2460
```

gcagccgaaa acaaccatct ggaagcagtg aagtacctca tcaaggctgg ggccctggtg 2520
gatcccaagg acgcagaggg ctctacgtgt ttgcacctgg ctgccaagaa aggccactac 2580
gaagtggtcc agtacctgct ttcaaatgga cagatggacg tcaactgtca ggatgacgga 2640
ggctggacac ccatgatctg ggccacagag tacaagcacg tggacctcgt gaagctgctg 2700
ctgtccaagg gctctgacat caacatccga gacaacgagg agaacatttg cctgcactgg 2760
gcggcgttct ccggctgcgt ggacatagcc gagatcctgc tggctgccaa gtgcgacctc 2820
cacgccgtga acatccacgg agactcgcca ctgcacattg ccgcccggga gaaccgctac 2880
gactgtgtcg tcctctttct ttctcgggat tcagatgtca ccttaaagaa caaggaagga 2940
gagacgcccc tgcagtgtgc gagcctcaac tctcaggtgt ggagcgctct gcagatgagc 3000
aaggctctgc aggactcggc ccccgacagg cccagccccg tggagaggat agtgagcagg 3060
gacatcgctc gaggctacga gcgcatcccc atcccctgtg tcaacgccgt ggacagcgag 3120
ccatgcccca gcaactacaa gtacgtctct cagaactgcg tgacgtcccc catgaacatc 3180
gacagaaata tcactcatct gcagtactgc gtgtgcatcg acgactgctc ctccagcaac 3240
tgcatgtgcg gccagctcag catgcgctgc tggtacgaca aggatggccg gctcctgcca 3300
gagttcaaca tggcggagcc tcccttgatc ttcgaatgca accacgcgtg ctcctgctgg 3360
aggaactgcc gaaatcgcgt cgtacagaat ggtctcaggg caaggctgca gctctaccgg 3420
acgcgggaca tgggctgggg cgtgcggtcc ctgcaggaca tcccaccagg cacctttgtc 3480
tgcgagtatg ttggggagct gatttcagac tcagaagccg acgttcgaga ggaagattct 3540
tacctctttg atctcgacaa taaggacggg gaggtttact gcatcgacgc gcggttctac 3600
gggaacgtca gccggttcat caaccaccac tgcgagccca acctggtgcc cgtgcgcgtg 3660
ttcatggccc accaggacct gcggttcccc cggatcgcct tcttcagcac ccgcctgatc 3720
gaggccggcg agcagctcgg gtttgactat ggagagcgct tctgggacat caaaggcaag 3780
ctcttcagct gccgctgcgg ctcccccaag tgccggcact cgagcgcggc cctggcccag 3840
cgtcaggcca gcgcggccca ggaggcccag gaggacggct tgcccgacac cagctccgcg 3900
gctgccgccg accccctatg agacgccgcc ggccagcggg gcgctcggga gccagggacc 3960
gccgcgtcgc cgattagagg acgaggagga gagattccgc acgcaaccga aagggtcctt 4020
cggggctgcg ccgccggctt cctggagggg tcggaggtga ggctgcagcc cctgcgggcg 4080
ggtgtggatg cctcccagcc accttcccag acctgcggcc tcaccgcggg cccagtgccc 4140
aggctggagc gcacactttg gtccgcgcgc cagagacgct gggagtccgc actggcatca 4200
ccttctgagt ttctgatgct gatttgtcgt tgcgaagttt ctcgtttctt cctctgacct 4260
ccgaggtccc cgctgcacca cggggttgct ctgttctcct gtccggccca gactcttctg 4320
tgtggcgccg ccgaagccac cgttagcgcg agctgctccg ttcgccctgc ccacggcctg 4380
cgtggctggg gccgagtccc aggggccgca cggagggcac agtctcctgt caggctcgga 4440
gaggtcagga gaccgacccc accactaact ttggagaaaa tgtgggtttg ctttttaaag 4500
gaatcctata tctagtccta tatatcaaac ctctaactga cgtttctttt cgaggaagtg 4560
gcttggtggg tgcagccccc gccggttccg ttgacgctgg caccttctgt tgattttta 4620
agccacatgc tatgatgaat aaactgattt attttctacc attactgaac attaggacaa 4680
acacaaaata aaaaacaaaa cacagacaac ggtgctgatt ctggtgtggt ttctactcac 4740
cacgtgaaat aaactatcaa ctgtataaag agaacaaagt gattttagaa taaaatgcag 4800
gaaaaacttt tttaaagatg ttagtcttgt agcgtgaata aatttgccat cacctttgt 4860 gtggtggcct ggcaggtcat atactttttt ttggcatata cctttttaaa gactgtaatt 4920
agtgcagtaa cagtggggtt ttttttgtgc aactcttcta aaaacattca taatgcagtc 4980
atgtttattt ttttctgtta aaatgttttt gacagtttta agagcagtct tttggctctg 5040
accatttctt gttctgtttc caatgaaatc aataaaaaaa aagaagtact ttaaa 5095

<210> SEQ ID NO 14
<211> LENGTH: 4133
<212> TYPE: DNA
<213> ORGANISM: Homo sapiens

<400> SEQUENCE: 14
agagatgcgg ggtctaccga gagggagggg gttgatgcgg gcccggggga ggggtcgtgc 60
ggcccctccg ggcagccgag gccgcggaag ggggggggccc cacagaggaa gaggtaggcc 120
ccggagccta ctctctcttc ccagggccca ggcatcctgg accccccaac tctctactgg 180
gctgaccagc cctcctgtcc cttgtctccc ctcccagggg gaggcccccg ctgagatggg 240
ggcgctgctg ctggagaagg aaaccagagg agccaccgag agagttcatg gctctttggg 300
ggacacccct cgtagtgaag aaaccctgcc caaggccacc cccgactccc tggagcctgc 360
tggcccctca tctccagcct ctgtcactgt cactgttggt gatgaggggg ctgacacccc 420
tgtaggggct acaccactca ttggggatga atctgagaat cttgagggag atggggacct 480
ccgtgggggc cggatcctgc tgggccatgc cacaaagtca ttcccctctt cccccagcaa 540
ggggggttcc tgtcctagcc gggccaagat gtcaatgaca ggggcgggaa aatcacctcc 600
atctgtccag agtttggcta tgaggctact gagtatgcca ggagcccagg gagctgcagc 660
agcagggtct gaaccccctc cagccaccac gagcccagag ggacagccca aggtccaccg 720
agcccgcaaa accatgtcca aaccaggaaa tggacagccc ccggtccctg agaagcggcc 780
ccctgaaata cagcatttcc gcatgagtga tgatgtccac tcactgggaa aggtgacctc 840
agatctggcc aaaaggagga agctgaactc aggaggtggc ctgtcagagg agttaggttc 900
tgcccggcgt tcaggagaag tgaccctgac gaaaggggac cccgggtccc tggaggagtg 960
ggagacggtg gtgggtgatg acttcagtct ctactatgat tcctactctg tggatgagcg 1020
cgtggactcc gacagcaagt ctgaagttga agctctaact gaacaactaa gtgaagagga 1080
ggaggaggaa gaggaggaag aagaagaaga ggaagaggag gaggaagagg aagaagaaga 1140
ggaagatgag gagtcaggga atcagtcaga taggagtggt tccagtggcc ggcgcaaggc 1200
caagaagaaa tggcgaaaag acagcccatg ggtgaagccg tctcggaaac ggcgcaagcg 1260
ggagcctccg cgggccaagg agccacgagg agtgaatggt gtgggctcct caggccccag 1320
tgagtacatg gaggtccctc tggggtccct ggagctgccc agcgagggga ccctctcccc 1380
caaccacgct ggggtgtcca atgacacatc ttcgctggag acagagcgag ggtttgagga 1440
gttgcccctg tgcagctgcc gcatggaggc acccaagatt gaccgcatca gcgagagggc 1500
ggggcacaag tgcatggcca ctgagagtgt ggacggagag ctgtcaggct gcaatgccgc 1560
catcctcaag cgggagacca tgaggccatc cagccgtgtg gccctgatgg tgctctgtga 1620
gacccaccgc gcccgcatgg tcaaacacca ctgctgcccg ggctgcggct acttctgcac 1680
ggcgggcacc ttcctggagt gccaccctga cttccgtgtg gcccaccgct tccacaaggc 1740
ctgtgtgtct cagctgaatg ggatggtctt ctgtccccac tgtggggagg atgcttctga 1800
agctcaagag gtgaccatcc cccggggtga cggggtgacc ccaccggccg gcactgcagc 1860

```
tcctgcaccc ccacccctgt cccaggatgt ccccgggaga gcagacactt ctcagcccag   1920
tgcccggatg cgagggcatg gggaaccccg gcgcccgccc tgcgatcccc tggctgacac   1980
cattgacagc tcagggccct ccctgaccct gcccaatggg ggctgccttt cagccgtggg   2040
gctgccactg gggccaggcc gggaggccct ggaaaaggcc ctggtcatcc aggagtcaga   2100
gaggcggaag aagctccgtt tccaccctcg gcagttgtac ctgtccgtga agcagggcga   2160
gctgcagaag gtgatcctga tgctgttgga caacctggac cccaacttcc agagcgacca   2220
gcagagcaag cgcacgcccc tgcatgcagc cgcccagaag ggctccgtgg agatctgcca   2280
tgtgctgctg caggctggag ccaacataaa tgcagtggac aaacagcagc ggacgccact   2340
gatggaggcc gtggtgaaca accacctgga ggtagcccgt tacatggtgc agcgtggtgg   2400
ctgtgtctat agcaaggagg aggacggttc cacctgcctc caccacgcag ccaaaatcgg   2460
gaacttggag atggtcagcc tgctgctgag cacaggacag gtggacgtca acgcccagga   2520
cagtgggggg tggacgccca tcatctgggc tgcagagcac aagcacatcg aggtgatccg   2580
catgctactg acgcggggcg ccgacgtcac cctcactgac aacgaggaga acatctgcct   2640
gcactgggcc tccttcacgg gcagcgccgc catcgccgaa gtccttctga atgcgcgctg   2700
tgacctccat gctgtcaact accatgggga cacccccctg cacatcgcag ctcgggagag   2760
ctaccatgac tgcgtgctgt tattcctgtc acgtggggcc aaccctgagc tgcggaacaa   2820
agagggggac acagcatggg acctgactcc cgagcgctcc gacgtgtggt ttgcgcttca   2880
actcaaccgc aagctccgac ttggggtggg aaatcgggcc atccgcacag agaagatcat   2940
ctgccgggac gtggctcggg gctatgagaa cgtgcccatt ccctgtgtca acggtgtgga   3000
tggggagccc tgccctgagg attacaagta catctcagag aactgcgaga cgtccaccat   3060
gaacatcgat cgcaacatca cccacctgca gcactgcacg tgtgtggacg actgctctag   3120
ctccaactgc ctgtgcggcc agctcagcat ccggtgctgg tatgacaagg atgggcgatt   3180
gctccaggaa tttaacaaga ttgagcctcc gctgattttc gagtgtaacc aggcgtgctc   3240
atgctggaga aactgcaaga accgggtcgt acagagtggc atcaaggtgc ggctacagct   3300
ctaccgaaca gccaagatgg gctgggggt ccgcgccctg cagaccatcc cacaggggac   3360
cttcatctgc gagtatgtcg gggagctgat ctctgatgct gaggctgatg tgagagagga   3420
tgattcttac ctcttcgact tagacaacaa ggatggagag gtgtactgca tagatgcccg   3480
ttactatggc aacatcagcc gcttcatcaa ccacctgtgt gaccccaaca tcattcccgt   3540
ccgggtcttc atgctgcacc aagacctgcg atttccacgc atcgccttct tcagttcccg   3600
agacatccgg actggggagg agctagggtt tgactatggc gaccgcttct gggacatcaa   3660
aagcaaatat ttcacctgcc aatgtggctc tgagaagtgc aagcactcag ccgaagccat   3720
tgccctggag cagagccgtc tggcccgcct ggacccacac cctgagctgc tgcccgagct   3780
cggctccctg ccccctgtca acacatgaga acggaccaca ccctctctcc ccagcatgga   3840
tggccacagc tcagccgcct cctctgccac cagctgctcg cagcccatgc ctgggggtgc   3900
tgccatcttc tctccccacc accctttcac acattcctga ccagagatcc cagccaggcc   3960
ctggaggtct gacagcccct ccctcccaga gctggttcct ccctgggagg gcaacttcag   4020
ggctggccac cccccgtgtt ccccatcctc agttgaagtt tgatgaattg aagtcgggcc   4080
tctatgccaa ctggttcctt ttgttctcaa taaatgttgg gtttggtaat aaa          4133
```

<210> SEQ ID NO 15
<211> LENGTH: 2654

<212> TYPE: DNA
<213> ORGANISM: Homo sapiens

<400> SEQUENCE: 15

```
gtttggcgct cggtccggtc gcgtccgaca cccggtggga ctcagaaggc agtggagccc     60
cggcggcggc ggcggcggcg cgcgggggcg acgcgcggga acaacgcgag tcggcgcgcg    120
ggacgaagaa taatcatggg ccagactggg aagaaatctg agaagggacc agtttgttgg    180
cggaagcgtg taaaatcaga gtacatgcga ctgagacagc tcaagaggtt cagacgagct    240
gatgaagtaa agagtatgtt tagttccaat cgtcagaaaa ttttggaaag aacggaaatc    300
ttaaaccaag aatggaaaca gcgaaggata cagcctgtgc acatcctgac ttctgtgagc    360
tcattgcgcg ggactaggga gtgttcggtg accagtgact tggattttcc aacacaagtc    420
atcccattaa agactctgaa tgcagttgct tcagtaccca taatgtattc ttggtctccc    480
ctacagcaga attttatggt ggaagatgaa actgttttac ataacattcc ttatatggga    540
gatgaagttt tagatcagga tggtactttc attgaagaac taataaaaaa ttatgatggg    600
aaagtacacg ggatagagaa atgtgggttt ataaatgatg aaatttttgt ggagttggtg    660
aatgcccttg gtcaatataa tgatgatgac gatgatgatg atggagacga tcctgaagaa    720
agagaagaaa agcagaaaga tctggaggat caccgagatg ataaagaaag ccgcccacct    780
cggaaatttc cttctgataa aatttttgaa gccatttcct caatgtttcc agataagggc    840
acagcagaag aactaaagga aaaatataaa gaactcaccg aacagcagct cccaggcgca    900
cttcctcctg aatgtacccc caacatagat ggaccaaatg ctaaatctgt tcagagagag    960
caaagcttac actcctttca tacgcttttc tgtaggcgat gttttaaata tgactgcttc   1020
ctacatcgta agtgcaatta ttcttttcat gcaacaccca acacttataa gcggaagaac   1080
acagaaacag ctctagacaa caaaccttgt ggaccacagt gttaccagca tttggaggga   1140
gcaaaggagt ttgctgctgc tctcaccgct gagcggataa agaccccacc aaaacgtcca   1200
ggaggccgca gaagaggacg gcttcccaat aacagtagca ggcccagcac ccccaccatt   1260
aatgtgctgg aatcaaagga tacagacagt gatagggaag cagggactga aacgggggga   1320
gagaacaatg ataaagaaga agaagagaag aaagatgaaa cttcgagctc ctctgaagca   1380
aattctcggt gtcaaacacc aataaagatg aagccaaata ttgaacctcc tgagaatgtg   1440
gagtggagtg gtgctgaagc ctcaatgttt agagtcctca ttggcactta ctatgacaat   1500
ttctgtgcca ttgctaggtt aattgggacc aaaacatgta gacaggtgta tgagtttaga   1560
gtcaaagaat ctagcatcat agctccagct cccgctgagg atgtggatac tcctccaagg   1620
aaaaagaaga ggaaacaccg gttgtgggct gcacactgca gaaagataca gctgaaaaag   1680
gacggctcct ctaaccatgt ttacaactat caaccctgtg atcatccacg gcagccttgt   1740
gacagttcgt gcccttgtgt gatagcacaa aatttttgtg aaaagttttg tcaatgtagt   1800
tcagagtgtc aaaaccgctt tccgggatgc cgctgcaaag cacagtgcaa caccaagcag   1860
tgcccgtgct acctggctgt ccgagagtgt gaccctgacc tctgtcttac ttgtggagcc   1920
gctgaccatt gggacagtaa aaatgtgtcc tgcaagaact gcagtattca gcggggctcc   1980
aaaaagcatc tattgctggc accatctgac gtggcaggct gggggatttt tatcaaagat   2040
cctgtgcaga aaaatgaatt catctcagaa tactgtggag agattatttc tcaagatgaa   2100
gctgacagaa gagggaaagt gtatgataaa tacatgtgca gctttctgtt caacttgaac   2160
aatgattttg tggtggatgc aacccgcaag ggtaacaaaa ttcgttttgc aaatcattcg   2220
```

gtaaatccaa actgctatgc aaaagttatg atggttaacg gtgatcacag gataggtatt 2280
tttgccaaga gagccatcca gactggcgaa gagctgtttt ttgattacag atacagccag 2340
gctgatgccc tgaagtatgt cggcatcgaa agagaaatgg aaatcccttg acatctgcta 2400
cctcctcccc cctcctctga aacagctgcc ttagcttcag gaacctcgag tactgtgggc 2460
aatttagaaa aagaacatgc agtttgaaat tctgaatttg caaagtactg taagaataat 2520
ttatagtaat gagtttaaaa atcaactttt tattgccttc tcaccagctg caaagtgttt 2580
tgtaccagtg aatttttgca ataatgcagt atggtacatt tttcaacttt gaataaagaa 2640
tacttgaact tgtc 2654

<210> SEQ ID NO 16
<211> LENGTH: 3509
<212> TYPE: DNA
<213> ORGANISM: Homo sapiens

<400> SEQUENCE: 16
agaggcagcc cgctcacttc ccgcggaggc gctccccggc gccgcgctcc gcggcagccg 60
cctgcccccg gcgctgcccc cgcccgccgc gccgccgccg ccgccgcgca cgccgcgccc 120
cgcagctctg ggcttcctct tcgcccgggt ggcgttgggc ccgcgcgggc gctcgggtga 180
ctgcagctgc tcagctcccc tcccccgccc cgcgccgcgc ggccgcccgt cgcttcgcac 240
agggctggat ggttgtattg ggcagggtgg ctccaggatg ttaggaactg tgaagatgga 300
agggcatgaa accagcgact ggaacagcta ctacgcagac acgcaggagg cctactcctc 360
cgtcccggtc agcaacatga actcaggcct gggctccatg aactccatga acacctacat 420
gaccatgaac accatgacta cgagcggcaa catgaccccg gcgtccttca acatgtccta 480
tgccaacccg ggcctagggg ccggcctgag tcccggcgca gtagccggca tgccgggggg 540
ctcggcgggc gccatgaaca gcatgactgc ggccggcgtg acggccatgg gtacggcgct 600
gagcccgagc ggcatgggcg ccatgggtgc gcagcaggcg gcctccatga atggcctggg 660
cccctacgcg gccgccatga acccgtgcat gagccccatg gcgtacgcgc cgtccaacct 720
gggccgcagc cgcgcgggcg gcggcggcga cgccaagacg ttcaagcgca gctacccgca 780
cgccaagccg ccctactcgt acatctcgct catcaccatg gccatccagc aggcgcccag 840
caagatgctc acgctgagcg agatctacca gtggatcatg gacctcttcc cctattaccg 900
gcagaaccag cagcgctggc agaactccat ccgccactcg ctgtccttca atgactgctt 960
cgtcaaggtg gcacgctccc cggacaagcc gggcaagggc tcctactgga cgctgcaccc 1020
ggactccggc aacatgttcg agaacggctg ctacttgcgc cgccagaagc gcttcaagtg 1080
cgagaagcag ccgggggccg gcggcggggg cgggagcgga agcgggggca gcggcgccaa 1140
gggcggccct gagagccgca aggacccctc tggcgcctct aaccccagcg ccgactcgcc 1200
cctccatcgg ggtgtgcacg ggaagaccgg ccagctagag ggcgcgccgg cccccgggcc 1260
cgccgccagc ccccagactc tggaccacag tggggcgacg gcgacagggg gcgcctcgga 1320
gttgaagact ccagcctcct caactgcgcc ccccataagc tccgggcccg gggcgctggc 1380
ctctgtgccc gcctctcacc cggcacacgg cttggcaccc cacgagtccc agctgcacct 1440
gaaaggggac ccccactact ccttcaacca cccgttctcc atcaacaacc tcatgtcctc 1500
ctcggagcag cagcataagc tggacttcaa ggcatacgaa caggcactgc aatactcgcc 1560
ttacggctct acgttgcccg ccagcctgcc tctaggcagc gcctcggtga ccaccaggag 1620
ccccatcgag ccctcagccc tggagccggc gtactaccaa ggtgtgtatt ccagacccgt 1680
cctaaacact tcctagctcc cgggactggg gggtttgtct ggcatagcca tgctggtagc 1740
aagagagaaa aaatcaacag caaacaaaac cacacaaacc aaaccgtcaa cagcataata 1800
aaatcccaac aactattttt atttcatttt tcatgcacaa cctttccccc agtgcaaaag 1860
actgttactt tattattgta ttcaaaattc attgtgtata ttactacaaa gacaacccca 1920
aaccaatttt tttcctgcga agtttaatga tccacaagtg tatatatgaa attctcctcc 1980
ttccttgccc ccctctcttt cttccctctt tcccctccag acattctagt ttgtggaggg 2040
ttatttaaaa aaacaaaaaa ggaagatggt caagtttgta aaatatttgt ttgtgctttt 2100
tccccctcct tacctgaccc cctacgagtt tacaggtctg tggcaatact cttaaccata 2160
agaattgaaa tggtgaagaa acaagtatac actagaggct cttaaaagta ttgaaagaca 2220
atactgctgt tatatagcaa gacataaaca gattataaac atcagagcca tttgcttctc 2280
agtttacatt tctgatacat gcagatagca gatgtcttta aatgaaatac atgtatattg 2340
tgtatggact taattatgca catgctcaga tgtgtagaca tcctccgtat atttacataa 2400
catatagagg taatagatag gtgatataca tgatacattc tcaagagttg cttgaccgaa 2460
agttacaagg accccaaccc ctttgtcctc tctacccaca gatggccctg ggaatcaatt 2520
cctcaggaat tgccctcaag aactctgctt cttgctttgc agagtgccat ggtcatgtca 2580
ttctgaggtc acataacaca taaaattagt ttctatgagt gtataccatt taaagaattt 2640
ttttttcagt aaaagggaat attacaatgt tggaggagag ataagttata gggagctgga 2700
tttcaaaacg tggtccaaga ttcaaaaatc ctattgatag tggccatttt aatcattgcc 2760
atcgtgtgct tgtttcatcc agtgttatgc actttccaca gttggacatg gtgttagtat 2820
agccagacgg gtttcattat tatttctctt tgctttctca atgttaattt attgcatggt 2880
ttattctttt tctttacagc tgaaattgct ttaaatgatg gttaaaatta caaattaaat 2940
tgttaatttt tatcaatgtg attgtaatta aaaatatttt gatttaaata acaaaaaataa 3000 taccagattt taagccgtgg aaaatgttct tgatcatttg cagttaagga ctttaaataa 3060
atcaaatgtt aacaaaagag catttctgtt atttttttc acttaactaa atccgaagtg 3120
aatatttctg aatacgatat ttttcaaatt ctagaactga atataaatga caaaaatgaa 3180
aataaaattg ttttgtctgt tgttataatg aatgtgtagc tagtaaaaag gagtgaaaga 3240
aattcaagta aagtgtataa gttgatttaa tattccaaga gttgagattt ttaagattct 3300
ttattcccag tgatgtttac ttcatttttt tttttttttt tgacaccggc ttaagccttc 3360
tgtgtttcct ttgagccttt tcactacaaa atcaaatatt aatttaacta cctttcctcc 3420
ttccccaatg tatcactttt ctttatctga gaattcttcc aatgaaaata aaatatcagc 3480
tgtggctgat agaattaagt tgtgtccaa 3509

<210> SEQ ID NO 17
<211> LENGTH: 5794
<212> TYPE: DNA
<213> ORGANISM: Homo sapiens

<400> SEQUENCE: 17
ctagcaaccg gggaagccgg gctgtgaagc gggcaatttc agtgtgagac tgagccgcga 60
gactgagctg cggctccgag cgctgcgcgg cggctcctcc cgcccagggt cagcgccccg 120
gcgcgcgcac gcgcaccccc gccgcccgag cgcgccccgc gccgcccgcg cagtcggtcg 180
gtcggtcgtc tgtcctgtcg ccgctgccgc cgccgccaca gcggccgccg cgggcgccac 240

-continued

```
ctgagggagt cgcctccgcg ggacgccaca agacctgacc ggactgcgcc gcccgaggcc    300
gtcggccgcc gtcagcgagg gcgccgagca acttcggttg gtcagcacat tgtctcaagt    360
agccttttga tgtcactgtg gccatggcca actggtagga ccagcacccc ataccccgaa    420
gccagttcag aatgaccgaa gaagcatgcc gaacacggag tcagaaacga gcgcttgaac    480
gggacccaac agaggacgat gtggagagca agaaaataaa aatggagaga ggattgttgg    540
cttcagattt aaacactgac ggagacatga gggtgacacc tgagccggga gcaggtccaa    600
cccaaggatt gctgagggca acagaggcca cggccatggc catgggcaga ggcgaagggc    660
tggtgggcga tgggcccgtg gacatgcgca cctcacacag tgacatgaag tccgagagga    720
gaccccccctc acctgacgtg attgtgctct ccgacaacga gcagccctcg agcccgagag    780
tgaatgggct gaccacggtg gccttgaagg agactagcac cgaggccctc atgaaaagca    840
gtcctgaaga acgagaaagg atgatcaagc agctgaagga agaattgagg ttagaagaag    900
caaaactcgt gttgttgaaa aagttgcggc agagtcaaat acaaaaggaa gccaccgccc    960
agaagcccac aggttctgtt gggagcaccg tgaccacccc tcccccgctt gttcggggca   1020
ctcagaacat tcctgctggc aagccatcac tccagacctc ttcagctcgg atgcccggca   1080
gtgtcatacc cccgcccctg gtccgaggtg ggcagcaggc gtcctcgaag ctggggccac   1140
aggcgagctc acaggtcgtc atgcccccac tcgtcagggg ggctcagcaa atccacagca   1200
ttaggcaaca ttccagcaca gggccaccgc ccctcctcct ggcccccccgg gcgtcggtgc   1260
ccagtgtgca gattcaggga cagaggatca tccagcaggg cctcatccgc gtcgccaatg   1320
ttcccaacac cagcctgctc gtcaacatcc cacagcccac cccagcatca ctgaagggga   1380
caacagccac ctccgctcag gccaactcca cccccactag tgtggcctct gtggtcacct   1440
ctgccgagtc tccagcaagc cgacaggcgg ccgccaagct ggcgctgcgc aaacagctgg   1500
agaagacgct actcgagatc cccccaccca agcccccagc cccagagatg aacttcctgc   1560
ccagcgccgc caacaacgag ttcatctacc tggtcggcct ggaggaggtg gtgcagaacc   1620
tactggagac acaagcaggc aggatgtcgg ccgccactgt gctgtcccgg gagccctaca   1680
tgtgtgcaca gtgcaagacg gacttcacgt gccgctggcg ggaggagaag agcggcgcca   1740
tcatgtgtga gaactgcatg acaaccaacc agaagaaggc gctcaaggtg gagcacacca   1800
gccggctgaa ggccgccttt gtgaaggcgc tgcagcagga acaggagatt gagcagcggc   1860
tcctgcagca gggcacggcc cctgcacagg ccaaggccga gcccaccgct gccccacacc   1920
ccgtgctgaa gcaggtcata aaaccccggc gtaagttggc gttccgctca ggagaggccc   1980
gcgactggag taacggggct gtgctacagg cctccagcca gctgtcccgg ggttcggcca   2040
cgacgccccg aggtgtcctg cacacgttca gtccgtcacc caaactgcag aactcagcct   2100
cggccacagc cctggtcagc aggaccggca gacattctga gagaaccgtg agcgccggca   2160
agggcagcgc cacctccaac tggaagaaga cgcccctcag cacaggcggg acccttgcgt   2220
ttgtcagccc aagcctggcg gtgcacaaga gctcctcggc cgtggaccgc cagcgagagt   2280
acctcctgga catgatccca ccccgctcca tcccccagtc agccacgtgg aaatagtgcg   2340
agccaggccc cgtggaagac gggctccctc ctcccccacc tggcccctgg tctagaagga   2400
cccactgcac caccctccgc tggctcggga agacaccgtg cccgccccaa gagcaagcac   2460
cggccatgct gcagaggcaa gacctcaatt cttggctgca aagtttcatc agggctaggg   2520
ggctggtgcc gcctcatagg cagacgagga tcatcgctgg gggacctttc ccgtgggctt   2580
tcttcctttc tctctttgcc tttagtttgc ccgacaccag cagaaaagtg gaccttgggg   2640
```

gctggttctg ctcctggccc ccttgttcag cccctgccgg cacacgggcg gctcaccctg 2700
gacactgtga tgcgcatggg caaggccagc gcccggggct tctgaaccga gcggggtgtt 2760
tcattttttt gcttttccct gtcttaggct cccagtcttt gactgccttc ccatggcgat 2820
ctataagttg aaagattttt ttttttttta atcacctcat gatgatggag ttaaaagtaa 2880
accgtgcaga ccctggggtc cctgttgtac gctgcatcat cccgctggcc ctgtgccctg 2940
gagggtgggc ggctcatggt gccacagccc ctggcaggga cggccggccc gcccccgtga 3000
ctgactgaca gatgcaggga tggccgaggc agccctcgct ccagctgaac gcctccattg 3060
ctgcttgttc tggagacccc cgcccccgca ccttccagac ttagcagaag aacaaactga 3120
agaacagacc cagccagaga agcagggatt ccagaagctg cccattaagg gagaaggaga 3180
ggatccggtc ggcagcagcc ctgagcagaa agctggaggg gggactgtcg cggggttttt 3240
ctgttgtggt ttattttatt aaattttttc ctttttttcta ttcatttcga tggacgcaat 3300
cttaagccac cctggccttg ctcctgggag gtgagcgtgc acaggtgtgt gcaggtcagg 3360
aggtgccgtc caggtgtgcg gcgagccgct gcgcacagat gtcaggattt ccgtttgggt 3420
ctagtttaga acctgtcctt aaacctaggg gttgctgtca ggatttgctt tcagactttt 3480
tttttttttg taattccctt tagagtctac aaaaatgttt ttaaaaggat caggtctgct 3540
tttagtttca tttttgtttc tttcccgtcc cactctttaa aaactggttc cgtgaggaaa 3600
ggcagaagcc gttccgtgtc tcttgcaggc tgggccggct tcatgccagt gcgagggcgt 3660
cccgtgccca cgtacatacg tatgtctcca tgagttctgg gctccactgg ttccaattga 3720
gctccagccc tggttttcct acccatgcag ttagggactt taatttaatt tttttttttgt 3780
agggccaccg ccttcaaaca caactgctac aacattctaa taaaggctca tttaaccccc 3840
aggctcctgt cgtgtgaata tcctcagtct gtaggaaact ttttttgaca cagcatagaa 3900
gacctagttt tggaaaacat tatctaattt tttgttgtgc aaatccccaa atttctcact 3960
aatttttgtt tttttgtgca taacttggat gggctgaagg aggtgaggac agattgggga 4020
agggtggctt tcattccaag atccagggat ttggggaaaa ggaaggaatt tgatgttttt 4080
tggggtggga ggggagggtg tgttttttac accaaaaaaa aaaaaaaaaa tcaagagtat 4140
gcaagcattt ctattcctcg catttttctg tgtgcctggc aaataaatac ctgtctccta 4200
cgaccctgag ctgttagccc tctctgttcc atgacagggg ccagatcttc cagctcctcc 4260
cagaaggagc acccaggctg gcttcttccc actgaaagcc ctccccagcg aaccaacctc 4320
agttctatgc agtggctggg gatcaggcat ccagaccgaa gtcacctctg cctgctccag 4380
cttgggtcag ctgggtctga ccagggggcc agatccgagc cgcacctgcc ggcccccagc 4440
cccagctcca gctcctgacc tctcccagcc tggcctggct gttcctccag ggctgatggc 4500
tgtcaaccca tccttgtgag ttcatatgga ctgctgcccc tcgaaaggga gagggtcggc 4560
cccatgtccc cagggagcat tccatcaggg acaacgtaca tactgtgatg taaacttttt 4620
tttttccccc ccagggggca aaagtgtgag atgccttaat ctttccttca tttctgctgt 4680
ctcgaacact ctagcccatt atttcctttc agttccttgc agcataacct ctacgataag 4740
ccccaagcgg gttgttgtat tatgacgttt atgatgttcc aggtgaaggc attattaagt 4800
acctctctgg gtgtggggtt tggacgcacc aggatagcta ttgattaatg ttaagggtgt 4860
tctacccaca gcaaagcaca ccctcttaaa ccaggcactg cctgggtcct ggtcccgaga 4920
gccctaccag gatcaggttc ctgcaagccg tcagaatgtg ggagccccca gcccaactga 4980
ttgtaactgt cccctgttac ctgtgacatg aacctccaac agcacctgga aacggttccc 5040
tctgtcagct gctctgtaga cagggctggg gagatctcag agttcacacc tcgcctgttg 5100
taggggaggt tgggggtagg gtttggaatg gccaagtgcc cttggaacct cccacagcta 5160
tggccgtcct gacctcatcc caggaactct acggtgacca ggaaccaccc ctctgacgag 5220
gtctgtagcg gcccttctca gagtggaaca gcccacagtg ctagttgtgc ctggtcttac 5280
ctgtactcca cggacctcgg tgaagcaaaa gcttcagggc agagggaatg aggcaaccca 5340
gtggcagccc cgctgggccc cgtggctcct gctctcctat tggacgtaga ggcaggggag 5400
agacttctct atacaaatat tctcatcaca gaagggatga tccttgctgc tctgccgtag 5460
ggtttttgat gctgagctat gctgcacatg acgttaacct aaagaacttg gactgagctt 5520
ttaaaaaagg acagcaaaca attttataat ccttaaagtg taatagacgg ttacactagt 5580
gcagggtatt ggggaggctc tttgggtgtg gaggctgtca cttgtattta ttgtgactct 5640
aaatctttga tagtaaaaca aatgtaaaaa gaaatgtttg ccaccagatg ggaatagaag 5700
ttccaataag caggctggaa tgggtggcta tacgttgtat cacgaggaag ttttagactc 5760
tgaaggataa taaatggatg atgtgtcaac tgga 5794

<210> SEQ ID NO 18
<211> LENGTH: 2204
<212> TYPE: DNA
<213> ORGANISM: Homo sapiens

<400> SEQUENCE: 18
agacgcggag ctgggaaaag ggaggcagag gaggcggagg cagaggcaga ggcagaggca 60
gagcccgagc ccggtgccga gaccaagcga cagaccggcg gggctgggcc tcgcaaagcc 120
ggctcggcga gctctcccga cacccgagcc ggggaggaaa agcagcgact cctcgctcgc 180
atccccggga gccgcactcc agactggccc ggtagtcagg ggctcaggag cagatcccga 240
ggcaggcttt gctcagcctc cgacgagggc tggccctttg gaaggcgcct tcaacagccg 300
gaccagacag gccaccatga ccgagaattc cacgtccgcc cctgcggcca agcccaagcg 360
ggccaaggcc tccaagaagt ccacagacca ccccaagtat tcagacatga tcgtggctgc 420
catccaggcc gagaagaacc gcgctggctc ctcgcgccag tccattcaga agtatatcaa 480
gagccactac aaggtgggtg agaacgctga ctcgcagatc aagttgtcca tcaagcgcct 540
ggtcaccacc ggtgtcctca agcagaccaa aggggtgggg gcctcggggt ccttccggct 600
agccaagagc gacgaaccca agaagtcagt ggccttcaag aagaccaaga aggaaatcaa 660
gaaggtagcc acgccaaaga aggcatccaa gcccaagaag gctgcctcca aagccccaac 720
caagaaaccc aaagccaccc cggtcaagaa ggccaagaag aagctggctg ccacgcccaa 780
gaaagccaaa aaacccaaga ctgtcaaagc caagccggtc aaggcatcca agcccaaaaa 840
ggccaaacca gtgaaaccca aagcaaagtc cagtgccaag agggccggca agaagaagtg 900
acaatgaagt cttttcttgc ggacactccc tcctgtctcc tattttctgt aaataatttt 960
ctcctttttt ctctcttgat gctcaccacc accttttgcc cccttctgtt ctgactttat 1020
aagagacagg atttggattc ttcagaaatt acagaataat tcatttttcc ttaaccagtt 1080
gtgcaaggac agcaacaacc aatctaatga tgagaatgta cttatatttt gttttgctat 1140
taacctactt acggggttag ggatttgcgg ggggggcttg tgtgttttgt tggcttgttt 1200
gccatgaagg tagatgtggg tggggagaag acacaaggca gtttgttctg gctagatgag 1260
agggaaccca ggaattgtga ggttagcagg aatatcttta gggtgagtga gttttctttg 1320

```
agttgggcac ccgttgtgag agtttcagaa cctttggcca gcaggagaga ggtggtaggg   1380

agcagccagc cggcaaagga aggaggggga aaaaaaccgc caccgggctg acttccacct   1440

cccagtggtg agcagtgggg gcccaaaccc agtttccttc tcatttttgt tagtttgcgc   1500

tttcggcctc cctattttct tagggaaggg gagtggggtc caagtgacag ctggatggga   1560

gaagccatag tttctcccag tcagctagga tgtagccatt gggggatctt tgtggcttca   1620

gcaaattctc ttgttaaacc ggagtgaaaa cttcagggga agggtgggga gtcagccaag   1680

tgcctcagtg tgccctgttg aaacttaggt ttttccacgc aatcgatgga ttgtgtccta   1740

ggaagacttt tcttttcctc tggatttttg ttcctcctgt acaagaggtg tctttgcttg   1800

gtttggtggg gctgcggcca cttaaaacct cccgatctct ttttgagtcc tttattataa   1860

gtagttgtag ctgcgggagg gggaggggga gtgggcgggc agtggatagt aagacttact   1920

gcagtcgatt tgggatttgc taagtagttt tacagagcta gatctgtgtg catgtgtgtg   1980

tttgtgtata tatacatatc tagggctagt acttagtttc acacccggga gctgggagaa   2040

aaaacctgta cagttgtctt tctcttattt ttaataaaat agaaaaatcg cgcacttgcg   2100

cgtccccccc ccaccccctt ttttaaacaa gtgttacttg tgccgggaaa attttgctgt   2160

ctttgtaatt ttaaaacttt aaaataaatt ggaaaaggga gaaa                    2204
```

<210> SEQ ID NO 19
<211> LENGTH: 3026
<212> TYPE: DNA
<213> ORGANISM: Homo sapiens

<400> SEQUENCE: 19

```
acggggtatt gtccggctcc ggcggcggcg gtcggtgctg cgagagcggc ggcggcggcg     60

cgggtcggca gcgggagggc gcgcggccga gcggaggcgg agtcggcgcc gagaacatgg    120

ctggaggcaa agctggaaag gacagtggga aggccaaggc taaggcagta tctcgctcac    180

agagagctgg gctacagttt cctgtgggcc gcatccacag acacttgaag actcgcacca    240

caagccatgg aagggtgggt gccactgctg ccgtgtacag tgctgcgatt ctggagtacc    300

tcactgcaga ggtgctggag ctggcaggta atgcttctaa ggatctcaaa gtaaagcgta    360

tcactccgcg tcacttgcag cttgcaatcc gtggtgatga agagttggat tctcttatca    420

aggctaccat agctgggggt ggtgtgatcc ctcacatcca caaatctctg attggaaaga    480

agggacagca gaaaactgct tagagggatg ctttaaccaa ccctcttcct ccccgtcatt    540

gtactgtaac tgggacagaa gaaataatgg ggatatgtgg aatttttaac aacagttaaa    600

tggaaaagca tagacaatta ctgtagacat gataaaagaa acatttgtat gttcttagac    660

tcgaagtttg ataaaagtac cttttcatgt ggtgacagtt gtgtgttgat tggctaggtt    720

tctcccgtgt gttttataca aaaatggaat tgataaacca ttttttacaa aattaatttg    780

tctcaaaact gttctgttca tgatgtatta gaaatatttt actcagactt taaatatttt    840

aaatctcaga ttggttattc agagtaacct tagaacagaa attgggaata tatctttaca    900

atgattgata ccatggtata ttgactctta gatgctattg atctgtagca ccattttta     960

caaacgacta aggaaaaaac ctgccaatta aatcatgata tgccatcaat tatgagacat   1020

cccaatttga gagatgttag attatagaaa agtatgcatt tatgactgaa atggtagtgg   1080

aattatttga attctacacc aagcacttac catgtgccag gccctttgca gagtgctcta   1140

ctgaccaaga aagttgttgc tgccacatta tagatgtgga gcctaagggt cacagaaatt   1200
```

```
gtgtgctatg ccaaaaaaca ttgaactggt agatagaaaa tgacagagct aggattcaaa   1260
cctagatctg gctgactcca gagcctagtt ttacctggaa ttgatgttca gtttatcaaa   1320
ggtttctcct tttggtttaa aatcccaatt tttggcctgg cattgtggtt tacgcctgta   1380
atcccaacac ttcgggagac cgaggctggt ggaacacttg aggtcaggag tttgagacca   1440
gcctggccaa catggtaaaa cgccgtctcg gccaggcgcg gtggctcacg cctgtaatcc   1500
cagcactttg ggaggccaag gtgggtgaat cacgaggtca ggaaatcgag accatcctgg   1560
ctaacatggt gaaaccccgt ctctatttaa aaaaatacaa aaaattagcc gggtgtggtg   1620
gcacgcgcct gtagtcccag ctactcagga ggctgaggca tgagaatgac gtgaacccgg   1680
gaggcggagc ttgcagtgag ccaagatggc gccactgcac tccagcttgg cgactgagca   1740
agactccctc tcaaaacaaa caaaaaaaag tctctactaa aaatacagaa attagccagg   1800
catggtacac acatgttgtc ccaactactt ggggcactgg ggcacaaaaa atcacttgaa   1860
cccaggaggc agaggttgca gtgagccaag atcacgccac tacactccag cctaggtgac   1920
agagtgtgac tctgtctcaa aaaaaaaaat cccaactttt agtagtctct tagtcatgca   1980
ataacagtaa tttgtacaat cttttaaaaa ttatatttat ttatcagttt ctaagaaact   2040
tttttgtttg ttttgagaca ggctcttgct cttttgccca ggttgaagtg cagtggcatg   2100
atcctggctc actgcagcct ccacctctca ggcccaagca atcctcttac ctcagccctg   2160
caaatagctg ggaccacagg cacatgccac catacctggc taattttttt tatttatgta   2220
agagacagag gtctccctat gttgcccagg ttggtattga actcctggct caagccatcc   2280
tcccaccttg gcctcccaaa gtactgggat tataggcata agccaccatg ccctgcgcta   2340
agtaactgtt acttgagtta atgtactagt taattgaccc ttagaaaatt atattttttct  2400
gcttgcaagt cttcattaaa gaaggaaatt ttaaaatatt ttatagtata atgctatcca   2460
aactcatttt taaaaacatt ttattatgga aattttcaca aatgcacaaa aagaatagca   2520
gaatgaagct ctgtgtaccc atcctccaac agctgtcctg tggtcagtct tgtttacctg   2580
catccccacc tatcccctgc cccaacccac agggatcagt ttgagtccca ttaacaggca   2640
tagtattttc atgtctgtgt gatcagagac attcaaatat aactccaaag atagggtact   2700
tttttgaaca taaccacaat accattgtgt aagactgcta aaacattttt tgatgccaag   2760
taccagtcaa tattcaaact tcctgattgt ctcgtaagtt ttttttaaca gttggtttat   2820
tcgagtcaag atccaggcaa gatctagatc ttgcattttg ttaatataat ctatagattt   2880
aactttcctg tttttaattt ttgaagaaac taagttgttt gtcctataga attgtccttc   2940
agtggatttt actgaatgta tcctaatggg atcatgtaca ccttttctgt cccctatatg   3000
ttctataaac tgacagatct agaggg                                         3026
```

<210> SEQ ID NO 20
<211> LENGTH: 1937
<212> TYPE: DNA
<213> ORGANISM: Homo sapiens

<400> SEQUENCE: 20

```
actggttcca gttcactcgg cagcggcgcc gggcggaggg ggagagcgcg ggccgcgcgg     60
gcgggaagcg aagaggcggg cgggccagcg aggagcgcgg agagaaaagg cgcgagcggc    120
caggagggct caggccgaga caccttgcag ctgccgccgc cgccaccgag ccgccgctgt    180
gctcactgat ccgcctccag ggccaccgcc atgtcgagcc gcggtgggaa gaagaagtcc    240
accaagacgt ccaggtctgc caaagcagga gtcatctttc ccgtggggcg gatgctgcgg    300
```

```
tacatcaaga aaggccaccc caagtacagg attggagtgg gggcacccgt gtacatggcc    360
gccgtcctgg aatacctgac agcggagatt ctggagctgg ctggcaatgc agcgagagac    420
aacaagaagg gacgggtcac accccggcac atcctgctgg ctgtggccaa tgatgaagag    480
ctgaatcagc tgctaaaagg agtcaccata gccagtgggg gtgtgttacc caacatccac    540
cccgagttgc tagcgaagaa gcggggatcc aaaggaaagt tggaagccat catcacacca    600
cccccagcca aaaaggccaa gtctccatcc cagaagaagc ctgtatctaa aaaagcagga    660
ggcaagaaag gggcccggaa atccaagaag cagggtgaag tcagtaaggc agccagcgcc    720
gacagcacaa ccgagggcac acctgccgac ggcttcacag tcctctccac caagagcctc    780
ttccttggcc agaagctgaa ccttattcac agtgaaatca gtaatttagc cggctttgag    840
gtggaggcca taatcaatcc taccaatgct gacattgacc ttaaagatga cctaggaaac    900
acgctggaga agaaaggtgg caaggagttt gtggaagctg tcctggaact ccggaaaaag    960
aacgggccct tggaagtagc tggagctgct gtcagcgcag gccatggcct gcctgccaag   1020
tttgtgatcc actgtaatag tccagtttgg ggtgcagaca agtgtgaaga acttctggaa   1080
aagacagtga aaaactgctt ggccctggct gatgataaga agctgaaatc cattgcattt   1140
ccatccatcg gcagcggcag gaacggtttt ccaaagcaga cagcagctca gctgattctg   1200
aaggccatct ccagttactt cgtgtctaca atgtcctctt ccatcaaaac ggtgtacttc   1260
gtgctttttg acagcgagag tataggcatc tatgtgcagg aaatggccaa gctggacgcc   1320
aactaggctg agcaatgaca gaaccagctg caccatgtac ccccaccttca gtttaaaaga   1380
aaaaaaaaat ccccttcact cctactggga ggtgggaccc ctttcatttt cagttttgct   1440
catctaggga aaataaggct ttggtttcca gtttaattgt ttttgacctt ctaaaatgtt   1500
tttatgttag cactgatagt tggcattact gttgttaagc actgtgttcc agaccgtgtc   1560
tgacttagtg taacctagga gattttatag ttttatttta atgaaaccct gattgacgca   1620
cagcagtggg gagaacagcg tcttttacct gtcaccgaag ccaggaagcc ccgtttgtaa   1680
gcgtgtgttg tggtgcttta ttgtacatcc tccagtggcg ttctttttac tctaatgttc   1740
ttttggtttc ccccctcaga agaatcatga atttgcaaca gacctaattt ttggttactt   1800
tttgtcttat tgatggattt gaaaatgaaa gatttaataa ggcaaagcag aatctgttgt   1860
ccttaattat atttgcaatt tggaatttgt gtgagttgat ttagtaaaat gttaaaccgt   1920
taaaaaaaaa aaaaaaa                                                  1937
```

<210> SEQ ID NO 21
<211> LENGTH: 9619
<212> TYPE: DNA
<213> ORGANISM: Homo sapiens

<400> SEQUENCE: 21

```
atggggtggc tggacgagag cagctcttgg ctcagcaaag aatgcacagt atgatcagct     60
cagtggatgt gaagtcagaa gttcctgtgg gcctggagcc catctcacct ttagacctaa    120
ggacagacct caggatgatg atgcccgtgg tggaccctgt tgtccgtgag aagcaattgc    180
agcaggaatt acttcttatc cagcagcagc aacaaatcca gaagcagctt ctgatagcag    240
agtttcagaa acagcatgag aacttgacac ggcagcacca ggctcagctt caggagcata    300
tcaagttgca acaggaactt ctagccataa aacagcaaca agaactccta gaaaaggagc    360
agaaactgga gcagcagagg caagaacagg aagtagagag gcatcgcaga gaacagcagc    420
```

```
ttcctcctct cagaggcaaa gatagaggac gagaaagggc agtggcaagt acagaagtaa    480
agcagaagct tcaagagttc ctactgagta aatcagcaac gaaagacact ccaactaatg    540
gaaaaaatca ttccgtgagc cgccatccca agctctggta cacggctgcc caccacacat    600
cattggatca aagctctcca ccccttagtg gaacatctcc atcctacaag tacacattac    660
caggagcaca agatgcaaag gatgatttcc cccttcgaaa aactgcctct gagcccaact    720
tgaaggtgcg gtccaggtta aaacagaaag tggcagagag gagaagcagc cccttactca    780
ggcggaagga tggaaatgtt gtcacttcat tcaagaagcg aatgtttgag gtgacagaat    840
cctcagtcag tagcagttct ccaggctctg gtcccagttc accaaacaat gggccaactg    900
gaagtgttac tgaaaatgag acttcggttt tgccccctac ccctcatgcc gagcaaatgg    960
tttcacagca acgcattcta attcatgaag attccatgaa cctgctaagt ctttatacct   1020
ctccttcttt gcccaacatt accttggggc ttcccgcagt gccatcccag ctcaatgctt   1080
cgaattcact caaagaaaag cagaagtgtg agacgcagac gcttaggcaa ggtgttcctc   1140
tgcctgggca gtatggaggc agcatcccgg catcttccag ccaccctcat gttactttag   1200
agggaaagcc acccaacagc agccaccagg ctctcctgca gcatttatta ttgaaagaac   1260
aaatgcgaca gcaaaagctt cttgtagctg gtggagttcc cttacatcct cagtctccct   1320
tggcaacaaa agagagaatt tcacctggca ttagaggtac ccacaaattg ccccgtcaca   1380
gacccctgaa ccgaacccag tctgcacctt tgcctcagag cacgttggct cagctggtca   1440
ttcaacagca acaccagcaa ttcttggaga agcagaagca ataccagcag cagatccaca   1500
tgaacaaact gctttcgaaa tctattgaac aactgaagca accaggcagt caccttgagg   1560
aagcagagga agagcttcag gggggaccagg cgatgcagga agacagagcg ccctctagtg   1620
gcaacagcac taggagcgac agcagtgctt gtgtggatga cacactggga caagttgggg   1680
ctgtgaaggt caaggaggaa ccagtggaca gtgatgaaga tgctcagatc caggaaatgg   1740
aatctgggga gcaggctgct tttatgcaac agcctttcct ggaacccacg cacacacgtg   1800
cgctctctgt gcgccaagct ccgctggctg cggttggcat ggatggatta gagaaacacc   1860
gtctcgtctc caggactcac tcttcccctg ctgcctctgt tttacctcac ccagcaatgg   1920
accgcccccct ccagcctggc tctgcaactg gaattgccta tgacccccttg atgctgaaac   1980
accagtgcgt ttgtggcaat tccaccaccc accctgagca tgctggacga atacagagta   2040
tctggtcacg actgcaagaa actgggctgc taaataaatg tgagcgaatt caaggtcgaa   2100
aagccagcct ggaggaaata cagcttgttc attctgaaca tcactcactg ttgtatggca   2160
ccaacccccct ggacggacag aagctggacc ccaggatact cctaggtgat gactctcaaa   2220
agttttttttc ctcattacct tgtggtggac ttggggtgga cagtgacacc atttggaatg   2280
agctacactc gtccggtgct gcacgcatgg ctgttggctg tgtcatcgag ctggcttcca   2340
aagtggcctc aggagagctg aagaatgggt ttgctgttgt gaggcccccct ggccatcacg   2400
ctgaagaatc cacagccatg ggttctgct tttttaattc agttgcaatt accgccaaat   2460
acttgagaga ccaactaaat ataagcaaga tattgattgt agatctggat gttcaccatg   2520
gaaacggtac ccagcaggcc ttttatgctg accccagcat cctgtacatt tcactccatc   2580
gctatgatga agggaacttt ttccctggca gtggagcccc aaatgaggtt ggaacaggcc   2640
ttggagaagg gtacaatata aatattgcct ggacaggtgg ccttgatcct cccatgggag   2700
atgttgagta ccttgaagca ttcaggacca tcgtgaagcc tgtggccaaa gagtttgatc   2760
cagacatggt cttagtatct gctggatttg atgcattgga aggccacacc cctcctctag   2820
```

gagggtacaa agtgacggca aaatgttttg gtcatttgac gaagcaattg atgacattgg 2880
ctgatggacg tgtggtgttg gctctagaag gaggacatga tctcacagcc atctgtgatg 2940
catcagaagc ctgtgtaaat gcccttctag gaaatgagct ggagccactt gcagaagata 3000
ttctccacca aagcccgaat atgaatgctg ttatttcttt acagaagatc attgaaattc 3060
aaagcaagta ttggaagtca gtaaggatgg tggctgtgcc aaggggctgt gctctggctg 3120
gtgctcagtt gcaagaggag acagagaccg tttctgccct ggcctcccta acagtggatg 3180
tggaacagcc ctttgctcag gaagacagca gaactgctgg tgagcctatg gaagaggagc 3240
cagccttgtg aagtgccaag tccccctctg atatttcctg tgtgtgacat cattgtgtat 3300
ccccccaccc cagtaccctc agacatgtct tgtctgctgc ctgggtggca cagattcaat 3360
ggaacataaa cactgggcac aaaattctga acagcagctt cacttgttct ttggatggac 3420
ttgaaagggc attaaagatt ccttaaacgt aaccgctgtg attctagagt tacagtaaac 3480
cacgattgga agaaactgct tccagcatgc ttttaatatg ctgggtgacc cactcctaga 3540
caccaagttt gaactagaaa cattcagtac agcactagat attgttaatt tcagaagcta 3600
tgacagccag tgaaattttg ggcaaaacct gagacatagt cattcctgac attctgatca 3660
gctttttttg gggtaatttg tttttcaaac agtcttaact tgtttacaag atttgctttt 3720
agctatgaac ggatcgtaat tccacccaga atgtaatgtt tcttgtttgt ttgttttgtt 3780
ttgttagggt ttttttctca actttaacac acagttcaac tgttcctagt aaaagttcaa 3840
gatggaggaa ctagcatgag gctttttttca gtatctcgaa gtccaaatgc caaaggaacc 3900
tcacacactg tttgtaatgg tgcaatattt tatatcactt tttttaaac atccccaaca 3960
tctttgtgtt ctcacacaca ggcaatttgc aatgttgcaa ttgtgttgga gaatgaagtc 4020
cccccacctc ccagccacac acacatcctt tgttctcatg acagtaggtc tgagcaaatg 4080
ttccaccaag cattttcagt gtctttgaaa agcacgtaac ttttcaaagg tggtcttaat 4140
ttgttgcata tctatcaagg acttattcac tcacctttcc ttttctgccc tctatcaatt 4200
gatttcttct tacctttcat cattcattcc ttcctttaga aaaactgaag attacccata 4260
atctcctctt attacttgag ggccttgact atttagttta ttttgtttac tttacaggtt 4320
aacacagttg ttttgtctga ttgcatttta ttaactgtga agccgttgaa atgaatatca 4380
cttaagcaac gttgctaaat ttctatgtgt ttgaaatgtg ttaatgaagg cactgcttat 4440
ttgtagtcac cttgaactga cttaacctag aagctgtgcc ttcttgtgaa aaaaaaaaaa 4500
aacaaaaaca aaaaacagcc tttaaacaag tttccttagt gtcaaaagtt aaaaataaag 4560
gacatttatt tctgagataa aaagtaactt actaaatata agtaggttat cctcctacct 4620
cctaaaattc gatttcaaca tataactcaa acacctaaac atattgaggt agaatatctc 4680
acagtattta atatctgaca atgcttttga aagagttgat gtttcttttt atatattttt 4740
ctaactcaaa ggatatatta aagccataag tgaagattgt catgctttta ttcagaaatc 4800
tgaaagaaac cttaattaaa acaaggtttt agggaaggcc atgatatgaa agatatggaa 4860
caatatggtt ttagttagag aggactctaa cctgtaaatc aaagatgaaa gatttcactc 4920
aagtagaatt atataactcc ctttgttata cagtcagacc atatttttca tgcatttggt 4980
ttttttagga ttaccatttt aattttaaag acttttatta catatacaaa aatggctcaa 5040
tacttggttt aacttcttag aaatttgaga caccctttga aataggaaat ctgaaatgga 5100
atgtaactta gtattaggta aaaattgctt tcattgcgta agggcaaatt cagtctagat 5160

```
tcatagtagt aatcaatttt ttataaattt tattttcatg agaaattcat accaatcata   5220
tttgctagct tatgttattt tgcagtgatt gcttgaggat atttacttaa aaaaatagta   5280
gagccaaagg cttaacaaaa gactctcccc cattttaaaa aggaaactca tgttttaatt   5340
agaaaaataa ttgtgtagtt ttaaaatcaa cttcataatt ataaatctct gtcattactt   5400
tttagtcctc ccagatattt ttttagttgt tgaataagaa aataaaacag tgtaatgcaa   5460
acatgctaat ttactaaagt ttcctacaac agtttagcca catgtttatg ccaagccatt   5520
aatctgataa agccaaatca ctaggacatc tccatggtta tttagattta aaacttgaca   5580
cattaatgag ttaatcacac atactcccat atgacaccat acccaattgg ttgcacttag   5640
agtctttaaa atacctggag aagcaaatga actgtggaga ggattatcca cagcatgtag   5700
ttgtaagaac agaatgccat tgctttttga ttataccatt acaagatgga gcatagccct   5760
gagggacaga atggaggctt tccgaaaata tcaacacttc ttttgaaata gaccagcact   5820
ttttgaaagg gtagtttcac ttggtatagt ttttcttcac ttacccgttt aaattttatt   5880
gctcgcagtt gttctgaatg agaggctaga agagtattat caattttgca tctccttgtg   5940
atacttactt tgaaggaaaa tcacatacgc tctctcatgg tctcatggta tctcatacag   6000
ggtgaataaa aatgattttt gataaatcta ctagtaaata atactaggaa tttaataagc   6060
tgtcaaacgt aggtataaaa agaaggctta aaaattaatt ttcccaattg tataatttgg   6120
ggctgtatat taaactaaaa aacacagaca gttttattaa atagtaacca aaatggactc   6180
aaataaaacc agaggctatg ttaccattgc ttagtaaatg gaaagaacat tgtgagatga   6240
actatcttta aatattgtaa caagtttata acatcaatag tggagacaga agtcagcttt   6300
ggagaaaata gagatattta tgaaaaaact actacaaatc acatttccat taccaatcct   6360
ggggatggaa atattgcctt cagtttttac tccagcccta tacgacactc tcactaacct   6420
ttcactgaca acatcatggc cttgaaagca gggatctcct cccacaaagg cttcagaaat   6480
tacaggactg gtctctctta atagtttagt cctgctttat ttccaaaggg caattataaa   6540
gcctcgtgga tttactgggt ttctttacag actccatatg gaagtaaaat agaatgatca   6600
tttggaaagt ctcctgggaa aaaattcctc ttcaatcagc attttaaaac tttttttattt  6660
ttgagtcaga gttttgctct tggtgcccag gctggagtgc aatggcgcaa tctcgactca   6720
ctgcaacctc cgcctcccgg gttcaagcaa ttctcctgac gagtagctgg gcatgcgcca   6780
ccacgtctgg ctaatttttg tatttttagt agagacgggg tttctccatg ttggtcaggc   6840
tggtctcaaa ctcccgacct caggtgatcc gcccgcctcg gcctcccaaa gtgctgaaat   6900
tacaggtgtg agccactgca cccggccaaa cttattgttt taatcccagc atttatgttt   6960
agaagaatta atttaaatat ttcttactat ttctctgtcg aatgtttact ctcatcttat   7020
ctcaatgaaa gaagtattaa aagtcttatg gccccaaaag aaacaagcca aactgtactg   7080
tcttaaaagt gattcattct gagcttgaaa cgactctgtc agtgtttgac attgtcattt   7140
ctagtggcat gtatcttaac attcttttcc tgcttcagga atgaaatcac ttgtcctgct   7200
gagaaaataa ggggaaaaca agatagaagt aaaaaacaac acacctgttg aactattttc   7260
ataaagatgg cgttttcact ttcaaaagaa atgaaaacca gatggtctat gctaagaagt   7320
gaaggcattt tgttgtcttc agaactgatc aacatggtca tgatcatcat caaatttctt   7380
gtttccaaag gccactattg tagtacagtc tccagcagga ttttgtacca tgtgctgcct   7440
ttggaataaa gtattataat gtatcttgtc accttcatca acaccaccat taaatatgta   7500
agttcctata tgtgactttt tctgggcata tttgcatcaa aaatcacagt ccttgcctcc   7560
```

```
ttgcttgctt ttactccatg aaacgcttca tgaagcagag catgattgtc aagtgaccag   7620
aggatgacat ttgtaagtga acgtggtata ctcacacatg ctatactcat actacataac   7680
ttagtttctc caaatcaact gcagtccgtt ttatctatga tattcctggc ttcgtataat   7740
ggttttgtaa aatacattaa atacaattaa gtccgttatt actatgctgg aaataactag   7800
gtcagacaat gaaaccttag acttttgatt ggggctgttt ggacttgatc caatgataag   7860
gtaataaggt tgttgcaatt tctcaaagca tcttaattct caaactgaaa catttagcaa   7920
atacatggtg aatctggtgt aaacttacaa tctaacaaat aattttcttt caactcttct   7980
ctttttctgc ctaacaatct atacgaaatt gccaatatct aagcaatcaa aagtttctga   8040
aatctctgtt tccttagtag aaatgacctt gacaacttat tttctgagat accactaggc   8100
ctactgtctt tcatgccatt ttatataaac attttgatag atactctgtc ttttgttttt   8160
tatctcttct cttttcaaga gtcacttgac tttttcaaat attcttaaaa gatagattta   8220
gttattgtat tttggtctac aattttggac ttggcagttt gttttactaa tgcagaatta   8280
ttctttttgt ttcaaacata gtttgccatc atctggctac tacctaatca tgttgtacta   8340
gttattgtgg aaagaaaatt gtacatacat ttccttgtcc tttgggagat gtctttgagt   8400
caaacccaca agcatgaact ctcacctgaa agaaaactgg aaaaggagaa actttaaatc   8460
agtatgtttt gaaaggaaga gatttccaga ctttttaaag caaattggaa tcgttttatt   8520
tttttgtttg ggccttaggc acaatagaag caaatgttgc aatattaaat ataataggga   8580
gagttcactg tttcctggga cattgtggtc atgtccttaa tccttcattg tgatgcccct   8640
tcttggagtt ggcattttgt gacaattcat agagatcttg cagcaatatt tggctattgg   8700
ttttattaac ttaaaattca acagaaatgg agtaattaaa aaaaaaaaca aaaaacagag   8760
aagaattgca aaatctgaag tggaatggca cttccttggg tatgtaaggg ttgtttttag   8820
ataaaactcc cgatttgttc ttcctacact ttaatagtct caaattcttt ctggggaagc   8880
aacgtcagtg tctacctcca cagtaactat gatataggaa attgtccttt cagtggtttc   8940
taggtataac aaacaagccg ttaaaaatga gtgaccattt tgtaggttac agcctcagca   9000
atctgtgtca tttgaaagca aatatcctga tatttttaaa taaggtgagc agggcaggca   9060
ggaaaccaat atttagtact tttgtgatta aacattctag accaggcttg ttgatatgta   9120
tgccaatagc ctagaatttt tggcttagtg taaaataaaa atgtcttttc tattgtggtc   9180
tgatatccgt ttctgtaata agatcagttt gttgtcctct gtgcaccagt ggttttgccc   9240
ttaatttttt ttggctagca tcaccaagat ctgtcatcca gagctgctga gaaaaataca   9300
tgttgccaaa cttttcttaa aattgtgctg ccagtggtat tttcccagat gtgaaaaata   9360
ataatctaat aaaggattaa tatctaataa caataccatt gttgaacatg ctcatggaat   9420
gtccaccttc ttctgattcc ttttttgtat ttgaaaatgc aatggtgtgt tccaaattat   9480
tgttggtgtt gttaatgtca tgactctcct ttgaatagaa taaaataacc ccttttgttt   9540
tgtgttttct actgaattag attttcctct agtcctatgt gaataaaaag ctatttgaaa   9600
taaaaaaaaa aaaaaaaaa                                                 9619
```

<210> SEQ ID NO 22
<211> LENGTH: 3714
<212> TYPE: DNA
<213> ORGANISM: Homo sapiens

<400> SEQUENCE: 22

-continued

```
ttatcagaga cattgagagg caaattcgga aaaaagaaaa cattcgtctt ttgggagaac     60
agattatttt gactgagcaa cttgaagcag aaagagagaa gatgttattg gcaaaaggat    120
ctcaaaaatc atgacttgaa tgtgaaatat ctgttggaca gacaacacga gtttgtgtgt    180
gtgtgttgat ggagagtagc ttagtagtat cttcatcttt ttttttggtc actgtccttt    240
taaacttgat caaataaagg acagtgggtc atataagtta ctgctttcag ggtcccttat    300
atctgaataa aggagtgtgg gcagacactt tttggaagag tctgtctggg tgatcctggt    360
agaagcccca ttagggtcac tgtccagtgc ttagggttgt tactgagaag cactgccgag    420
cttgtgagaa ggaagggatg gatagtagca tccacctgag tagtctgatc agtcggcatg    480
atgacgaagc cacgagaaca tcgacctcag aaggactgga ggaaggtgaa gtggagggag    540
agacgctcct gatcgtcgaa tccgaggatc aggcatcagt ggacttatcg cacgaccaga    600
gtggggattc cctcaacagt gatgaaggag acgtgtcttg gatggaggag cagctgtcct    660
acttctgtga caagtgccaa aaatggatac cagccagtca gctgagggaa cagctcagtt    720
accttaaggg tgataatttt tttaggttta cttgttcgga ttgctcagca gatggcaagg    780
agcagtatga aaggctgaag ctgacatggc agcaagtcgt catgttggca atgtacaact    840
tgtctctgga aggaagtgga cgtcaaggtt atttcaggtg gaaagaagat atctgtgctt    900
ttattgagaa acattggact tttttactag ggaataggaa aaagacgtct acctggtgga    960
gcaccgtggc aggttgcctc agcgtgggaa gtcccatgta cttccgttca ggtgctcagg   1020
aatttggaga gccaggatgg tggaaacttg ttcataacaa gcccccaacg atgaaacctg   1080
aaggagagaa gttgtctgcc tctactttga aaataaaagc agcctcaaaa ccaactttag   1140
atcccatcat tactgttgag ggacttagaa aacgagcaag tcggaatcct gtggaatctg   1200
ccatggaatt aaaagagaaa aggtctcgaa ctcaggaagc aaaagacatt agaagagccc   1260
agaaggaggc cgctggcttt cttgacagga gcacatcttc taccccctgta aaattcataa   1320
gccgaggccg caggccagat gtgattctgg aaaaaggcga agtgattgac ttttcctcct   1380
tgagctcctc tgaccgcacc ccgctgacaa gcccatctcc ttctccttct ctggatttct   1440
ctgcccctgg tacacctgcc tctcattctg ccacacctag cttgctttca gaagcagatc   1500
tgattccaga tgtgatgccc ccacaagcct tgtttcatga tgacgatgag atggaaggcg   1560
atggagtcat agacccaggg atggagtacg tcccaccccc tgctgggtca gtagcttctg   1620
ggccagtggt tgggggcaga aagaaggtca gaggccctga acagataaag caggaggtag   1680
agagtgagga ggaaaaaccc gacaggatgg atattgacag tgaagacaca gattcaaaca   1740
catctttgca aacaagggct agagaaaaga ggaagcctca gctggagaag gacacaaagc   1800
cgaaagagcc caggtatact cccgtgagca tctacgagga aaagctgctg ctcaagaggc   1860
tggaagcttg tcccggtgct gttgccatga ctccggaagc tcggagactg aaacgcaaac   1920
tgattgtcag acaagcgaaa agggataggg gattaccact ttttgacttg gatcaagttg   1980
ttaatgctgc tcttttgtta gttgacggga tttatggagc caaagaagga ggaatttcca   2040
gacttccagc tggacaagcc acgtacagaa ccacctgtca ggacttcaga atccttgacc   2100
gataccagac ttccttgccg tccaggaagg gatttcgaca ccagaccacc aagtttttgt   2160
atcgcttggt aggatcagaa gatatggctg tggaccagag tattgtcagc ccttatacct   2220
ctcggatctt gaaaccttat atcaggcgtg attatgaaac aaagccaccc aaactgcagc   2280
tcctgtcaca gattcgttcc cacctgcaca ggagcgaccc tcactggacg ccggagcccg   2340
acgcacctct cgattactgt tatgtgcggc caaatcacat cccaacgatc aactccatgt   2400
```

gtcaggagtt tttttggcct ggcattgacc tgtctgagtg tctgcagtac ccagacttca 2460
gtgttgttgt tctttataaa aaagtcatca ttgcctttgg cttcatggtt cctgatgtga 2520
aatacaatga agcttacatt tcatttctgt tcgtccaccc tgaatggaga agagcaggga 2580
ttgcaacttt catgatctat catctgattc agacctgcat gggcaaggac gtaacccttc 2640
acgtctcagc aagcaacccc gctatgctac tgtaccagaa gtttggattc aagactgaag 2700
aatatgtatt agatttctat gataaatatt acccattgga gagtacagag tgtaaacacg 2760
cattctttct gaggctccgg cgctgatgcg aatacagctc acagagaaac gcatgtgcta 2820
ttggagaaca ggtctttgtg gagatctaaa ggcagtgatt gatttcacag ggagctctaa 2880
tctctgtgat tacatggtcc ttcaaactcc caaccaaagt gagaaaagcg gcatgcagtg 2940
aaatgagcag tgagcagccc tttagcaaaa tcgccctcca gtccttcctg gagatgcctt 3000
cagccagcat cccagactcc acagttattt atgaatgatg tcgtgattct ccctccacct 3060
gacagtttgt aagagtgaaa gagcatctaa cctgatgctc ttggagagag ataacctgtc 3120
tgtcataact taaaggatga gaaaatgtgg tgtagctatt aaagattcat gcagtcccaa 3180
aaggcactgt cctgggatga tgagagatta taaggtgatt tcataaaagg aatccaaccc 3240
tgtgcccggc cattgatgtg ttgtcattga atccaggagg atttctaggg cactgaagtt 3300
ttgttgtttc ttttgctgac tttggttaca gtcagaaaaa ataaactaga tgtttgtgtc 3360
tacatgttct acctgttgta cctattagca tcttcctgca gggacttggg cccatggcct 3420
gggaggttgg tttgggattg gggttgttgg gcagcctgcc attcacctgg cctatcctgg 3480
cccttctcat gcccaagaca gttgtttcac aggagtggaa gtgtgggtga tgcaagtaga 3540
accctctaga tgtaccctgt gtggtctgca ggactggact gtttgctgtg tttgtggatg 3600
ttggcgatag actgtcaatt aggttgtttg tgatccaaca agaacatttc caaaagtatc 3660
taggtgttct caaataaaaa gctttctttg cacaacccat ggccagagcg tcaa 3714

<210> SEQ ID NO 23
<211> LENGTH: 8314
<212> TYPE: DNA
<213> ORGANISM: Homo sapiens

<400> SEQUENCE: 23
agtgtcatgt cggattcatg tcaacgacaa caacaggggg acacaaaatg gcggcggctt 60
agctcctacc cctggcggcg gcggcagcgg tggcggaggc gacggcacct cctccaggcg 120
gcagccgcag tttctcaggc agcggcagcg cccccggcag gcgcggtggc ggtggcgcgc 180
agccagattt gcctgaagac ctggataatc tccatttttg tcatggactg ttaaaacgtt 240
tgaagttcca attctggtct tgatttccca gttaaagatg ttcttcaccc gaatgcagtc 300
tttcctgttg gtaaaataag acaaccatca acattgcctg tttgtctgct tttgaatctc 360
ttaaggatgg atgtttgtaa gatgttgctt aatacagtct ggaatactct gtccatttgt 420
tgaattgtaa atgactttca aatgtgcaag ttctgttaaa tacaaagaga acctctatgg 480
gtaacttttg tgttgaagaa gtcatttgtc aaccatggta aaacttgcaa acccacttta 540
tacagagtgg attcttgaag ctatacagaa aataaaaaag caaaagcaaa ggccctctga 600
agagagaatc tgccatgcgg tcagtacttc ccatgggttg gataagaaga cagtctctga 660
acagctggaa ctcagtgttc aggatggctc agttctcaaa gtcaccaaca aaggccttgc 720
ctcctataag gacccagaca accctgggcg cttttcatca gttaaaccag gcacttttcc 780

```
taagtcagcc aaggggtcta gaggatcatg taatgatctc cgcaatgtgg attggaataa    840
acttttaagg agagcaattg aaggacttga ggagccgaat ggctcctccc tgaagaacat    900
agagaagtat ctcagaagtc aaagtgatct cacaagcacc accaacaacc cagcctttca    960
gcagcggctg cgactggggg ccaaacgcgc tgtgaataat gggaggttac tgaaagacgg   1020
accgcagtac agggtcaatt atgggagctt agatggcaaa ggggcacctc agtatcccag   1080
tgcattccca tcctcgctcc cacctgtcag ccttctaccc catgagaaag accagccccg   1140
tgctgatccc attccaatat gtagcttctg tttggggact aaagaatcaa atcgtgaaaa   1200
gaaaccagaa gaactcctct cttgtgcaga ttgtggcagt agtggacacc catcctgttt   1260
gaaattttgt cctgaattaa caacaaatgt aaaggcctta aggtggcagt gcatcgaatg   1320
caagacatgc agtgcctgta gagtccaagg cagaaatgct gataatatgc tttttgtga    1380
ttcctgtgat agaggatttc atatggaatg ctgtgaccca ccactttcca gaatgccaaa   1440
agggatgtgg atttgccaag tctgcagacc aaagaaaaag ggaagaaaac tacttcatga   1500
gaaagctgca caaataaaac gacgatatgc aaaacccatt ggacgaccga aaataaatt    1560
aaagcaacga ttgttgtctg taaccagtga tgaaggatcc atgaatgcat tcacaggaag   1620
ggggtcacct ggtaggggtc aaaagactaa agtctgtacc acaccttcat ctggtcatgc   1680
tgcatctggg aaggactcaa gcagcagatt ggctgttaca gaccccactc ggcctggtgc   1740
caccaccaaa atcaccacca cctccaccta catttctgcc tctacactta aagttaacaa   1800
gaaaaccaaa gggctcattg atggccttac taagtttttt acaccatcac ctgatggtcg   1860
cagatcacga ggtgaaatta tagacttttc aaagcactat cgtccaagga aaaaggtctc   1920
tcagaaacag tcatgcactt ctcatgtgtt ggctacaggt accacacaaa agctaaaacc   1980
tccaccttct tcacttccac ccccaacccc catctccggt cagagcccca gttcacaaaa   2040
gtccagcacg gccacttctt ctccctctcc ccagagttct tccagccagt gcagtgtgcc   2100
ctccctgagc agccttacca ctaacagcca gctgaaggca ctctttgatg ggctttctca   2160
tatctatacc actcagggac agtctcgcaa aaagggacac ccgagttatg caccacccaa   2220
acgtatgcgt cgtaaaactg aattatcttc cacggcaaaa tctaaagccc acttctttgg   2280
caaaagagat attagaagtc ggtttatttc tcactcctcc tcctctagct gggggatggc   2340
tagaggaagt atttttaaag caattgctca cttcaagcga acaactttcc ttaaaaagca   2400
caggatgcta ggcagattaa aatataaagt gacccctcag atggggaccc cctcaccagg   2460
gaaggggagc ttgacagacg gaaggattaa acctgatcag gatgatgata ctgaaataaa   2520
aataaacatc aaacaagaaa gtgcagatgt aaatgtgatt ggaaacaagg atgtcgttac   2580
tgaagaggat ttggatgttt ttaagcaggc ccaggaactt tcttgggaga aaatagagtg   2640
tgagagtggg gtggaagact gtggccggta cccttctgtg attgaatttg gtaaatatga   2700
aatccaaacc tggtactcct cgccttaccc acaggaatat gcaagattac caaagcttta   2760
cctgtgtgaa ttctgtctta aatatatgaa aagtaaaaat attttgctaa gacactccaa   2820
gaagtgtgga tggtttcatc ctccagcaaa tgaaatttac cgaaggaaag acctttcagt   2880
atttgaggtt gatgggaata tgagcaaaat ttattgccaa aacctttgct tgttagccaa   2940
gctcttcctg gaccacaaaa cgttgtatta tgatgtcgag ccattccttt tttatgtcct   3000
tacaaaaaat gatgaaaagg gctgtcatct ggttggatac ttctctaagg aaaagctttg   3060
ccagcagaag tataatgtct cctgcataat gatcatgccc cagcaccaaa ggcaaggatt   3120
tggacggttt ctcattgatt tcagctattt gctttctaga agagaaggcc aagcagggtc   3180
```

tcctgaaaag cctctctccg atctgggccg tctctcctac ctggcatatt ggaagagcgt 3240
catcttggag tatctctacc accaccatga gaggcacatc agcatcaagg caattagcag 3300
agcgacgggc atgtgcccac atgacattgc caccactctg cagcacctcc acatgatcga 3360
caagagagat ggcagatttg tcatcattag acgggaaaag ttgatattga gccacatgga 3420
aaagctgaaa acctgttcca gagccaatga acttgatcca gacagtctga ggtggacccc 3480
aattttaatt tctaatgctg cagtgtctga agaagagcga gaagctgaga aagaggctga 3540
gcggctaatg gaacaagcta gctgctggga gaaggaggaa caagaaatcc tgtcaactag 3600
agctaacagt aggcaatcac ctgcaaaagt acaatcgaaa aataaatatt tgcattcccc 3660
ggagagccgg ccagtcacag gggagcgagg gcagctgctg gagctgtcta aagagagcag 3720
tgaagaagaa gaggaggagg aggacgagga ggaggaagaa gaggaggaag aagaggaaga 3780
ggatgaagag gaggaagaag aggaagaaga agaagaagaa gaagaaaata ttcaaagctc 3840
tcccccaaga ttgacgaaac cacagtcagt tgccataaag agaaagaggc cttttgtact 3900
aaagaagaaa aggggtcgta aacgcaggag gatcaacagc agtgtaacaa cagagaccat 3960
ttcagagacg acagaagtac tgaatgagcc ctttgacaac tcagatgaag agaggccaat 4020
gccacagctg gagcctacct gtgagattga agtggaggaa gatggcagga agccagtcct 4080
gagaaaagca ttccagcatc agcctgggaa gaaaagacaa acagaggaag aggaaggaaa 4140
agacaatcat tgcttcaaga atgctgaccc ttgtagaaac aatatgaatg atgattcaag 4200
taacttgaaa gaaggcagta aagacaatcc cgaacctcta aagtgcaaac aagtgtggcc 4260
aaaaggaaca aagcgcggtc tatctaagtg gaggcaaaac aaagagagga agaccggatt 4320
taaactgaat ttgtacaccc cgccagaaac acccatggag cctgacgagc aggtaacagt 4380
ggaagaacag aaggagactt cagaaggaaa aaccagcccc agtcccatca ggattgagga 4440
ggaggtcaag gaaactgggg aagccctgtt gcctcaagag gaaaacagaa gggaagaaac 4500
atgtgcccct gtaagtccaa acacatcacc aggtgaaaaa ccagaagatg atctcatcaa 4560
acctgaggaa gaggaagagg aggaggagga ggaagaggaa gaagaggaag aagaggaagg 4620
ggaagaagaa gaaggaggag gaaatgtaga aaaagatcca gatggtgcta aaagccaaga 4680
aaaagaggaa ccagaaatct ccacggaaaa agaagactct gcacgtttgg atgatcacga 4740
agaggaggag gaagaggatg aagagccatc ccacaacgag gaccatgatg ccgatgacga 4800
ggatgacagc cacatggagt ctgccgaagt ggagaaggaa gagctgccca gagaaagctt 4860
caaagaagta ctggaaaacc aggagacttt tttagacctt aatgtgcagc ctggtcactc 4920
gaacccagag gtcttaatgg actgtggcgt cgacctgaca gcttcttgta acagtgagcc 4980
caaggagctt gctggggacc ctgaagctgt acccgaatct gacgaggagc cacccccagg 5040
agaacaggca cagaagcagg accaaaagaa cagcaaggaa gtcgatacag agttcaaaga 5100
gggaaaccca gcaaccatgg aaatcgactc tgagactgtc caggccgttc agtctttgac 5160
ccaggagagc agcgaacagg acgacacctt tcaggattgt gccgagactc aagaggcctg 5220
tagaagccta cagaactaca cccgtgcaga ccaaagtcca cagattgcca ccacgctcga 5280
cgattgccaa cagtcggacc acagtagccc agtttcatcc gtccactccc atcctggcca 5340
gtccgtacgt tctgtcaaca gcccaagtgt ccctgctctg gaaaacagct acgcccaaat 5400
cagcccagat caaagtgcca tctcagtgcc atctctgcag aacatggaaa ccagtcccat 5460
gatggatgtc ccatcagttt cagatcattc acagcaagtc gtagacagtg gatttagtga 5520

-continued

```
cctgggcagt atcgagagca caactgagaa ctacgaaaac ccaagcagct acgattctac   5580
tatgggaggc agcatctgtg gaaacggctc ttcacagaac agctgctcct atagcaacct   5640
cacctccagc agtctgacac agagcagctg tgctgtcacc cagcagatgt ccaacatcag   5700
cgggagctgc agcatgctgc agcaaaccag catcagctcc cctccgacct gcagcgtcaa   5760
gtctcctcaa ggctgtgtgg tggagaggcc tccgagcagc agccagcagc tggctcagtg   5820
cagcatggct gctaacttca ccccacccat gcagctggct gaaatccccg agacgagcaa   5880
cgccaacatt ggcttatacg agcgaatggg tcagagtgat tttggggctg ggcattaccc   5940
gcagccgtca gccaccttca gccttgccaa actgcagcag ttaactaata cacttattga   6000
tcattcattg ccttacagcc attccgctgc tgtgacttcc tatgcaaaca gtgcctcttt   6060
gtccacacca ttaagtaaca cagggcttgt tcaactttct cagtctccac actccgtccc   6120
tgggggaccc caagcacaag ctaccatgac ccccaccccc aacctgactc ctcctccaat   6180
gaatctgccg ccgcctcttt tgcaacggaa catggctgca tcaaatattg gcatctctca   6240
cagccaaaga ctgcaaaccc agattgccag caagggccac atctccatga gaaccaagtc   6300
agcgtctctg tcaccagccg ctgccaccca tcagtcacaa atctatgggc gctcccagac   6360
tgtagccatg cagggtcctg cacggacttt aacgatgcaa agaggcatga acatgagtgt   6420
gaacctgatg ccagcgccag cctacaatgt caactctgtg aacatgaaca tgaacactct   6480
caacgccatg aatgggtaca gcatgtccca gccaatgatg aacagtggct accacagcaa   6540
tcatggctat atgaatcaaa cgccccaata ccctatgcag atgcagatgg gcatgatggg   6600
cacccagcca tatgcccagc agccaatgca gaccccaccc cacggtaaca tgatgtacac   6660
ggcccccgga catcacggct acatgaacac aggcatgtcc aaacagtctc tcaatggctc   6720
ctacatgaga aggtagacaa cgtgggcagt ccacaaaacc tacggggcat cactattgga   6780
ttgatctgca caaatacctt tgaagagtac gatttcaaaa ccagcaattg gtgtgaatgc   6840
aaaaacattt gttggcacca tttatttaaa aaaaaaaaaa gctgtatgca gcagaaagcc   6900
ttatacaagt tgtttttctt tttttccttt ttcttttttt tggtaccttc atttctgtta   6960
cttttatata aaattctctg caaaggaagg cctctctttg gactacaatt tggaggcagc   7020
cacttgttgt gcctgcttct gttaaacaat gtggatatca agccccccca aattatctgt   7080
tttaatattg aacctagagc ttttttttttc ccttccctgt ccactccatg taaatgcctt   7140
tagcatttca gttattgtat attttgttta aggtgacact tcagcatgcc gctaatgtct   7200
ttgttagtga cagtgcattt tgtagtactg tacaagtgtt gtgctaacag taagccattt   7260
cttaagtttt ttgccttgat tagggtgccc taatttgagg gttttaaaaa aaactatatt   7320
tttgttaatt ataaaactgt aaagagctat aaaagctatt cccatttggt tagtcaaaag   7380
ggttttattg ctaaatgttt ggtgtaaagt tgagaccctt ttccattttg gtgacagatt   7440
tctttgggga aaaaaggcag ctttctgttt tataaatgca gacttctgtt tattgaatga   7500
agcatatctc agtgtttatc tgtcaggttt tgaaacattt catatatgtc caaatacttg   7560
gcaggattta aaaaaaaata gtgaatttgg tgtaaagttg ctattttatg gaaatgcctc   7620
taactttaca ttttcattcc atctgtagat ttttctatct ttataaaata ttggagttat   7680
tttttaagga aaaatagaaa agtagcttgt gaatagctca aactaagctt acaaatcgca   7740
tgtaaaaaag caaaaaagtt atttgtgtct gtttatattg cttccttttt tgtagccttt   7800
gtacctgtac agggtgacag taagggccaa gcaggagagg cgtaatcctt gtataaaata   7860
ggatccagcg acactcttgt atttatctgt tctcttttta gtcagtcact tcaaaaaaac   7920
```

aaaaaacaaa caaaaaaaag ctgtacattt taacataaaa taaattatga tgagccattt 7980
ttagcctctt gtgtcctgtc atattatgat tgatagagaa tgaccaatgg aactgtatca 8040
tgtgtcacgc ctcagaacac atacacattt tgggaaaata aattatttag tgtaaattgg 8100
agttatggga ttttctgatt tgttttgact ttgggggagg ggttggcaat aaataagagt 8160
aatatctaat aaaaccatca catataccaa atacctattt aataaattaa tttataatgg 8220
attttaatgc ttttcatgaa agtttatttt atgcgagtgc ataccttctg tatgccaatc 8280
attgtcttta aaataaagtg aaattgtttt tttc 8314

<210> SEQ ID NO 24
<211> LENGTH: 9514
<212> TYPE: DNA
<213> ORGANISM: Homo sapiens

<400> SEQUENCE: 24
gcagaacgct ccagacgctg agaggcagga ggcactaggg atcgtccgca ggattgggac 60
tgatacagag gccgccacgg agcccgccgg agccaccgtt cctgctgctg ccgccgctgc 120
ccgaatcgga accgtcgggc cgcagccgcc ggcaatgccg cgaaggaaga ggaatgcagg 180
cagtagttca gatggaaccg aagattccga tttttctaca gatctcgagc acacagacag 240
ttcagaaagt gatggcacat cccgacgatc tgctcgagtc acccgctcct cagccaggct 300
aagccagagt tctcaagatt ccagtcctgt tcgaaatctg cagtcttttg gcactgagga 360
gcctgcttac tctaccagaa gagtgacccg tagtcagcag cagcctaccc cagtgacacc 420
gaaaaaatac cctcttcggc agactcgttc atctggttca gaaactgagc aagtggttga 480
tttttcagat agagaaacta aaaatacagc tgatcatgat gagtcaccgc ctcgaactcc 540
aactggaaat gcgccttctt ctgagtctga catagacatc tccagcccca atgtatctca 600
cgatgagagc attgccaagg acatgtccct gaaggactca ggcagtgatc tctctcatcg 660
ccccaagcgc cgtcgcttcc atgaaagcta caacttcaat atgaagtgtc ctacaccagg 720
ctgtaactct ctaggacacc ttacaggaaa acatgagaga catttctcca tctcaggatg 780
cccactgtat cataacctct cagctgacga atgcaaggtg agagcacaga gccgggataa 840
gcagatagaa gaaaggatgc tgtctcacag gcaagatgac aacaacaggc atgcaaccag 900
gcaccaggca ccaacggaga gacagcttcg atataaggaa aaagtggctg aactcaggaa 960
gaaaagaaat tctggactga gcaaagaaca gaaagagaaa tatatggaac acagacagac 1020
ctatgggaac acacgggaac ctcttttaga aaacctgaca agcgagtatg acttggatct 1080
tttccgaaga gcacaagccc gggcttcaga ggatttggag aagttaaggc tgcaaggcca 1140
aatcacagag ggaagcaaca tgattaaaac aattgctttt ggccgctatg agcttgatac 1200
ctggtatcat tctccatatc ctgaagaata tgcacggctg ggacgtctct atatgtgtga 1260
attctgttta aaatatatga agagccaaac gatactccgc cggcacatgg ccaaatgtgt 1320
gtggaaacac ccacctggtg atgagatata tcgcaaaggt tcaatctctg tgtttgaagt 1380
ggatggcaag aaaaacaaga tctactgcca aaacctgtgc ctgttggcca aacttttct 1440
ggaccacaag acattatatt atgatgtgga gcccttcctg ttctatgtta tgacagaggc 1500
ggacaacact ggctgtcacc tgattggata tttttctaag gaaaagaatt cattcctcaa 1560
ctacaacgtc tcctgtatcc ttactatgcc tcagtacatg agacagggct atggcaagat 1620
gcttattgat ttcagttatt tgctttccaa agtcgaagaa aaagttggct ccccagaacg 1680

```
tccactctca gatctggggc ttataagcta tcgcagttac tggaaagaag tacttctccg   1740
ctacctgcat aattttcaag gcaaagagat ttctatcaaa gaaatcagtc aggagacggc   1800
tgtgaatcct gtggacattg tcagcactct gcaagccctt cagatgctca aatactggaa   1860
gggaaaacac ctagttttaa agagacagga cctgattgat gagtggatag ccaaagaggc   1920
caaaaggtcc aactccaata aaaccatgga tcccagctgc ttaaaatgga cccctcccaa   1980
gggcacttaa agtgacctgt cattccgagc cagcgaaccc cagcagtagg aatccgtacc   2040
ctagggatct gtctgtcatt tctctgttgc tcttgtgatt ggcaagtaca gtatcctttg   2100
ggaaggccat ccccctcagg actgtcctgg ctccgacctt tgtgtacact gcagacgctg   2160
gttctgagga actgttgttt cggcctcagt gaggttgcct ggatgggatc tgtattagac   2220
ttgagtgcag gtctctcagc actgacccaa ggagttctgt tatggtactg tacctgtcca   2280
gtcactggtt ctctcctcat gtcctctcgc cccatgaggt tgtgttgtgt cttctaagcg   2340
tggtactagt gcttgccacc tggtcaccag acctccaaat atggctgcca ccaccaggac   2400
ctttccagtt actccttata tgtgtgttct atggaggggc agggaaaagg tggcacttgt   2460
gagtgtgtgt ggattggcag gggtccatt cactttgggt tccatcttgc tttaaatttc   2520
ttcattttga ttaagagacc tctttttgat ctgtattggg ctaaccagag ccaaatactt   2580
ttgaagagtt tcccagggac tagtcatggt aatagcatat aattgatctg aatgagatgg   2640
agagaagaat gaaggggtgg tggttctggg tttgatttga gttcacctgt gggcagtggg   2700
cagtgggcag tgtcttggtg aaagggaacg gatactactt tttgcctcac cgtaaagtac   2760
tcactagtaa atatttcctt ctctctttac tcccactttt tacgtttgca ggtgccaaag   2820
taatgtccac ttttcccttt catgctgcat attaactggt taattatact gcagaaacct   2880
tttcacctcc actagtctga tacagtacat ctgtacttcc atataccttg cactgatttt   2940
gtctgagtgc cctgggagaa gtagaaaatg attgaaagtg acttccgtat ctcagcccat   3000
gactcagcaa ggcagaatgg ccacccctgc caaagtttgc ttctcttttc aacagtgcct   3060
caccctccct ctaggattaa agtgcttctg cccttccacg aactcctcct ccatttcctt   3120
tttgggattt gtcaccatcc ttctattctc tggtcttcta tttttggtgt tgttcaagtg   3180
aaggaagaga tgttccctct aatttctctc tagcccatta taacctgcta tcttggggca   3240
acttttgatg tatgacatgt caccccttccc aacttggtct cctccaacat gctgtcttca   3300
tgtggagccc tcaccacaat ccctgactcc ggtcatttgt gcctttctct tgtcatctct   3360
gtacactact tatattcact gtgggttggg ggagctaatt ttaagcatgt tcagtggcag   3420
ctcccctcca gtttcagtgt cactgttaaa atttatcaaa aagcaacttc actaggggtt   3480
ttcttaaggg ataaaggcct tttacagaag ctaaaccctt ccccacatgt ggtagaatgt   3540
gctcttctat atctactcct caataaagca tgttctctgc tcaagtctgt ttcatctggg   3600
ggctctcatt tatatatgaa aatgatgcac acgatctgct actaatagta aatgcacttg   3660
ggatttgctt tccctagcag taaactgttg agggatgtgg tttgtggcta tggaatgttt   3720
ttccctgtga tacaggctgt ctgtaaagat caagggagtg ctcactctga acttctctag   3780
atggtggcac aaatttgatc tgcctcactt tggttccagc taatcagtat acgtagcaat   3840
gattagtcag tattacccat tctttcacta agtgccattt tccactgatt ttaggggcaa   3900
aggaaccaat aggaaattag gatatatggg ggtacagttg atgcctgtag gagatgggaa   3960
cagacattcc ttctcatctc caagctcatt caccagtatt gagcagtgtc acctctaatt   4020
attgactctc tcgcaggttg aaattattct ttttgaaaat agctgcattt tcatgtaaga   4080
```

tatacccagc acaggaaaag ggtggctgag cactaacctc cgtatggtgg aaaggaggag 4140
gctgggaatt gtatgtgctg gaatggtttc actcactgtg accagtagtg gtgagaaccc 4200
atacagttga agtttttgc acagtcctga tcccaggtct ccactcgctt tgccatccca 4260
ctttactccc taaaaataaa aggatttatt atctcattta aaccccaca ggtgtggaaa 4320
cagagtttca cttgccttgg caactttgca tgagactatc ccatttcatt ccgtttttt 4380
ttttttgagt cagagtctgg ctctgttgcc caggttggag tgcagtggcg cagttttggc 4440
tcacaacctc tgcctcccgg gttcaagtga ttcttctgtc tcagccttcc gaatagctgg 4500
gattacaggt gcctgtcacc atgcccagct aatttttgta tttttagtag agacagggtt 4560
tcgtcatgtt ggtcaggctg atctcgaact cctgacctca ggtgatccgc ccaccttggc 4620
ctcccaaagt gctgggatta caggcgtgag ccactgcacc cgacctattt tttttttttt 4680
tttttttttt ttttttaaaa aaagacagtc tcactctatc atccagtccg gaatgcagtg 4740
gcatgatctc agctcactgc aatgtctgcc tcctggattc cagtgattct cctgcctcag 4800
cctctcaagt agctgggatt acaggtgcag gccacctggc taatttttgt atgtttagta 4860
gagacagggt tttgccatgt tggccaggcc agtctcaaac tcttgacctc aagtgatcac 4920
ccgcctcatc ctcccaaagt gctgggatta cagccgtgag cctctgcacc cagcttttaa 4980
ctccctctta tctgcataac agaagcttag ctgcttaagc tcctttatta gaagagcaaa 5040
agtctgaaat tattcctgaa acctgctcaa tggaagtacc tactctattg gttgcttccc 5100
atatggttgt cactgtacct tcatactgcc tcatttgacc ctcatattag ccctgtacag 5160
tagatgggta cactggtttg ccaaaggaga cctggaatcc aaggtggaag taagcagcaa 5220
agccagaaac ttcaattctg gtctgtctac cttgatagcc tgcaccctcc cctctaccgt 5280
tttcttccac tatttttgat tccttaatga tgaatcatcc tctcccttct agttggattt 5340
gtttctaatg gcttccatta caaggataat aatgaaactg gtgaaaactt tcaggcaaaa 5400
ggattttctt tttatatttt ttcttattat tttttaatta ttaaccaaat taactcatta 5460
cagtaaaaag gactgatttt taagccagct gtgatagctc tgtaatagtc tgtaatctca 5520
gcactttggg aggccaaggc gggcagatcg cttgagtcca ggaattcgag actagcctgg 5580
gcagcatggt gaaaccccag ctctacaaaa aatagaaaaa tcagacgtgg gcacatgcct 5640
gtagtctcag ctacttggga ggctgaggca cgagaatcgc ctgaacctgg gaggcagaag 5700
ttgcaatgag ctgagatgat gccactgcac tccagcctgg gtgacagagt gagaccctgt 5760
ctcaaaaaca aaaaacagaa ttgattgatg ttagttggct ttagaagcag caagtttagg 5820
gggctacaga gctaaaccag gaagcaaaag atgtgcctca ttctggcatt gtttctgatt 5880
taggaataaa ctgttcagta agcactgtcc ctttacttcc atggttttct tcattcctca 5940
ccacagcaca gtaaggtgga tattatagtc ttcttctaga tgaaaaattg aggctcatag 6000
tggtcttgct gctgtgtcat agcaatagaa tgagagagcc ttgcttccct gagtccaaat 6060
cccatacttt tggcattgtt atgaggtctg gtcacctgat gcttccatgc tattttccca 6120
tttcttatct ggggataatg agtcatatta agtaattttt ttttttgaga cggagtttcg 6180
ttctgtcacc caggctggag tgcagtggtg cgatcttggc tcactgcaag ctctgcctcc 6240
cgggttcatg ccattcttct gcttcagtct cccgagtagc tgggactaca ggtgcccacc 6300
accacgccca gctaattttt tgtattttta gtagaatgag gtttcaccgt gttagccagg 6360
atgatctcga tctcctgacc tcgtgatcca ctcgcctcag cctcccaaag tgctgggatt 6420

-continued

```
acaggcgtga gccattgcac ccagccattt tttttttttt taagacgacg tctcactctg   6480
tcacctatgc tggagtgcag tggcgtgatc taggctcatt gcaacctctg cctcccaggt   6540
tcaagcgatt ttcctgcctc agcctcccaa gtagctggga ttacaggtgc ccaccacctc   6600
gcctggctaa tttttgtatt tttagtagag atgaggtttt gccctgttgg ctaggttggt   6660
cttgaactcc tgacctcagg tgatccactc acctcagcct cccaaagtgc tgggattaca   6720
ggcaggagcc actgcgccca gccaagtaac ttttaacagt gtggtataac ctttaaatga   6780
caaggtgatg cttttgactt gtcctcaact ttgatttgta ctgatttgtc cctatagttc   6840
tgggtggggt gggtcaaaac aaagtctcga gctgtaccag gatcaagcag cacagctcag   6900
ccatgatcct tttaccactt ttttcttctg tccttgagac tctaattaaa gcactggatt   6960
tttaaaaatc acccttgtaa atatgcacac atttgtctat agttgaggaa attgtgccgt   7020
tgaagtccat tcttggacat ggagttaaga aaccctggtt tgagaaaaag ccccagtgag   7080
acagcaggaa tccttttacc atacaaccct caactagttt agtgtgctca agctcaaata   7140
accaatccca tcaagtgaaa agaatggcag cagggagaag gcctggctca ctgaggctct   7200
cagcattagt ttcctctacc tcttgtgtct cacaggtgca catatgtaca gcatatcaaa   7260
gtgttgaatg tcatgagaat aaaatatgaa aactactttg ctgaatgata gtatgtgatg   7320
tgtgctagga cttctagaag ccaccctttg ctttgctgtt cattgggatc atggaatcgg   7380
acctcagctg gttttgcctc agcactttct ttcacaaaat tatgtgtgac tgcctcctcc   7440
agactgtttc ctgctgatag gggcagttta atagccttct tcctgtgtgg tatctgcaac   7500
aaaatcccaa tgaatgtcac caagaaggaa acaaaggatt gcccagcgat gagaaatgtc   7560
cctggtgcca aaacatcagt ttgcccctaa cctcttgtgc aataccttta agtccaggtc   7620
atgttgttac catttggggg tttgcggatt tgtttacttg tgcccaagaa tggagaaaat   7680
aacctgtact attgtacaac tctggctcca tggctcctca caaatgttcc atgtgagata   7740
taaacatctt tatcctcgac aagtcatgtt cattccaaga aaccagtctt tgttcttaat   7800
tggacatttg tttctgcaaa cagcttacca tacattcaat tccaaagtta tcagaaacct   7860
acactcttat ctcacaaatt tagaggtgtg gtagatcatc tccaaagatg gccaccaaca   7920
gttgctctca tcctctgtgc acgtgctatt tccaataagg tctatttttt tctacagtga   7980
gggctgaact tgtgacttgt tttgactaat aggatatgga agtgatattt tggcagcttc   8040
cacttttgct cttgaaaata agctgacacg tttccaaacg agaagcttgg gctaaattac   8100
tgaatggtga gagacgatgc ataggagaac caaggtgctc tagtcacagc actaaaagcc   8160
cagacttgtg tctcttgaag gtttcaaccc cgccagactc ccagctgaac gcaccctcat   8220
gagtggccct tgctggtacc acatgacact aaagacatct agctgagtcc tgttaaccca   8280
gagaattatg agaatactgt tttaaccaca cgttttggaa tggtttgata catggcaatg   8340
gagaagtgaa acaaggggac ttcggaaact aaagggctgg aattcagttt gccttgtagg   8400
ttgattggaa gccagatgtg cctagaggaa ggctaccacc ttgtgcaatt ccaggggaca   8460
ctgtttatgt tccgtgtaaa tggcagcctc agttcacctc atttggttat ttatcgtgtc   8520
ttcgctgtca gtcaaattgc ttctgagata actggctggc cttggaattc ttagccacct   8580
ccttaagcgg atcaggaaaa ctgaagaata tccttctgta tgtatgtatg tatttattga   8640
ttgatcgatt tatgagacag ggtctccttc tgtcacccag gctggagtgc agtggtacga   8700
tcacggctca ctgctgcgtc gccttcccag gctccagcta tcctcccacc tcaacctcca   8760
gagtagttga gaccacaggc gtgcactacc acgcccggct acctttttgt attttcagta   8820
```

gagacgaggt ttcgccgtgt tgcccaggct ggttcaagcg gagctcaagc aatcagcctg 8880
cctcggcctc ccaaagtgtt gggattacag gcatgagccg ctgcgcccaa ccttcttctg 8940
ctgtcgagat actgctcatc acctgcctgc tccagaattc atgtggcttc tcattgctca 9000
atggattaag ttcatgttta tcctggcttt caagtctttc cgtaagctga ctcaacctac 9060
atagctttca tcattccctt acacataacc tcaacgtgca acaggattag tctattattc 9120
cctttcttgt gtttactgag aaagcctcca cttcaacgtt ccatgaagtg tgttccatta 9180
aataccaaag tataggcaaa aagttctgtg gtcaaataaa tttggaaaac acagagtgtt 9240
tccaaagtta gtatcaggcc aggcatggtg ggaggatcac ttgagcccag gagttcgaga 9300
ccagcctggg caacataggg agacccaatc cctacaaaaa aattagttgg gcatggtggt 9360
gtgcacccgt agtgccagct actcaggagg ctgaggtagg aggatcacct gagcccagga 9420
agtcaaggct gtggtcagct gagatcccac cagtgtgctc cagcctgggt gacagagcaa 9480
gaccctgtct caaaaaataa aaaaataaag ataa 9514

<210> SEQ ID NO 25
<211> LENGTH: 5604
<212> TYPE: DNA
<213> ORGANISM: Homo sapiens

<400> SEQUENCE: 25
agggctcggt cgccagcaac cgagcggggc ccggcccgag cggggcctgg gggtgcgacg 60
ccgagggcgg gggagagcgc gccgctgctc ccggaccggg ccgcgcacgc cgcctcagga 120
accatcactg ttgctggagg cacctgacaa atcctagcga atttttggag catctccacc 180
caggaacctc gccatccaga agtgtgcttc ccgcacagct gcagccatgg ggtctgagga 240
ccacggcgcc cagaacccca gctgtaaaat catgacgttt cgcccaacca tggaagaatt 300
taaagacttc aacaaatacg tggcctacat agagtcgcag ggagcccacc gggcgggcct 360
ggccaagatc atcccccga aggagtggaa gccgcggcag acgtatgatg acatcgacga 420
cgtggtgatc ccggcgccca tccagcaggt ggtgacgggc cagtcgggcc tcttcacgca 480
gtacaatatc cagaagaagg ccatgacagt gggcgagtac cgccgcctgg ccaacagcga 540
gaagtactgt accccgcggc accaggactt tgatgacctt gaacgcaaat actggaagaa 600
cctcaccttt gtctccccga tctacggggc tgacatcagc ggctctttgt atgatgacga 660
cgtggcccag tggaacatcg ggagcctccg gaccatcctg gacatggtgg agcgcgagtg 720
cggcaccatc atcgagggcg tgaacacgcc ctacctgtac ttcggcatgt ggaagaccac 780
cttcgcctgg cacaccgagg acatggacct gtacagcatc aactacctgc actttgggga 840
gcctaagtcc tggtacgcca tcccaccaga gcacggcaag cgcctggagc ggctggccat 900
cggcttcttc cccgggagct cgcagggctg cgacgccttc ctgcggcata agatgaccct 960
catctcgccc atcatcctga agaagtacgg gatccccttc agccggatca cgcaggaggc 1020
cggggaattc atgatcacat ttccctacgg ctaccacgcc ggcttcaatc acgggttcaa 1080
ctgcgcagaa tctaccaact tcgccaccct gcggtggatt gactacggca aagtggccac 1140
tcagtgcacg tgccggaagg acatggtcaa gatctccatg gacgtgttcg tgcgcatcct 1200
gcagcccgag cgctacgagc tgtggaagca gggcaaggac ctcacggtgc tggaccacac 1260
gcggcccacg gcgctcacca gccccgagct gagctcctgg agtgcatccc gggcctcgct 1320
gaaggccaag ctcctccgca ggtctcaccg gaaacggagc cagcccaaga agccgaagcc 1380

```
cgaagacccc aagttccctg gggagggtac ggctggggca gcgctcctag aggaggctgg   1440
gggcagcgtg aaggaggagg ctgggccgga ggttgacccc gaggaggagg aggaggagcc   1500
gcagccactg ccacacggcc gggaggccga gggcgcagaa gaggacggga ggggcaagct   1560
gcggccaacc aaggccaaga gcgagcggaa gaagaagagc ttcggcctgc tgcccccaca   1620
gctgccgccc ccgcctgctc acttcccctc agaggaggcg ctgtggctgc catccccact   1680
ggagcccccg gtgctgggcc caggccctgc agccatggag gagagccccc tgccggcacc   1740
ccttaatgtc gtgcccccctg aggtgcccag tgaggagcta gaggccaagc ctcggcccat   1800
catccccatg ctgtacgtgg tgccgcggcc gggcaaggca gccttcaacc aggagcacgt   1860
gtcctgccag caggcctttg agcactttgc ccagaagggt ccgacctgga aggaaccagt   1920
ttcccccatg gagctgacgg ggccagagga cggtgcagcc agcagtgggg caggtcgcat   1980
ggagaccaaa gcccgggccg gagaggggca ggcaccgtcc acattttcca aattgaagat   2040
ggagatcaag aagagccggc gccatcccct gggccggccg cccacccggt ccccactgtc   2100
ggtggtgaag caggaggcct caagtgacga ggaggcatcc cctttctccg gggaggaaga   2160
tgtgagtgac ccggacgcct tgaggccgct gctgtctctg cagtggaaga acagggcggc   2220
cagcttccag gccgagagga agttcaacgc agcggctgcg cgcacggagc cctactgcgc   2280
catctgcacg ctcttctacc cctactgcca ggccctacag actgagaagg aggcacccat   2340
agcctccctc ggagagggct gcccggccac attaccctcc aaaagccgtc agaagacccg   2400
accgctcatc cctgagatgt gcttcacctc tggcggtgag aacacggagc cgctgcctgc   2460
caactcctac atcggcgacg acgggaccag cccccctgatc gcctgcggca agtgctgcct   2520
gcaggtccat gccagttgct atggcatccg tcccgagctg gtcaatgaag gctggacgtg   2580
ttcccggtgc gcggcccacg cctggactgc ggagtgctgc ctgtgcaacc tgcgaggagg   2640
tgcgctgcag atgaccaccg ataggaggtg gatccacgtg atctgtgcca tcgcagtccc   2700
cgaggcgcgc ttcctgaacg tgattgagcg ccaccctgtg gacatcagcg ccatccccga   2760
gcagcggtgg aagctgaaat gcgtgtactg ccggaagcgg atgaagaagg tgtcaggtgc   2820
ctgtatccag tgctcctacg agcactgctc cacgtccttc cacgtgacct gcgcccacgc   2880
cgcaggcgtg ctcatggagc cggacgactg gccctatgtg gtctccatca cctgcctcaa   2940
gcacaagtcg gggggtcacg ctgtccaact cctgagggcc gtgtccctag gccaggtggt   3000
catcaccaag aaccgcaacg ggctgtacta ccgctgtcgc gtcatcggtg ccgcctcgca   3060
gacctgctac gaagtgaact tcgacgatgg ctcctacagc gacaacctgt accctgagag   3120
catcacgagt agggactgtg tccagctggg acccccttcc gagggggagc tggtggagct   3180
ccggtggact gacggcaacc tctacaaggc caagttcatc tcctccgtca ccagccacat   3240
ctaccaggtg gagtttgagg acgggtccca gctgacggtg aagcgtgggg acatcttcac   3300
cctggaggag gagctgccca agagggtccg ctctcggctg tcactgagca cgggggcacc   3360
gcaggagccc gccttctcgg gggaggaggc caaggccgcc aagcgcccgc gtgtgggcac   3420
cccgcttgcc acggaggact ccgggcggag ccaggactac gtggccttcg tggagagcct   3480
cctgcaggtg cagggccggc ccggagcccc cttctaggac agctggccgc tcaggcgacc   3540
ctcagcccgg cggggaggcc atggcatgcc ccgggcgttc gcttgctgtg aattcctgtc   3600
ctcgtgtccc cgacccccga gaggccacct ccaagccgcg ggtgcccccct agggcgacag   3660
gagccagcgg gacgccgcac gcggccccag actcagggag cagggccagg cgggctcggg   3720
ggccggccag gggagcaccc cactcaacta ctcagaattt taaaccatgt aagctctctt   3780
```

```
cttctcgaaa aggtgctact gcaatgccct actgagcaac ctttgagatt gtcacttctg   3840
tacataaacc acctttgtga ggctctttct ataaatacat attgtttaaa aaaaagcaag   3900
aaaaaaagga aaacaaagga aaatatcccc aaagttgttt tctagatttg tggctttaag   3960
aaaaacaaaa caaaacaaac acattgtttt tctcagaacc aggattctct gagaggtcag   4020
agcatctcgc tgttttttg ttgttgtttt aaaatattat gatttggcta cagaccaggc   4080
agggaaagag acccggtaat tggagggtga gcctcggggg gggggcagga cgccccggtt   4140
tcggcacagc ccggtcactc acggcctcgc tctcgcctca ccccggctcc tgggctttga   4200
tggtctggtg ccagtgcctg tgcccactct gtgcctgctg ggaggaggcc caggctctct   4260
ggtggccgcc cctgtgcacc tggccagggg aagcccgggg gtctggggcc tccctccgtc   4320
tgcgcccacc tttgcagaat aaactctctc ctggggtttg tctatctttg tttctctcac   4380
ctgagagaaa cgcaggtgtt ccagaggctt ccttgcagac aaagcacccc tgcacctcct   4440
atggctcagg atgagggagg cccccaggcc cttctggttg gtagtgagtg tggacagctt   4500
cccagctctt cgggtacaac cctgagcagg tcgggggaca cagggccgag gcaggccttc   4560
ggggcccctt tcgcctgctt ccgggcaggg acgaggcctg gtgtcctcgc tccacccacc   4620
cacgctgctg tcacctgagg ggaatctgct tcttaggagt gggttgagct gatagagaaa   4680
aaacggcctt cagcccaggc tgggaagcgc cttctccagg tgcctctccc tcaccagctc   4740
tgcacccctc tggggagcct tccccacctt agctgtctcc tgccccaggg agggatggag   4800
gagataattt gcttatatta aaaacaaaaa atggctgagg caggagtttg ggaccagcct   4860
gggctatata gcaagacccc atcactacaa attttttaca aattagctag gtgtggtggt   4920
gcgcacctgt ggtcccagct actcgggagg ctgtggtggg aggattgctt gagtccagga   4980
ggttgaggct gcagtcagct cagattgcac cactgcactc cagcctgggc aacagagcga   5040
gaccctgtct ccaaaaaaaa aaaaaagcaa tgtttatatt ataaaagagt gtcctaacag   5100
tccccgggct agagaggact aaggaaaaca gagagagtgt tacgcaggag caagcctttc   5160
atttccttgg tgggggaggg gggcggttgc cctggagagg gccggggtcg gggaggttgg   5220
ggggtgtcag ccaaaacgtg gaggtgtccc tctgcacgca gccctcgccc ggcgtggcgc   5280
tgacactgta ttcttatgtt gtttgaaaat gctatttata ttgtaaagaa gcgggcgggt   5340
gcccctgctg cccttgtccc ttgggggtca cacccatccc ctggtgggct cctgggcggc   5400
ctgcgcagat gggccacaga agggcaggcc ggagctgcac actctcccca cgaaggtatc   5460
tctgtgtctt actctgtgca aagacgcggc aaaacccagt gccctggttt ttccccaccc   5520
gagatgaagg atacgctgta tttttgcct aatgtccctg cctctaggtt cataatgaat   5580
taaaggttca tgaacgctgc gaaa                                        5604
```

<210> SEQ ID NO 26
<211> LENGTH: 2951
<212> TYPE: DNA
<213> ORGANISM: Homo sapiens

<400> SEQUENCE: 26

```
gcgggcgttt gaaatcagtg ccttagagta gaccctaaac ctcattttat accttcaaga     60
accaattact taatgtctct tccgtctttt ccgtccccga ccccctccca gactccttca    120
ttccggtact gcgtggacgg aaagccccgg gtagccgaca ccacgtcccc ggctagcggg    180
agagagcgtg gaaaaggatt acaccaaact gtttaaatcc aacgactcct gcttccatcc    240
```

-continued

```
tttctcctga gctagaacca acaaacctag agagttgggc ttcggaaaaa ctagtgtttt    300
catttaattg gatatgaaga aagaacaaat atgtacgggg caaccacgat ctttacaaag    360
aacataagtt ccaggaaagc aggaaccttg tctctcttgt tcactgggtg tatcctctgc    420
atatagaaca gtgcctggca cataataggt gctgaatttt gttctaaaca ctgaggacat    480
tctctgctac atttgggtcg tacccccagg tctgagtaat tcaatagact taagaagaca    540
gagcccagca gcaaccgaaa cataacagag ttgcaggatc agctaacgtc aatgcctggg    600
caaagctgct gcccagagtg gaatctcact agtgaataaa caagcccaag aaagattatc    660
atctcatttg caaaaaaaaa agtacgctgg tagatcctgc tacctcatag ataacaccag    720
tcaaattttt ttttaaagta gcattttcct acattgtcaa ctatctagaa catacctaaa    780
aactaagagt ttactgctta ttaaatggaa actatgaagt ctaaggccaa ctgtgcccag    840
aatccaaatt gtaacataat gatatttcat ccaaccaaag aagagtttaa tgattttgat    900
aaatatattg cttacatgga atcccaaggt gcacacagag ctggcttggc taagataatt    960
ccacccaaag aatggaaagc cagagagacc tatgataata tcagtgaaat cttaatagcc   1020
actcccctcc agcaggtggc ctctgggcgg gcaggggtgt ttactcaata ccataaaaaa   1080
aagaaagcca tgactgtggg ggagtatcgc catttggcaa acagtaaaaa atatcagact   1140
ccaccacacc agaatttcga agatttggag cgaaaatact ggaagaaccg catctataat   1200
tcaccgattt atggtgctga catcagtggc tccttgtttg atgaaaacac taaacaatgg   1260
aatcttgggc acctgggaac aattcaggac ctgctggaaa aggaatgtgg ggttgtcata   1320
gaaggcgtca atacacccta cttgtacttt ggcatgtgga aaaccacgtt tgcttggcat   1380
acagaggaca tggaccttta cagcatcaac tacctgcacc ttggggagcc caaaacttgg   1440
tatgtggtgc ccccagaaca tggccagcgc ctggaacgcc tggccaggga gctcttccca   1500
ggcagttccc ggggttgtgg ggccttcctg cggcacaagg tggccctcat ctcgcctaca   1560
gttctcaagg aaaatgggat tcccttcaat cgcataactc aggaggctgg agagttcatg   1620
gtgacctttc cctatggcta ccatgctggc ttcaaccatg gtttcaactg cgcagaggcc   1680
atcaattttg ccactccgcg atggattgat tatggcaaaa tggcctccca gtgtagctgt   1740
ggggaggcaa gggtgacctt ttccatggat gccttcgtgc gcatcctgca acctgaacgc   1800
tatgacctgt ggaaacgtgg gcaagaccgg gcagttgtgg accacatgga gcccagggta   1860
ccagccagcc aagagctgag cacccagaag gaagtccagt tacccaggag agcagcgctg   1920
ggcctgagac aactcccttc ccactgggcc cggcattccc cttggcctat ggctgcccgc   1980
agtgggacac ggtgccacac ccttgtgtgc tcttcactcc cacgccgatc tgcagttagt   2040
ggcactgcta cgcagccccg ggctgctgct gtccacagct ctaagaagcc cagctcaact   2100
ccatcatcca cccctggtcc atctgcacag attatccacc cgtcaaatgg cagacgtggt   2160
cgtggtcgcc ctcctcagaa actgagagct caggagctga ccctccagac tccagccaag   2220
aggcccctct tggcgggcac aacatgcaca gcttcgggcc cagaacctga gcccctacct   2280
gaggatgggg ctttgatgga caagcctgta ccactgagcc cagggctcca gcatcctgtc   2340
aaggcttctg ggtgcagctg ggcccctgtg ccctaagtcc acgggctgtc tttatatccc   2400
actgccctgc tgtgtgacag tttgatgaaa ctggttacat ttacatccca aaactttggt   2460
tgagtttgca ggactctagg catgcatgaa agagcccccc tggtgatgcc cttggatgct   2520
gccaagtcca tggtagtttt caattttgcc atacttttgt tcttcctacc ggaccctgga   2580
atgtctttgg atattgctaa aatctatttc tgcagctgag gttttatcca ctggacacat   2640
```

ttgtgtgtga gaactaggtc ttgttgaggt tagcgtaacc tggtatatgc aactaccatc 2700
ctctgggcca actgtggaag ctgctgcact tgtgaagaat cctgagcttt gattcctctt 2760
cagtctacgc atttctctct tcccctccct cacccccttt ttcttataaa actaggttct 2820
ttatacagat aaggtcagta gagttccaga ataaaagata tgacttttct gagttattta 2880
tgtacttaaa atatgttgtc acagtatttg ttcccaaata tattaaaggt aaccaaaatg 2940
ttaaaatctg a 2951

<210> SEQ ID NO 27
<211> LENGTH: 9220
<212> TYPE: DNA
<213> ORGANISM: Homo sapiens

<400> SEQUENCE: 27
agtcggcgag cggagtagcg agcgagcgtg tgtgtgtttt ttaaagatgg ccggagcggc 60
ggcggcggtg gccgcgggag cagcagctgg agccgccgcg gcagccgtgt cggtggcggc 120
tcccggccgg gcctcggcgc ctccgccgcc cccgcccgtg tactgtgtgt gccggcagcc 180
gtacgacgtg aaccgcttca tgatcgagtg cgatatctgc aaggactggt tccacggcag 240
ctgtgttgga gtagaagaac atcatgctgt tgacattgac ctgtatcact gtcccaactg 300
tgcagtttta catggttcct ccttgatgaa aaaaaggagg aactggcaca gacatgacta 360
cacagaaatt gatgatggtt ccaaaccagt gcaagctgga actagaactt tcattaagga 420
attacgctct cgagtcttcc caagtgccga tgaaataatt ataaagatgc atggcagcca 480
gctgacacaa agatatctgg agaaacatgg atttgatgtc cctattatgg tcccaaaatt 540
agatgatcta ggactcaggc tcccttcacc tacattttct gtgatggatg tggaacgtta 600
tgtaggtggt gacaaagtga tagatgtcat tgatgtggcg aggcaggcag acagcaaaat 660
gacacttcac aattatgtta aatacttcat gaatcctaac agaccaaaag tgttaaatgt 720
gatcagcctt gaattttcag atacaaagat gtctgaattg gtggaggtcc ctgatatagc 780
caaaaaactt tcctgggtgg aaaattattg gccagatgat tcagtctttc ccaagccatt 840
tgttcagaaa tattgcttaa tgggagttca agacagctat acagatttcc acattgactt 900
cggtggaact tcagtctggt accatgtcct ctggggtgag aagatttttt atttaataaa 960
gccaacagat gaaaatttgg cacgttatga atcttggagt tcatctgtga cccagagtga 1020
ggtgttcttt ggagataagg tggataaatg ctacaaatgt gtggtaaagc agggacatac 1080
cttatttgtt cctacagggt ggatccatgc tgtgctcact tctcaggact gtatggcttt 1140
tggggggaac ttcctgcaca accttaacat tggcatgcag ctcaggtgtt atgagatgga 1200
gaaaaggcta aaaacaccag atcttttcaa attccctttc tttgaagcca tatgttggtt 1260
tgtagccaaa aacttgctgg aaaccctgaa agaactgaga gaagatggtt tccagcctca 1320
aacttaccta gtacagggag tgaaagcact gcatactgct ttaaaattat ggatgaaaaa 1380
agaacttgta tctgaacatg cctttgaaat tccagacaat gttagacctg gacaccttat 1440
taaagaactt tctaaagtaa ttcgagcaat agaggaggaa aacggcaaac cagttaaatc 1500
tcagggaatt cctattgtgt gtccagtttc acgatcctca aatgaagcaa cttccccata 1560
ccattcccga agaaagatga ggaaacttcg agatcataat gtccgaactc cttctaacct 1620
agacatccta gagctccaca caagggaggt cctcaaaaga ttagagatgt gtccatggga 1680
agaggacatc ttgagctcta aactgaatgg aaaattcaac aaacatctcc aaccatcctc 1740

-continued

```
cacagtacct gaatggagag cgaaagataa tgatctacga ttactgctga caaatggaag   1800
aataattaaa gatgaaaggc agccctttgc agatcaaagt ctttatacag cagatagtga   1860
aaatgaagag gataaaagaa ggacaaaaaa ggcaaaaatg aagatagaag agagttcagg   1920
agtagaggga gtggaacatg aagaatctca aaaaccactg aatgggtttt ttacacgtgt   1980
gaaatcagaa ctcaggagta gatcatcagg atattctgat atttctgagt cagaagactc   2040
cggacccgag tgcactgcac tgaaaagtat ctttaccact gaagagtctg aaagttcagg   2100
tgatgaaaag aaacaagaaa taacatccaa ctttaaggag gaatctaatg tgatgaggaa   2160
cttccttcaa aagagccaga agccatctag aagtgaaatt ccaattaaaa gggaatgtcc   2220
tacctcgacg agcacagagg aagaagctat tcagggcatg ctgtctatgg cagggttgca   2280
ctattccacg tgtttacaaa ggcaaataca aagcacagac tgcagtggtg aaagaaactc   2340
tctccaggat cccagcagct gccatggcag taaccatgag gttaggcagt tgtatcgcta   2400
tgataaacca gtggaatgtg gataccatgt caagactgaa gatccagact tgaggacttc   2460
ctcctggatt aaacagtttg atacttccag atttcatcct caggatctaa gtagaagcca   2520
gaaatgcatc agaaaggaag gttcatcaga aattagtcag agggtacaaa gtaggaatta   2580
tgtggacagc agcggctcaa gccttcagaa tggaaagtat atgcagaatt caaacctgac   2640
ttcgggggcg tgccagataa gtaatggcag tctaagccca gaaaggccag ttggtgaaac   2700
ttccttctcg gtgccccttc accccaccaa gagaccggca tcaaatccac cacctatcag   2760
caaccaggca acaaaaggta aacgtccaaa aaaaggaatg gcaacagcca aacaacgtct   2820
tgggaagatc cttaagttga acagaaatgg ccatgcacgt ttctttgtgt gacagagctg   2880
ctgttgcagc cattcttccc tttggagacc agtctagggg tgcaggagcc tggagcttcc   2940
gctgtccccc tgcctggagc agtttgtgtg tatagtaaga acactgcccg aagaacagaa   3000
tgaacctgat gctgcatttt cactgtgcca cacccactca gcaataacca ttttggacct   3060
ggtgggggag aggaagaagg agggtagaac cttaaaaaga gaccttgaac tggaaagggt   3120
ctcttgtcag ggcttgaatt ttattttgtt gttggtagtg tcttgatgta ttttcagtgg   3180
tagggtaaag aattatcaat aatttattta acagattttt ttttaaagtt aacagctttt   3240
aaattctttt tttaaagcta tttatttgga agatttctgg agaaatatct cactaattta   3300
gatgtaagaa tgtgaaggtt tttaaattat ttttgatagt gtgtgtgtta catgtgggga   3360
agggccacag taacagtaac tagtctggac tcttaaattt gatattcagg ttaaagtctt   3420
aaacagggat ttgatgcatt aattatttta aattaagatg tatatgaaaa tcattttatt   3480
ttatatattt catgtgtttt ttataagcta ttagcttcgc ttttgctaac atccaaggtg   3540
catactgtta tccaggttga ttaccttata tcccaccttc cctctgcact ccccatcatt   3600
ttgtgatgac ccagtaagac tcttctcttt gcagggaaac actttcgtag ccaatgtgta   3660
agaactccat gaaagatccc tcatttctca tttcgtttga cattgtgatt ttcttctcaa   3720
cattaaaaaa aataggcttt tgcattttca tttctgctga tgatatctgg gtcccaaaga   3780
gagcagcttt aatatatttt tcctacttgt gggaaaagta ttataagttt ggttaaattg   3840
tcatgtttat agtttttcca agtacatttg taactacagc aggccttctt cgtactgctg   3900
ctgttggaca acaggactgg cacctgctgc agaggttata ccttatgata cttttatgct   3960
ccatacctga tttgttggga aatgttattt aggatattca aatctgcatc ataagccgta   4020
atataatagg attaatacta cattaagttg tatagaagca agcatgttgg aatagatctt   4080
ttgtgtgtat ttactttttt tatttcttaa ttttctaaag aattacttaa gatatggatt   4140
```

```
tggagtaaaa tgggtgcttt tggcagtttc ttccatctat cctaacctga ccagtacata   4200
ttgaggttaa gtatctggtt aaactttaag gtattcattt atctccttta tgtatgattt   4260
ttactaaatg ccagttttca tttgcttata gtagcttcta ttttcccttt tttccatcca   4320
tggcataaaa ataagtgatt tctgggggtg gggcagaaat gttcccaagt ctgacaatag   4380
agcattttac aaattcctac aaagaaaata taggcaaata gataaaattt atttttatgg   4440
agaagaaata tggccatatt atggatttgt cttttttta ctcagcaaga tagcaggact   4500
taccottctc tattaagtat cacttgaatt gctaagaaga aaaaagtctg taccatcatc   4560
tttcatggtt gcattcaaat gtatatttc aaagagaaat acttcttgtg tccccattcc   4620
aaaatgtcat gggataaata tgaaatagtt tatgaagtag cctttctggt tcagagtgac   4680
tggaccaaag tctgaatctt atctgggtat caggaaaaag aatttttatg gaaatcctta   4740
gtgtctataa acaacccgtg taaaccctgt ctacactatg ccaaaaccag tggaaagatg   4800
ggtagagtca tcttatctca ggatgtcaaa aatctgggtt tgactgattc ccctaccttc   4860
ccacacagta tattcttgtg atttttgctt ttctgtagat cctgagtcgg tgttacaata   4920
gtcatgtttt tattttgggt taagaaatac gaggtgtaag agctataatt tccttttcgt   4980
gttatatcat gatctgggtt ttcttttttc ctttacgttt ttcacagctc ttgagtattt   5040
tctatttttt tctttagtca caaaaattaa aattaaactt tatttttatg aattaaaatg   5100
aaatttaatt tatttttatg aattaaaatt gtggccagta tccactgtgt ccttaggctg   5160
agaagtacta atttggagta gcccgtgtgt ggaattctaa agtgaaggta ctgtggattc   5220
atttttagta gttttagccc cttaataagt ggctaagtta gaaaactttc agcgaggtaa   5280
tagaaccact tgaatagaat ccatgtgtct ttttctgaat tggtgaaaat tcggccactg   5340
atccagtgac tcctggtcaa acgtcttata acattactgg ccataatgca tccctttatc   5400
tcatggaaat ggctgaactt tgtggtagct gctgcgagta cctgggctta acagtaatag   5460
agaacctcat ttataccata cagacacagc aacttaggaa gacagcactg atagcattta   5520
gctagttgta accaaataca aatatgtaaa attgagaatt atgattaaca tatgcaactt   5580
tagtaatagg aatagatgat aattttcctg tattgtttca aataagtgac tgttcagctg   5640
ggatccattg gattataatt tacaatgtca cataatatta tgcttttcaa tattgatgag   5700
tgatgtaaac aatataaagt tggcagtttg tagtagttca gtatcctaga aatacattga   5760
acttcataag tatcagttca tttttaagca tacagaattg aagattctga ctgaaatcat   5820
aaactcagag gaaacaagcc catctttatc actaattact tagcttgaat acttttctat   5880
ttttaaataa tcctaattat tgccttttca attatagtct actgtattta tttatatggg   5940
atcaacaggt atttatcaaa catctactgt gtgcccagca ctacctagta ctgttgggga   6000
acatcaattt gcagttgtgg tctctgccct tgaaggtatc ttctccagga aattagcagt   6060
attattttca cttctaagca aacatgagca aaagaggacc tgttcattaa aaaacatgct   6120
gactttttta gtttcaactg agatatgcca ctgtagaagt gaaagtaatt tcacaattaa   6180
agaaatgctt caacttggta attaatatgg tcatacaggg acttggtgta gcatgcaagg   6240
aagcagaaga cctgggcttt tgtcgaagtt ctgccattta ggtatcagct gtgtaacctt   6300
gaataagtca cttaactctt tctcttagtt ttctcatttg taaatttgga ttaaagtgtt   6360
tattatgata atcaattaag aaaatctctt aacacttcat acatacagag aacttatcat   6420
taagttaaaa ctggcaatta atgcaccttt atatatattt ttaaatgaaa actaatacta   6480
```

```
ttcatgatgt ttattttata tcaaatatat gcccagggca tgctacttta aaaatccgag   6540
gaatctccaa caaggtgctg gattaaaatc agatttcgtg cttgaagtgg aagaaaaatg   6600
aagttgttta tggataagag agtgagaatg tgtatcctca agtacgttaa gatgatttaa   6660
ctgaaagatg gctttaggtt tttcttgaag aattaggaaa gtaccatccc cacagattca   6720
gcatactctt caggtactag ataaaggtga aggaagtcat ggaattaaaa tgacttagca   6780
actccccagg gaacttgtgg ggagaatgag gtggttagaa aggtgagaat gcacaaagac   6840
agctctgggt tgggtaccaa cagtttgctt ggtagaaaga aaccagtgta ggaaaggaga   6900
cgccaccaga catcttcaac agacaagatt ctttctgcct ttttcaaaag atgctctctg   6960
cagcagtaag actatagata gagttgattg gaatatcatg tgacccagta tgctactgct   7020
aggcataatt atcaaaaatt catttttctc attaaatatt gttaattgct cgccacataa   7080
agagaagcta gagctcacca gtcttggtgg tgtcctagac cttcctctaa agcagtcttg   7140
ggaagctgga tcatcagatc tttagcctag acagagtgtc gctggtaaat aaaggagaca   7200
caggtaaccc agagtggaca gtgatttgcg tggggagaca cagtggatct ggggcctctg   7260
atactttgct tcctaaaaca gcccccagtt ttcggcttgc cctatgagat gatgttcatg   7320
tgcttccttg aaaccaggtg gaaagaaagg ggaagaatta attttctcat tctgttgctg   7380
ttgaacgtaa tgtaatctta atactgtagc cttcctagaa gcccttccct ctttttcatg   7440
ctgtaaagtc aaatatttga tatccttaac ataaatttta aaaattaagg tcattaggaa   7500
gcaaatgtct atttccaaag caatgagctt gttgtgactg tgattttatt cttctatagt   7560
atttttttcc tcattttaac tgagaggaga aaataatact cttttgcaat atccttaggt   7620
tctccccttc cccctggtgc cccttctagt gtcttaagac tttgtcttaa caagtataac   7680
attacatttt gttgttaaaa cctttcgaaa ctgtattcag tgattcttcc aagtttatct   7740
gctctgcact atttcactaa taaaccctgg ctaccacgta gcccttgatc tccaagtagt   7800
ttacctatgc aagacctgtg acactctgaa ttcacttctc tttctttcag aaagtagtca   7860
taaatggagc ttaattataa aggtaaaact tgtctccaac cagtttcatt ttggccattt   7920
ctttttcaaa atgtcagctg ttttcctcca agatttttca ccaaaacaat gatcataagt   7980
gctggaatat ataatacttt gcaggcataa aataacccag acatactctc atatttcttt   8040
ggtgtatttt ggttggtaaa acttaccagc attaaatgta aaatataatg aggagttaat   8100
tccttaccta gaactatttc ttccttttaa gattcataag taacctttta tttttacaga   8160
gctacgtata acttccacat tacagtcagg gacctgaggt gtaacttact aagtgaaccc   8220
caaggttatt ttatcttgca aaagaaacct aaaccaaact aagggcctta cagtttatgg   8280
ttagactgaa tcaaaagcta taacctcaat ttttccaaaa acagcttctg actgcaaaag   8340
caagtcatac agttgttagg tatgaaatag cactgatcag gaaatgcatc ttcgcagatg   8400
gtatttcctt cagaaaagac ttttctactt ttaatataaa ttaagccata acagtttcat   8460
gctgtggaaa gagggtgaaa aggttcattt taagagatta tataatatga actttcacat   8520
ttactgtgaa atgtctaact ttgccagtgc ttcagcaagt ttttttgggg ggtgatgggg   8580
aggggtagta ttggttttag aggtttcaaa tctgtgaact ttggagaggg gacagttgtt   8640
ggctctggta tttactagtt ttgtagtaac gttttgctag cctgactgac ttttcttact   8700
ggtttttatg cccacggtcc gaggggactg ttcttcttgt tgggggtgtc tgcggaatag   8760
cgtctcgtct tgtttgtata ggcagtcaat gtgtgtgaca tgtgtgtcct ttcagtccgg   8820
aagcccactg tgtgacaatg gcgtggggtg tggctgggag gtggggtgct gaagcttgaa   8880
```

```
gagcatttct ttgctgattc ataacagtat ttcccatctt ttgcctgcag gcagggaaag   8940

tgtacagtat ttattttgtt tctgttttac tttaaatttg taagtcttta agtagcttac   9000

attgattatt ataggggagg acaagtgact tgtttaaagt tgtatttagt attctttcca   9060

atttctgtat tttaaaatat tgaaattaaa attgtattac ttctgttttg atttttttag   9120

cacttagtgt atttttttgct cattttgttt gaaagtataa atgttgaaaa ttgtataaaa   9180

tgcgtccttg aaagaaaaag aatctgaatt ctatatccaa                        9220
```

<210> SEQ ID NO 28
<211> LENGTH: 5462
<212> TYPE: DNA
<213> ORGANISM: Homo sapiens

<400> SEQUENCE: 28

```
gctgagatgt tggaggggcg tctagcgcgc atgtgcgaag gtgtccaaac tgacaatgct     60

ggagagatag cgagtgtgga ttgagagaaa gggagagagg gagggagaga gagtgaaaga    120

agaaaataca gagagtgagt gtgtggaaga gagagagaaa caggagagaa acaggaggga    180

gggagagaga gagagagaga gagagagaga gagagagaga gagagagaga gagagagaca    240

ggagagagag ggagggagcg agagggagag caaaagaagg aaaggatcca agaaaaaaaa    300

gccccaacca cacaccagcg gctgcaggac tgggcacagc atgagatcca aaggcagggc    360

aaggaaactg gccacaaata atgagtgtgt atatggcaac taccctgaaa tacctttgga    420

agaaatgcca gatgcagatg gagtagccag cactccctcc ctcaatattc aagagccatg    480

ctctcctgcc acatccagtg aagcattcac tccaaaggag ggttctcctt acaaagcccc    540

catctacatc cctgatgata tccccattcc tgctgagttt gaacttcgag agtcaaatat    600

gcctggggca ggactaggaa tatggaccaa aaggaagatc gaagtaggtg aaaagtttgg    660

gccttatgtg ggagagcaga ggtcaaacct gaaagacccc agttatggat gggagatctt    720

agacgaattt tacaatgtga agttctgcat agatgccagt caaccagatg ttggaagctg    780

gctcaagtac attagattcg ctggctgtta tgatcagcac aaccttgttg catgccagat    840

aaatgatcag atattctata gagtagttgc agacattgcg ccgggagagg agcttctgct    900

gttcatgaag agcgaagact atccccatga aactatggcg ccggatatcc acgaagaacg    960

gcaatatcgc tgcgaagact gtgaccagct ctttgaatct aaggctgaac tagcagatca   1020

ccaaaagttt ccatgcagta ctcctcactc agcattttca atggttgaag aggactttca   1080

gcaaaaactc gaaagcgaga atgatctcca agagatacac acgatccagg agtgtaagga   1140

atgtgaccaa gtttttcctg atttgcaaag cctggagaaa cacatgctgt cacatactga   1200

agagagggaa tacaagtgtg atcagtgtcc caaggcattt aactggaagt ccaatttaat   1260

tcgccaccag atgtcacatg acagtggaaa gcactatgaa tgtgaaaact gtgccaaggt   1320

tttcacggac cctagcaacc ttcagcggca cattcgctct cagcatgtcg gtgcccgggc   1380

ccatgcatgc ccggagtgtg gcaaaacgtt tgccacttcg tcgggcctca aacaacacaa   1440

gcacatccac agcagtgtga agccctttat ctgtgaggtc tgccataaat cctatactca   1500

gttttcaaac ctttgccgtc ataagcgcat gcatgctgat tgcagaaccc aaatcaagtg   1560

caaagactgt ggacaaatgt tcagcactac gtcttcctta aataaacaca ggaggttttg   1620

tgagggcaag aaccattttg cggcaggtgg atttttggc caaggcattt cacttcctgg   1680

aaccccagct atggataaaa cgtccatggt taatatgagt catgccaacc cgggccttgc   1740
```

-continued

```
tgactatttt ggcgccaata ggcatcctgc tggtcttacc tttccaacag ctcctggatt   1800
ttcttttagc ttccctggtc tgtttccttc cggcttgtac cacaggcctc ctttgatacc   1860
tgctagttct cctgttaaag gactatcaag tactgaacag acaaacaaaa gtcaaagtcc   1920
cctcatgaca catcctcaga tactgccagc tacacaggat attttgaagg cactatctaa   1980
acacccatct gtaggggaca ataagccagt ggagctccag cccgagaggt cctctgaaga   2040
gaggcccttt gagaaaatca gtgaccagtc agagagtagt gaccttgatg atgtcagtac   2100
accaagtggc agtgacctgg aaacaacctc gggctctgat ctggaaagtg acattgaaag   2160
tgataaagag aaatttaaag aaaatggtaa aatgttcaaa gacaaagtaa gccctcttca   2220
gaatctggct tcaataaata ataagaaaga atacagcaat cattccattt tctcaccatc   2280
tttagaggag cagactgcgg tgtcaggagc tgtgaatgat tctataaagg ctattgcttc   2340
tattgctgaa aaatactttg gttcaacagg actggtgggg ctgcaagaca aaaaagttgg   2400
agctttacct taccttcca tgtttcccct cccatttttt ccagcattct ctcaatcaat    2460
gtacccattt cctgatagag acttgagatc gttacctttg aaaatggaac cccaatcacc   2520
aggtgaagta aagaaactgc agaagggcag ctctgagtcc ccctttgatc tcaccactaa   2580
gcgaaaggat gagaagccct tgactccagt cccctccaag cctccagtga cacctgccac   2640
aagccaagac cagcccctgg atctaagtat gggcagtagg agtagagcca gtgggacaaa   2700
gctgactgag cctcgaaaaa accacgtgtt tgggggaaaa aaaggaagca acgtcgaatc   2760
aagacctgct tcagatggtt ccttgcagca tgcaagaccc actcctttct ttatggaccc   2820
tatttacaga gtagagaaaa gaaaactaac tgacccactt gaagctttaa aagagaaata   2880
cttgaggcct tctccaggat tcttgtttca cccacaattc caactgcctg atcagagaac   2940
ttggatgtca gctattgaaa acatggcaga aaagctagag agcttcagtg ccctgaaacc   3000
tgaggccagt gagctcttac agtcagtgcc ctctatgttc aacttcaggg cgcctcccaa   3060
tgccctgcca gagaaccttc tgcggaaggg aaaggagcgc tatacctgca gatactgtgg   3120
caagattttt ccaaggtctg caaacctaac acggcacttg agaacccaca caggagagca   3180
gccttacaga tgcaaatact gtgacagatc atttagcata tcttctaact tgcaaaggca   3240
tgttcgcaac atccacaata aagagaagcc atttaagtgt cacttatgtg ataggtgttt   3300
tggtcaacaa accaatttag acagacacct aaagaaacat gagaatggga acatgtccgg   3360
tacagcaaca tcgtcgcctc attctgaact ggaaagtaca ggtgcgattc tggatgacaa   3420
agaagatgct tacttcacag aaattcgaaa tttcattggg aacagcaacc atggcagcca   3480
atctcccagg aatgtggagg agagaatgaa tggcagtcat tttaaagatg aaaaggcttt   3540
ggtgaccagt caaaattcag acttgctgga tgatgaagaa gttgaagatg aggtgttgtt   3600
agatgaggag gatgaagaca atgatattac tggaaaaaca ggaaaggaac cagtgacaag   3660
taatttacat gaaggaaacc ctgaggatga ctatgaagaa accagtgccc tggagatgag   3720
ttgcaagaca tccccagtga ggtataaaga ggaagaatat aaaagtggac tttctgctct   3780
agatcatata aggcacttca cagatagcct caaaatgagg aaaatggaag ataatcaata   3840
ttctgaagct gagctgtctt cttttagtac ttcccatgtg ccagaggaac ttaagcagcc   3900
gttacacaga aagtccaaat cgcaggcata tgctatgatg ctgtcactgt ctgacaagga   3960
gtccctccat tctacatccc acagttcttc caacgtgtgg cacagtatgg ccagggctgc   4020
ggcggaatcc agtgctatcc agtccataag ccacgtatga cgttatcaag gttgaccaga   4080
gtgggaccaa gtccaacagt agcatggctc tttcatatag gactatttac aagactgctg   4140
```

agcagaatgc cttataaacc tgcagggtca ctcatctaaa gtctagtgac cttaaactga 4200
atgatttaaa aaagaaaaga aagaaaaaag aaactattta ttctcgatat tttgttttgc 4260
acagcaaagg cagctgctga cttctggaag atcaatcaat gcgacttaaa gtgattcagt 4320
gaaaacaaaa aacttggtgg gctgaaggca tcttccagtt taccccacct tagggtatgg 4380
gtgggtgaga agggcagttg agatggcagc attgatatga atgaacactc catagaaact 4440
gaattctctt ttgtacaaga tcacctgaca tgattgggaa cagttgcttt taattacaga 4500
tttaattttt ttcttcgtta aagttttatg taatttaacc ctttgaagac agaagtagtt 4560
ggatgaaatg cacagtcaat tattatagaa actgataaca gggagtactt gttcccccttt 4620 ttgccttctt aagtacattg tttaaaacta gggaaaaagg gtatgtgtat attgtaaact 4680
atggatgtta acactcaaag aggttaagtc agtgaagtaa cctattcatc accagtaccg 4740
ctgtaccact aataaattgt ttgccaaatc cttgtaataa catcttaatt ttagacaatc 4800
atgtcactgt ttttaatgtt tattttttttg tgtgtgttgc gtgtatcatg tatttatttg 4860
ttggcaaact attgtttgtt gattaaaata gcactgttcc agtcagccac tactttatga 4920
cgtctgaggc acaccccttt ccgaatttca aggaccaagg tgacccgacc tgtgtatgag 4980
agtgccaaat ggtgtttggc ttttcttaac attccttttt gtttgtttgt tttgttttcc 5040
ttcttaatga actaaatacg aatagatgca acttagtttt tgtaatactg aaatcgattc 5100
aattgtataa acgattataa tttctttcat ggaagcatga ttcttctgat taaaaactgt 5160
actccatatt ttatgctggt tgtctgcaag cttgtgcgat gttatgttca tgttaatcct 5220
atttgtaaaa tgaagtgttc ccaaccttat gttaaaagag agaagtaaat aacagactgt 5280
attcagttat tttgcccttt attgaggaac cagatttgtt ttctttttgt ttgtaatctc 5340
attttgaaat aatcagcaag ttgaggtact ttcttcaaat gctttgtaca atataaactg 5400
ttatgccttt cagtgcatta ctatgggagg agcaactaaa aaataaagac ttacaaaaag 5460
ga 5462

<210> SEQ ID NO 29
<211> LENGTH: 4587
<212> TYPE: DNA
<213> ORGANISM: Homo sapiens

<400> SEQUENCE: 29
gtcatagaag actactcgga gagcgctgcc tctgggttgg cgggctggca ggctgtagcc 60
gagcgcgggc aggactcgtc ccggcagggt tccagagcca tgggagcgga aaggaggctg 120
ctgtcgatta aggaggcctt tcggctggcg cagcagccgc accagaacca ggcgaagctg 180
gtggtggcgc tgagccgcac ctaccgcacg atggatgata agacagtttt tcatgaggag 240
ttcattcatt accttaaata tgttatggtg gtctataaac gtgaaccagc tgtggagagg 300
gtaatagaat ttgcagcaaa gtttgttacc tcatttcacc aatcagatat ggaagatgat 360
gaggaagagg aagatggtgg ccttttaaat tatttgttta cttttctctt aaagtctcat 420
gaagcaaaca gcaatgcagt gagatttaga gtgtgcctgc tcataaacaa gcttttggga 480
agtatgccag aaaatgctca gattgatgat gatgtgtttg ataaaattaa taaagccatg 540
cttattagat tgaaagataa gattccaaat gtgagaatac aggcagttct ggcgctttca 600
cgacttcagg atcccaagga tgatgaatgc ccagtggtta atgcatatgc tactttgatt 660
gaaaatgatt caaatccaga agttagacgg gcagtgttat catgtattgc accatcagca 720

-continued

```
aagactttgc caaaaattgt agggcgcacc aaggatgtga aagaggctgt cagaaagctg    780
gcttatcagg ttttagctga aaaggttcat atgagagcta tgtccattgc tcagagagta    840
atgctccttc aacaaggtct taatgacaga tcagatgctg tgaaacaagc tatgcagaag    900
catcttcttc aaggctggtt acggttctct gaaggaaata tcttagagtt gctccatcgg    960
ttggatgtag aaaattcttc tgaagtggca gtctctgttc tcaatgcctt gttttcaata   1020
actcctctca gtgaactggt gggactctgt aaaaacaatg atggcaggaa attgattcca   1080
gtggaaacat taactcctga aattgctttg tattggtgtg ccctttgtga atatttgaaa   1140
tcaaaaggag atgaaggtga agaattttta gagcagattt tgccagagcc tgtagtatat   1200
gcagactatt tattgagtta catccagagc attccagttg ttaatgaaga acacagaggt   1260
gatttttcct atattggaaa tttgatgaca aaagaattca taggtcaaca attgattcta   1320
attattaagt ctttggatac cagtgaagaa ggaggaagaa aaaaactgct ggctgtttta   1380
caggagattc ttattttacc cacaatccca atatccctgg tttcttttct tgttgaaaga   1440
ctactccaca tcattataga tgataataag agaacacaaa ttgttacaga aattatctca   1500
gagattcggg cgcccattgt tactgttggt gttaataacg atccagctga tgtaagaaag   1560
aaagaactca agatggctga aataaaagtt aagcttatcg aagccaaaga agctttggaa   1620
aattgcatta ccttacagga ttttaatcgg gcatcagaat taaaagaaga aataaaagca   1680
ttagaagatg ccagaataaa ccttttgaaa gagacagagc aacttgaaat taaagaagtc   1740
cacatagaga agaatgatgc tgaaacattg cagaaatgtc ttattttatg ctatgaactg   1800
ttgaagcaga tgtccatttc aacaggctta agtgcaacca tgaatggaat catcgaatct   1860
ttgattcttc ctggaataat aagtattcat cctgttgtaa gaaacctggc tgttttatgc   1920
ttgggatgct gtggactaca gaatcaggat tttgcaagga aacacttcgt attactattg   1980
caggttttgc aaattgatga tgtcacaata aaaataagtg ctttaaaggc aatctttgac   2040
caactgatga cgttcgggat tgaaccattt aaaactaaaa aaatcaaaac acttcattgt   2100
gaaggtacag aaataaacag tgatgatgag caagaatcaa aagaagttga agagactgct   2160
acagctaaga atgttctgaa actcctttct gatttcttag atagtgaggt atctgaactt   2220
aggactggag ctgcagaagg actagccaag ctgatgttct ctgggctttt ggtcagcagc   2280
aggattcttt ctcgtcttat tttgttatgg tacaatcctg tgactgaaga ggatgttcaa   2340
cttcgacatt gcctaggcgt gttcttcccc gtgtttgctt atgcaagcag gactaatcag   2400
gaatgctttg aagaagcttt tcttccaacc ctgcaaacac tggccaatgc ccctgcatct   2460
tctcctttag ctgaaattga tatcacaaat gttgctgagt tacttgtaga tttgacaaga   2520
ccaagtggat taaatcctca ggccaagact tcccaagatt atcaggcctt aacagtacat   2580
gacaatttgg ctatgaaaat ttgcaatgag atcttaacaa gtccgtgctc gccagaaatt   2640
cgagtctata caaaagcctt gagttcttta gaactcagta gccatcttgc aaaagatctt   2700
ctggttctat tgaatgagat tctggagcaa gtaaaagata ggacatgtct gagagctttg   2760
gagaaaatca agattcagtt agaaaaagga aataaagaat ttggtgacca agctgaagca   2820
gcacaggatg ccaccttgac tacaactact ttccaaaatg aagatgaaaa gaataaagaa   2880
gtatatatga ctccactcag gggtgtaaaa gcaacccaag catcaaagtc tactcagcta   2940
aagactaaca gaggacagag aaaagtgaca gtttcagcta ggacgaacag gaggtgtcag   3000
actgctgaag ccgactctga aagtgatcat gaagttccag aaccagaatc agaaatgaag   3060
atgagactac caagacgagc caaaaccgca gcactagaaa aaagtaaact taaccttgcc   3120
```

caatttctca atgaagatct aagttaggaa agacgatgga ggtggaatcc tttaagatta 3180
tgtccagtta tttgctttaa taaagaagaa gttacccttg tcaaaatcag aacaaacctg 3240
atgtctttct gaagattttc tgctgtgcgc ttccacgtta ctttggcctg tattaaagca 3300
gtagagcagc atcagttatt atagtccaga aaaagtgtgc atcagtcagt cacacagatt 3360
tatcacaatc tgaggtgggc ctaggaatct catttttaaa tagtctctcc aagtgattct 3420
tatgaactct ttatgtttaa aatcatgtca ttatggaaaa cttacaagtg taactagcta 3480
gtagcttgca tttgagaagc ttatgactta gatgggcaga atcaacaaag atgaaaccgc 3540
ctgaggacac atttaacaag taacatttct agggaaaatg aaggaagtac cacaaactgg 3600
ctagaaagga gcttatcaat caccagtgag gaagaccagt ataacgttca acaacagtta 3660
ttttgacaaa aacttatttt gtgattccta cagtgaaaac atttttggtg atatctgcct 3720
gggaaatctc tcttcctaaa gtatttgtat atgggagtcc ttgtttgtga atgtttcctg 3780
gattagggag gtgtcaacat aaatgtatta ttaaccatga agctgctcgc tatatttttg 3840
gcataacaaa ataatattta tttactgtgg ataataattc tagtgggaat ataatgtgac 3900
aggaacttct ctttatatac gctaccaatt tatgagcact attcactgtc aatttcattt 3960
cttgtctttt gaaattgaca cttggcctga cttacgaaac ttgtactata tgaaattggt 4020
cctcttttct gcaataccca acgaaacacc ttttctcttt attattcaga aatgtcctaa 4080
catggatctg tttgttttaa taattgtgct ttttttaggc ttatcatcta ctagaggcca 4140
tttacttaag gtgaaatttt aagatggagc taaagtaaga tcactggttt ttagaaccaa 4200
attgctatac atatgtgcct catagaactt ataaaaggag tcaaagtttc aaagcaagat 4260
agttattaag caaaaggaaa aatggtaatg atagaaagtc agttaaaaat agatgattgt 4320
tcttcattct gtttgttggc tctgtgttct cctgtgcttc agattcctta tgtgttgttg 4380
ttttaaagac aatttgcagg gggttgggag aaggactgaa aaggtacatt aagtgtgctg 4440
taaggaaaag tcttagaaac ataataagct aaaatcccat tcacacatgg ccaggctatc 4500
caaaaagaaa ggagccatgt tctcatgtgg tttaccatac caaagcttgc tttctctggc 4560
atgggaaaaa taaatttaag caccaaa 4587

<210> SEQ ID NO 30
<211> LENGTH: 2927
<212> TYPE: DNA
<213> ORGANISM: Homo sapiens

<400> SEQUENCE: 30
cacggttcca aacagccgtg gcccgcggtg tctggcgctc ggtgggtgtg gttgccccta 60
gtttgaggcc tgcccgatta cccgcaagac ttgggcagcc ccgggcgccg ctccgaccac 120
gacagggaaa ggaaccttaa tctcatcttt aaaataagga gaattactga gtgacctgaa 180
ggaccctttt cagctggaaa gtctgaactg accaacactg gatgaatttg accatttctt 240
aggagactgg aatgttaagt ttctataaat gaatgaacca gttctctctt gtttggagca 300
atgctgaaat tccaagaggc agctaagtgt gtgagtggat caacagccat ttccacttat 360
ccaaagacct tgattgcaag aagatacgtg cttcaacaaa aacttggcag tggaagtttt 420
ggaactgtct atctggtttc agacaagaaa gccaaacgag gagaggaatt aaaggtactt 480
aaggaaatat ctgttggaga actaaatcca aatgaaactg tacaggccaa tttggaagcc 540
caactcctct ccaagctgga ccacccagcc attgtcaagt tccatgcaag ttttgtggag 600

-continued

```
caagataatt tctgcattat cacggagtac tgtgagggcc gagatctgga cgataaaatt    660
caggaatata aacaagctgg aaaaatcttt ccagaaaatc aaataataga atggtttatc    720
cagctgctgc tgggagttga ctacatgcat gagaggagga tacttcatcg agacttaaag    780
tcaaagaatg tatttctgaa aaataatctc cttaaaattg gagattttgg agtttctcga    840
cttctaatgg gatcctgtga cctggccaca actttaactg gaactcccca ttatatgagt    900
cctgaggctc tgaaacacca aggctatgac acaaagtcgg acatctggtc actggcatgc    960
attttgtatg agatgtgctg catgaatcat gcattcgctg gctccaattt cttatccatt   1020
gttttaaaaa ttgttgaagg tgacacacct tctctccctg agagatatcc aaaagaacta   1080
aatgccatca tggaaagcat gttgaacaag aatccttcat taagaccatc tgctatcgaa   1140
attttaaaaa tcccttacct tgatgagcag ctacagaacc taatgtgtag atattcagaa   1200
atgactctgg aagacaaaaa tttggattgt cagaaggagg ctgctcatat aattaatgcc   1260
atgcaaaaaa ggatccacct gcagactctg agggcactgt cagaagtaca gaaaatgacg   1320
ccaagagaaa ggatgcggct gaggaagctc caggcggctg atgagaaagc caggaagctg   1380
aaaaagattg tggaagaaaa atatgaagaa aatagcaaac gaatgcaaga attgagatct   1440
cggaactttc agcagctgag tgttgatgta ctccatgaaa aaacacattt aaaaggaatg   1500
gaagaaaagg aggagcaacc tgagggaaga ctttcttgtt caccccagga cgaggatgaa   1560
gagaggtggc aaggcaggga agaggaatct gatgaaccaa ctttagagaa cctgcctgag   1620
tctcagccta ttccttccat ggacctccac gaacttgaat caattgtaga ggatgccaca   1680
tctgaccttg gataccatga gatcccagaa gacccacttg tggctgaaga gtactacgct   1740
gatgcatttg attcctattg tgaagagagt gatgaggagg aagaagaaat agcgttagaa   1800
agaccagaga aagaaatcag gaatgaggga tcccagcctg cttacagaac aaaccaacag   1860
gacagtgata tcgaagcgtt ggccaggtgt ttggaaaatg tcctgggttg cacttctcta   1920
gacacaaaga ccatcaccac catggctgaa gacatgtccc caggaccacc aattttcaac   1980
agtgtgatgg ccaggaccaa gatgaaacgc atgagggaat cagccatgca gaagctgggg   2040
acagaagtat ttgaagaggt ctataattac ctcaagagag caaggcatca gaatgctagc   2100
gaagcagaga tccgcgagtg tttggaaaaa gtggtgcctc aagccagcga ctgttttgaa   2160
gtggaccagc tcctgtactt tgaagagcag ttgctgatca cgatgggaaa agaacctact   2220
ctccagaacc atctctaggc aactatcaaa aagaagcaga agttcaagtg gacaaattta   2280
tgtgaaaatt catttaacat ataagctgaa ctctattatg gggaatggat acaaaagcag   2340
agctcccatc ttgactttca attcctcatc agaagtactg gcttctttag agagtagtaa   2400
gcatggctgc ctatgcttgg agtcataagt gttatttgga ctataccctg agataagctt   2460
atagatcaag tttggctccc ttgaaaagca tttctctcat gtgcgccctc agggcttcca   2520
gcaggattga gtcaccctga cgatgaccgg ggagaagccg tgtgctcttc attattttca   2580
gctggaggac agagctcagt gcctgactgc ctagggtctc atggactgta ggcagcctgc   2640
cagtgaaggt cactggactc tagcctacaa catgctgagc tacagcccag aagccagaca   2700
tgcctgtctt agctgacctg tttttggtcc acttttgccc ttccatgact aataaggaag   2760
atatgtgtgt atttcataca cacacaagga cctggattaa aaatccaaaa agtgattctc   2820
ttctatgatt tatttcaaac tcatccatag ataattcaag atttgtattc aaaataaaca   2880
tagttttcac agttacaaaa taaatcacct attttatctt ttcctta                  2927
```

<210> SEQ ID NO 31
<211> LENGTH: 1741
<212> TYPE: DNA
<213> ORGANISM: Homo sapiens

<400> SEQUENCE: 31
gtagggcccc agcgcccggg ccatggcggc ggcggtggcg ggagctgctg tctgagcagc 60
ggttgcggac cgagcgaact tggcccagga gcccgggcct agggagaggc gcggcggcgg 120
cgggagcgcg aacggctgga gctggccttc ttcgccttct cctcggctgt ggagccctgg 180
tggggggtct gcgcccggtc accatgacga cgccggcgaa tgcccagaat gccagcaaaa 240
cgtgggaact gagtctgtat gagctgcacc ggaccccgca ggaagccata atggatggca 300
cagagattgc tgtttcccct cggtcactgc attcagaact catgtgccct atctgcctgg 360
acatgctgaa gaatacgatg accaccaagg agtgcctcca cagattctgc tctgactgca 420
ttgtcacagc cctacggagc gggaacaagg agtgtcctac ctgccgaaag aagctggtgt 480
ccaagcgatc cctacggcca gaccccaact ttgatgccct gatctctaag atctatccta 540
gccgggagga atacgaggcc catcaagacc gagtgcttat ccgcctgagc cgcctgcaca 600
accagcaggc attgagctcc agcattgagg aggggctacg catgcaggcc atgcacaggg 660
cccagcgtgt gaggcggccg ataccagggt cagatcagac cacaacgatg agtggggggg 720
aaggagagcc cggggaggga gaaggggatg gagaagatgt gagctcagac tccgcccctg 780
actctgcccc aggccctgct cccaagcgac cccgtggagg gggcgcaggg gggagcagtg 840
tagggacagg gggaggcggc actggtgggg tgggtggggg tgccggttcg gaagactctg 900
gtgaccgggg agggactctg ggagggggaa cgctgggccc cccaagccct cctggggccc 960
ccagcccccc agagccaggt ggagaaattg agctcgtgtt ccggccccac cccctgctcg 1020
tggagaaggg agaatactgc cagacgaggt atgtgaagac aactgggaat gccacagtgg 1080
accacctctc caagtacttg gccctgcgca ttgccctcga gcggaggcaa cagcaggaag 1140
caggggagcc aggagggcct ggagggggcg cctctgacac cggaggacct gatgggtgtg 1200
gcggggaggg tgggggtgcc ggaggaggtg acggtcctga ggagcctgct ttgcccagcc 1260
tggagggcgt cagtgaaaag cagtacacca tctacatcgc acctggaggc ggggcgttca 1320
cgacgttgaa tggctcgctg accctggagc tggtgaatga gaaattctgg aaggtgtccc 1380
ggccactgga gctgtgctat gctcccacca aggatccaaa gtgaccccac caggggacag 1440
ccagaggaag gggaccatgg ggtatccctg tgtcctggtc tatcacccca gcttctttgt 1500
cccccagtac ccccagccca gccagccaat aagaggacac aaatgaggac acgtggcttt 1560
tatacaaagt atctatatga gattcttcta tattgtacag agtggggcaa aacacgcccc 1620
catctgctgc cttttctatt gccctgcaac gtcccatcta tacgaggtgt tggagaaggt 1680
gaagaaccct cccattcacg cccgcctacc aacaacaaac gtgctttttt cctctttgaa 1740
a 1741

<210> SEQ ID NO 32
<211> LENGTH: 3989
<212> TYPE: DNA
<213> ORGANISM: Homo sapiens

<400> SEQUENCE: 32
gttggaagcg gagtgattcc ccacccctgc tccatctagc tctttccagt gcagccactg 60
ccgccgccca ggagccctcg tcccctgcct tgtcccccta ctcgttcccg ctcccacggc 120

-continued

```
atggagcagg acactgccgc agtggcagcc accgtggcag ccgcggatgc gaccgccact    180
atcgtggtca tagaggacga gcagcccggg ccgtccacct ctcaggagga gggagcggcc    240
gccgcggcca ccgaagccac cgcggccacg gagaagggcg agaagaagaa ggagaaaaac    300
gtttcttcat ttcaactcaa acttgctgct aaagcgccta aatctgaaaa ggaaatggac    360
ccagaatatg aagagaaaat gaaagccgac cgagcaaaga gatttgaatt tttactgaag    420
cagacagaac tttttgcaca tttcattcag ccttcagcac agaaatctcc aacatctcca    480
ctgaacatga aattgggacg tccccgaata aagaaagatg aaaagcagag cttaatttct    540
gctggagact accgccatag gcgcacagag caagaagaag atgaagagct actgtctgag    600
agtcggaaaa catctaatgt gtgtattaga tttgaggtgt caccttcata tgtgaaaggg    660
gggccactga gagattatca gattcgagga ctgaattggt tgatctcttt atatgaaaat    720
ggagtcaatg gcattttggc tgatgaaatg ggccttggga aaactttaca aacaattgct    780
ttgcttggtt acctgaaaca ctaccgaaat attcctggac ctcacatggt tttagttcca    840
aagtctactt tacacaactg gatgaatgaa tttaaacgat gggtcccatc tctccgtgtc    900
atttgttttg tcggagacaa ggatgccaga gctgctttta ttcgtgatga aatgatgcca    960
ggagagtggg atgtttgcgt tacttcttat gagatggtaa ttaaagaaaa atctgtattc   1020
aaaaagtttc actggcgata cctggtcatt gatgaagctc acagaataaa gaatgaaaaa   1080
tctaagcttt cagagattgt tcgtgagttc aagtcgacta accgcttgct cctaactgga   1140
acacctttgc agaataacct gcatgaactg tgggccttac tcaacttttt attgcctgat   1200
gtctttaatt ctgcagatga ctttgattct tggtttgaca ctaaaaattg tcttggtgat   1260
caaaaactcg tggaaagact tcatgcagtt ttaaaaccat ttttgttacg ccgtataaaa   1320
actgatgtag agaagagtct gccacctaaa aaggaaataa agatttactt ggggctgagt   1380
aagatgcaac gagaatggta tacaaaaatc ctgatgaaag atattgatgt tttaaactct   1440
tctggcaaga tggacaagat gcgactctta aacattctga tgcagcttcg aaagtgttgt   1500
aatcatccat atctgtttga tggtgctgaa cctggtccac cttataccac tgatgagcat   1560
attgtcagca acagtggtaa aatggtagtt ctggataaac tattggccaa actcaaagaa   1620
cagggttcaa gggttctcat tttcagccag atgactcgct tgctggatat tttggaagat   1680
tattgcatgt ggcgtggtta tgagtattgt cgactggatg gacaaacccc gcatgaagaa   1740
agagaggata aattcctaga agtggaattt ctgggtcaaa gggaagcaat agaggctttt   1800
aatgctccta atagtagcaa attcatcttt atgctaagta ccagggctgg aggtctcgga   1860
attaacctgg caagtgctga tgtggttata ctatatgatt cagactggaa cccacaggtt   1920
gatctacaag ctatggatcg agcacatcgt attggtcaga agaaaccagt acgtgtattc   1980
cgtctcatca ctgacaacac tgttgaagag aggattgtag aaagagctga gataaaactg   2040
agactcgatt caattgttat acaacaagga agactcattg accaacagtc taacaagctg   2100
gcaaaagagg aaatgttaca aatgatacgg catggagcca cccatgtttt tgcttctaaa   2160
gagagtgagt tgacagatga agacattaca actattctgg aaagagggga aaagaagact   2220
gcagagatga atgaacgcct gcaaaaaatg ggagagtctt ctctaagaaa ttttagaatg   2280
gacattgaac aaagtttata caaatttgag ggagaagatt atagagaaaa acagaagctt   2340
ggcatggtgg aatggattga acctcctaaa cgagaacgca aagcaaacta cgcagtggat   2400
gcctacttta gagaggcttt gcgtgtcagc gagccaaaga ttccaaaggc tccacggcct   2460
ccaaaacagc caaatgttca ggattttcaa tttttcccac cacgcttatt tgagctcctg   2520
```

```
gaaaaggaaa ttctttatta tcggaagaca ataggctata aggttccaag gaatcctgat   2580
atcccaaatc cagctctggc tcaaagagaa gagcaaaaaa agattgatgg agctgaacct   2640
cttacaccag aagagactga agaaaaggaa aaacttctca cacaaggttt cacaaactgg   2700
actaaacgag attttaacca gtttattaaa gctaatgaga aatatggaag agatgacatt   2760
gataacatag ctcgagaggt agagggcaaa tcccctgagg aggtcatgga gtattcagct   2820
gtattttggg aacgttgcaa tgaattacag gacattgaga aaattatggc tcaaattgaa   2880
cgtggagaag caagaattca acgaaggatc agtatcaaga aagccctgga tgccaaaatt   2940
gcaagataca aggctccatt tcatcagttg cgcattcagt atggaaccag caaaggaaag   3000
aactatactg aggaagaaga tagattcttg atttgtatgt tacacaaaat gggctttgat   3060
agagaaaatg tatatgaaga attaagacag tgtgtacgaa atgctcccca gtttagattt   3120
gactggttta tcaagtctag gactgccatg gaattccaga gacgctgtaa cactctgatt   3180
tcattgattg agaaagaaaa tatggaaatt gaggaaagag agagagcaga aaagaagaaa   3240
cgggcaacta aaactccaat gtcacagaaa agaaaagcag agtcagctac tgagagctct   3300
ggaaagaagg atgtcaagaa ggtgaaatcc taaagcctag aaataaagtt ttaaatggga   3360
aactgctatt ttcttgttcc catcttcaaa tgctaattgc cagttccagt gtattcatgg   3420
tactctaaga aaaatctctt tggttttgat ttcttgcata ttttatatat tttacaatgc   3480
tttctacctg aaatgtgtag ctttatattt tatggcattc tagtattttt gtgtactgta   3540
ttttgtgcat ttcatgtctt catcaaaatc ctctcagtcc ttgttctttt gaagcttgtg   3600
ctgaggtttt agcttttcta tgttttatat gccgctgctt tgaaagagaa cctagattct   3660
atagttgtat tattgttgtt tcatacttta aatttatatg gctgtggaaa aacgaattaa   3720
aatgttttga ggagaaagac tttttcactt ctttgttgct ttcttttcta ttgagtctgg   3780
gcttgtttgt gttactgcat actgtgatta gcataataat tgtttctttg aggtcatcta   3840
aatatttttt tcctaaagga ataaagggtg aggaaagaaa aatattaaaa aagctaatat   3900
ttgatactgt gcttgctgtc agtatgcatt acatttaaat tattctctat tcaagtggga   3960
aaatataata aagaaatgtc tataagaaa                                      3989
```

<210> SEQ ID NO 33
<211> LENGTH: 5090
<212> TYPE: DNA
<213> ORGANISM: Homo sapiens

<400> SEQUENCE: 33

```
ggcggggccc gagccggaga agatggcggt gcggaagaag gacggcggcc ccaacgtgaa     60
gtactacgag gccgcggaca ccgtgaccca gttcgacaac gtgcggctgt ggctcggcaa    120
gaactacaag aagtatatac aagctgaacc acccaccaac aagtccctgt ctagcctggt    180
tgtacagttg ctacaatttc aggaagaagt ttttggcaaa catgtcagca atgcaccgct    240
cactaaactg ccgatcaaat gtttcctaga tttcaaagcg ggaggctcct tgtgccacat    300
tcttgcagct gcctacaaat tcaagagtga ccagggatgg cggcgttacg atttccagaa    360
tccatcacgc atggaccgca atgtggaaat gtttatgacc attgagaagt ccttggtgca    420
gaataattgc ctgtctcgac ctaacatttt tctgtgccca gaaattgagc ccaaactact    480
agggaaatta aaggacatta tcaagagaca ccagggaaca gtcactgagg ataagaacaa    540
tgcctcccat gttgtgtatc ctgtcccggg gaatctagaa gaagaggaat gggtacgacc    600
```

```
agtcatgaag agggataagc aggttcttct gcactggggc tactatcctg acagttacga    660
cacgtggatc ccagcgagtg aaattgaggc atctgtggaa gatgctccaa ctcctgagaa    720
acctaggaag gttcatgcaa agtggatcct ggacaccgac accttcaatg aatggatgaa    780
tgaggaagac tatgaagtaa atgatgacaa aaaccctgtc tcccgccgaa agaagatttc    840
agccaagaca ctgacagatg aggtgaacag cccagattca gatcgacggg acaagaaggg    900
gggaaactat aagaagagga agcgctcccc ctctccttca ccaaccccag aagcaaagaa    960
gaaaaatgct aagaaaggtc cctcaacacc ttacactaag tcaaagcgtg gccacagaga   1020
agaggagcaa gaagacctga caaaggacat ggacgagccc tcaccagtcc ccaatgtaga   1080
agaggtgaca cttcccaaaa cagtcaacac aaagaaagac tcagagtcgg ccccagtcaa   1140
aggcggcacc atgaccgacc tggatgaaca ggaagatgaa agcatggaga cgacgggcaa   1200
ggatgaggat gagaacagta cggggaacaa gggagagcag accaagaatc cagacctgca   1260
tgaggacaat gtgactgaac agacccacca catcatcatt cccagctacg ctgcctggtt   1320
tgactacaat agtgttcatg ccattgagcg gagggctctc cccgagttct tcaacggcaa   1380
gaacaagtcc aagactccag agatctacct ggcctatcga aactttatga ttgacactta   1440
ccgactgaac ccccaagagt atcttacctc taccgcctgc cgccgaaacc tagcgggtga   1500
tgtctgtgcc atcatgaggg tccatgcctt cctagaacag tggggtctta ttaactacca   1560
ggtggatgct gagagtcgac caaccccaat ggggcctccg cctacctctc acttccatgt   1620
cttggctgac acaccatcag ggctggtgcc tctgcagccc aagacacctc agggccgcca   1680
ggttgatgct gataccaagg ctgggcgaaa gggcaaagag ctggatgacc tggtgccaga   1740
gacggctaag ggcaagccag agctgcagac ctctgcttcc caacaaatgc tcaactttcc   1800
tgacaaaggc aaagagaaac caacagacat gcaaaacttt gggctgcgca cagacatgta   1860
cacaaaaaag aatgttccct ccaagagcaa ggctgcagcc agtgccactc gtgagtggac   1920
agaacaggaa accctgcttc tcctggaggc actggaaatg tacaaagatg actggaacaa   1980
agtgtccgag catgtgggaa gccgcacaca ggacgagtgc atcttgcatt ttcttcgtct   2040
tcccattgaa gacccatacc tggaggactc agaggcctcc ctaggccccc tggcctacca   2100
acccatcccc ttcagtcagt cgggcaaccc tgttatgagc actgttgcct tcctggcctc   2160
tgtcgtcgat ccccgagtcg cctctgctgc tgcaaagtca gccctagagg agttctccaa   2220
aatgaaggaa gaggtaccca cggccttggt ggaggcccat gttcgaaaag tggaagaagc   2280
agccaaagta acaggcaagg cggaccctgc cttcggtctg gaaagcagtg gcattgcagg   2340
aaccacctct gatgagcctg agcggattga ggagagcggg aatgacgagg ctcgggtgga   2400
aggccaggcc acagatgaga agaaggagcc caaggaaccc cgagaaggag gggtgctat    2460
agaggaggaa gcaaaagaga aaccagcgga ggctcccaag aaggatgagg agaaagggaa   2520
agaaggcgac agtgagaagg agtccgagaa gagtgatgga gacccaatag tcgatcctga   2580
gaaggagaag gagccaaagg aagggcagga ggaagtgctg aaggaagtgg tggagtctga   2640
gggggaaagg aagacaaagg tggagcggga cattggcgag ggcaacctct ccaccgctgc   2700
tgccgccgcc ctggccgccg ccgcagtgaa agctaagcac ttggctgctg ttgaggaaag   2760
gaagatcaaa tctttggtgg ccctgctggt ggagacccag atgaaaaagt tggagatcaa   2820
acttcggcac tttgaggagc tggagactat catggaccgg gagcgagaag cactggagta   2880
tcagaggcag cagctcctgg ccgacagaca agccttccac atggagcagc tgaagtatgc   2940
ggagatgagg gctcggcagc agcacttcca acagatgcac caacagcagc agcagccacc   3000
```

accagccctg cccccaggct cccagcctat ccccccaaca ggggctgctg ggccacccgc 3060
agtccatggc ttggctgtgg ctccagcctc tgtagtccct gctcctgctg gcagtggggc 3120
ccctccagga agtttgggcc cttctgaaca gattgggcag gcagggtcaa ctgcagggcc 3180
acagcagcag caaccagctg gagcccccca gcctggggca gtcccaccag gggttccccc 3240
ccctggaccc catggcccct caccgttccc caaccaacaa actcctccct caatgatgcc 3300
aggggcagtg ccaggcagcg ggcacccagg cgtggcgggt aatgctcctt tgggtttgcc 3360
ttttggcatg ccgcctcctc ctcctcctcc tgctccatcc atcatcccat ttggtagtct 3420
agctgactcc atcagtatta acctccccgc tcctcctaac ctgcatgggc atcaccacca 3480
tctcccgttc gccccgggca ctctcccccc acctaacctg cctgtgtcca tggcgaaccc 3540
tctacatcct aacctgccgg cgaccaccac catgccatct tccttgcctc tcgggccggg 3600
gctcggatcc gccgcagccc aaagccctgc cattgtggca gctgttcagg gcaacctcct 3660
gcccagtgcc agcccactgc cagacccagg caccccccctg cctccagacc ccacagcccc 3720
gagcccaggc acggtcaccc ctgtgccacc tccacagtga ggagccagcc agacatctct 3780
ccccctcacc ccctgtggac atcacggttc caggaacagc ccttccccca ccactgggac 3840
cctccccagc ctggagagtt catcactacg taaggaaagc tccttccgcc cctccaaagc 3900
cctcaccatg cctaacagag gcatgcattt ttatatcaga ttattcaagg acttctgttt 3960
aaaagatgtt tataatgtct gggagagagg ataggatggg aatgctgccc taaaggaagg 4020
gctggtgaaa ggtgtttata caaggttcta ttaaccactt ctaagggtac acctccctcc 4080
aaactactgc attttctatg gattaaaaaa aaaaaaaaaa agtagatttt aaaaagccac 4140
attggagctc ccttctaccc actaaaaaat aaccaatttt tacatttttt gagggggagt 4200
gagttttagg aaaggggaat taagattcca gggagagctc tggggataga acagggcgca 4260
gattccatct ctccccaagc cccttttttag tgactaagtc aaggccccaa ctcccctccc 4320
ccaccctacg ctgagcttat tcgagttcat tcgtactaat aatccctcct gcggcttcct 4380
cattgttgct gttttaggcc accccagctc agccaatgat tcctttccct ctgaatgtca 4440
gttttgtttt taaaagtcac ttgcttagtt gatgtcagcg tatgtgtatt tggtggggaa 4500
aacctaattt cggggatttc tgtggtaggt aataggagaa gaaagggcac tgggggctgt 4560
tctccttcct tccctgggct gtatccatgg actcctggaa ggcacagaga agggagctat 4620
aagaggatgt gaagttttaa aacctgaaat tgttttttaa agcacttaag cacctccata 4680
ttatgacttg gtgggtcacc ccttagcttc ctccctctcc caccaagact atgagaactt 4740
cagctgatag ctgggggctc cccagatgag gatgcaggga tttgggagca gtggaagagg 4800
gtgcccaacc ttgggttgga ccaacccttg gctcgcagct caactctgct tcccgcattc 4860
ctgctccacg tgtcccagct tctcccctgt gacgggaagg caggtgtgac tccaggctct 4920
gcactggttc ttcttggttc ctcccaccag gccctttgtt cctcatgtcc ccatgtttct 4980
ctccctctgc gtcttagcac ctttcttctg ttcaaagttt tctgtaaatt ttctcttttt 5040
ttctttcttt cttttttttt tttttataaa ttaatttgct ttcagttcca 5090

<210> SEQ ID NO 34
<211> LENGTH: 1907
<212> TYPE: DNA
<213> ORGANISM: Homo sapiens

<400> SEQUENCE: 34

```
actccgctcg agtagaagtg tgagagagcc cagcaggact cagaggggag agttggagga     60
aaaaaaaagg cagaaaaggg aaagaaagag gaagagagag agagagtgag aggagccgct    120
gagcccaccc cgatggccgc ggacgaagtt gccggagggg cgcgcaaagc cacgaaaagc    180
aaactttttg agtttctggt ccatggggtg cgcccccggga tgccgtctgg agcccggatg    240
ccccaccagg gggcgcccat gggccccccg ggctccccgt acatgggcag ccccgccgtg    300
cgacccggcc tggcccccgc gggcatggag cccgcccgca agcgagcagc gccccccgccc    360
gggcagagcc aggcacagag ccagggccag ccggtgccca ccgcccccgc gcggagccgc    420
agtgccaaga ggaggaagat ggctgacaaa atcctccctc aaaggattcg ggagctggtc    480
cccgagtccc aggcttacat ggacctcttg gcatttgaga ggaaactgga tcaaaccatc    540
atgcggaagc gggtggacat ccaggaggct ctgaagaggc ccatgaagca aaagcggaag    600
ctgcgactct atatctccaa cacttttaac cctgcgaagc ctgatgctga ggattccgac    660
ggcagcattg cctcctggga gctacgggtg gaggggaagc tcctggatga tcccagcaaa    720
cagaagcgga agttctcttc tttcttcaag agtttggtca tcgagctgga caaagatctt    780
tatggccctg acaaccacct cgttgagtgg catcggacac ccacgaccca ggagacggac    840
ggcttccagg tgaaacggcc tggggacctg agtgtgcgct gcacgctgct cctcatgctg    900
gactaccagc ctccccagtt caaactggat ccccgcctag cccggctgct ggggctgcac    960
acacagagcc gctcagccat tgtccaggcc ctgtggcagt atgtgaagac caacaggctg   1020
caggactccc atgacaagga atacatcaat ggggacaagt atttccagca gatttttgat   1080
tgtccccggc tgaagttttc tgagattccc cagcgcctca cagccctgct attgcccccct   1140
gacccaattg tcatcaacca tgtcatcagc gtggaccctt cagaccagaa gaagacggcg   1200
tgctatgaca ttgacgtgga ggtggaggag ccattaaagg ggcagatgag cagcttcctc   1260
ctatccacgg ccaaccagca ggagatcagt gctctggaca gtaagatcca tgagacgatt   1320
gagtccataa accagctcaa gatccagagg gacttcatgc taagcttctc cagagacccc   1380
aaaggctatg tccaagacct gctccgctcc cagagccggg acctcaaggt gatgacagat   1440
gtagccggca accctgaaga ggagcgccgg gctgagttct accaccagcc ctggtcccag   1500
gaggccgtca gtcgctactt ctactgcaag atccagcagc gcaggcagga gctggagcag   1560
tcgctggttg tgcgcaacac ctaggagccc aaaaataagc agcacgacgg aactttcagc   1620
cgtgtcccgg gccccagcat tttgccccgg gctccagcat cactcctctg ccaccttggg   1680
gtgtggggct ggattaaaag tcattcatct gacagcagcc gtgtggtcat tggaaactgg   1740
ggaggggagg gggagagaag ggaaagggaa gaaggtgggg aggcagtggg tccctcggga   1800
cgactcccca ttcccttccc ttggattctt ctccttactc aattttccct agacctaaaa   1860
acagtttggc agaagacatg tttaataaca ttttcatatt taaaaaa                  1907
```

<210> SEQ ID NO 35
<211> LENGTH: 4233
<212> TYPE: DNA
<213> ORGANISM: Homo sapiens

<400> SEQUENCE: 35

```
gataacgcgg gtgaggcgtg gagggcggcg ccatggccca cctggagctg ctgcttgtgg     60
aaaatttcaa gtcgtggcgg ggccgccagg tcattggccc cttccggagg ttcacctgca    120
tcatcggccc caacggctct ggaaaatcta atgtaatgga tgcacttagt tttgtaatgg    180
gagagaaaat agctaattta agagtgaaaa atattcaaga actcattcat ggagcacata    240
```

```
ttggaaaacc tatttcttct tctgcaagtg taaaaattat atatgtggag gaaagtggcg    300
aagagaaaac atttgcaagg attatccgag ggggatgctc agaatttcgc tttaatgata    360
atcttgtgag tcgttctgtt tacattgcag agttggaaaa gataggcata atagtcaaag    420
cacaaaattg tttggttttt cagggaactg tagagtcaat ttcagtgaag aaacccaaag    480
aaaggaccca gtttttgag gaaatcagca cttcaggaga gcttatagga gaatatgaag    540
aaaagaaaag aaagttacaa aaagccgaag aggatgcaca gtttaacttt aataagaaaa    600
aaaatatagc ggcagagcgc agacaagcaa aattagagaa ggaagaggca gaacgttacc    660
agagtctcct tgaagaactg aaaatgaaca agatacaact gcagcttttt caactatacc    720
ataatgagaa aaagattcat ctcctgaaca ccaagttaga gcatgtgaat agggatttga    780
gtgtcaaaag agagtctttg tctcatcatg aaaacatagt taaagccagg aaaaaggaac    840
atggaatgct aactagacaa ctacaacaaa cagaaaaaga attaaaatcg gttgaaaccc    900
ttttaaatca gaagaggcct cagtacatta aagccaaaga aaacacttct caccacctta    960
agaaattaga tgtggctaag aaatcaataa aggacagcga aaaacaatgt tctaaacagg   1020
aagatgatat aaaagccctg gagacagagc tggctgattt agatgctgca tggagaagtt   1080
ttgaaaagca gattgaggaa gaaattttac ataaaaagcg agacattgaa ctggaagcca   1140
gtcagctgga tcgttataaa gaacttaagg aacaagtaag aaagaaagta gctacaatga   1200
ctcaacaact ggaaaaactg cagtgggaac agaagacaga tgaagaaaga ctggcatttg   1260
aaaagaggag gcatggagaa gttcagggaa atctaaaaca aataaaagaa caaatagaag   1320
atcataaaaa acgaatagag aagttagagg agtatacaaa gacatgcatg gattgcttga   1380
aagagaaaaa acagcaagag gaaaccctag tggatgaaat tgaaaaaaca aaatcaagaa   1440
tgtctgaagt taatgaagaa ttgaatctta ttagaagtga attgcagaat gctgggattg   1500
atacccatga gggaaaacgt cagcaaaaga gagcagaggt tctggaacac cttaaaagac   1560
tgtacccaga ttctgtgttt ggaagactat ttgacctgtg tcatcctatt cataagaaat   1620
accagctggc tgttactaag gtttttggcc ggttcatcac tgccattgtt gtagcctctg   1680
aaaaggtagc aaaagattgt attcgatttc tgaaggagga aagagctgaa cctgagacat   1740
tcctcgctct agattacctt gatatcaagc caatcaatga aagactaagg gagcttaaag   1800
gctgtaaaat ggtgattgat gtcataaaga ctcagtttcc tcagctgaag aaagtgattc   1860
agtttgtgtg tggaaatggt cttgtttgtg agactatgga agaagcaagg catattgcac   1920
tcagtggacc tgaaagacag aaaacagtag ctcttgatgg aacattattt ttaaaatctg   1980
gagtgatctc tggagggtca agtgacttaa aatacaaggc tagatgctgg gatgagaaag   2040
agttaaagaa tctaagagac agacgaagcc agaaaatcca agagctaaag ggtttaatga   2100
agacactccg caaagaaaca gatttgaaac aaatacagac cctgatacag ggaactcaaa   2160
cacgactcaa atattcacaa aatgaactag agatgattaa gaagaagcac cttgttgctt   2220
tttaccagga acaatctcag ttacaaagtg aactactaaa tattgagtct caatgtatta   2280
tgttgagtga aggaatcaag gaacgacaac gaagaattaa agaatttcaa gaaaagatag   2340
ataaggtaga agacgatatc ttccaacact tctgtgaaga aattggcgtg gaaaatattc   2400
gtgaatttga gaacaaacat gttaaacggc aacaagaaat tgatcaaaaa agattagaat   2460
ttgaaaaaca aaaaactcgg cttaatgttc aacttgagta tagtcgcagt caccttaaga   2520
agaaactgaa taagatcaac acattaaaag aaactatcca gaaaggtagt gaagatattg   2580
```

-continued

```
atcacctaaa gaaggctgaa gaaaactgtc tgcagacagt gaatgaactc atggcaaagc   2640

agcagcaact taaggacata cgtgtcactc agaactccag tgccgagaaa gttcaaactc   2700

aaattgaaga ggaacggaag aagtttctgg ctgttgatag ggaagtgggg aaattgcaaa   2760

aagaagttgt aagtattcaa acttctctgg aacagaaacg attagagaag cataacttgc   2820

tgcttgattg caaagtgcaa gacattgaga taatcctttt gtcggggtca ctggatgaca   2880

tcattgaagt ggagatggga actgaagcag aaagtaccca ggcaacaatt gatatctatg   2940

aaaaagaaga agcctttgaa atagactaca gctctctaaa agaggatttg aaggctctac   3000

agtctgatca agaaatcgag gcccacctta ggctcttatt gcagcaagta gcatcccagg   3060

aagatatctt actgaaaaca gcagccccaa acctacgagc actggagaac ttaaagactg   3120

tcagagacaa gtttcaagag tccacagatg cttttgaggc cagcagaaag gaagccagac   3180

tgtgtaggca agagttcgag caagtgaaaa aaaggagata cgatcttttc acccagtgtt   3240

ttgagcatgt ctcaatctca attgatcaaa tctacaagaa gctctgcaga aacaacagcg   3300

cccaagcatt tcttagccca gagaaccctg aagaacctta cttggaggga attagctata   3360

actgtgtggc ccccaggcaaa cggtttatgc caatggacaa tttgtcaggg ggagaaaagt   3420

gtgtggcagc cttggctctc ctgtttgctg tgcacagttt tcgtcctgcc ccattctttg   3480

ttttagatga agtggatgca gccctagaca atactaacat aggcaaagtg tcaagttaca   3540

tcaaagagca aactcaagac cagtttcaga tgatagtcat ctccctaaaa gaagagttct   3600

attccagagc cgacgcgctg atcggcatct atcctgagta cgatgactgc atgttcagcc   3660

gagttttgac cctagatctt tctcagtatc cagacactga aggccaagaa agcagcaaga   3720

gacacggaga gtcccgctag ggcagtcct gcagcagtca cctgatcact gttcagttcc   3780

cactctaata ctcacacagc tcctccacag gagacttctg gagcaagcag gaccagcctg   3840

gtgcaccctt taagagaaac cttagtcgtt ctagccaaag aggctgtggc tcactttagt   3900

tgagtgttca gacctcattc tagtagggaa agttttcagt gagagctggt gtcaaatgag   3960

tttttaaaaa acaaacaaaa ggtacaattt tgtactataa ttctaacttc tattttgaaa   4020

taagctagtt tggttggaaa aattttgaat tcagcttcat cttcactctg atcttgcctt   4080

gcacccaagt aatcttgaag ggaacttctc ttggttttta aacatactag ttataagatt   4140

gttaataaac tgttgaacct ggcttttggg aaattgtttc agagaaacta tgttagtatt   4200

gaaaatatca ataaaaaatg ttctaatttc aaa                                 4233
```

<210> SEQ ID NO 36
<211> LENGTH: 4385
<212> TYPE: DNA
<213> ORGANISM: Homo sapiens

<400> SEQUENCE: 36

```
agtgttaaat aactgccgcg ctggcctgac agtctctgag atgacaatag ggagaatgga     60

gaacgtggag gtcttcaccg ctgagggcaa aggaaggggt ctgaaggcca ccaaggagtt    120

ctgggctgca gatatcatct ttgctgagcg ggcttattcc gcagtggttt ttgacagcct    180

tgttaatttt gtgtgccaca cctgcttcaa gaggcaggag aagctccatc gctgtgggca    240

gtgcaagttt gcccattact gcgaccgcac ctgccagaag gatgcttggc tgaaccacaa    300

gaatgaatgt tcggccatca agagatatgg gaaggtgccc aatgagaaca tcaggctggc    360

ggcgcgcatc atgtggcggg tggagagaga aggcaccggg ctcacggagg gctgcctggt    420

gtccgtggac gacttgcaga accacgtgga gcactttggg gaggaggagc agaaggacct    480
```

```
gcgggtggac gtggacacat tcttgcagta ctggccgccg cagagccagc agttcagcat    540
gcagtacatc tcgcacatct tcggagtgat taactgcaac ggttttactc tcagtgatca    600
gagaggcctg caggccgtgg gcgtaggcat cttccccaac ctgggcctgg tgaaccatga    660
ctgttggccc aactgtactg tcatatttaa caatggcaat catgaggcag tgaaatccat    720
gtttcatacc cagatgagaa ttgagctccg ggccctaggc aagatctcag aaggagagga    780
gctgactgtg tcctatattg acttcctcaa cgttagtgaa gaacgcaaga ggcagctgaa    840
gaagcagtac tactttgact gcacatgtga acactgccag aaaaaactga aggatgacct    900
cttcctgggg gtgaaagaca accccaagcc ctctcaggaa gtggtgaagg agatgataca    960
attctccaag gatacattgg aaaagataga caaggctcgt tccgagggtt tgtatcatga   1020
ggttgtgaaa ttatgccggg agtgcctgga gaagcaggag ccagtgtttg ctgacaccaa   1080
catctacatg ctgcggatgc tgagcattgt ttcggaggtc ctttcctacc tccaggcctt   1140
tgaggaggcc tcgttctatg ccaggaggat ggtggacggc tatatgaagc tctaccaccc   1200
caacaatgcc caactgggca tggccgtgat gcgggcaggg ctgaccaact ggcatgctgg   1260
taacattgag gtggggcacg ggatgatctg caaagcctat gccattctcc tggtgacaca   1320
cggaccctcc caccccatca ctaaggactt agaggccatg cgggtgcaga cggagatgga   1380
gctacgcatg ttccgccaga acgaattcat gtactacaag atgcgcgagg ctgccctgaa   1440
caaccagccc atgcaggtca tggccgagcc cagcaatgag ccatccccag ctctgttcca   1500
caagaagcaa tgaggactgc ccagtggagg aggggcgatg tggctgggga gctagggaga   1560
gactctggag gtggtgggtc tctcgggaga cccctaatga ggaagttgag gtaatgctta   1620
acattgttgc tgtgagaatt tactgcccta tgtttcccag agccattttg gctcaattca   1680
agtctattca attcaagtta actctagccc agcccagatc aactcctcct acaaatatta   1740
ttggatgata ggccctagaa cccaataaag gagctccaaa tgtcgttggg tggggaagca   1800
aaatgtagag aaacatttaa agcacactgt aataataaat gcaattataa actatatgga   1860
ggagggtgca gaggagggaa tgtgtctggt gtgtgatgtg tgtgtgtgca gtgggggtat   1920
cacagagagt atgacatctg agttgagggt agcaggtgcc tggagtctca ggtggctgct   1980
cacccatctg tgcaggtgtc tctggggctg ctggtctcac ctgtggtctg cagtagacac   2040
aattggctga gcaggatatg tgatactgtg tggttggtgt ggagttttga agaaggggct   2100
gtgtttgggc cacgtaggct ctactcagag acctgaaacc acttcagaat ggtgcatatg   2160
tcgaaagagc tggctggggg ccttgcccaa accaactgag gtcttaaagt ccagggaaaa   2220
aaagtctggg ttccaactag aattctagaa atatttctag aacacacaga gagggaataa   2280
gtccctctat caccctttatt accaagcctt gtggttccct gtgattttag ataatgtctg   2340
atatttttct ggctatttgc ctagtaggat ttaaaaaata ttttcaaagt gaagctgaga   2400
gagaatcttg gaaacacaca tacctgttga tcatgggccc tgcagaattg gcccttgggg   2460
gctttatttg gttacatgtg cctgggtggt ctttaccagc ttagactcta tcatgggccc   2520
ccatgaagct ccattctcaa tactgaataa ttattacttc ccttgttgag tttctttttc   2580
tgtcatgccc tgggggcttc tgctcttctc accagaaaga acatttgaat ctggattctt   2640
gtacacctgg gttagaccct gttcagaggt gtggccaatt tatcccgatc tcctggaagg   2700
ctgttgtgat ttccatctaa gaaatgaggg tcttgagaat caaccagtcc caagattagc   2760
ctgttatcct gttatctact gagaccccaa atttctcacc aatgttttgg gagatcctgg   2820
```

```
aaaagatccc ttcagtttgg ggtgtcacca agacttctac acaacccagg actaccattg   2880
acctcagagc tgtaccccac atcttgaagt aaattgatcc caccaggtcc cacgtttgtt   2940
atctctgcct aaatgttagc ttctccatcc tcaccacatg atgacctgct gtgtccctct   3000
gagcactacc cagtggctga aaactctgca aatgggccac acttttgcaa aatacttgta   3060
tctgacactt aggtcttgtt tgaagaattt cctttctgga aggttttaca agaagactga   3120
tagtctttca agcccccaca tcacaggctt agggacggca ctaactttct cccagggatc   3180
taactggcta gttcaaatta tcactctttt accttcatat aaaatgtctc ccccaaacct   3240
ttttcccttc tttgtcattg ttatctgcta agcccctggt catttcccca tattcgtagt   3300
cttttttttcc atcctatctt tctaatattt gttgtcttta acaaactgtg ttctgtgtct   3360
gtgctcctcc ttccctctca gaccactgga atgcaagtcc ttcttccctt tggaatgtac   3420
tctggatccc ttcccctgct ttgaccccca gactttgctc catctattat tgcttctcca   3480
tcctggatcc ttgacatttg tcaccccact ggccttctca ggtgcaatca gtaaaaatgc   3540
tgagaactct tggatcttaa tcttcatgac tgagtttttt ttagttgtat agttatcatc   3600
tgcctttctt cactttgcat ttcttcttga atccattgca gattgacttc cactcccact   3660
ccttcactaa aagggctctt accaagatca aatctaatgg gtacatttta gttcctatgt   3720
gatttggcct ttcgatgtca atcatcactc ccagccattg attttggtga cccacttccc   3780
tgtgatgatc ttctgatcta gtttctcagg ttccttcgct ggtccttttt ctttccctgc   3840
ccctgacata ttgacatttc ctggagttgg ttttgtcctt gattcattct catgtcattc   3900
tgcacacagt ctctgcatga actcaggcag acccttcatt taatgaccac cttagggctg   3960
atgattctca aatctgtatt ccccgatctt gcatttgagc tccagcccca ctcatcctct   4020
cggatgttct gcaggcccag caaactcatc atgtccaaag tgaaactttt tctctttcct   4080
gtctcctctc ctctgatctg ttctttcttg gaacaccacc caagaacgtc acctcctcca   4140
tcagattgtg agctcctgga gggcaggagc tgtgtccttc tattcatctt cctatcccca   4200
gaaccttgca cagatcctgg aatgtggtag gtgctcagta aatgtgtgtt gaataaatga   4260
atgaatgaat gaacaaatga atgaatttgc ttacttcaag gcaaaagaac catgaaactg   4320
tattttgagt ttctatgtta tagcagtcag caaatcctat taaatacttt gtgtttccaa   4380
gcaaa                                                               4385
```

```
<210> SEQ ID NO 37
<211> LENGTH: 3259
<212> TYPE: DNA
<213> ORGANISM: Homo sapiens

<400> SEQUENCE: 37

ggctcagccg caagatggcg gcgctggcgg aggagcagac ggaggtggcg gtcaagctag     60
agcctgaggg accgccaacg ctgctacctc cgcaggcggg ggacggcgca ggcgagggta    120
gcggcggcac taccaacaac ggccccaacg gcggcggcgg gaacgttgcg gcgtcgtcgt    180
ccactggcgg ggatggcggg acccccaagc ccacggtggc tgtctccgcc gctgccccgg    240
cgggggcggc cccggtgccc gccgctgctc cggacgccgg cgctccgcat gaccgacaga    300
ctctactggc cgtgctgcag ttcctacggc agagcaaact ccgcgaggcc gaagaggcgc    360
tgcgccgtga ggccgggctg ctggaggagg cagtggcggg ctccggagcc ccgggagagg    420
tggacagcgc cggcgctgag gtgaccagcg cgcttctcag ccgggtgacc gcctcggccc    480
ctggccctgc ggcccccgac cctccgggca ctggcgcttc gggggccacg gtcgtctcag    540
```

```
gttcagcctc aggtcctgcg gctccgggta aagttggaag tgttgctgtg gaagaccagc    600
cagatgtcag tgccgtgttg tcagcctaca accaacaagg agatcccaca atgtatgaag    660
aatactatag tggactgaaa cacttcattg aatgttccct ggactgccat cgggcagagt    720
tgtcccaact tttttatcct ctgtttgtgc acatgtactt ggagctagtc tacaatcaac    780
atgagaatga agcaaagtca ttctttgaga agttccatgg agatcaggaa tgttattacc    840
aggatgacct acgagtatta tctagtctta ccaaaaagga acacatgaaa gggaatgaga    900
ccatgttgga ttttcgaaca agtaaatttg ttctgcgtat ttcccgtgac tcgtaccaac    960
tcttgaagag gcatcttcag gagaaacaga acaatcagat atggaacata gttcaggagc   1020
acctctacat tgacatcttt gatgggatgc cgcgtagtaa gcaacagata gatgcgatgg   1080
tgggaagttt ggcaggagag gctaaacgag aggcaaacaa atcaaaggta tttttttggtt  1140
tattaaaaga accagaaatt gaggtacctt tggatgacga ggatgaagag ggagaaaatg   1200
aagaaggaaa acctaaaaag aagaagccta aaaaagatag tattggatcc aaaagcaaaa   1260
aacaagatcc caatgctcca cctcagaaca gaatccctct tcctgagttg aaagattcag   1320
ataagttgga taagataatg aatatgaaag aaaccaccaa acgagtgcgc cttgggccgg   1380
actgcttacc ctccatttgt ttctatacat ttctcaatgc ttaccagggt ctcactgcag   1440
tggatgtcac tgatgattct agtctgattg ctggaggttt tgcagattca actgtcagag   1500
tgtggtcggt aacacccaaa aagcttcgta gtgtcaaaca agcatcagat cttagtctta   1560
tagacaaaga atcagatgat gtcttagaaa gaatcatgga tgagaaaaca gcaagtgagt   1620
tgaagatttt gtatggtcac agtgggccctg tctacggagc cagcttcagt ccggatagga  1680
actatctgct ttcctcttca gaggacggaa ctgttagatt gtggagcctt caaacattta   1740
cttgtttggt gggatataaa ggacacaact atccagtatg ggacacacaa ttttctccat   1800
atggatatta ttttgtgtca gggggccatg accgagtagc tcggctctgg gctacagacc   1860
actatcagcc tttaagaata tttgccggcc atcttgctga tgtgaattgt accagattcc   1920
atccaaattc taattatgtt gctacgggct ctgcagacag aactgtgcgg ctctgggacg   1980
tcctgaatgg taactgtgta aggatcttca ctggacacaa gggaccaatt cattccttga   2040
cattttctcc caatgggaga ttcctggcta caggagcaac agatggcaga gtgcttcttt   2100
gggatattgg acatggtttg atggttggag aattaaaagg ccacactgat acagtctgtt   2160
cacttaggtt tagtagagat ggtgaaattt tggcatcagg ttcaatggat aatacagttc   2220
gattatggga tgctatcaaa gcctttgaag atttagagac cgatgacttt actacagcca   2280
ctgggcatat aaatttacct gagaattcac aggagttatt gttgggaaca tatatgacca   2340
aatcaacacc agttgtacac cttcatttta ctcgaagaaa cctggttcta gctgcaggag   2400
cttatagtcc acaataaacc atcggtatta aagacctttt ggaagctact gtttttaaaa   2460
agggagacta aaagcaaata cctcagtgat taatatttaa gctacagaga atgtttttgt   2520
ctatatggat ctggaagtat gctgcttgga aaaatctgaa caggacagtt ccacgtttct   2580
atagcaacca catttgacta atttccgtta gttgaataag aggtattatg atcatggagg   2640
ggacatttat ggtgctttgg attgtgtgga aactatgcat tttctgttca aatgctattt   2700
taatttatta catttagaaa aaaagttgat ttcaataatt catcctgctt caagattcaa   2760
attcagaaat atactatcat cttgaatttt agctgaagaa tcctatgagc atgtatgttt   2820
ctgctgtaaa aacgtagtta ctgtatggca ctcaaaaact atgttaaatg atccactaac   2880
```

```
ttttttttc ttggcccatg attaatggaa tgtatgtaac taggtagggt tcctttctta   2940

gatctagagg aagtacagcc acccactgac atctgaattt atatacctgt tgagttttga   3000

gtgcacccaa acactcgata aaccaggtga agaaatttag cttccatgtt ctacttcagc   3060

taaaacagct acatacaacc tagtacactt gaagtcagac agacatttca gttgcttacc   3120

tccagtactg agccttgctt tgggaaacta aaagatttag accaagtcac tgccagtttt   3180

tgcctttgtt gcattttgta cagtttttat atttttgata tcttgtaaat aaagacaacc   3240

agcttttcca ggttcataa                                               3259
```

<210> SEQ ID NO 38
<211> LENGTH: 5695
<212> TYPE: DNA
<213> ORGANISM: Homo sapiens

<400> SEQUENCE: 38

```
aaccgacgcg cgtctgtgga gaagcggctt ggtcgggggt ggtctcgtgg ggtcctgcct     60

gtttagtcgc tttcagggtt cttgagcccc ttcacgaccg tcaccatgga agtgtcacca    120

ttgcagcctg taaatgaaaa tatgcaagtc aacaaaataa agaaaaatga agatgctaag    180

aaaagactgt ctgttgaaag aatctatcaa aagaaaacac aattggaaca tattttgctc    240

cgcccagaca cctacattgg ttctgtggaa ttagtgaccc agcaaatgtg ggtttacgat    300

gaagatgttg gcattaacta tagggaagtc acttttgttc ctggtttgta caaaatcttt    360

gatgagattc tagttaatgc tgcggacaac aaacaaaggg acccaaaaat gtcttgtatt    420

agagtcacaa ttgatccgga aaacaattta attagtatat ggaataatgg aaaaggtatt    480

cctgttgttg aacacaaagt tgaaaagatg tatgtcccag ctctcatatt tggacagctc    540

ctaacttcta gtaactatga tgatgatgaa aagaaagtga caggtggtcg aaatggctat    600

ggagccaaat tgtgtaacat attcagtacc aaatttactg tggaaacagc cagtagagaa    660

tacaagaaaa tgttcaaaca gacatggatg gataatatgg gaagagctgg tgagatggaa    720

ctcaagccct tcaatggaga agattataca tgtatcacct ttcagcctga tttgtctaag    780

tttaaaatgc aaagcctgga caaagatatt gttgcactaa tggtcagaag agcatatgat    840

attgctggat ccaccaaaga tgtcaaagtc tttcttaatg gaaataaact gccagtaaaa    900

ggatttcgta gttatgtgga catgtatttg aaggacaagt tggatgaaac tggtaactcc    960

ttgaaagtaa tacatgaaca agtaaaccac aggtgggaag tgtgtttaac tatgagtgaa   1020

aaaggctttc agcaaattag ctttgtcaac agcattgcta catccaaggg tggcagacat   1080

gttgattatg tagctgatca gattgtgact aaacttgttg atgttgtgaa gaagaagaac   1140

aagggtggtg ttgcagtaaa agcacatcag gtgaaaaatc acatgtggat ttttgtaaat   1200

gccttaattg aaaacccaac ctttgactct cagacaaaag aaaacatgac tttacaaccc   1260

aagagctttg gatcaacatg ccaattgagt gaaaaattta tcaaagctgc cattggctgt   1320

ggtattgtag aaagcatact aaactgggtg aagtttaagg cccaagtcca gttaaacaag   1380

aagtgttcag ctgtaaaaca taatagaatc aagggaattc ccaaactcga tgatgccaat   1440

gatgcagggg gccgaaactc cactgagtgt acgcttatcc tgactgaggg agattcagcc   1500

aaaactttgg ctgtttcagg ccttggtgtg gttgggagag acaaatatgg ggtttttccct   1560

cttagaggaa aaatactcaa tgttcgagaa gcttctcata agcagatcat ggaaaatgct   1620

gagattaaca atatcatcaa gattgtgggt cttcagtaca agaaaaacta tgaagatgaa   1680

gattcattga agacgcttcg ttatgggaag ataatgatta tgacagatca ggaccaagat   1740
```

ggttcccaca tcaaaggctt gctgattaat tttatccatc acaactggcc ctctcttctg 1800
cgacatcgtt ttctggagga atttatcact cccattgtaa aggtatctaa aaacaagcaa 1860
gaaatggcat tttacagcct tcctgaattt gaagagtgga agagttctac tccaaatcat 1920
aaaaaatgga aagtcaaata ttacaaaggt ttgggcacca gcacatcaaa ggaagctaaa 1980
gaatactttg cagatatgaa aagacatcgt atccagttca aatattctgg tcctgaagat 2040
gatgctgcta tcagcctggc ctttagcaaa aaacagatag atgatcgaaa ggaatggtta 2100
actaatttca tggaggatag aagacaacga aagttacttg ggcttcctga ggattacttg 2160
tatggacaaa ctaccacata tctgacatat aatgacttca tcaacaagga acttatcttg 2220
ttctcaaatt ctgataacga gagatctatc ccttctatgg tggatggttt gaaaccaggt 2280
cagagaaagg ttttgtttac ttgcttcaaa cggaatgaca agcgagaagt aaaggttgcc 2340
caattagctg gatcagtggc tgaaatgtct tcttatcatc atggtgagat gtcactaatg 2400
atgaccatta tcaatttggc tcagaatttt gtgggtagca ataatctaaa cctcttgcag 2460
cccattggtc agtttggtac caggctacat ggtggcaagg attctgctag tccacgatac 2520
atctttacaa tgctcagctc tttggctcga ttgttatttc caccaaaaga tgatcacacg 2580
ttgaagtttt tatatgatga caaccagcgt gttgagcctg aatggtacat tcctattatt 2640
cccatggtgc tgataaatgg tgctgaagga atcggtactg ggtggtcctg caaaatcccc 2700
aactttgatg tgcgtgaaat tgtaaataac atcaggcgtt tgatggatgg agaagaacct 2760
ttgccaatgc ttccaagtta caagaacttc aagggtacta ttgaagaact ggctccaaat 2820
caatatgtga ttagtggtga agtagctatt cttaattcta caaccattga aatctcagag 2880
cttcccgtca gaacatggac ccagacatac aaagaacaag ttctagaacc catgttgaat 2940
ggcaccgaga agacacctcc tctcataaca gactataggg aataccatac agataccact 3000
gtgaaatttg ttgtgaagat gactgaagaa aaactggcag aggcagagag agttggacta 3060
cacaaagtct tcaaactcca aactagtctc acatgcaact ctatggtgct ttttgaccac 3120
gtaggctgtt taaagaaata tgacacggtg ttggatattc taagagactt ttttgaactc 3180
agacttaaat attatggatt aagaaaagaa tggctcctag gaatgcttgg tgctgaatct 3240
gctaaactga ataatcaggc tcgctttatc ttagagaaaa tagatggcaa aataatcatt 3300
gaaaataagc ctaagaaaga attaattaaa gttctgattc agaggggata tgattcggat 3360
cctgtgaagg cctggaaaga agcccagcaa aaggttccag atgaagaaga aaatgaagag 3420
agtgacaacg aaaaggaaac tgaaaagagt gactccgtaa cagattctgg accaaccttc 3480
aactatcttc ttgatatgcc cctttggtat ttaaccaagg aaaagaaaga tgaactctgc 3540
aggctaagaa atgaaaaaga acaagagctg gacacattaa aaagaaagag tccatcagat 3600
ttgtggaaag aagacttggc tacatttatt gaagaattgg aggctgttga agccaaggaa 3660
aaacaagatg aacaagtcgg acttcctggg aaaggggga aggccaaggg gaaaaaaaca 3720
caaatggctg aagttttgcc ttctccgcgt ggtcaaagag tcattccacg aataaccata 3780
gaaatgaaag cagaggcaga aaagaaaaat aaaaagaaaa ttaagaatga aaatactgaa 3840
ggaagccctc aagaagatgg tgtggaacta gaaggcctaa aacaaagatt agaaaagaaa 3900
cagaaaagag aaccaggtac aaagacaaag aaacaaacta cattggcatt taagccaatc 3960
aaaaaaggaa agaagagaaa tccctggtct gattcagaat cagataggag cagtgacgaa 4020
agtaattttg atgtccctcc acgagaaaca gagccacgga gagcagcaac aaaaacaaaa 4080

-continued

| | |
|---|---|
| ttcacaatgg atttggattc agatgaagat ttctcagatt ttgatgaaaa aactgatgat | 4140 |
| gaagattttg tcccatcaga tgctagtcca cctaagacca aaacttcccc aaaacttagt | 4200 |
| aacaaagaac tgaaaccaca gaaaagtgtc gtgtcagacc ttgaagctga tgatgttaag | 4260 |
| ggcagtgtac cactgtcttc aagccctcct gctacacatt tcccagatga aactgaaatt | 4320 |
| acaaacccag ttcctaaaaa gaatgtgaca gtgaagaaga cagcagcaaa aagtcagtct | 4380 |
| tccacctcca ctaccggtgc caaaaaaagg gctgccccaa aaggaactaa aagggatcca | 4440 |
| gctttgaatt ctggtgtctc tcaaaagcct gatcctgcca aaaccaagaa tcgccgcaaa | 4500 |
| aggaagccat ccacttctga tgattctgac tctaattttg agaaaattgt ttcgaaagca | 4560 |
| gtcacaagca agaaatccaa gggggagagt gatgacttcc atatggactt tgactcagct | 4620 |
| gtggctcctc gggcaaaatc tgtacgggca aagaaaccta taaagtacct ggaagagtca | 4680 |
| gatgaagatg atctgtttta aaatgtgagg cgattatttt aagtaattat cttaccaagc | 4740 |
| ccaagactgg ttttaaagtt acctgaagct cttaacttcc tcccctctga atttagtttg | 4800 |
| gggaaggtgt ttttagtaca agacatcaaa gtgaagtaaa gcccaagtgt tctttagctt | 4860 |
| tttataatac tgtctaaata gtgaccatct catgggcatt gttttcttct ctgctttgtc | 4920 |
| tgtgttttga gtctgctttc ttttgtcttt aaaacctgat ttttaagttc ttctgaactg | 4980 |
| tagaaatagc tatctgatca cttcagcgta aagcagtgtg tttattaacc atccactaag | 5040 |
| ctaaaactag agcagtttga tttaaaagtg tcactcttcc tccttttcta ctttcagtag | 5100 |
| atatgagata gagcataatt atctgtttta tcttagtttt atacataatt taccatcaga | 5160 |
| tagaacttta tggttctagt acagatactc tactacactc agcctcttat gtgccaagtt | 5220 |
| tttctttaag caatgagaaa ttgctcatgt tcttcatctt ctcaaatcat cagaggccga | 5280 |
| agaaaaacac tttggctgtg tctataactt gacacagtca atagaatgaa gaaaattaga | 5340 |
| gtagttatgt gattatttca gctcttgacc tgtcccctct ggctgcctct gagtctgaat | 5400 |
| ctcccaaaga gagaaaccaa tttctaagag gactggattg cagaagactc ggggacaaca | 5460 |
| tttgatccaa gatcttaaat gttatattga taaccatgct cagcaatgag ctattagatt | 5520 |
| cattttggga aatctccata atttcaattt gtaaactttg ttaagacctg tctacattgt | 5580 |
| tatatgtgtg tgacttgagt aatgttatca acgtttttgt aaatatttac tatgtttttc | 5640 |
| tattagctaa attccaacaa ttttgtactt taataaaatg ttctaaacat tgcaa | 5695 |

METHODS OF TREATMENTS BASED UPON ANTHRACYCLINE RESPONSIVENESS

CROSS-REFERENCE TO RELATED APPLICATIONS

This application is a national stage of PCT Patent Application No. PCT/US2020/025842, entitled "Methods of Treatments Based Upon Anthracycline Responsiveness," filed Mar. 30, 2020, which claims priority to U.S. Provisional Patent Application No. 62/826,775 entitled "Methods of Treatments Based Upon Anthracycline Responsiveness," filed Mar. 29, 2019, the disclosures of which are incorporated herein by reference.

STATEMENT REGARDING FEDERALLY SPONSORED RESEARCH OR DEVELOPMENT

This invention was made with Government support under contract W81XWH-16-1-0084 and W81XWH-16-1-0083 awarded by the Department of Defense; and under contract CA163915 awarded by the National Institutes of Health. The Government has certain rights in the invention

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Mar. 30, 2020, is named "05739 Seq List_ST25.txt" and is 238,079 bytes in size.

FIELD OF THE INVENTION

The invention is generally directed to methods of treatments based upon a neoplasm's responsiveness to anthracycline, and more specifically to treatments based upon a neoplasm's molecular architecture indicative of anthracycline responsiveness.

BACKGROUND

Anthracyclines are a class of chemotherapeutic molecules that are used to treat a number of neoplasms, especially cancers. In practice, doxorubicin and epirubicin are used in treatments of breast cancer, childhood solid tumors, soft tissue sarcomas, and aggressive lymphomas. Daunorubicin and idarubicin are often used to treat lymphomas, leukemias, myeloma, and breast cancer. Other anthracyclines include valrubicin, nemorubicin, pixantrone, and sabarubicin, which are each used to treat various neoplasms.

Anthracyclines are considered non-cell specific drugs and have multiple mechanisms of action on neoplastic tissue. These mechanisms include inhibition of DNA and RNA synthesis by intercalation, generation of toxic free oxygen radicals, alteration in histone regulation of DNA, and inhibition of the topoisomerase II enzyme, which assists in DNA and RNA synthesis. Unfortunately, anthracyclines are toxic to various healthy tissues, especially heart muscle. This cardiotoxicity can result in heart failure. Additionally, anthracyclines use is associated with an increased risk of secondary malignancy.

SUMMARY OF THE INVENTION

Many embodiments are directed to methods of treatment of neoplasms and cancer based upon diagnostics that utilize chromatin availability and/or chromatin regulatory gene expression data to infer treatment. In many of these embodiments, an anthracycline is administered when appropriate, as determined by chromatin openness or accessibility and/or chromatin regulatory gene expression data. Various embodiments are also directed towards identification of chromatin regulatory genes that provide robust indication of anthracycline benefit.

In an embodiment to treat an individual having cancer, a biopsy is obtained from an individual. Chromatin accessibility or expression levels of a set of chromatin regulatory genes of the biopsy is assessed. The likelihood of survival of the individual with anthracycline treatment is determined utilizing a first survival model and the chromatin accessibility or the expression levels of the set of chromatin regulatory genes. The likelihood of survival of the individual without anthracycline treatment is determined utilizing a second survival model and the chromatin accessibility or the expression levels of the set of chromatin regulatory genes. The likelihood of survival of the individual with anthracycline treatment is determined to be greater than the likelihood of survival of the individual without anthracycline treatment. The individual is treated with a treatment regimen including anthracycline based upon the determination that the likelihood of survival of the individual with anthracycline treatment is greater than the likelihood of survival of the individual without anthracycline treatment.

In another embodiment, the biopsy is a liquid biopsy or a solid tissue biopsy extracted from a tumor or collection of cancerous cells.

In yet another embodiment, the biopsy is an excision of a tumor performed during a surgical procedure.

In a further embodiment, the chromatin accessibility is assessed by DNase I hypersensitivity, micrococcal nuclease (MNase) patterns, or Assay for Transposase-Accessible Chromatin (ATAC).

In still yet another embodiment, the expression levels of the set of chromatin regulatory genes is assessed by nucleic acid hybridization, RNA-seq, RT-PCR, or immunodetection.

In yet a further embodiment, the set of chromatin regulatory genes comprises at least one of the following genes: ACTL6A, ACTR5, AEBP2, APOBEC1, APOBEC2, APOBEC3C, ARID1A, ARID5B, ATF7IP, ATM, BAZ1B, BAZ2A, BCL11A, BCL7A, CBX2, CCNA2, CDK1, CECR2, CHARC1, CHD4, CHD5, CHD8, DNMT3A, DPF1, DPF3, EED, EHMT1, EHMT2, EZH2, FOXA1, GATAD2A, H1-0, H2AZ2, H2AFX, MACROH2A1, HCFC1, HDAC11, HDAC5, HDAC6, HDAC7, HDAC9, HEMK1, HIST1H2AJ, HIST1H4D, HMG20B, ING3, INO80B, KAT14, KAT2B, KAT6B, KAT7, KDM2A, KDM3B, KDM4A, KDM4B, KDM4C, KDM4D, KDM5C, KDM6B, KDM7A, KMT2A, MAP3K12, MBD2, MBD3, MCRS1, MECOM, MIER2, MTF2, NCAPG, NCAPH2, NCOA3, NEK11, NSD1, PCGF2, PHF1, PHF2, PRDM2, RING1, RSF1, RUVBL2, SAP18, SAP30, SETD1A, SMARCA1, SMARCA2, SMARCC2, SMARCD1, SMARCD3, SMC1B, SMC2, SMC3, SMYD1, SRCAP, SUPT3H, TAF1, TAF5, TAF5L, TAF6L, TOP1, TOP2A, TOP3A, TOP3B, UCHL5, UTY, YY1.

In an even further embodiment, the set of chromatin regulatory genes comprises the following genes: ACTL6A, AEBP2, APOBEC1, ARID5B, ATM, BCL11A, CBX2, CCNA2, CDK1, CECR2, CHARC1, EED, EHMT1, EHMT2, EZH2, FOXA1, GATAD2A, H1-0, H2AZ2, MACROH2A1, HDAC9, KAT14, KAT6B, KAT7, KDM4B, KDM4D, KDM7A, MECOM, NCAPG, NEK11, RING1, SMARCA1, SMARCC2, SMARCD3, SMC1B, SMYD1, TAF5, and TOP2A.

In yet an even further embodiment, the set of chromatin regulatory genes comprises the following genes: ATM, BCL11A, CCNA2, EZH2, FOXA1, MACROH2A1, HDAC9, KAT6B, KDM4B, MECOM, NCAPG, NEK11, SMARCC2 and TAF5.

In still yet an even further embodiment, the set of chromatin regulatory genes comprises the following genes: HDAC9, KAT6B, and KDM4B.

In still yet an even further embodiment, the likelihood of survival with anthracycline treatment and the likelihood of survival without anthracycline treatment are each determined utilizing a survival model select from the group consisting of: Cox proportional hazard model, Cox regularized regression, LASSO Cox model, ridge Cox model, elastic net Cox model, multi-state Cox model, Bayesian survival model, accelerated failure time model, survival trees, survival neural networks, bagging survival trees, random survival forest, survival support vector machines, and survival deep learning models.

In still yet an even further embodiment, the likelihood of survival with anthracycline treatment and the likelihood of survival without anthracycline treatment each incorporate at least one of: tumor grade, metastatic status, lymph node status, and treatment regime.

In still yet an even further embodiment, the likelihood of survival with anthracycline treatment and the likelihood of survival without anthracycline treatment each incorporate gene expression of at least one DNA repair gene, at least one apoptosis regulatory gene, at least one cancer immunology gene, at least one hypoxia response gene, at least one TOP2 localization gene, or at least one drug resistance factor gene.

In still yet an even further embodiment, the contrast between the likelihood of survival of the individual with anthracycline treatment and the likelihood of survival of the individual without anthracycline treatment is above a threshold.

In still yet an even further embodiment, the cancer is acute non lymphocytic leukemia, acute lymphoblastic leukemia, acute myeloblastic leukemia, acute myeloid leukemia Wilms' tumor, soft tissue sarcoma, bone sarcoma, breast carcinoma, transitional cell bladder carcinoma, Hodgkin's lymphoma, malignant lymphoma, bronchogenic carcinoma, ovarian cancer, Kaposi's sarcoma, or multiple myeloma.

In still yet an even further embodiment, the cancer is a Stage I, II, IIIA, IIB, IIC, or IV breast cancer.

In still yet an even further embodiment, the cancer is HER2-positive, ER-positive, or triple negative breast cancer.

In still yet an even further embodiment, the anthracycline is daunorubicin, doxorubicin, epirubicin, idarubicin, valrubicin or mitoxantrone.

In still yet an even further embodiment, the treatment regimen includes non-anthracycline chemotherapy, radiotherapy, immunotherapy or hormone therapy.

In still yet an even further embodiment, the treatment regimen is an adjuvant treatment regimen or a neoadjuvant treatment regimen.

In an embodiment to treat an individual having a cancer, a biopsy is obtained from an individual. The likelihood of survival of the individual with anthracycline treatment is determined utilizing a first survival model and the chromatin accessibility or the expression levels of the set of chromatin regulatory genes. The likelihood of survival of the individual without anthracycline treatment is determined utilizing a second survival model and the chromatin accessibility or the expression levels of the set of chromatin regulatory genes. The likelihood of survival of the individual with anthracycline treatment is determined to not be a threshold greater than the likelihood of survival of the individual without anthracycline treatment. The individual is treated with a treatment regimen excluding anthracycline based upon the determination that the contrast between the likelihood of survival of the individual with anthracycline treatment and the likelihood of survival of the individual without anthracycline treatment is below the threshold.

In another embodiment, the likelihood of survival of the individual with anthracycline treatment is not greater than the likelihood of survival of the individual without anthracycline treatment.

In yet another embodiment, the treatment regimen includes non-anthracycline chemotherapy, radiotherapy, immunotherapy or hormone therapy.

In a further embodiment, the treatment regimen comprises one of: cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, denosumab, bevacizumab, cetuximab, trastuzumab, alemtuzumab, ipilimumab, nivolumab, ofatumumab, panitumumab, or rituximab.

In an embodiment to determine anthracycline responsiveness of neoplastic cells, the expression level of each gene within a set of chromatin regulatory genes within neoplastic cells is determined utilizing a biochemical assay. The set of chromatin regulatory genes comprises HDAC9, KAT6B, and KDM4B. The biochemical assay is nucleic acid hybridization, RNA-seq, RT-PCR, or immunodetection. High expression of KAT6B and KDM4B and low expression of BCL11A indicates the neoplastic cells are responsive to anthracycline.

In another embodiment, the expression of KAT6B and KDM4B is high and that the expression of BCL11 is low within the neoplastic cells is determined. Anthracycline is administered to the neoplastic cells.

In yet another embodiment, the expression of BCL11A is determined via nucleic acid hybridization utilizing a nucleic acid probe comprising a sequence between ten and fifty bases complementary to SEQ. ID No. 6.

In a further embodiment, the expression of KAT6B is determined via nucleic acid hybridization utilizing a nucleic acid probe comprising a sequence between ten and fifty bases complementary to SEQ. ID No. 23.

In still yet another embodiment, the expression of KDM4B is determined via nucleic acid hybridization utilizing a nucleic acid probe comprising a sequence between ten and fifty bases complementary to SEQ. ID No. 25.

In yet a further embodiment, the expression of BCL11A is determined via RT-PCR amplification utilizing a set of primers to produce an amplicon comprising a sequence between fifty and one thousand bases complementary to SEQ. ID No. 6.

In an even further embodiment, the expression of KAT6B is determined via RT-PCR amplification utilizing a set of primers to produce an amplicon comprising a sequence between fifty and one thousand bases complementary to SEQ. ID No. 23.

In yet an even further embodiment, the expression of KDM4B is determined via RT-PCR amplification utilizing a set of primers to produce an amplicon comprising a sequence between fifty and one thousand bases complementary to SEQ. ID No. 25.

In an embodiment of a kit for determining anthracycline responsiveness of neoplastic cells via RT-PCR, the kit includes a plurality of primer sets. Each primer set to produce an amplicon of a chromatin regulatory gene. The plurality of primer sets include a primer set to detect BCL11A expression. The BCL11A primer set produces an amplicon comprising a sequence between fifty and one thousand bases complementary to SEQ. ID No. 6. The plurality of primer sets include a primer set to detect KAT6B expression. The KAT6B primer set produces an amplicon comprising a sequence between fifty and one thousand bases complementary to SEQ. ID No. 23. The plurality of primer sets include a primer set to detect KDM4B expression. The KDM4B primer set produces an amplicon comprising a sequence between fifty and one thousand bases complementary to SEQ. ID No. 25.

In an embodiment of a kit for determining anthracycline responsiveness of neoplastic cells via nucleic acid hybridization, the kit includes a plurality of hybridization probes. Each hybridization probe comprises a sequence complementary to chromatin regulatory gene. The plurality of hybridization probes include a hybridization probe to detect BCL11A expression. The BCL11A hybridization probe comprises a sequence between ten and fifty bases complementary to SEQ. ID No. 6. The plurality of hybridization probes include a hybridization probe to detect KAT6B expression. The KAT6B hybridization probe comprises a sequence between ten and fifty bases complementary to SEQ. ID No. 23. The plurality of hybridization probes include a hybridization probe to detect KDM4B expression. The KDM4B hybridization probe comprises a sequence between ten and fifty bases complementary to SEQ. ID No. 25.

In an embodiment for identifying chromatin genes indicative of anthracycline responsiveness, data results of a treatment a panel of neoplastic cell lines with an anthracycline to determine each cell line's responsiveness to anthracyclines is obtained. Differential analysis is performed on the expression of chromatin regulatory genes between anthracycline-sensitive and anthracycline-resistant cell lines. Chromatin regulatory genes indicative of anthracycline responsiveness are identified from the differential analysis.

In an embodiment for identifying chromatin genes indicative of anthracycline responsiveness, data results from a collection of treated individuals having a neoplasm to determine each individual's neoplasm's responsiveness to the individual's treatment is obtained. Analysis on the association among expression of chromatin regulatory genes, treatment regime, and survival on the data results is performed. Chromatin regulatory genes that are indicative of anthracycline response are identified from the analysis.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
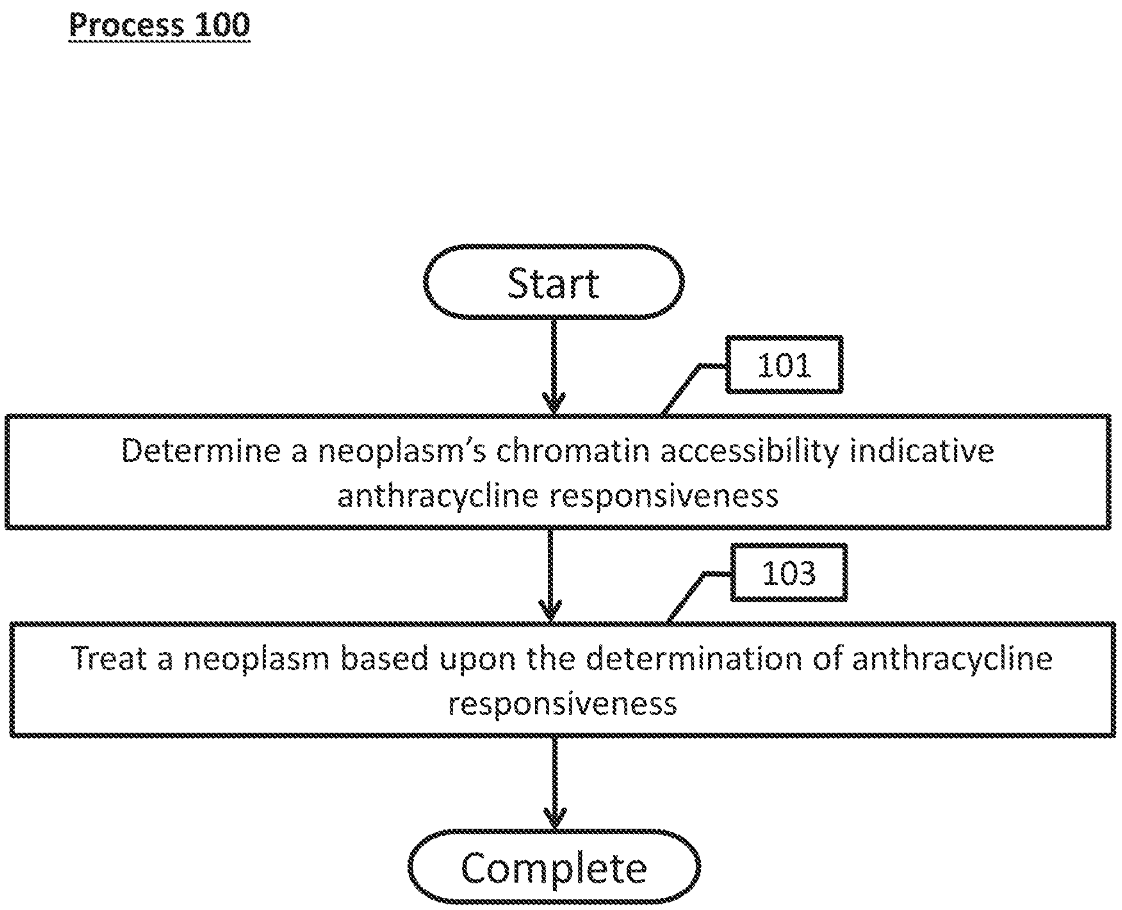
FIG. 1 provides a flow diagram of a method to treat a neoplasm based upon anthracycline responsiveness in accordance with an embodiment of the invention.

Turning now to the drawings and data, methods of treating neoplasms taking into account the ability to respond to anthracycline are provided. Many embodiments are directed to obtaining an indication of whether a neoplasm (e.g., cancer) would be sensitive to or resistant of anthracycline treatment and then treating that neoplasm accordingly. In various embodiments, particular chromatin states within neoplastic cells provide an indication of anthracycline responsiveness. In some embodiments, the chromatin architecture within these cells are determined by their expression levels of chromatin regulatory genes (CRGs) to provide an indication of anthracycline responsiveness (i.e., high or low expression of various CRGs indicate anthracycline sensitivity, and vice versa). In some embodiments, the chromatin states within these cells are determined by their chromatin accessibility to provide an indication of anthracycline responsiveness (i.e., open chromatin is sensitive to anthracycline whereas condensed chromatin is resistant). In accordance with multiple embodiments, neoplasms exhibiting an ability to respond to anthracycline, as determined by their CRG expression or chromatin accessibility, are treated with an anthracycline chemotherapeutic. In accordance with many embodiments, neoplasms exhibiting resistance to anthracycline, as determined by their CRG expression or chromatin accessibility, are treated by alternative therapies and agents other than anthracycline.

A number of embodiments are directed to utilizing a computational and/or statistical models to identify CRGs and expression levels that are indicative of anthracycline responsiveness. Accordingly, embodiments are directed to the use of chromatin accessibility and/or identified sets of one or more CRGs within these models to determine whether a particular neoplasm will respond to anthracycline and treat the neoplasm accordingly. In many embodiments, survival models incorporating chromatin accessibility and/or CRG expression data is utilized to determine the likelihood of a survival outcome with and without anthracycline treatment. When survival models suggest that the likelihood of survival is greater with anthracycline treatment, then the individual is to be treated with anthracycline. Conversely, when the survival models suggest that the likelihood of survival is not greater with anthracycline treatment, then the individual is to be treated with an alternative other than anthracycline. Survival models include (but are not limited to) Cox proportional hazard model, Cox regularized regression, LASSO Cox model, ridge Cox model, elastic net Cox model, multi-state Cox model, Bayesian survival model, accelerated failure time model, survival trees, survival neural networks, ensemble models including bagging survival trees or random survival forest, kernel models including survival support vector machines, or survival deep learning models. Various survival outcomes can be utilized, including (but not limited to) overall survival, disease-specific survival, relapse-free survival, and distant relapse-free survival.

Anthracyclines such as doxorubicin and epirubicin have played an important role in chemotherapy for early-stage breast cancer for nearly 30 years. The use of anthracyclines, however, can have unwanted side effects, including increased risk of cardiac events and death, as well as a risk (<1%) of treatment-related leukemia or myelodysplastic syndrome. Given the risks associated with anthracycline treatment, there remains a critical need to understand the biological mechanisms that dictate potential anthracycline benefit. In some cases, it may be of benefit to treat with other classes of chemotherapeutics, such as taxanes. Anthracyclines are also often used to treat individuals that have a high likelihood of cancer relapse.

Anthracyclines are thought to work through several mechanisms, including inhibition of topoisomerase II (TOP2) religation, which prevents DNA double-stranded breaks from repairing, resulting in an accumulation of DNA breaks and ultimately leading to cell death. TOP2 performs decatenation and torsional stress of DNA by strand cleavage followed by strand passage and religation of the DNA. TOP2 requires chromatin regulators to create accessible chromatin in order to cleave DNA. Accordingly, TOP2 religation inhibitors can only promote cell death when TOP2 is interacting with accessible DNA. Thus, various embodiments of the invention take advantage of the fact that alterations in expression of various CRGs can alter chromatin accessibility and reduce the ability of TOP2 to access DNA, which in turn results in anthracycline resistance.

Accordingly, several embodiments are directed to determining chromatin accessibility and/or expression levels of a set of one or more CRGs that indicate responsiveness to anthracycline treatment of a neoplasm. In many of these embodiments, a neoplasm with a more open chromatin state (also referred to as relaxed or accessible chromatin) indicates sensitivity to anthracycline and thus confers anthracycline cytotoxicity of the neoplasm. Conversely, in many of these embodiments, a neoplasm with a more closed chromatin state (also referred to as condensed or inaccessible chromatin) indicates a lack of sensitivity to anthracycline and thus the neoplasm is likely to resist anthracycline toxicity.

Anthracycline Treatment of Neoplasia Determined by Chromatin Accessibility or Chromatin Regulatory Gene Expression A number of embodiments are directed to treating neoplasms (e.g., cancer) by determining whether the neoplasm to be treated is responsive to anthracycline as indicated by the neoplasm's chromatin architecture. In some embodiments, a neoplasm having an open chromatin architecture indicates that the neoplasm is likely to respond favorably to anthracycline treatment (i.e., anthracycline will be more cytotoxic in neoplasms having relaxed chromatin). Conversely, in some embodiments, a neoplasm having a closed chromatin architecture indicates that the neoplasm is anthracycline resistant (i.e., anthracycline will not have a cytotoxic effect in neoplasm having condensed chromatin). In various embodiments, determination of chromatin accessibility and/or expression levels of a set of one or more CRGs of a neoplasm are used to determine the neoplasm's chromatin status and thus an appropriate course of treatment for that neoplasm.

A neoplasm's chromatin accessibility can be determined via various assays, including (but not limited to) DNase I hypersensitivity, micrococcal nuclease (MNase) patterns, and Assay for Transposase-Accessible Chromatin (ATAC). As detailed herein, chromatin accessibility is regulated by CRGs and their expression levels can be used to infer chromatin accessibility. Furthermore, based on studies described herein, it is now known that CRG expression levels of a cancer correlate directly with its responsiveness to anthracycline treatment. CRG expression levels thus provide a diagnostic tool to determine whether a cancer will respond to anthracycline treatment and to inform appropriate treatment.

A list of CRGs within the human genome have been identified from gene ontology analysis (Table 1). Of these CRGs, a number of CRGs have been further identified to be robust indicators of anthracycline responsiveness (Table 2). In accordance with various embodiments, expression levels of a set CRGs by a neoplasm is determined utilizing a biochemical technique, including (but not limited to) nucleic acid hybridization, RNA-seq, RT-PCR, and immunodetection. In several embodiments, the determined CRG expression levels are utilized to determine appropriate treatment based on the neoplasm's anthracycline responsiveness.

Provided in FIG. 1 is an embodiment of an overview method to treat a neoplasm (e.g., cancer). As depicted, process 100 can begin by determining (101) a neoplasm's chromatin accessibility indicative anthracycline responsiveness. In several embodiments, a neoplasm is responsive anthracycline treatment when its chromatin is more accessible. Conversely, in many embodiments, a neoplasm is less responsive to anthracycline when its chromatin is more condensed and less accessible. In some embodiments, chromatin accessibility can be determined by various genomic DNA accessibility assays. In various embodiments, chromatin accessibility is inferred by expression levels of a set of CRGs. It should be noted that expression levels of a number CRGs have been identified that associate with anthracycline responsiveness. Accordingly, many embodiments are directed to determining expression levels of a set of one or more CRGs to indicate anthracycline responsiveness.

Determination of genomic DNA accessibility can be determined by a number of known biochemical assays in the art. These accessibility assays include (but are not limited to) DNase I hypersensitivity, micrococcal nuclease (MNase) patterns, and Assay for Transposase-Accessible Chromatin (ATAC). Accordingly, genomic DNA from neoplastic cells can be examined using an accessibility assay. Results displaying a high a level of chromatin accessibility indicate that anthracycline would be toxic to the neoplasm. Conversely, results displaying a low level of chromatin accessibility indicate that the neoplasm is anthracycline resistant and thus an alternative treatment would be more beneficial.

Expression levels of CRGs have been found to correlate with a neoplasm's ability to respond to anthracycline treatments. As is discussed in further detail below, anthracycline sensitivity is indicated by high expression of some CRGs and low expression of some other CRGs, and vice versa. Accordingly, by determining the expression level of a set of one or more CRGs, the anthracycline responsiveness of a neoplasm can be determined.

Expression of CRGs can be determined by a number of ways, in accordance with several embodiments and as understood by those in the art. Typically, RNA and/or proteins are examined directly in the neoplastic cells or in an extraction derived from the neoplastic cells. Expression levels of RNA can be determined by a number of methods, including (but not limited to) hybridization techniques (e.g., in situ hybridization (ISH)), nucleic acid proliferation techniques (e.g., RT-PCR), and sequencing (e.g., RNA-seq). Expression levels of proteins can be determined by a number of methods, including (but not limited to) immunodetection (e.g., enzyme-linked immunosorbent assay (ELISA)) and spectrometry (e.g., mass spectrometry).

In several embodiments, genomic DNA accessibility and/or gene expression levels are defined relative to a known expression result. In some instances, genomic DNA accessibility and/or gene expression levels of a test sample is determined relative to a control sample or molecular signature (i.e., a sample/signature with a known anthracycline responsiveness). A control sample/signature can either be highly resistant (i.e., null control), highly sensitive (i.e., positive control), or any other level of responsiveness that can be relatively quantified. Accordingly, when the genomic DNA accessibility and/or the CRG expression level of a test sample is compared to one or more controls, the relative genomic DNA accessibility and/or expression level can indicate whether the test sample is responsive to anthracycline. In some instances, CRG expression levels are determined relative to a stably expressed biomarker (i.e., endogenous control). Accordingly, when CRG expression levels exceed a certain threshold relative to a stably expressed biomarker, the level of expression is indicative of anthracycline responsiveness. In some instances, genomic DNA accessibility and/or CRG expression level is determined on a scale. Accordingly, various genomic DNA accessibility expression level thresholds and ranges can be set to classify anthracycline responsiveness and thus used to indicate a test sample's responsiveness. It should be understood that methods to define expression levels can be combined, as necessary for the applicable assessment. For example, standard quantitative reverse transcriptase polymerase chain reaction (RT-PCR) assessments often utilize both control samples and stably expressed biomarkers to elucidate expression levels.

Returning to FIG. 1, a neoplasm is treated (103) based upon the determination of anthracycline responsiveness. In a number of embodiments, an individual having a neoplasm is treated to remove and/or kill the neoplasm. In various embodiments, a treatment entails chemotherapy, radiotherapy, immunotherapy, a dietary alteration, physical exercise, or any combination thereof. Embodiments are directed to treatment regimens comprising the chemotherapeutic anthracycline for a neoplasm that is sensitive to anthracycline. Various embodiments encompass treatment regimens that exclude anthracycline when it has been determined that a neoplasm is resistant to anthracycline.

Chromatin Regulatory Genes Indicative of Anthracycline Responsiveness

Several embodiments are directed to the use of expression levels of a set of one or more CRGs that are indicative of anthracycline responsiveness. Accordingly, responsiveness of a neoplasm to anthracycline can be determined by measuring the RNA and/or protein expression levels of CRGs.

Provided in Table 1 is a list of over 400 genes classified as CRGs, as determined by from the literature and gene ontology annotation. In this description, a CRG is a gene involved in modifying or maintaining (including assisting in modifying and maintaining) genomic chromatin architecture. Accordingly, as it would be understood in the art, the precise list of genes classified as CRGs can be altered, as enlightening knowledge surrounding chromatin regulators is further understood.

Provided in Table 2 is a list of CRGs found to be significant in various clinical and biological studies. The significant CRGs were discovered utilizing a consensus of in vitro assays including 87 breast cancer cell lines across 11 cell line/response datasets and three evaluations of a metacohort study of 760 early-stage breast cancer patients. Three genes were found to be significant in the in vitro assay and all three evaluations of the metacohort study (HDAC9, KAT6B, and KDM4B). Ten genes were found to be significant in the in vitro assay and at least one evaluation of the metacohort (ATM, BCL11A, CCNA2, EZH2, FOXA1, MACROH2A1, HDAC9, KAT6B, KDM4B, MECOM, NCAPG, NEK11, SMARCC2 and TAF5). Thirty eight genes were found to be significant in the in vitro studies (ACTL6A, AEBP2, APOBEC1, ARID5B, ATM, BCL11A, CBX2, CCNA2, CDK1, CECR2, CHARC1, EED, EHMT1, EHMT2, EZH2, FOXA1, GATAD2A, H1-0, H2AZ2, MACROH2A1, HDAC9, KAT14, KAT6B, KAT7, KDM4B, KDM4D, KDM7A, MECOM, NCAPG, NEK11, RING1, SMARCA1, SMARCC2, SMARCD3, SMC1B, SMYD1, TAF5, and TOP2A). For further description of these studies, please see the Exemplary Embodiment Section. Please also see Table 10 and the Sequence Listing for gene sequences.

As shown in Table 2, several CRGs were found to positively correlate with anthracycline response (i.e., high expression of CRG correlates with ability of anthracycline to kill neoplastic cells, whereas low expression correlates with anthracycline resistance). Likewise, several CRGs were found to inversely correlate with anthracycline response (i.e., high expression of CRG correlates with anthracycline resistance, whereas low expression correlates with ability of anthracycline to kill neoplastic cells).

In a number of embodiments, expression levels of a set of one or more of CRGs identified as significant is used to determine anthracycline response. In many of these embodiments, RNA and/or protein expression levels from a neoplasm is examined. Accordingly, based on the expression levels of the set of significant CRGs, a neoplasm is treated with anthracycline when the expression levels are indicative of anthracycline sensitivity. Alternatively, a neoplasm is not treated with anthracycline when the expression levels are indicative of anthracycline response.

Methods of Detecting Chromatin Regulatory Gene Expression

Expression of CRGs can be detected by a number of methods in accordance with various embodiments of the invention, as would be understood by those skilled in the art. In several embodiments, expression of CRGs is detected at the RNA level. In many embodiments, expression of CRGs is detected at the protein level.

The source of biomolecules (e.g., RNA and protein) to determine expression can be derived de novo (i.e., from a biological source). Several methods are well known to extract biomolecules from biological sources. Generally, biomolecules are extracted from cells or tissue, then prepped for further analysis. Alternatively, RNA and proteins can be observed within cells, which are typically fixed and prepped for further analysis. The decision to extract biomolecules or fix tissue for direct examination depends on the assay to be performed, as would be understood by those skilled in the art.

In several embodiments, biomolecules are extracted and/or examined in a biopsy derived from cells and/or tissues to be treated. In many cases, the cells to be treated are neoplastic cells of a neoplasia (e.g., cancer) of an individual and thus the biopsy is the collection of neoplastic cells or excised neoplastic tissue. In some embodiments, a liquid biopsy is utilized, in which cell-free nucleic acid molecules (i.e., cfDNA or cfRNA) within blood are extracted. When a liquid biopsy is utilized, extracted cell-free nucleic acids are to include nucleic acids derived from neoplastic cells of a neoplasia. The precise source and method to extract and/or examine biomolecules ultimately depends on the assay to be performed and the availability of biopsy.

A number of assays are known to measure and quantify expression of biomolecules. Expression levels of RNA can be determined by a number of methods, including (but not limited to) hybridization techniques, nucleic acid proliferation techniques, and sequencing. A number of hybridization techniques can be used, including (but not limited to) ISH, microarrays (e.g., Affymetrix, Santa Clara, CA), nanoString nCounter (Seattle, WA), and Northern blot. Likewise, a number of nucleic acid proliferation and sequencing techniques can be used, including (but not limited to) RT-PCR and RNA-seq. In several embodiments, the RNA sequences to be detected are CRGs that have been identified to be significantly correlated in anthracycline response, such as the genes listed in Table 2. Accordingly, some embodiments are directed to identifying CRG sequences of the associated Sequence ID Nos. listed in Table 10. Specifically, in accordance with a number of embodiments, primers and probes capable of hybridizing with the sequences listed in Tables 2 and 10 can be utilized for detection and expression quantification.

As understood in the art, only a portion of the gene may need to be detected in order to have a positive detection. In some instances, genes can be detected with identification of as few as ten nucleotides. In many hybridization techniques, detection probes are typically between ten and fifty bases, however, the precise length will depend on assay conditions and preferences of the assay developer. In many application techniques, amplicons are often between fifty and one-thousand bases, which will also depend on assay conditions and preferences of the assay developer. In many sequencing techniques, genes are identified with sequence reads between ten and several hundred bases, which again will depend on assay conditions and preferences of the assay developer.

It should be understood that minor variations in gene sequence and/or assay tools (e.g., hybridization probes, amplification primers) may exist but would be expected to provide similar results in a detection assay. These minor variations are to include (but not limited to) minor insertions, minor deletions, single nucleotide polymorphisms, and other variations due to assay design. In some embodiments, detections assays are able to detect CRGs, such as those listed in Tables 2 and 10, having high homology but not perfect homology (e.g., 70%, 80%, 90% or 95% homology).

Expression levels of proteins can be determined by a number of methods, including (but not limited to) immunodetection and spectrometry (e.g., mass spectrometry). A number of immunodetection techniques can be used, including (but not limited to) ELISA, immunohistochemistry (IHC), flow cytometry, dot blot and western blot.

It should also be understood that several genes, including many of which are listed in Table 2, have a number of isoforms that are expressed. As understood in the art, many alternative isoforms would be understood to confer similar indication of anthracycline responsiveness. Accordingly, alternative isoforms of CRGs that are significantly correlated in anthracycline response are also covered in some embodiments. Furthermore, sequences that are not explicitly provided in the Sequence Listing but are of an isoform of a CRG indicative of anthracycline response are to be covered in various embodiments of the invention, as it would be understood in the art.

In many embodiments, an assay is used to measure and quantify gene expression. The results of the assay can be used to determine relative gene expression of a tissue of interest. For example, the nanoString nCounter, which can quantify up to 800 hundred nucleic acid molecule sequences in one assay utilizing a set of complement nucleic acids and probes, which can be used to determine the relative expression of a set of CRGs. The resulting expression can be compared to a control sample and/or molecular signature having a known anthracycline response, thus determining the anthracycline response on the tissue of interest. Based on the CRG expression profile, a patient can be treated accordingly. In some embodiments the expression of a plurality of CRG genes is utilized to compose a CRG gene expression signature that is predictive of response via statistical or classifier methods as described herein.

In several embodiments, kits are used to determine the ability of a neoplasm to respond to anthracycline treatments. A nucleic acid detection kit, in accordance with various embodiments, includes a set of hybridization-capable complement sequences (e.g., cDNA) and/or amplification primers specific for a set of CRGs. In some embodiments, probes and/or amplification primers span across an exon junction such that it cannot detect genomic sequence. A peptide detection kit, in accordance with various embodiments, includes a set of antigen-detecting biomolecules (e.g., antibodies) having specificity and affinity for a set of CRGs. In some instances, a kit will include further reagents sufficient to facilitate detection and/or quantitation of a set of CRGs. In some instances, a kit will be able to detect and/or quantify for at least 5, 10, 15, 20, 25, 30, 40 50, 60, 70, 80, 90, or 100 CRGs.

In a number of embodiments, a set of hybridization-capable complement sequences are immobilized on an array, such as those designed by Affymetrix. In many embodiments, a set of hybridization-capable complement sequences are linked to a "bar code" to promote detection of hybridized species and provided such that hybridization can be performed in solution, such as those designed by NanoString. In several embodiments, a set of primers (and, in some cases probes) to promote amplification and detection of amplified species are provided such that a PCR can be performed in solution, such as those designed by Applied Biosystems of ThermoScientific (Foster City, CA). In some embodiments, a set of antibodies to bind CRG peptides such that binding of a CRG protein (or peptide thereof) by an antibody can be detected, such as those designed by Abcam (Cambridge, UK).

Clinical Methods to Inform Cancer Treatment

It is now understood that success of anthracycline treatment for cancer is influenced by the cancer's chromatin accessibility. When the cancer chromatin is more relaxed, anthracyclines have higher toxicity on the cancer cells. Likewise, when the cancer chromatin is more condensed, anthracyclines are less toxic on the cancer cells and thus have less effective. Because anthracyclines have undesired side effects, including cardiotoxicity, that could severely harm a treatment recipient, it is advantageous to understand whether that individual would benefit from the treatment.

Figure 2:
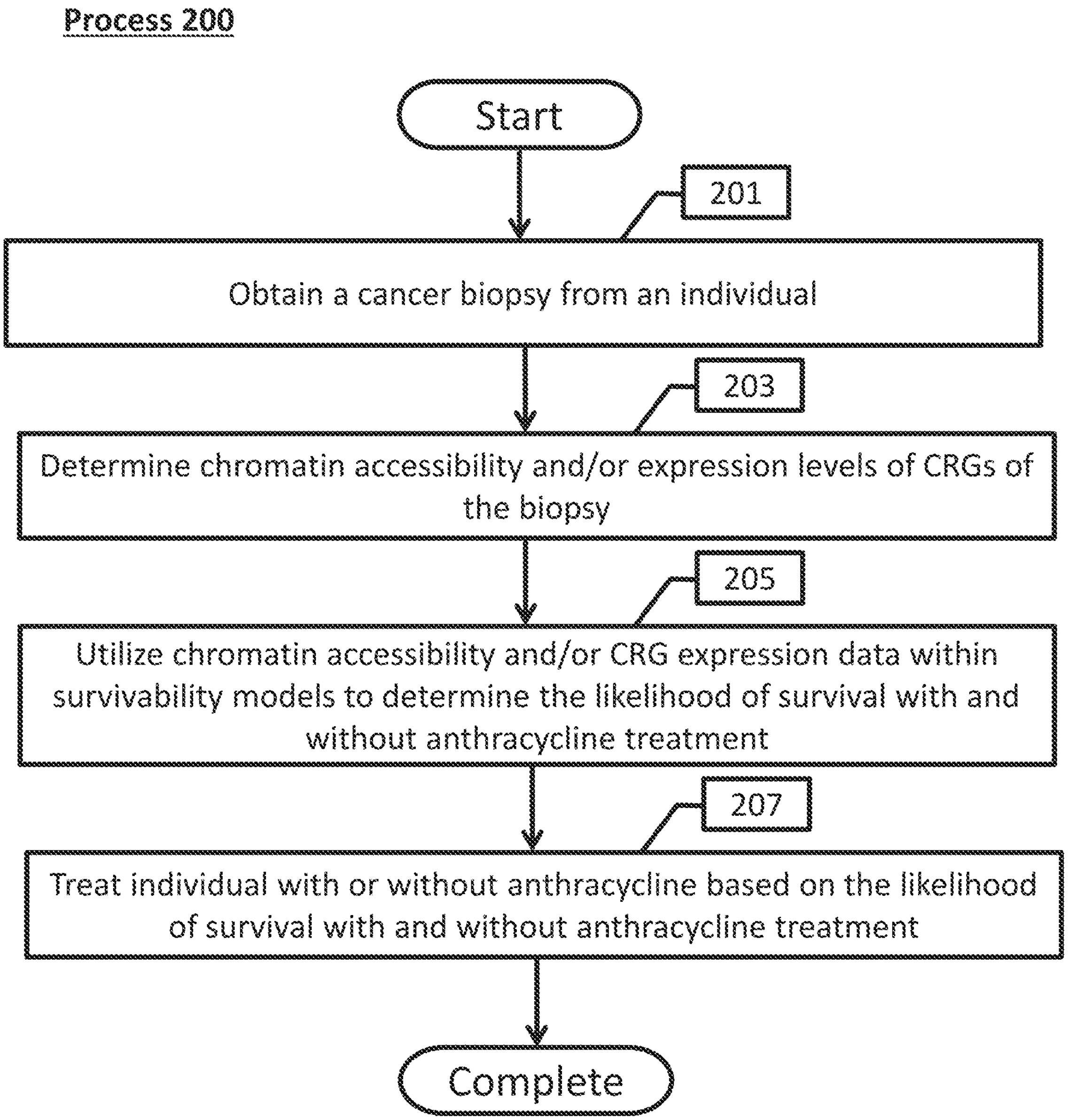
FIG. 2 provides a flow diagram of a clinical method to assess and treat an individual having cancer based upon anthracycline responsiveness in accordance with an embodiment of the invention.

Provided in FIG. 2 is an embodiment of a method to determine whether an individual having cancer would benefit from anthracycline treatment, and then treating that individual accordingly. The method can begin by obtaining (201) a cancer biopsy of an individual. Any appropriate cancerous biopsy can be extracted, such as (for example) a biopsy of a tumor, collection of cancerous cells, or a liquid biopsy (e.g., blood extraction) that includes cell-free nucleic acids derived from cancerous cells. In some instances, a biopsy can be an excision of a tumor performed during a surgical procedure to remove cancerous tissue.

Utilizing the cancer biopsy, chromatin accessibility and/or expression levels of CRGs of the biopsy are determined (203). Any appropriate means to determine chromatin accessibility and/or expression levels can be utilized, including various methods described herein. Chromatin accessibility can be determined via various assays, including (but not limited to) DNase I hypersensitivity, micrococcal nuclease (MNase) patterns, and Assay for Transposase-Accessible Chromatin (ATAC). Expression levels of a set CRGs by a neoplasm is determined utilizing a biochemical technique, including (but not limited to) nucleic acid hybridization, RNA-seq, RT-PCR, and immunodetection. In many embodiments, the set of CRGs to be examined are those determined to correlate with anthracycline responsiveness, such as the CRGs listed in Tables 2 and 10.

In several embodiments, chromatin DNA, RNA transcripts and/or peptide products are extracted from the biopsy and processed for analysis. Any appropriate means for extracting biomolecules can be utilized, as appreciated in the art. In some embodiments, chromatin DNA, RNA transcripts and/or peptide products are examined within the cellular source, as described by methods herein.

The resultant chromatin accessibility and/or CRG expression data is utilized (205) within statistical or classifier survival models to determine the likelihood of survival with and without anthracycline treatment. In many instances, survival models are utilized to determine the likelihood of survival with anthracycline treatment and the likelihood of survival without anthracycline treatment. Any appropriate type of survival model can be utilized, including (but not limited to) Cox proportional hazard model, Cox regularized regression, LASSO Cox model, ridge Cox model, elastic net Cox model, multi-state Cox model, Bayesian survival model, accelerated failure time model, survival trees, survival neural networks, ensemble models including bagging survival trees or random survival forest, kernel models including survival support vector machines, or survival deep learning models. In various embodiments, the survival models are used to compute an outcome.

Cox proportion hazard models are statistical survival models that relate the time that passes to an event and the covariates associated with that quantity in time (See D. R. Cox, *J. R. Stat. Soc. B* 34, 187-220 (1972), the disclosure of which is herein incorporated by reference). To utilize Cox proportional hazards models, in some embodiments, clinical, molecular, and integrative subtype features are included. In some embodiments, features can be linear and/or polynomial transformed and interaction can include variable selection. In some embodiments, to further simplify the model, stepwise variable selection can be incorporated into the cross validation scheme. Any appropriate computational package can be utilized and/or adapted, such as (for example), the RMS package (https://www.rdocumentation.org/packages/rms).

A multi-state Cox model could be utilized to account for different timescales (time from diagnosis and time from relapse), competing causes of death (cancer death or other causes), clinical covariates or age effects, and distinct baseline hazards for different histopathologic or molecular subgroups (see Rueda et al. Nature 2019. H. Putter, M. Fiocco, & R. B. Geskus, Stat. Med. 26, 2389-430 (2007); O. Aalen, O. Borgan, & H. Gjessing, Survival and Event History Analysis—A Process Point of View. (Springer-Verlag New York, 2008); and T. M. Therneau & P. M. Grambsh, Modeling Survival Data: Extending the Cox Model. (Springer-Verlag New York, 2000); the disclosures of which are each herein incorporated by reference). In many embodiments, a multistate statistical model is fit to the dataset, such that the chronology of cancer and competing risks of death due to cancer or other causes are accounted. In some embodiments, the hazards of occurrence of each of these states are modeled with a non-homogenous semi-Markov Chain with two absorbent states (Death/Cancer and Death/Other).

Shrinkage based methods include (but not limited to) regularized lasso (R. Tibshirani *Stat. Med.* 16, 385-95 (1997), the disclosure of which is herein incorporated by reference), lassoed principal components (D. M. Witten and R. Tibshirani *Ann. Appl. Stat.* 2, 986-1012 (2008), the disclosure of which is herein incorporated by reference), and shrunken centroids (R. Tibshirani, et al., *Proc. Natl. Acad. Sci. USA* 99, 6567-72 (2002), the disclosure of which is herein incorporated by reference). Any appropriate computation package can be utilized and/or adapted, such as (for example), the PAMR package for shrunken centroid (https://www.rdocumentation.org/packages/pamr/versions/1.56.1).

Tree based models include (but not limited to) survival random forest (H. Ishwaran, et al., *Ann. Appl. Stat.* 2, 841-60 (2008), the disclosure of which is herein incorporated by reference) and random rotation survival forest (L. Zhou, H. Wang, and Q. Xu, *Springerplus* 5, 1425 (2016), the disclosure of which is herein incorporated by reference). In some embodiments, the hyperparameter corresponds to the number of features selected for each tree. Any appropriate setting for the number of trees can be utilized, such as (for example) 1000 trees. Any appropriate computation package can be utilized and/or adapted, such as (for example), the RRotSF package for random rotation survival forest (https://github.com/whcsu/RRotSF).

Bayesian methods include (but are not limited to) Bayesian survival regression (J. G. Ibrahim, M. H. Chen, and D. Sinha, Bayesian Survival Analysis, Springer (2001), the disclosure of which is herein incorporated by reference) and Bayes mixture survival models (A. Kottas *J. Stat. Pan. Inference* 3, 578-96 (2006), the disclosure of which is herein incorporated by reference). In some embodiments, sampling is performed with a multivariate normal distribution or a linear combination of monotone splines (See B. Cai, X. Lin, and L. Wang, *Comput. Stat. Data Anal.* 55, 2644-51 (2011), the disclosure of which is herein incorporated by reference). Any appropriate computation package can be utilized and/or adapted, such as (for example), the ICBayes package (https://www.rdocumentation.org/packages/ICBayes/versions/1.0/topics/ICBayes).

Kernel based methods include (but not limited to) survival support vector machines (L. Evers and C. M. Messow, *Bioinformatics* 24, 1632-38 (2008), the disclosure of which is herein incorporated by reference), kernel Cox regression (H. Li and Y. Luan, *Pac. Symp. Biuocomp.* 65-76 (2003), the disclosure of which is herein incorporated by reference), and multiple kernel learning (O. Dereli, C. Oguz, and M. Gonen *Bioinformatics* (2019), the disclosure of which is herein incorporated by reference). It is to be understood that kernel based methods can include support vector machines (SVM) and survival support vector machines with polynomial and Gaussian kernel, where hyperparameter C specifies regularization (See L. Evers and C. M. Messow, cited supra). In some embodiments, multiple kernel learning (MLK) approaches combine features in kernels, including kernels embed clinical information, molecular information and integrative subtype. Any appropriate computation package can be utilized and/or adapted, such as (for example), the path2surv package (https://github.com/mehmetgonen/path2surv).

Neural network methods include (but not limited to) DeepSury (J. L. Katzman, et al., *BMC Med. Res. Methodol.* 18, 24 (2018), the disclosure of which is herein incorporated by reference), and SuvivalNet (S. Yousefi, et al., *Sci. Rep.* 7, 11707 (2017), the disclosure of which is herein incorporated by reference). Any appropriate computation package can be utilized and/or adapted, such as (for example), the Optunity package (https://pypi.org/project/Optunity/).

In several embodiments, in order to ensure that a model is not overfitted, models are trained using an X-times, and cross validated X-fold scheme (e.g., 10-fold training, 10-fold cross validation). Sample data can be split into subsets, and some data is used to train the model and some data is used to evaluate the model. By using this method, it can be assured that all data are validated at least once and no sample is used for both training and validation at the same time, all while the X-fold cross validation minimized sampling bias. A training/cross-validation approach also enables evaluation of the stability of the predictions by calculating confidence intervals, which facilitates model comparisons. Additionally, an internal cross validation scheme can be employed for hyperparameter specification.

Within a survival model, various survival outcomes can be utilized, including (but not limited to) overall survival, disease-specific survival, relapse-free survival, and distant relapse-free survival, dependent on the type of outcome that is desired. Overall survival is the time from diagnosis to death (any death, including non-cancer related deaths). Disease specific survival is time from diagnosis to death from cancer. Relapse-free survival is time from diagnosis until tumor recurrence (local or distant) or death. Distant relapse-free survival is time from diagnosis until distal tumor recurrence (metastasis) or death.

A number of parameters can be incorporated into the model, including (but not limited to) CRG expression or chromatin accessibility levels, tumor grade, metastatic status, lymph node status, treatment regime, and expression of other genes that can impact cancer progression and/or treatment. In regards to CRG expression and chromatin accessibility, appropriate parameter definitions can be utilized. For example, CRG expression can include any appropriate set of CRGs, where each CRG its own parameter. The expression level can be entered into the model on an appropriate scale, or can be entered in categorically (e.g., high expression vs. low expression) Alternatively, CRG expression levels of sets of CRGs can be analyzed and then clustered together and/or tallied, and then utilized as a single scalar or categorical parameter within the model. In another example, chromatin accessibility can be determined and then utilized as a scalar or categorical parameter within the model.

In many embodiments, the CRGs to be utilized in the survival model include one or more CRGs provided in Table 2. In some embodiments, CRGs to be utilized in the model include HDAC9, KAT6B, and KDM4B. In some embodiments, CRGs to be utilized in the model include ATM, BCL11A, CCNA2, EZH2, FOXA1, MACROH2A1, HDAC9, KAT6B, KDM4B, MECOM, NCAPG, NEK11, SMARCC2 and TAF5. In some embodiments, CRGs to be utilized in the model include ACTL6A, AEBP2, APOBEC1, ARID5B, ATM, BCL11A, CBX2, CCNA2, CDK1, CECR2, CHARC1, EED, EHMT1, EHMT2, EZH2, FOXA1, GATAD2A, H1-0, H2AZ2, MACROH2A1, HDAC9, KAT14, KAT6B, KAT7, KDM4B, KDM4D, KDM7A, MECOM, NCAPG, NEK11, RING1, SMARCA1, SMARCC2, SMARCD3, SMC1B, SMYD1, TAF5, and TOP2A.

In a number of embodiments, expression levels of other classes of genes that can impact cancer progression and/or treatment are utilized within the survival model. Other classes of genes that can be utilized include (but are not limited to) DNA repair genes (e.g., BRCA1 or BRCA2), apoptosis regulatory genes (e.g., TP53 or BCL2), cancer immunology genes (e.g., IL2), hypoxia response genes (e.g., HIF1A), TOP2 localization genes (e.g., LATM4B), and drug resistance factor genes (e.g., ABCB1).

A survival model can be developed by various appropriate means. Generally, data describing the parameters to be included within model and the survival outcomes are to be collected from two cohorts of patients: those that receive anthracycline treatment and those that did not. In many embodiments, patient data is to include CRG expression and/or chromatin accessibility of their cancer biopsy. Utilizing these data, a survival model can be built that determines the likelihood of survival for patients receiving anthracycline treatment and the likelihood of survival for patients receiving an alternative treatment. Examples of building survival models are described within the Exemplary Embodiments.

Based on the likelihood of survival with and without anthracycline treatment, an individual can be treated (207) accordingly. In many instances, an individual that has a higher chance of survival with anthracycline compared to likelihood of survival without anthracycline treatment is treated with anthracycline. Likewise, an individual that does not have a higher chance of survival with anthracycline compared to likelihood of survival without anthracycline treatment is treated with an alternative treatment.

In several embodiments, a threshold is utilized to determine whether an individual is treated with anthracycline. Accordingly, the likelihood of survival with anthracycline is contrasted with the likelihood of survival without anthracycline, and when the contrast is greater than a threshold, then the individual is treated with anthracycline. Likewise, when the contrast is less than a threshold, then the individual is treated with an alternative treatment. Any appropriate means of comparison between likelihoods can be utilized, such as (for example) numerical difference or statistical significance. In addition, a threshold can be determined by any appropriate means. In some instances, a threshold is set to maximize a percentage of individuals that would benefit from treatment with anthracycline (e.g., 60%, 70%, 80, 90%, 95%, or 99% of patients benefit from anthracycline treatment).

While specific examples of processes for determining anthracycline benefit and treating a cancer are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for determining anthracycline benefit and treating a cancer appropriate to the requirements of a given application can be utilized in accordance with various embodiments of the invention.

Methods of Treatment

Various embodiments are directed to treatments based on anthracycline responsiveness. As described herein, chromatin accessibility and/or expression levels of a set of CRGs can be used to determine whether a neoplasm would be sensitive to anthracyclines. Based on their responsiveness to anthracyclines, neoplasms (or individuals having a neoplasm) can be treated accordingly.

Several embodiments are directed to the use of medications to treat a neoplasm based on the neoplasm's responsiveness to anthracycline. In some embodiments, medications are administered in a therapeutically effective amount as part of a course of treatment. As used in this context, to "treat" means to ameliorate at least one symptom of the disorder to be treated or to provide a beneficial physiological effect. For example, one such amelioration of a symptom could be reduction of neoplastic cells and/or tumor size.

A therapeutically effective amount can be an amount sufficient to prevent reduce, ameliorate or eliminate the symptoms of diseases or pathological conditions susceptible to such treatment, such as, for example, neoplasms, cancer, or other diseases that may be responsive to anthracycline treatment. In some embodiments, a therapeutically effective amount is an amount sufficient to reduce to induce toxicity in a neoplasm.

As described herein, various neoplasms and cancers can be treated with an anthracycline. Anthracyclines used in treatments include (but are not limited to) daunorubicin, doxorubicin, epirubicin, idarubicin, valrubicin and mitoxantrone. In various embodiments, anthracyclines can be utilized in an adjuvant or a neoadjuvant treatment regime. An adjuvant treatment comprises utilizing anthracycline after surgical excision of a tumor. A neoadjuvant treatment comprises utilizing anthracycline prior to surgical intervention, which may reduce tumor size or improve tumor margins.

In several embodiments, any class of neoplasms having variable responsiveness to anthracycline can be treated, including (but not limited to) acute non lymphocytic leukemia, acute lymphoblastic leukemia, acute myeloblastic leukemia, acute myeloid leukemia Wilms' tumor, soft tissue sarcoma, bone sarcoma, breast carcinoma, transitional cell bladder carcinoma, Hodgkin's lymphoma, malignant lymphoma, bronchogenic carcinoma, ovarian cancer, Kaposi's sarcoma, and multiple myeloma. In many embodiments, breast cancer is to be treated, as the variability of anthracycline responsiveness is well known. Accordingly, any appropriate breast cancer can be treated, including Stage I, II, IIIA, IIB, IIC, and IV breast cancer. Breast cancer with positive and/or negative status for estrogen receptor (ER), progesterone receptor (PR) and human epidermal growth factor 2 (Her2) can also be treated in accordance with various embodiments of the invention.

Anthracyclines may be administered intravenously, intraarterially, or intravesically. The appropriate dosing of anthracyclines is often determined by body surface are and varies by neoplasm type and the selected anthracycline. Generally, anthracyclines can be administered intravenously at dosages from 10 $mg/m^2$ to 300 $mg/m^2$ per week. The following are specific examples of treatment regimens utilizing doxorubicin:

- Acute lymphoblastic leukemia: IV administration at 60 to 75 $mg/m^2$ repeated every 21 days as a single agent OR 40 to 75 $mg/m^2$ repeated every 21 days if combined with other chemotherapeutic agents. Cumulative does not to exceed 550 $mg/m^2$.
- Acute myelogenous leukemia: IV administration at 60 to 75 $mg/m^2$ repeated every 21 days as a single agent OR 40 to 75 $mg/m^2$ repeated every 21 days if combined with other chemotherapeutic agents. Cumulative does not to exceed 550 $mg/m^2$.
- Hodgkin's lymphoma: IV administration at 25 $mg/m^2$ on weeks 1, 3, 5, 7, 9 and 11 in combination with mechlorethamine, vinblastine, vincristine, bleomycin, and prednisone. Total duration is 12 weeks.
- Bladder cancer: Intravesical administration at 50 to 150 mg in 150 ml of saline instilled into bladder and retained for 30 minutes.
- HER2+ breast cancer: IV administration of 60 mg/m2 in combination with cyclophosphamide 600 mg/m2 every 14 days for 4 cycles followed by paclitaxel plus trastuzumab or paclitaxel plus trastuzumab and pertuzumab. Concurrent use of trastuzumab and pertuzumab with an anthracycline should be avoided, as this could increase cardiotoxicity in some individuals.
- ER+ breast cancer: IV administration of 60 mg/m2 in combination with cyclophosphamide 600 mg/m2 every 14 days for 4 cycles followed by paclitaxel every two weeks.
- Triple negative breast cancer: Standard neoadjuvant treatment with IV administration of taxane, alkylator and anthracycline-based chemotherapy.

It is to be understood that these listed treatment regimens are merely examples and several other variations in dosing and schedule of an anthracycline treatment regime may be utilized within various embodiments.

A number of additional or alternative treatments and medications are available to treat neoplasms and cancers, such radiotherapy, chemotherapy, immunotherapy, and hormone treatments. Classes of anti-cancer or chemotherapeutic agents can include alkylating agents, platinum agents, taxanes, vinca agents, anti-estrogen drugs, aromatase inhibitors, ovarian suppression agents, endocrine/hormonal agents, bisphosphonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, and tykerb. Accordingly, an individual may be treated, in accordance with various embodiments, by a single medication or a combination of medications described herein. For example, common treatment combination is cyclophosphamide, methotrexate, and 5-fluorouracil (CMF). Furthermore, several embodiments of treatments further incorporate immunotherapeutics, including denosumab, bevacizumab, cetuximab, trastuzumab, pertuzumab, alemtuzumab, ipilimumab, nivolumab, ofatumumab, panitumumab, and rituximab. Various embodiments include a prolonged hormone/endocrine therapy in which fulvestrant, anastrozole, exemestane, letrozole, and tamoxifen may be administered.

Dosing and therapeutic regimens can be administered appropriate to the neoplasm to be treated, as understood by those skilled in the art. For example, 5-FU can be administered intravenously at dosages between 25 $mg/m^2$ and 1000 $mg/m^2$. Methotrexate can be administered intravenously at dosages between 1 $mg/m^2$ and 500 $mg/m^2$.

Methods to Identify of Chromatin Regulatory Genes Indicative of Anthracycline Responsiveness Many embodiments are directed to methods that identify CRGs indicative of anthracycline responsiveness. In general, identification of CRGs can be performed using neoplastic cells having varying responsiveness to anthracycline treatments. In many embodiments, a number of neoplastic cell lines are cultivated in vitro and treated with an anthracycline to determine their response to a treatment of anthracycline. In some embodiments, expression data derived from anthracycline treatment of cohorts of individuals having are examined and compared with expression data from an alternative treatment of cohorts of individuals having a neoplasm, identifying which expressed profiles of CRGs are indicative of anthracycline responsiveness.

Figure 3:
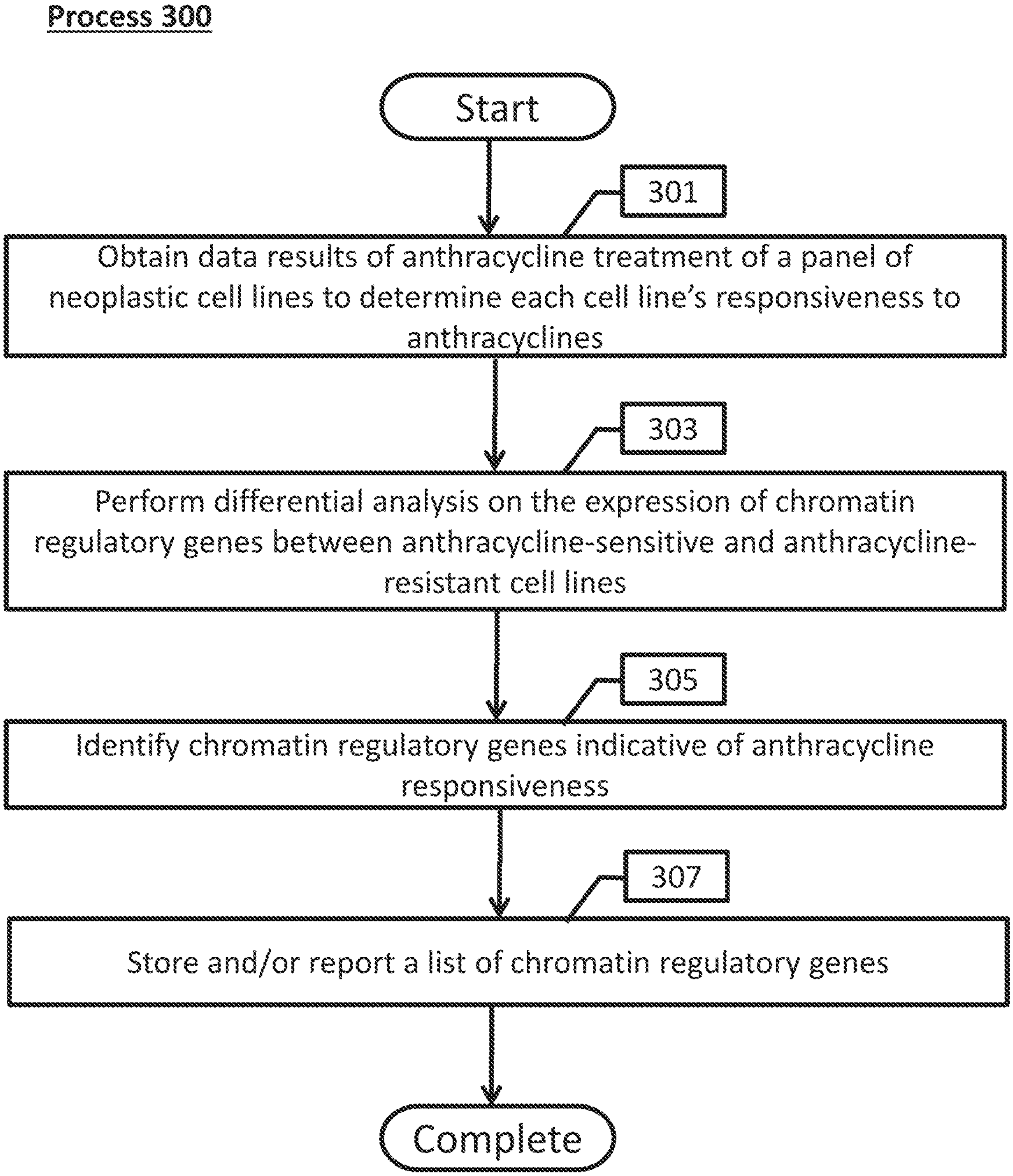
FIG. 3 provides a flow diagram of a method to identify chromatin regulatory genes indicative of anthracycline responsiveness in accordance with various embodiments of the invention.

Provided in FIG. 3 is an embodiment of a process to identify CRGs from a panel of neoplastic cell lines. Process 300 begins with obtaining (301) data results of anthracycline treatment of a panel of neoplastic cell lines to determine each cell line's responsiveness to anthracyclines. In many embodiments, data results derived from cell line experiments include CRG expression level data and the corresponding anthracycline response.

Neoplastic cell lines to be used can be any appropriate cell line representative of a neoplasm. In many embodiments, a cell line derived from or that mimics a cancer is used. Cell lines can be derived from an individual having a neoplasm by extracting a biopsy from the individual and culturing the cells in vitro by methods understood in the art. Extracted cells can then be used to measure direct sensitivity to anthracyclines or for measurement of CRG expression levels. In various embodiments, transformed cell lines are utilized, which will typically have some features that mimic a neoplasia, such as (for example) increased growth rate, anaplasia, chromosomal abnormalities, or increased survival when stressed.

To perform analysis, several embodiments utilize a panel of neoplastic cell lines defined by a particular characteristic. In some embodiments, a panel of neoplastic cell lines is defined by a particular neoplasm type, such as a particular cancer (e.g., breast cancer). In various embodiments, a panel of neoplastic cell lines is defined as pan-cancer (i.e., sampling of a number of different cancers such that it signifies a panel covering cancers generally). In some embodiments, panels are defined by particular molecular characteristics (e.g., HER2 status). It should be understood that a number of variations of panel constituencies can be used such that the panel has a defining characteristic such that anthracycline response can be evaluated in relation to that characteristic.

In many embodiments, a panel of neoplastic cell lines are to be treated with an anthracycline, such as (for example) doxorubicin, epirubicin, idarubicin, valrubicin or mitoxantrone. The precise dose of treatment will often depend on the anthracycline selected and the constituency of the panel of neoplastic cell lines. For example, anthracycline responsive breast cancer cell lines can be treated with doxorubicin within a range of approximately 100 nM to 100 μM to achieve the desired cytotoxic effects. The precise concentration of anthracycline for cell line studies can be optimized using techniques known in the art.

In several embodiments, the anthracycline treatment provides a varied response from the various cell lines within a panel. Accordingly, some cell lines can be anthracycline sensitive and thus the anthracycline will be cytotoxic at certain concentrations. Some cell lines can be anthracycline resistant and thus the anthracycline will not produce a cytotoxic response at certain concentrations. Utilizing a particular concentration of anthracycline, in accordance with a number of embodiments, a panel will have a set of anthracycline-sensitive and a set of anthracycline-resistant cell lines.

In several embodiments, CRG expression levels are defined relative to a known expression result. In some instances, CRG expression level of a cell line is determined relative to a control sample and/or relative to a panel of cell lines. A control sample can either be highly resistant (i.e., null control), highly sensitive (i.e., positive control), or any other level of responsiveness that can be relatively quantified. Accordingly, when the CRG expression level of a cell line is compared to one or more controls, the relative expression level can indicate whether the cell line is responsive to anthracycline. In some instances, CRG expression level is determined relative to a stably expressed biomarker (i.e., endogenous control). Accordingly, when CRG expression levels exceed a certain threshold relative to a stably expressed biomarker, the level of expression is indicative of anthracycline responsiveness. In some instances, CRG expression level is determined on a scale. Accordingly, various expression level thresholds and ranges can be set to classify anthracycline responsiveness and thus used to indicate a cell line's responsiveness. It should be understood that methods to define expression levels can be combined, as necessary for the applicable assessment. For example, standard RT-PCR assessments often utilize both control samples and stably expressed biomarkers to elucidate expression levels.

Expression of CRGs can be determined by a number of ways, in accordance with several embodiments and as understood by those in the art. Typically, RNA and/or proteins are examined directly in the neoplastic cells or in an extraction derived from the neoplastic cells. Expression levels of RNA can be determined by a number of methods, including (but not limited to) hybridization techniques (e.g., ISH), nucleic acid proliferation techniques (e.g., RT-PCR), and sequencing (e.g., RNA-seq). Expression levels of proteins can be determined by a number of methods, including (but not limited to) immunodetection (e.g., ELISA) and spectrometry (e.g., mass spectrometry).

Process 300 also performs (303) differential analysis on the expression of genes, including CRGs, between a set of one or more anthracycline-sensitive and a set of one or more anthracycline-resistant cell lines. Typically, anthracycline responsiveness of cell lines will vary along a spectrum. Accordingly, various embodiments are directed to categorizing cell lines as anthracycline responsiveness on a threshold measure. In some embodiments, a half maximal inhibitory concentration ($IC_{50}$), half maximal growth inhibitory concentration ($GI_{50}$), or half maximal effective concentration ($EC_{50}$) is used to measure responsiveness. In various embodiments, cell lines are divided by a percentile or quantile (e.g., median, tertile, quartile, etc.). In some embodiments, a top percentile or quantile of responsiveness is defined as anthracycline-sensitive while a bottom percentile or quantile of responsive is defined as anthracycline-resistant. In various embodiments, statistical analysis is used to determine differential gene expression, many of which are known in the art. In some embodiments, the computational program limma is used to facilitate differential statistical analysis. For more on limma, see M. E. Ritchie *Nucleic Acids Res.* 43, e47 (2015), the disclosure of which is herein incorporated by reference.

Utilizing the differential analysis, chromatin regulatory genes are identified (305) that are indicative of anthracycline responsiveness. In many embodiments, the gene expression levels of a set of anthracycline-sensitive cell lines are compared to a set of anthracycline-resistant cell lines. Several statistical and computational methods are known to compare expression levels of two categorical sets of data. In various embodiments, a computational program that infers CRG activity from expression profile data and CRG networks based upon estimates of activities of the various CRGs, such as the program Virtual Inference of Protein-activity by Enriched Regulon analysis (VIPER), is used to identify CRGs that are associated with anthracycline responsiveness. In some embodiments, CRG networks are built using Algorithm for the Reconstruction of Accurate Cellular Networks (ARACNE). For more on ARACNE and VIPER, see A. A. Margolin, et al., *BMC Bioinformatics* 7 Suppl 1, S7 (2006) and M. J. Alvarez, et al., *Nat. Genet.* 48, 838-847 (2016), respectively, the disclosures of which are herein incorporated by reference.

Process 300 also stores and/or reports (307) a list of chromatin regulatory genes that have been identified as responsive to anthracycline activity. As is discussed herein, CRG expression levels can be used to determine anthracycline responsiveness and thus can be utilized to treat a neoplasm accordingly.

While specific examples of processes for identifying anthracycline-sensitive and anthracycline-resistant CRGs from a panel of neoplastic cells are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for identifying anthracycline-sensitive and anthracycline-resistant CRGs from a panel of neoplastic cells appropriate to the requirements of a given application can be utilized in accordance with various embodiments of the invention.

Figure 4:
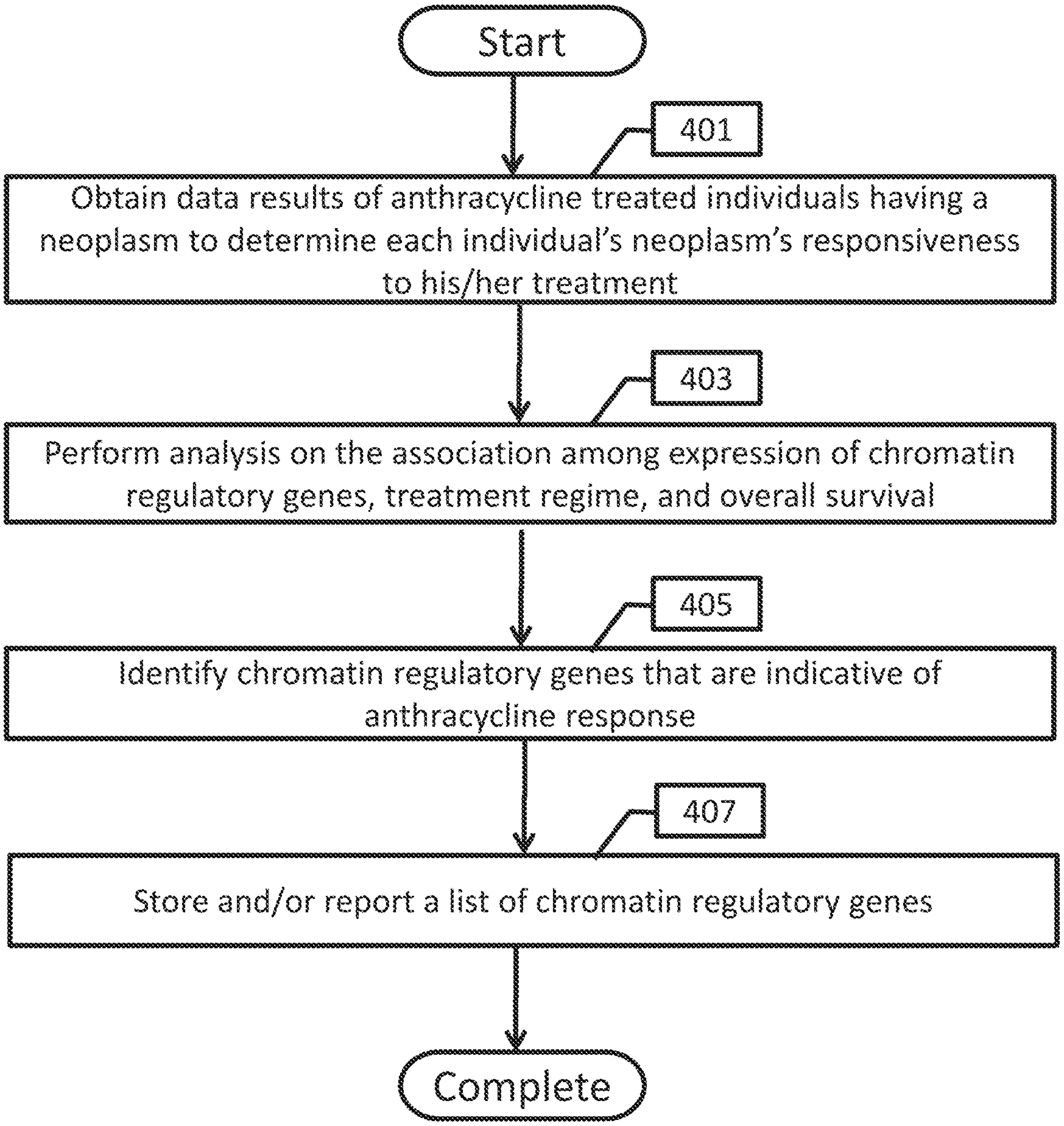
FIG. 4 provides a flow diagram of a method to identify chromatin regulatory genes indicative of anthracycline responsiveness in accordance with various embodiments of the invention.

Provided in FIG. 4 is an embodiment of a process to identify anthracycline responsive CRGs from clinical data. Process 400 begins with obtaining (401) data results of anthracycline treated individuals having a neoplasm to determine each individual's neoplasm's responsiveness to his/her treatment. In many embodiments, data results are to include CRG expression level data, overall survival, and treatment regime. In some embodiments, data results include neoplasia-defining characteristics.

Neoplasms to be analyzed can be any appropriate neoplasm. In many embodiments, a neoplasm is a cancer, such as (for example) breast, colon, lung, skin, pancreatic, and liver. In various embodiments, a collection of neoplasms examined is defined as pan-cancer (i.e., sampling of a number of different cancers such that it signifies a collection covering all cancers). In some embodiments, a collection of neoplasms examined is defined by a particular cancer (e.g., breast). In some embodiments, panels are defined by certain molecular characteristics (e.g., HER2 status). It should be understood that a number of variations of neoplasm collection constituencies can be used such that the collection has a defining characteristic such that treatment response can be evaluated in relation to that characteristic.

In many embodiments, a collection of neoplasms to be analyzed can include those treated with an anthracycline, such as (for example) doxorubicin, epirubicin, idarubicin, valrubicin or mitoxantrone. In an analysis, anthracycline treatments can be compared with other treatment regimes, such as (for example), any treatment lacking anthracycline, other chemotherapies (e.g., CMF, taxane), immunotherapies, radiotherapies, and lack of intervention (i.e., untreated).

In several embodiments, the data includes varied anthracycline treatment results of the treated individuals. Accordingly, some individuals' neoplasms can be anthracycline sensitive and thus the anthracycline will improve neoplasm eradication and overall survival. Some individual's neoplasms can be anthracycline resistant and thus the anthracycline will not inhibit neoplasm progression and thus decrease overall survival.

In several embodiments, CRG expression levels are defined relative to a known expression result. In some instances, CRG expression level of an individual's biopsy is determined relative to a control sample and/or relative to a collection of biopsies. A control sample can either be highly resistant (i.e., null control), highly sensitive (i.e., positive control), or any other level of responsiveness that can be relatively quantified. Accordingly, when the CRG expression level of an individual's biopsy is compared to one or more controls, the relative expression level can indicate whether the corresponding neoplasm is responsive to anthracycline. In some instances, CRG expression level is determined relative to a stably expressed biomarker (i.e., endogenous control). Accordingly, when CRG expression levels exceed a certain threshold relative to a stably expressed biomarker, the level of expression is indicative of anthracycline responsiveness. In some instances, CRG expression level is determined on a scale. Accordingly, various expression level thresholds and ranges can be set to classify anthracycline responsiveness and thus used to indicate a neoplasm's responsiveness. It should be understood that methods to define expression levels can be combined, as necessary for the applicable assessment. For example, standard RT-PCR assessments often utilize both control samples and stably expressed biomarkers to elucidate expression levels.

Expression of CRGs can be determined by a number of ways, in accordance with several embodiments and as understood by those in the art. Typically, RNA and/or proteins are examined directly in the neoplastic cells, in an extraction derived from the neoplastic cells, or from an extraction of a non-neoplastic biopsy representative of the neoplasm. Expression levels of RNA can be determined by a number of methods, including (but not limited to) hybridization techniques (e.g., ISH), nucleic acid proliferation techniques (e.g., RT-PCR), and sequencing (e.g., RNA-seq). Expression levels of proteins can be determined by a number of methods, including (but not limited to) immunodetection (e.g., ELISA) and spectrometry (e.g., mass spectrometry).

Process 400 also performs (403) analysis on the association among expression of chromatin regulatory genes, treatment regime, and overall survival. In some embodiments, a computational classifier or statistical model (e.g., Cox Proportional Hazard model, accelerated failure time model, survival trees, or survival random forest) is used to evaluate the interaction between CRG expression and treatment and their association with a parameter, such as overall survival. In some embodiments, parameters used in association studies include (but are not limited to) overall survival, survival of a specific disease, relapse survival, and distant relapse survival. In various embodiments, a classifier or statistical model is adjusted for various neoplasm characteristics known to be associated with patient survival. For example, in breast cancer, ER status, PR status, HER2 status, tumor size, and lymph node status is known to associate with survival in breast cancer. For more description of the Cox Proportional Hazard model, see P. M. Rothwell *Lancet* 365, 176-186 (2005), the disclosure of which is herein incorporated by reference.

Utilizing the comparison between anthracycline treatment and an alternative treatment, CRGs are identified (405) that are indicative of anthracycline responsiveness. Several statistical and classifier methods are known to compare expression levels of two categorical sets of cell lines. In various embodiments, a statistical or classifier model (e.g., Cox Proportional Hazard model, accelerated failure time model, survival trees, or survival random forest) is used to identify CRGs that are associated with anthracycline responsiveness from clinical patient data.

Process 400 also stores and/or reports (407) a list of chromatin regulatory genes that have been identified as responsive to anthracycline activity. As is discussed herein, CRG expression levels can be used to determine anthracycline responsiveness and thus can be utilized to treat a neoplasm accordingly.

While specific examples of processes for identifying anthracycline-sensitive and anthracycline-resistant CRGs from clinical patient data are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for identifying anthracycline-sensitive and anthracycline-resistant CRGs from clinical patient data appropriate to the requirements of a given application can be utilized in accordance with various embodiments of the invention.

EXEMPLARY EMBODIMENTS

The embodiments of the invention will be better understood with the several examples provided within. Many exemplary results of processes that identify chromatin regulatory genes involved in anthracycline responses are described. Validation results are also provided.

Example 1: Chromatin Regulatory Genes are Associated with Anthracycline Sensitivity In Vitro A list of over four hundred CRGs has been derived from the literature and gene ontology annotation (Table 1). The list is based on a defined set of Gene Ontology functions, including: a) Histone lysine methyltransferase activity (GO: 0018024), b) histone demethylation (GO:0032452), c) histone deacetylation (GO:0004407), d) histone acetyltransferase activity (GO:0004402), e) histone phosphorylation (GO: 0016572), f) PRC1 complex (GO:0035102), g) PRC2 complex (GO:0035098), h) SWI/SNF complex (GO: 0016514 plus other members not included in this GO category), i) ISWI complex members (NURF, ACG, CHRAC, WICH, NORC, RSF and CERF complex members, j) Chromodomain and NURD-Mi-2 complex, k) INO80 complex (GO:0031011 l) SWR1 complex m) PR-DUB complex, n) CAF1 complex (GO:0033186), o) Cohesins, p) Condensins, q) Topoisomerases (GO: 0003916), r) DNA methyltransferases (GO:0006306), DNA demethylases (GO:0080111), Histone proteins, and chromatin pioneer factors.

Figure 5:
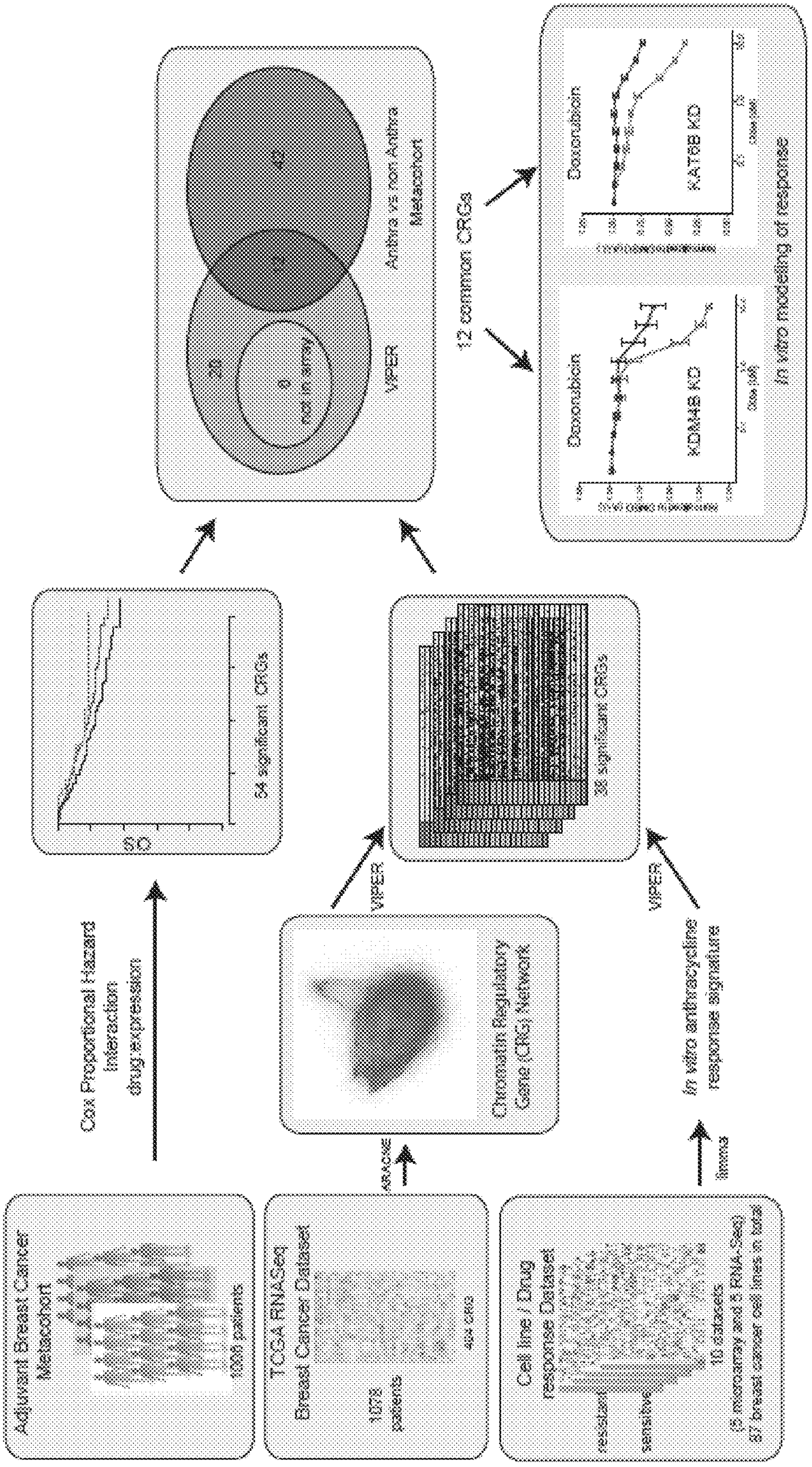
FIG. 5 provides a schematic overview of methods to identify chromatin regulatory genes from in vitro and clinical data in accordance with various embodiments of the invention.
Figure 6:
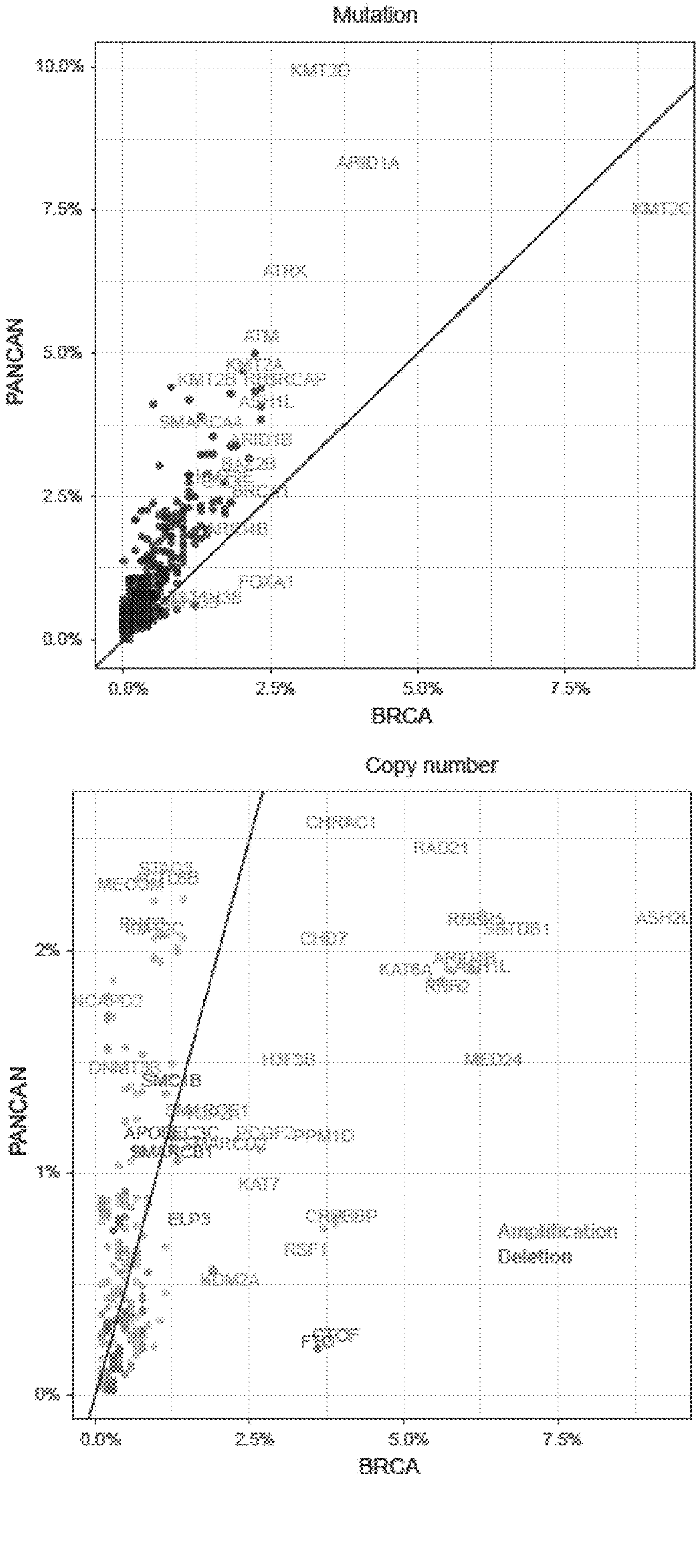
FIG. 6 provides data charts indicative of abnormal copy number variations in breast cancer, used in accordance with an embodiment of the invention.

In order to evaluate the association between the expression of CRGs and anthracycline response in human breast cancers, data were combined from multiple sources, including the TCGA breast cancer cohort (Cancer Genome Atlas *Nature* 520, 239-242 (2015), the disclosure of which is herein incorporated by reference), breast cancer cell line expression and growth inhibition ($GI_{50}$) data (J. C. Costello, et al., *Nat. Biotechnol.* 32, 1202-1212 (2014); M. Hafner, et al., *Scientific Data,* 4, 170166 (2017); P. M. Haverty, et al., *Nature,* 533, 333 (2016); J. Barretina, et al., *Nature,* 483, 603 (2012); B. Seashore-Ludlow, et al., *Cancer Discovery,* 5, 1210-1223 (2015); F. Iorio, et al., *Cell,* 166, 740-754 (2016); and J. P. Mpindi, et al., *Nature,* 540, E5 (2016); the disclosures of which are each herein incorporated by reference), and a metacohort of expression profiles and clinical covariates for 1006 early-stage breast cancer patients (FIG. 5). CRG expression levels were examined instead of mutation status because CRGs are infrequently mutated in breast cancer, but often copy number amplified or deleted (FIG. 6), presumably effecting expression changes and consistent with breast tumors being copy number driven.

The TCGA breast cancer RNA-seq dataset (N=1079 patients) was downloaded from gdc.cancer.gov (January 2018). RPKM count data was normalized using variance stabilizing transformation (VST) from the package DESeq2 (M. I. Love, W. Huber, and S. Anders *Genome Biol.* 15, 550 (2014), the disclosure of which is herein incorporated by reference) within R Bioconductor. The breast cancer cell line response datasets, including gene expression microarray, RNASeq and drug response information were downloaded from the publications: Data, 4, 170166 (2017); P. M. Haverty, et al., *Nature,* 533, 333 (2016); J. Barretina, et al., *Nature,* 483, 603 (2012); B. Seashore-Ludlow, et al., *Cancer Discovery,* 5, 1210-1223 (2015); F. Iorio, et al., *Cell,* 166, 740-754 (2016); and J. P. Mpindi, et al., *Nature,* 540, E5 (2016), which included a total of 87 cell lines. Drug response information was recorded as $-\log 10(GI_{50})$ for Heiser dataset (where $GI_{50}$ was the concentration that inhibited cell growth by 50% after 72 hours of treatment or AUC (Area under the dose-response curve). Each dataset was divided into the top tertile and bottom tertile sensitive to doxorubicin cell lines. The limma method was used for normalization, the microarray datasets used weighted samples (arrayWeight function) to avoid bias, and the RNASeq was voom transformed (voom function) to obtain both a signature for doxorubicin response and a null model of the signature by permuting the sample labels 1000 times.

To obtain the metacohort of expression profiles and clinical covariates, raw CEL files were downloaded from the Gene Expression Omnibus (GEO) Database for the datasets KAO (GSE20685), IRB/JNR/NUH (GSE45255), MAIRE (GSE65194), UPS (GSE3494) and STK (GSE1456) (See Y. Lie, et al. *Nat. Med.* 16, 214-218 (2010); K. J. Kao, et al. *Genome Biol.* 14, R34 (2013); S. Nagalla, et al. *Genome Biol.* 14, R34 (2013); V. Maire, et al., *Cancer Res* 73, 813-823 (2013); L. D. Miller, et al., *Proc. Natl. Acad. Sci. U.S.A* 102, 13550-13555 (2005); Y. Pawitan, et al., *Breast Cancer Res.* 7, R953-964 (2005); the disclosures of which are each herein incorporated by reference). These datasets were each profiled on the Affymetrix platform (hgu133plus2, hgu133a and hgu133b) and were reprocessed using the rma function from the affy package and quantile normalized (L. Gautier, et al., *Bioinformatics* 20, 307-315 (2004), the disclosure of which is herein incorporated by reference). COMBAT was used to remove batch effects (W. E. Johnson, C. Li, and A. Rabinovic *Biostatistics* 8, 118-127 (2007), the disclosures of which are herein incorporated by reference). Patients who received an anthracycline (doxorubicin or epirubicin) as a component of their treatment regimen were classified as "anthracycline-treated", while patients who received a chemotherapy regimen that did not contain anthracyclines, who received endocrine therapy alone, or who received no therapy were classified as "not anthracycline-treated". ER, PR and Her2 status were inferred using a Gaussian mixture model of the probes 205225_at, 208305_at, and 216836_s_t, respectively. MKI67 values were obtained from probe 212023_s_at. Lymph node positivity is a binary feature obtained from: Number of nodes>0, or N-stage≥1. T-stage was a factor feature obtained from either the actual T-stage, as reported in (n=327 cases), or as inferred from the reported size of the tumor (T1<2 cm, T2≤5 cm, T3>5 cm) (n=520 cases)). For the STK cohort, neither size, T-stage, lymph node status or N-stage was available, however the authors reports that mean size of the cohort is 22 mm and 62% of samples have size<21 mm and 38% samples are lymph node negative. The t-stage 2 and lymph node negative status were inferred for all samples in this cohort.

Figure 7:
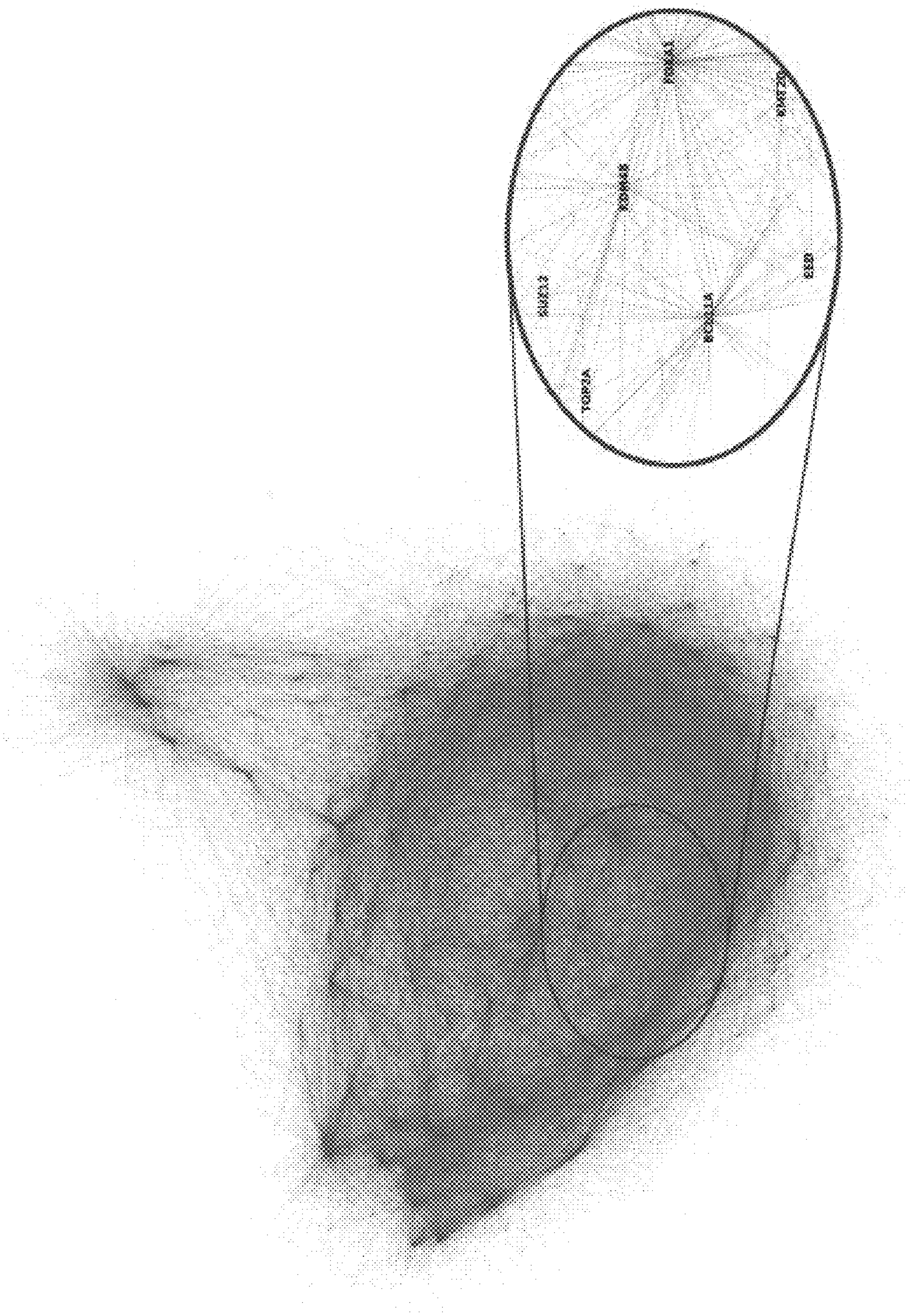
FIG. 7 provides a network diagram of a chromatin regulatory network, generated in accordance with an embodiment of the invention.

After compilation of the data, CRGs that have a central regulatory role in breast cancer were identified using graph theoretical approaches. A genome-wide regulatory network from The Cancer Genome Atlas (TCGA) breast tumor RNA-seq data (N=1079 patients) was generated using the Algorithm for the Reconstruction of Accurate Cellular Networks (ARACNE) (FIG. 7). To generate this network, it was assumed that each gene from the expression dataset is a regulatory element. ARACNE was run with the default parameters (p<1 E−8). Significant networks were calculated from 10 bootstrap iterations for the genome-wide network and from 100 bootstraps for the CRG network. The network for posterior analyses was obtained by using the edges with adjusted p-values<0.05. The regulon was composed of 396 CRGs and the median number of targets per CRG was 94. In order to evaluate the centrality of the CRGs, the degree, betweenness and page rank centrality was calculated for each gene in the genome-wide network. 10,000 combinations of 404 genes were randomly selected to obtain a centrality score for each centrality measure by aggregating the values of all 404 genes. The centrality score for the CRGs was compared with the null distribution, with those over 5% of the tail for degree, betweenness and page rank considered significant.

Figure 8:
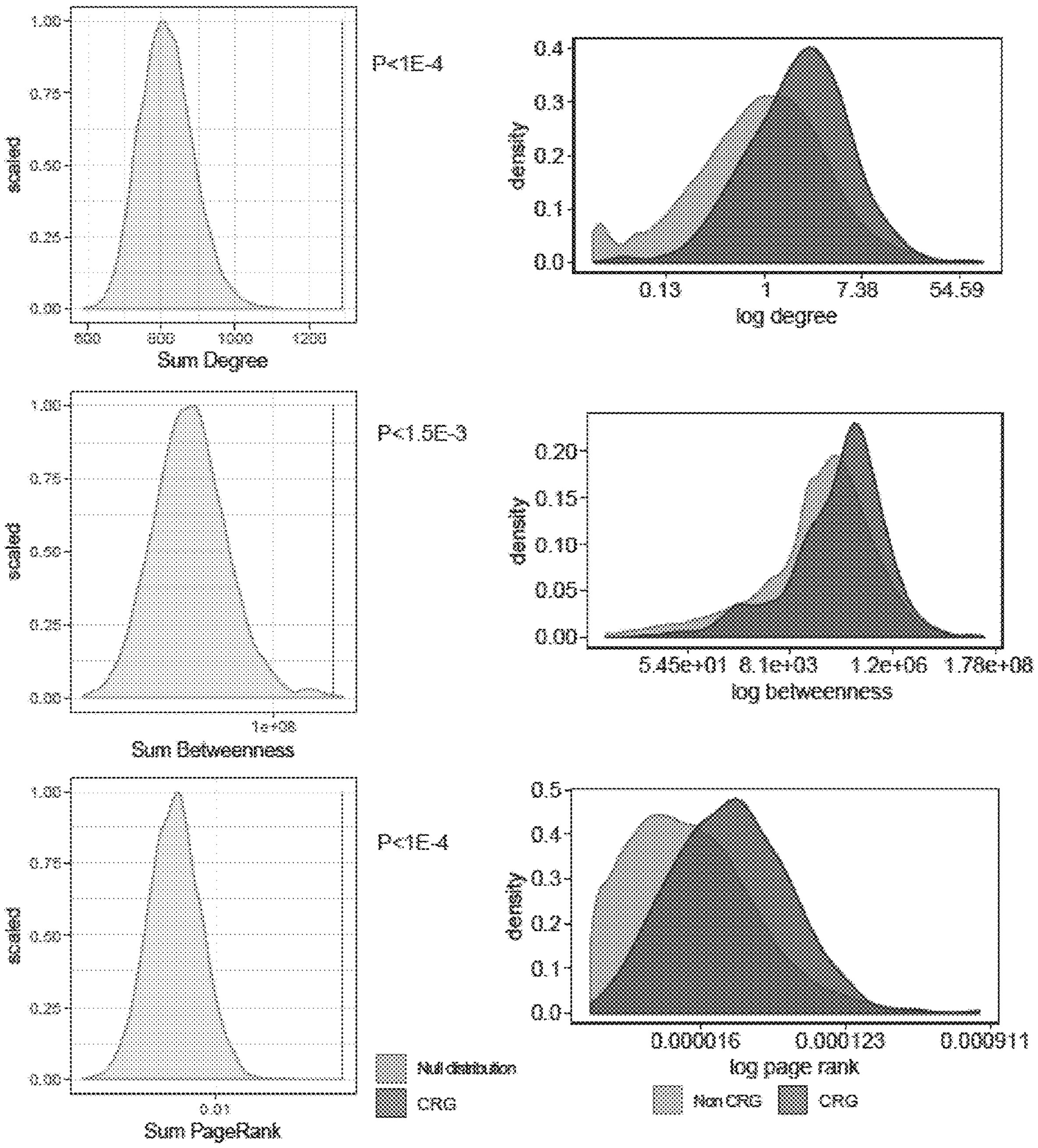
FIG. 8 provides diagrams to exemplify the connectivity of chromatin regulatory genes, generated in accordance with an embodiment of the invention.

The set of CRGs exhibited significantly high centrality (degree 3.26±4.37 for CRGs versus 2.04±3.7 for nonCRGs) in the transcriptional network and this was significantly greater (p<1 E−4, p<1.5 E−3, p<1 E−4, respectively) than that observed for a null distribution generated via 10,000 bootstrap iterations with random genes (404 out of 24,919) (FIG. 8). In order to identify the sets of target genes directly regulated by each CRG, ARACNE was used to generate a breast cancer chromatin regulatory network, where CRGs correspond to nodes (See FIG. 5).

Figure 9:
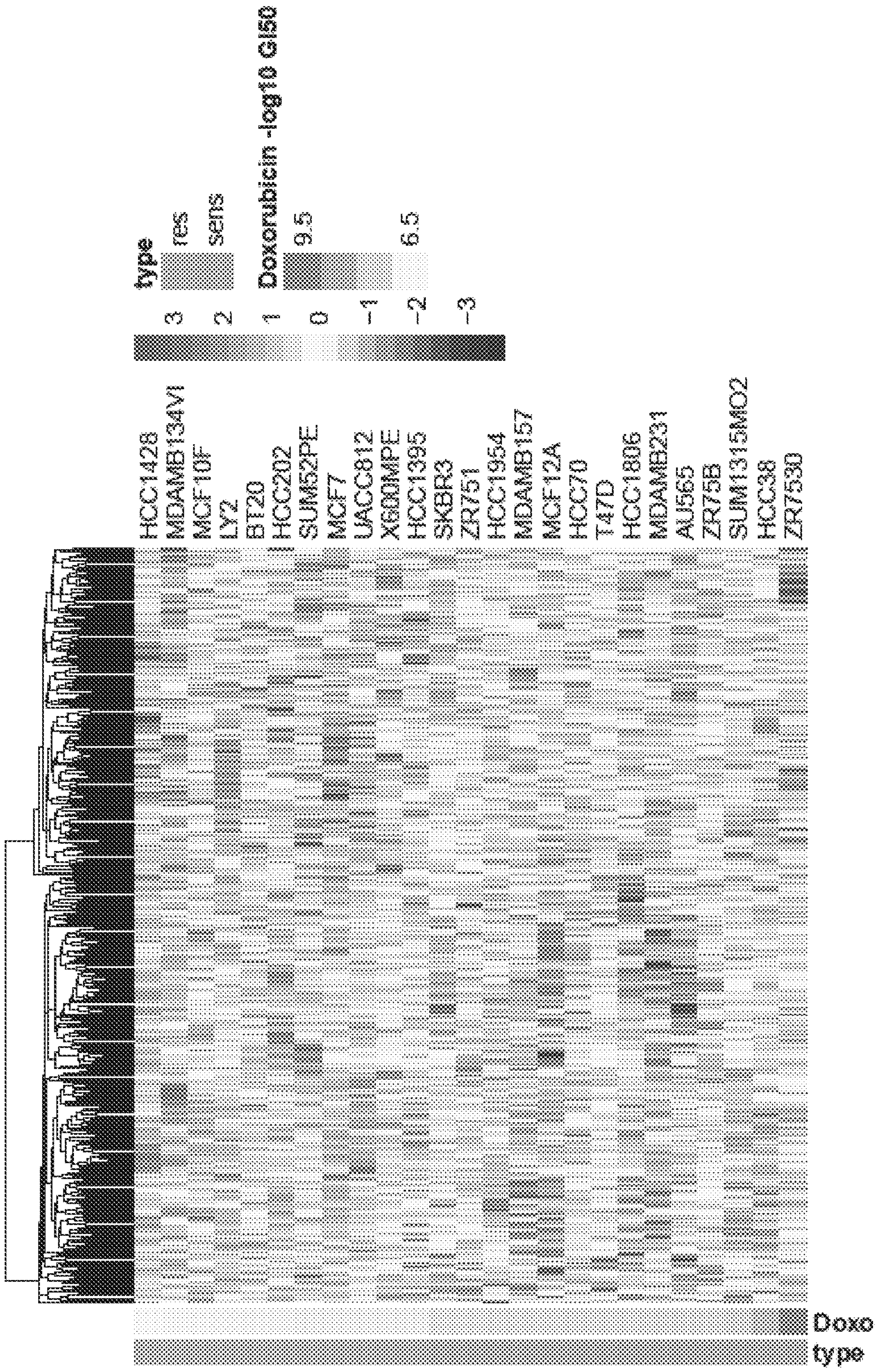
FIG. 9 provides a heat map diagram of chromatin regulatory gene expression in breast cancer cell lines treated with doxorubicin, generated in accordance with various embodiments of the invention.
Figure 10:
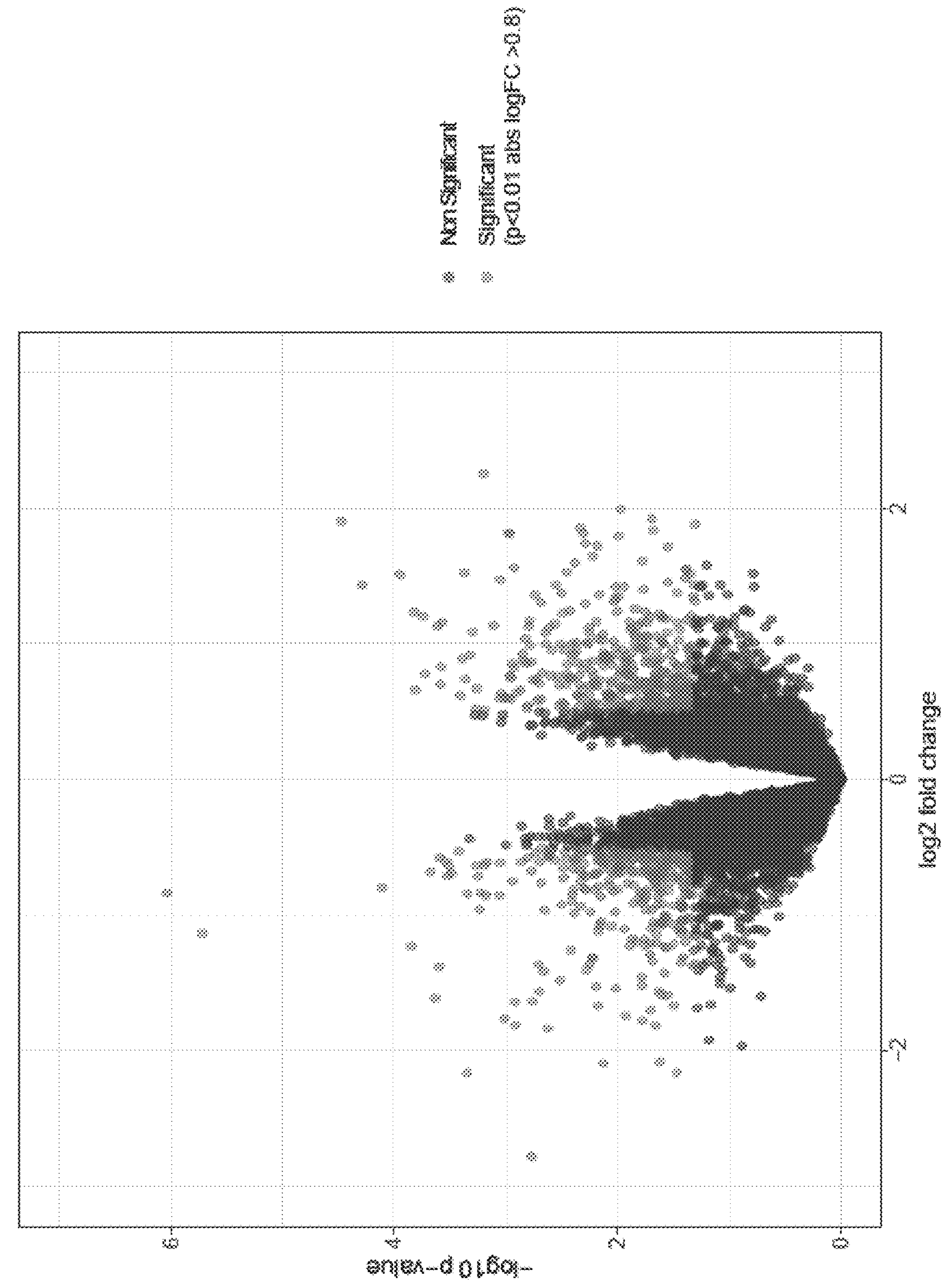
FIG. 10 provides a diagram of differential gene expression of anthracycline-resistant and anthracycline-sensitive breast cancer cell lines, generated in accordance with various embodiments of the invention.
Figure 11A:
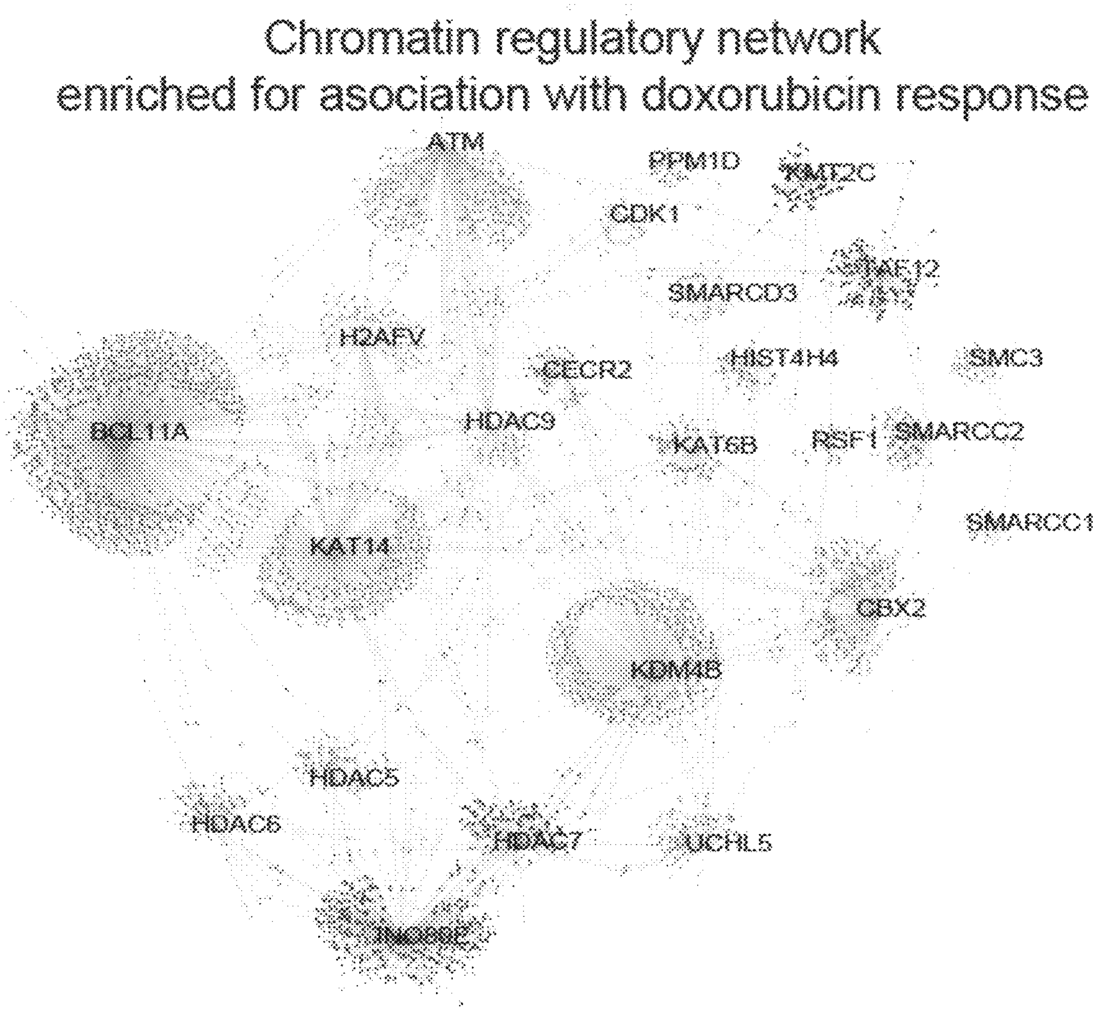
FIGS. 11A and 11B provide data depicting the activation of chromatin regulatory genes indicative of anthracycline responsiveness, generated in accordance with various embodiments of the invention.
Figure 11B:
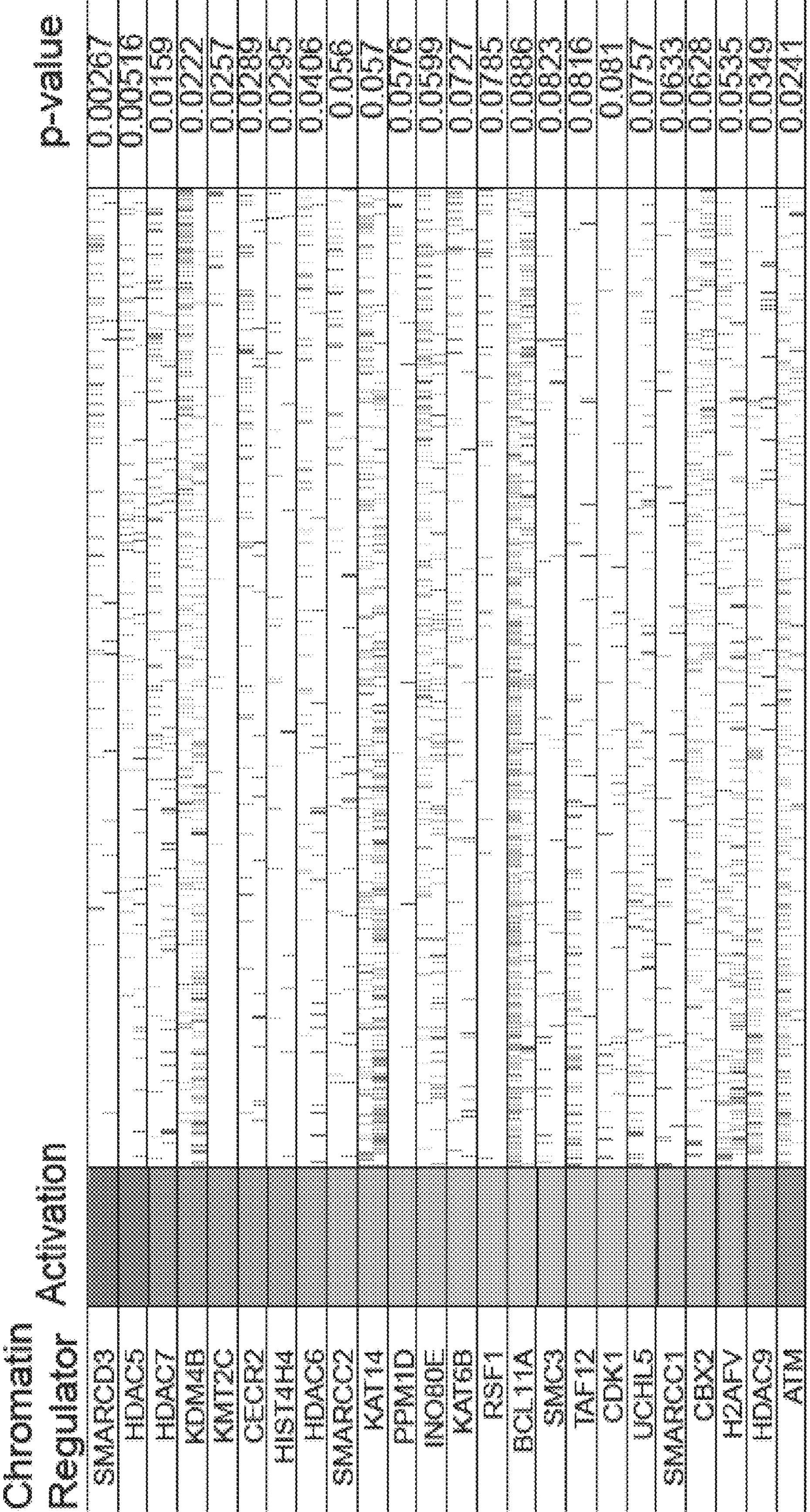

It was hypothesized that CRGs involved in anthracycline response could be identified by examining the association with the expression levels of their target genes. Using a panel of 87 breast cancer cell lines with available expression data and doxorubicin $GI_{50}$ values, a genome-wide signature of anthracycline response was defined in which the F-statistic (per gene) was used as a measure of treatment response (See FIG. 5). This signature of anthracycline response was identified by performing differential expression analysis between cell lines that were resistant (bottom tertile of $-\log_{10} GI_{50}$ values) and sensitive (top tertile of $-\log_{10} GI_{50}$ values) to doxorubicin (FIGS. 9 & 10). Virtual Inference of Protein-activity by Enriched Regulon analysis (VIPER) was used to identify genes from the ARACNE breast cancer chromatin regulatory network whose putative targets were significantly enriched in the anthracycline response signature. While VIPER was originally designed to identify protein activity associated with a specific transcriptional regulatory program or phenotype, in this analysis VIPER was adapted to identify CRGs that were associated with the genome-wide anthracycline response signature. By evaluating the set of genes that were up- or down-regulated in the anthracycline response signature amongst genes in the chromatin regulatory network, 24 CRGs associated (p<0.1) with anthracycline response in vitro were identified (FIGS. 11A and 11B, Table 3). In these analyses a positive association refers to a chromatin regulator in which its RNA expression level positively correlates with ability to respond to anthracycline. Conversely, negative association refers to a chromatin regulator in which its RNA expression level inversely correlates with ability to respond to anthracycline.

Example 2: Chromatin Regulatory Genes are Indicative Anthracycline Benefit in Early-Stage Breast Cancer Patients The associations between the 404 CRGs and anthracycline benefit was evaluated in a metacohort of 1006 early-stage breast cancer patients. Each patient was clinically evaluated for tumor characteristics, outcome (overall survival), treatment, and gene expression data were available (FIG. 5). A Cox Proportional Hazard model was used to study the interaction between gene expression and treatment and their association with overall survival in the breast cancer metacohort. In particular, the associations between CRG expression with patient outcome under the following sets of drug conditions were compared: (1) anthracycline-treated vs not anthracycline-treated (including patients who received non-anthracycline chemotherapy, only endocrine therapy, or no therapy), (2) anthracycline-treated vs CMF-treated (cyclophosphamide, methotrexate, and 5-fluorouracil), and (3) anthracycline-treated vs taxane-treated (alone or in combination with other non-anthracycline agents). The model was adjusted for age, tumor size (t-stage), lymph node status (positive or negative), cohort, MKI67 expression, and estrogen receptor (ER), progesterone receptor (PR) and human epidermal growth factor 2 (Her2) status with the exception of the stratified clinical analysis, where ER, PR or Her2 were removed accordingly. Hormone therapy was also included in ER-positive samples. In HER2-positive tumors, trastuzumab treatment was not included as a covariate since it was not reported. The maxstat algorithm from survminer (https://cran.r-project.org/web/packages/survminer/index.html) package was used to obtain the optimal threshold to divide high and low expression profiles for visualization in the Kaplan-Meier plots (T. Hothorn and A. Zeileis *Biometrics* 64, 1263-1269 (2008), the disclosure of which is herein incorporated by reference). For comparing the contrast and Cox Proportional Hazard probability plots, "high" was defined as one standard deviation above the median and "low" was defined as one standard deviation below the median. The rms (https://cran.r-project.org/web/packages/rms/index.html) and survival (https://cran.r-project.org/web/packages/survival/index.html) packages were used for outcome analysis.

Figure 12A:
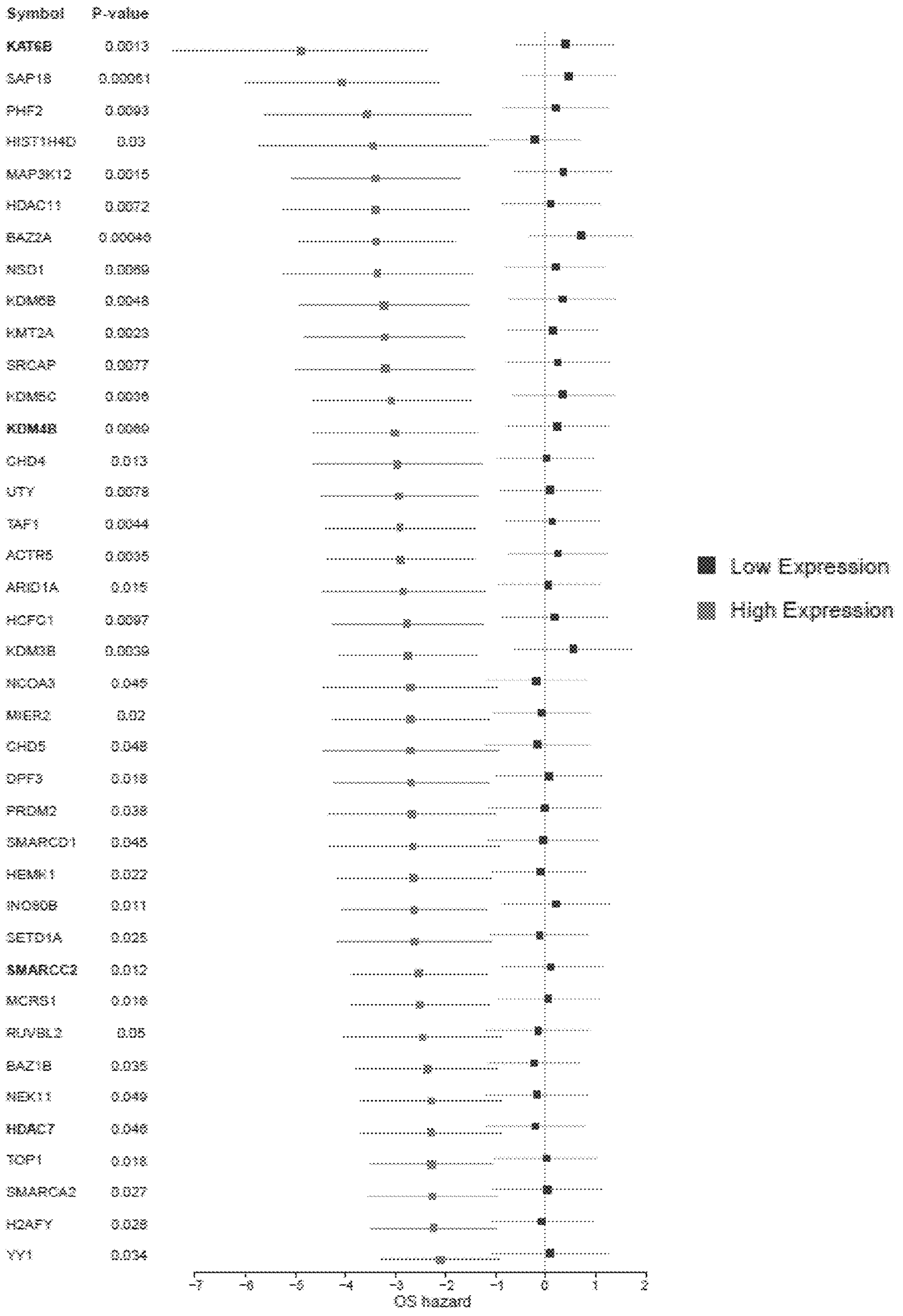
FIGS. 12A and 12B provide data charts depicting expression levels of chromatin regulatory genes indicative of anthracycline responsiveness derived from a cohort of breast cancer patients, generated in accordance with various embodiments of the invention.
Figure 12B:
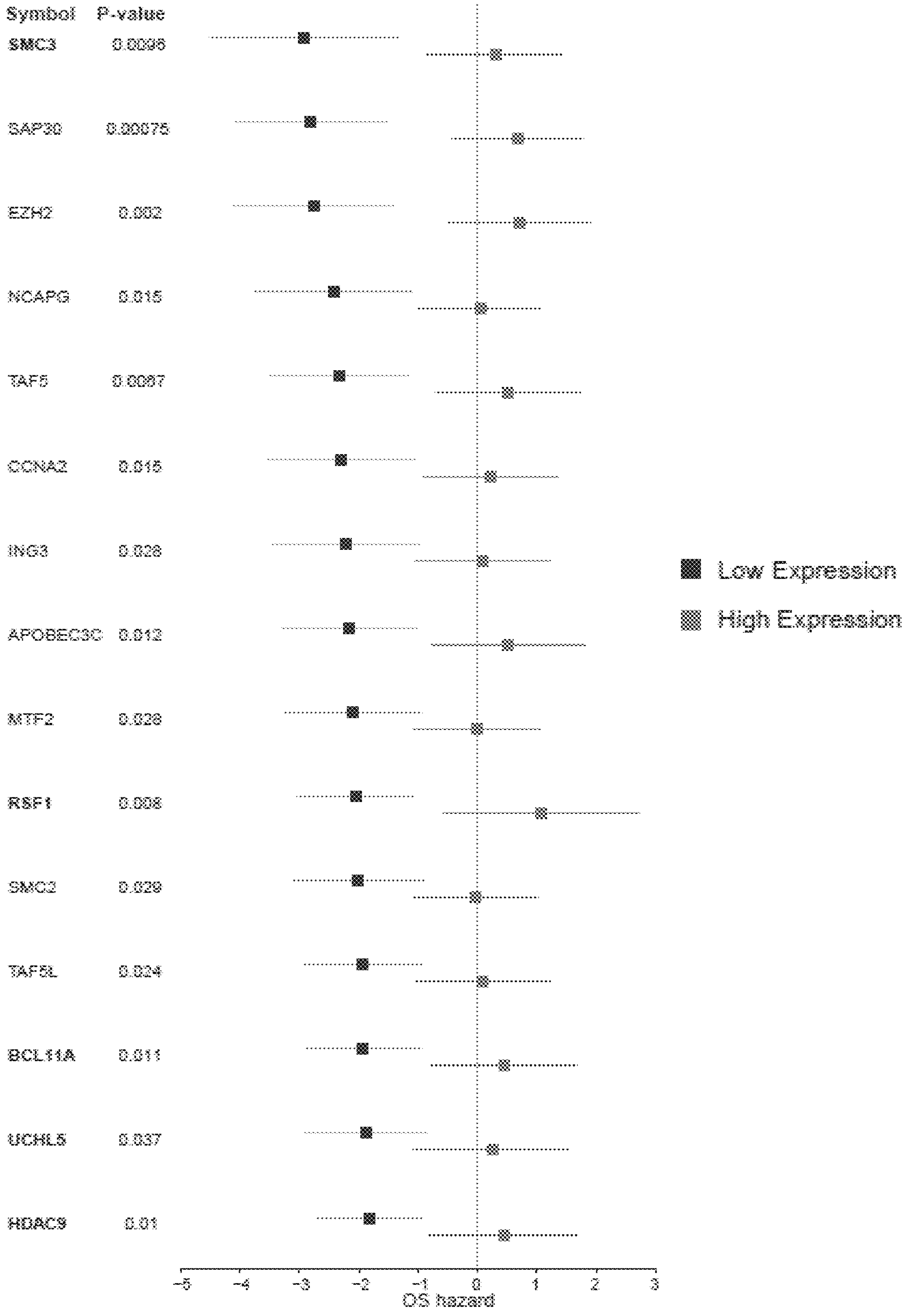

Patients that were treated with anthracyclines (N=218) were compared with patients not treated with anthracycline (N=542). Fifty-four CRGs were found with an interaction (p<0.05) between their expression and treatment (anthracycline vs no anthracycline) in predicting overall survival (FIGS. 12A and 12B, Table 4). There was a striking positive enrichment of gene/drug interactions associated (p<0.05)

with outcome among CRGs (Fisher Exact one tail test P=0.00062, OR:1.54). Notably, a subset of CRGs were found to be associated with reduced anthracycline benefit when their expression levels were below the median; many of these CRGs typically promote open chromatin. This list includes Trithorax-group proteins, including the BAF complex subunits ARID1A, SMARCD3, SMARCD1, and SMARCA2, COMPASS complex subunits such as KMT2A, as well as genes that promote open chromatin through histone modifications such as the histone lysine acetyltransferase KAT6B, and histone demethylases KDM6B and KDM4B. In addition, a separate subset of CRGs were found to be associated with greater anthracycline benefit when their expression levels were below the median. These inversely correlated CRGs include the Polycomb gene EZH2, the histone deacetylase HDAC9, histone chaperone RSF1, and BCL11A whose role in chromatin accessibility is less clear.

Overall, the observation that lower expression of BAF complex subunits, or higher expression of Polycomb subunits, are associated with anthracycline resistance is interesting when considering their respective structures and functions. TOP2 proteins function as dimers of approximately 340 kD that require accessible chromatin to bind DNA. In particular, a functional BAF complex is necessary for TOP2 to associate with DNA at about half of its sites in the genome (and thus a dysfunctional BAF complex renders cells insensitive to TOP2 inhibitors), while the Polycomb complex antagonizes the BAF complex conferring TOP2 inhibitor resistance. These data suggest that additional CRGs such as other Trithorax-group complexes may also mediate DNA accessibility for TOP2.

Figure 13:
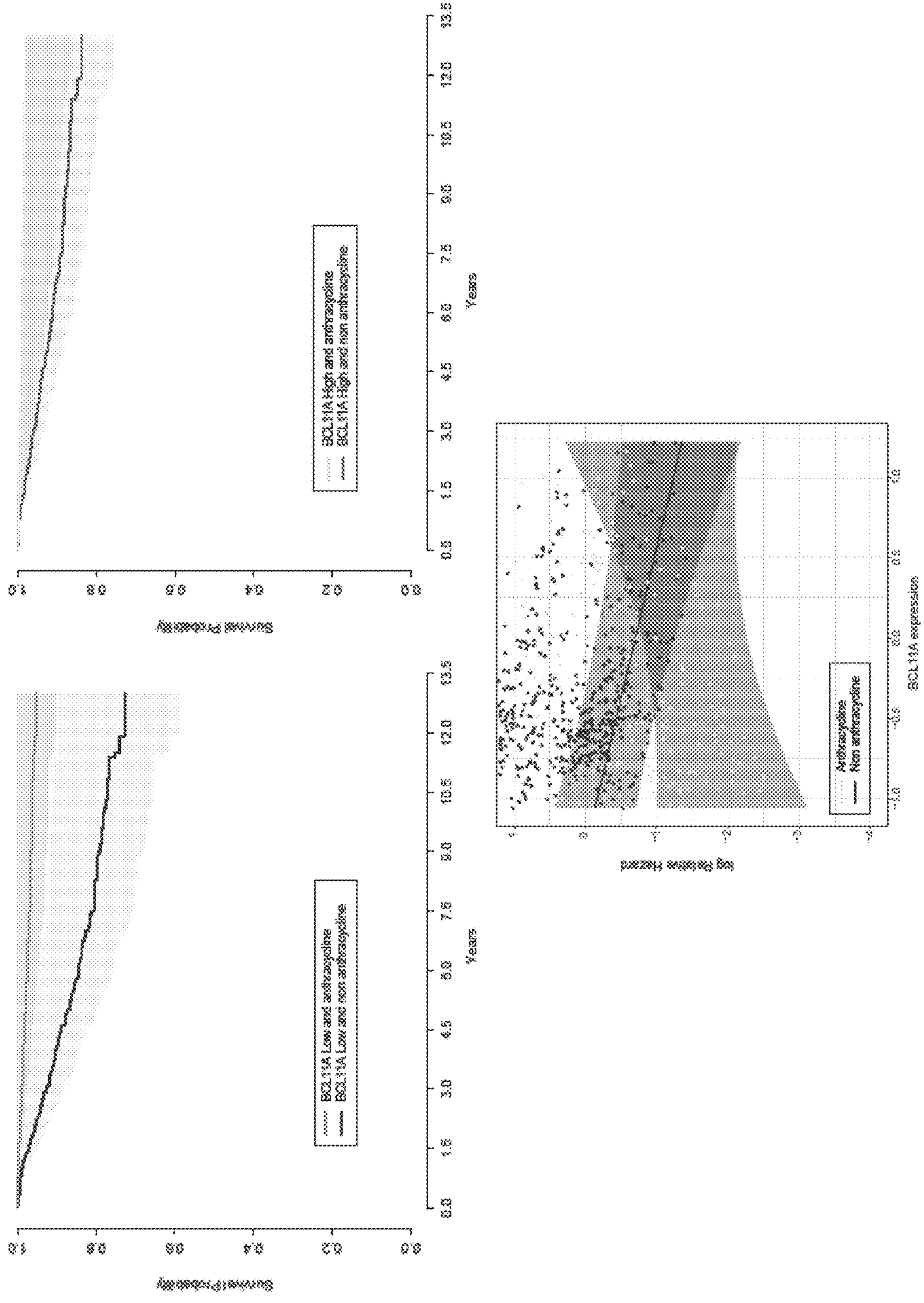
FIG. 13 provides Cox Hazard plots of BCL11A, generated in accordance with various embodiments of the invention.
Figure 14:
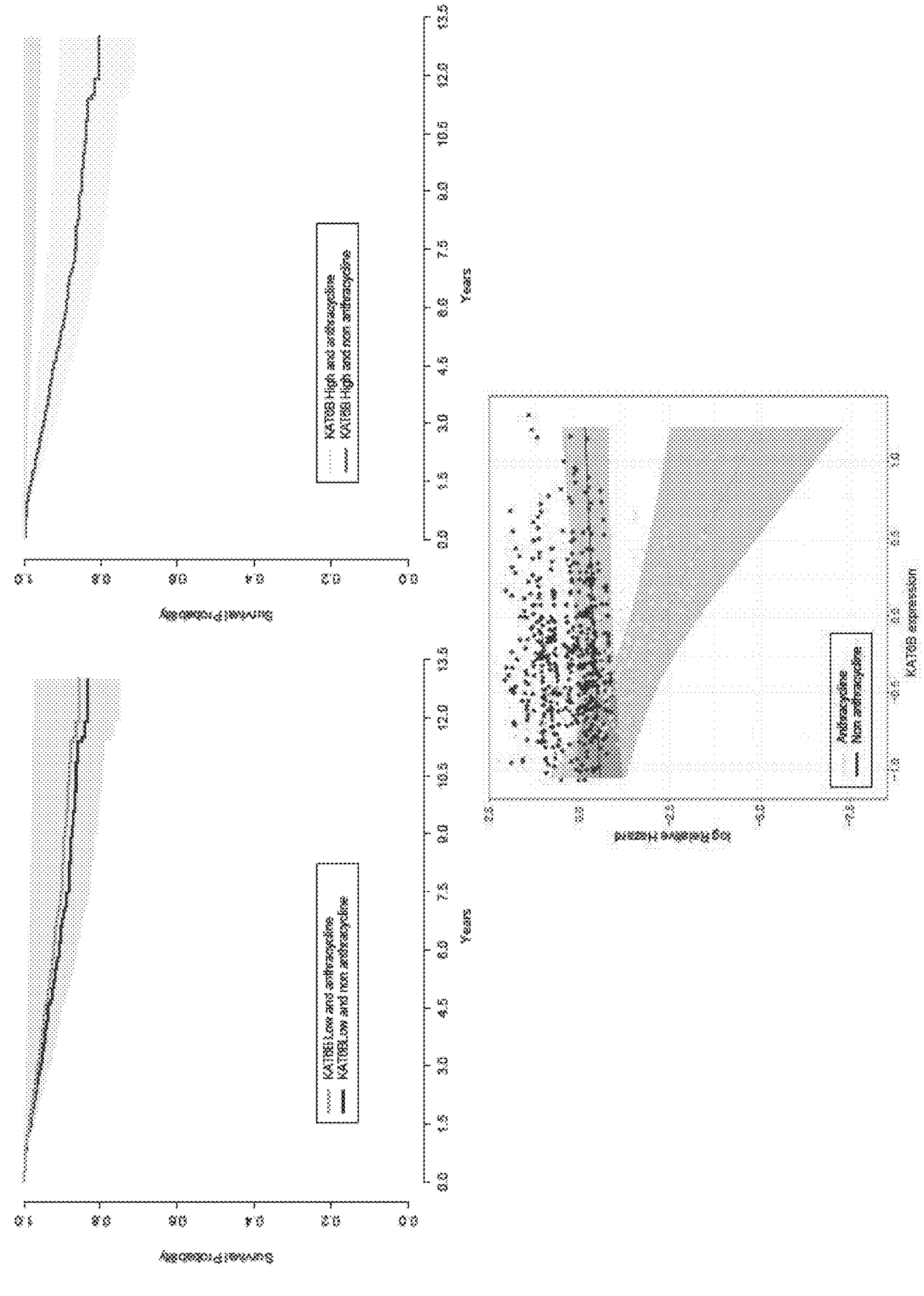
FIG. 14 provides Cox Hazard plots of KAT6B, generated in accordance with various embodiments of the invention.
Figure 15:
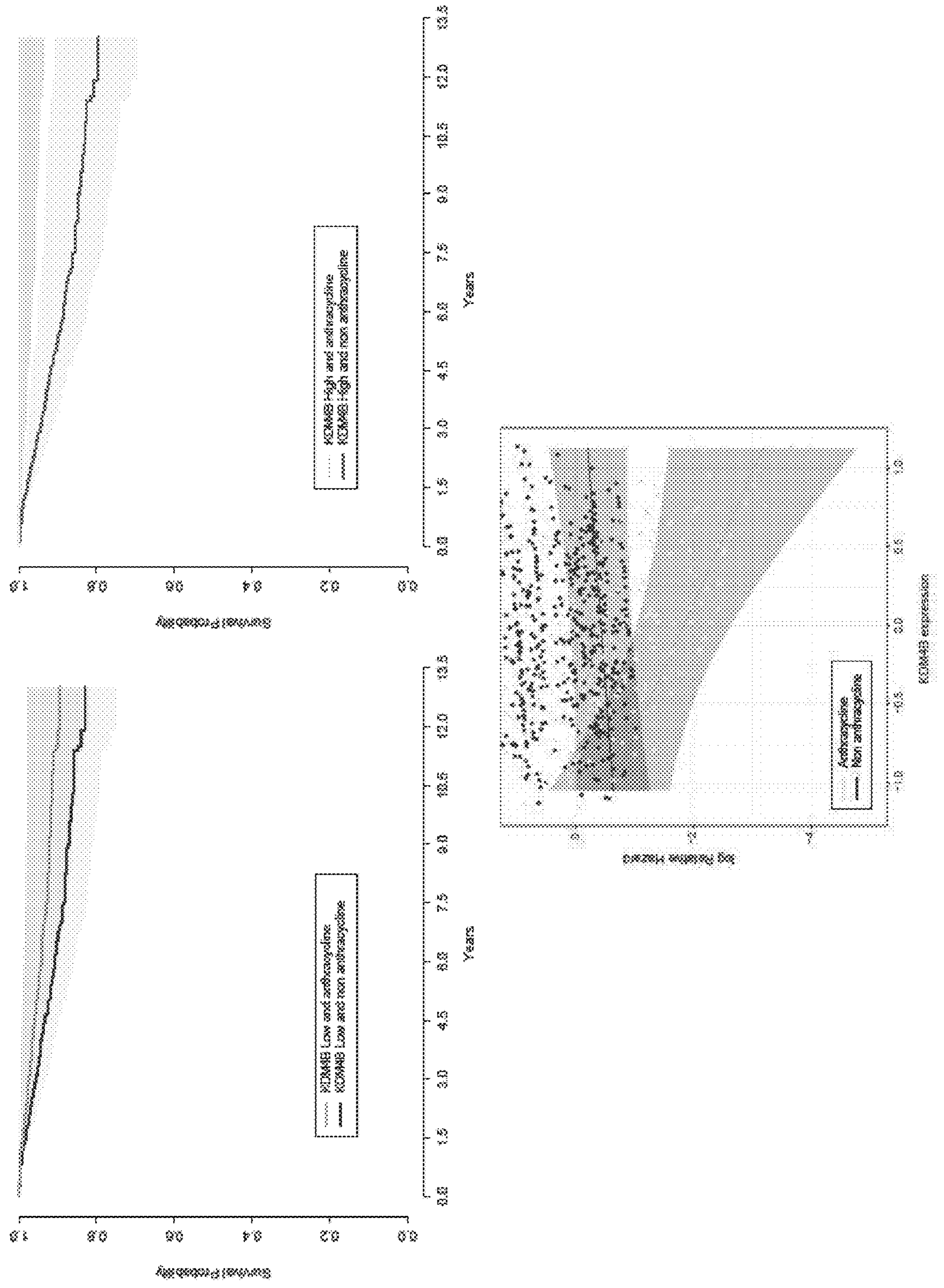
FIG. 15 provides Cox Hazard plots of KDM4B, generated in accordance with various embodiments of the invention.

Provided in FIGS. 13 to 15 are plots of Cox Proportional Hazards model of the probability of overall survival (adjusted by hormone, her2, lymph node status, size and cohort) and Hazard plots illustrating the Cox Proportional log relative Hazard by CRG expression levels in treated versus untreated samples. As can be seen in FIG. 13, anthracycline treatment of patients having tumors with low expression of BCL11A had greater survival rates. Accordingly, the lower expression of BCL11A resulted in a lower relative hazard score in the anthracycline treatment group but not in the non-anthracycline treatment group. Conversely, as shown in FIGS. 14 and 15, anthracycline treatment of patients having tumors with high expression of KAT6B or KDM4B had greater survival rates. Accordingly, the higher expression of KAT6B or KDM4B resulted in a lower relative hazard score in the anthracycline treatment group but not in the non-anthracycline treatment group.

Figure 16:
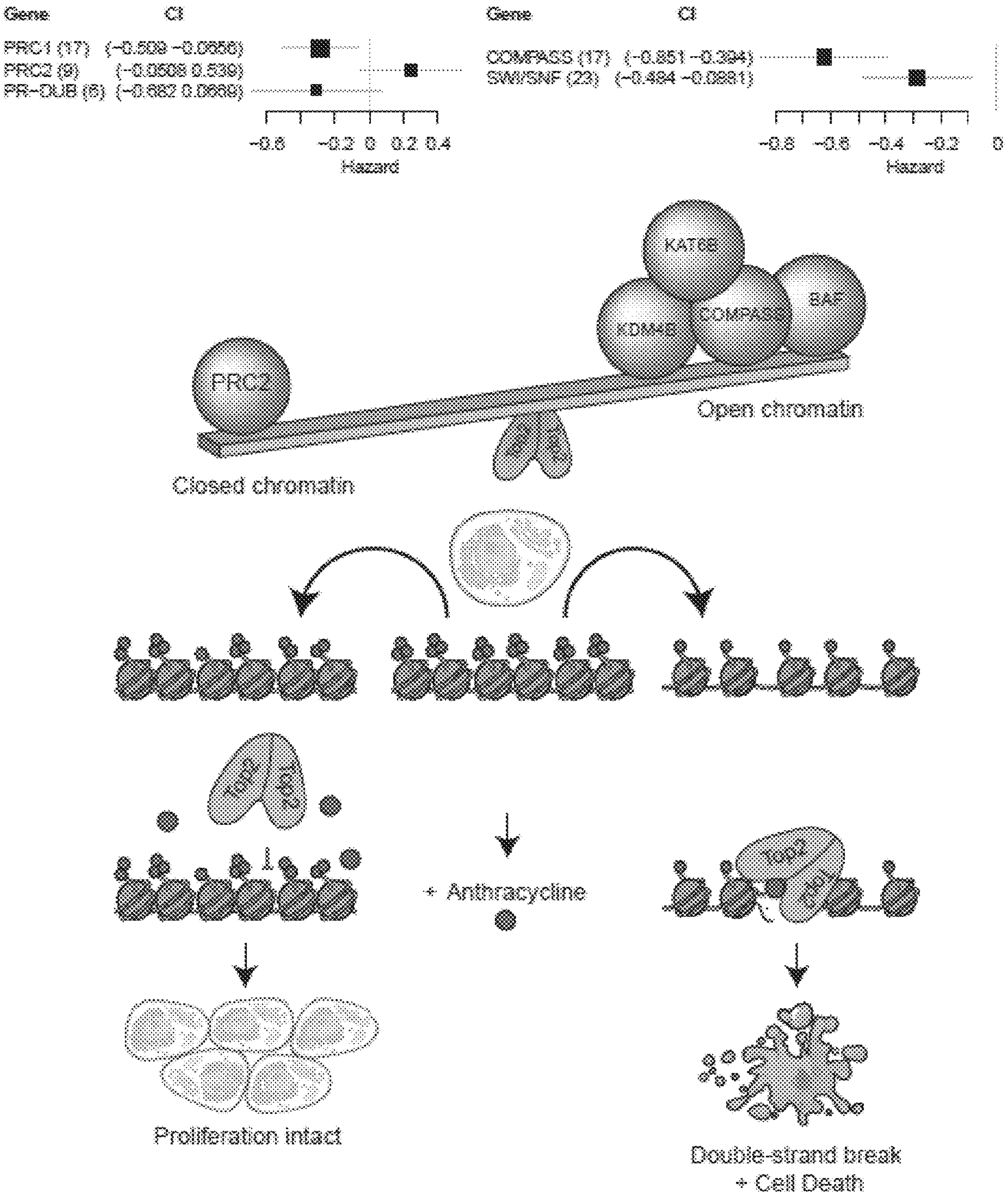
FIG. 16 provides data charts depicting expression of PRC2 and COMPASS/BAF complexes and also provides a schematic exemplifying the roles of PRC2 and COMPASS/BAF complexes in chromatin architecture, generated in accordance with various embodiments of the invention.

Because the BAF complex, a member of the trithorax group, influences TOP2 recruitment and accessibility, and opposes polycomb group complexes, the roles of these two complex families in mediating anthracycline benefit were evaluated. To this end, the p-values and hazard ratios from the breast cancer metacohort for all genes in each complex family were summarized. It was found that higher expression of PRC2 genes are generally associated with a higher hazard ratio, whereas higher expression of both BAF and COMPASS, members of trithorax class of genes, are generally associated with lower hazard ratios in the presence of anthracyclines (FIG. 16). Changes in PRC1 levels do not lead to concomitant changes in accessibility, consistent with the lack of a change in hazard ratio for PRC1 or PR-DUB genes. Thus, CRGs for which high expression was associated with greater anthracycline benefit were generally associated with increased DNA accessibility, while those for which high expression was associated with lesser anthracycline benefit were associated with decreased DNA accessibility. These findings are consistent with a model where an imbalance of CRG expression in a patient's tumor mediates anthracycline benefit. The Trithorax proteins, including BAF and COMPASS complexes, KDM4B and others open the DNA fiber for TOP2 binding, thereby increasing anthracycline sensitivity. Conversely, an opposing set of CRGs including Polycomb group proteins (PRC2 complex) and others close the DNA fiber to TOP2 binding, thereby decreasing anthracycline sensitivity (FIG. 16).

Figure 17A:
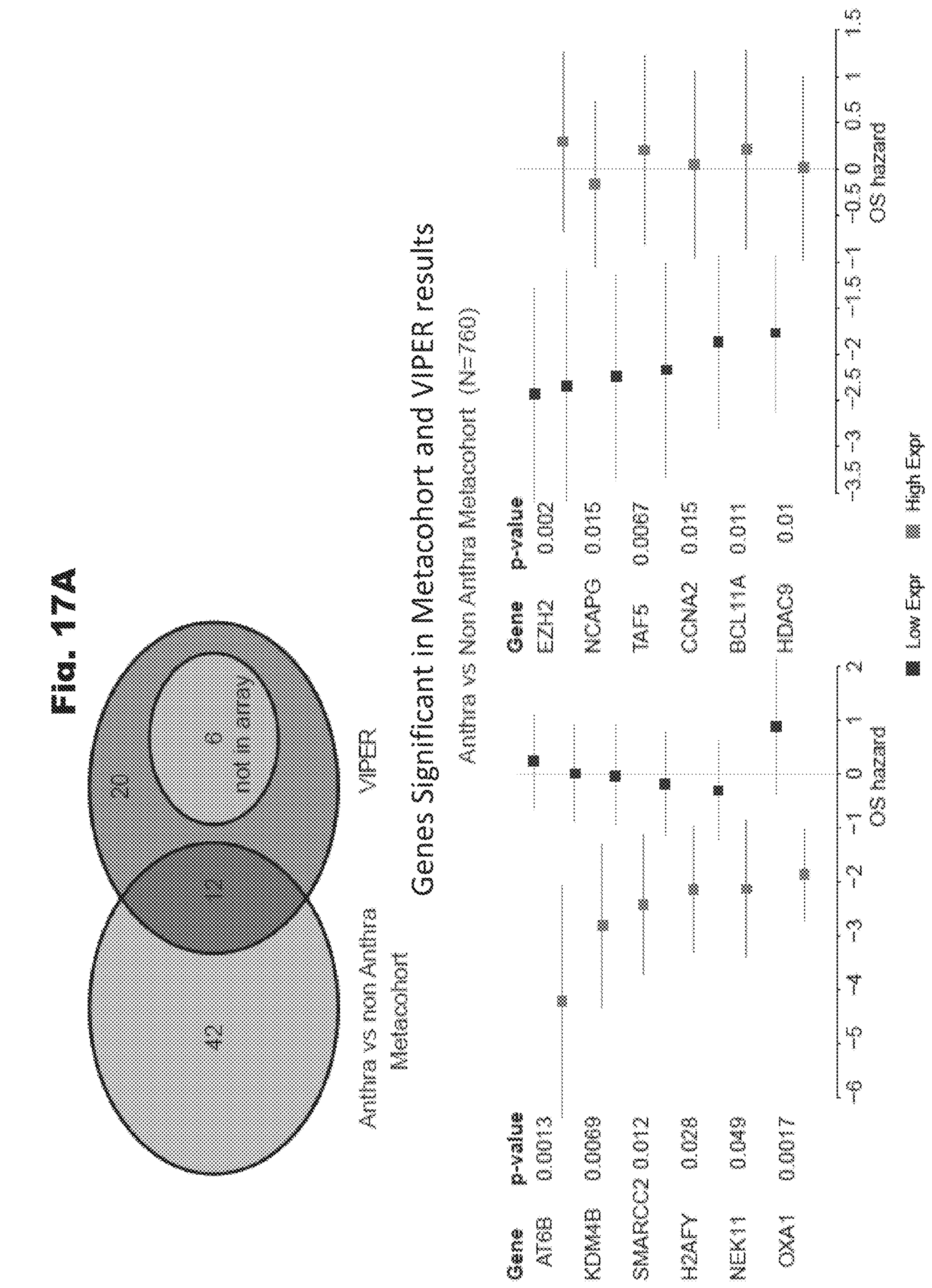
FIG. 17A provides data charts depicting expression levels of chromatin regulatory genes indicative of anthracycline responsiveness derived from anthracycline vs. non-anthracycline treated patients, generated in accordance with various embodiments of the invention.
Figure 17B:
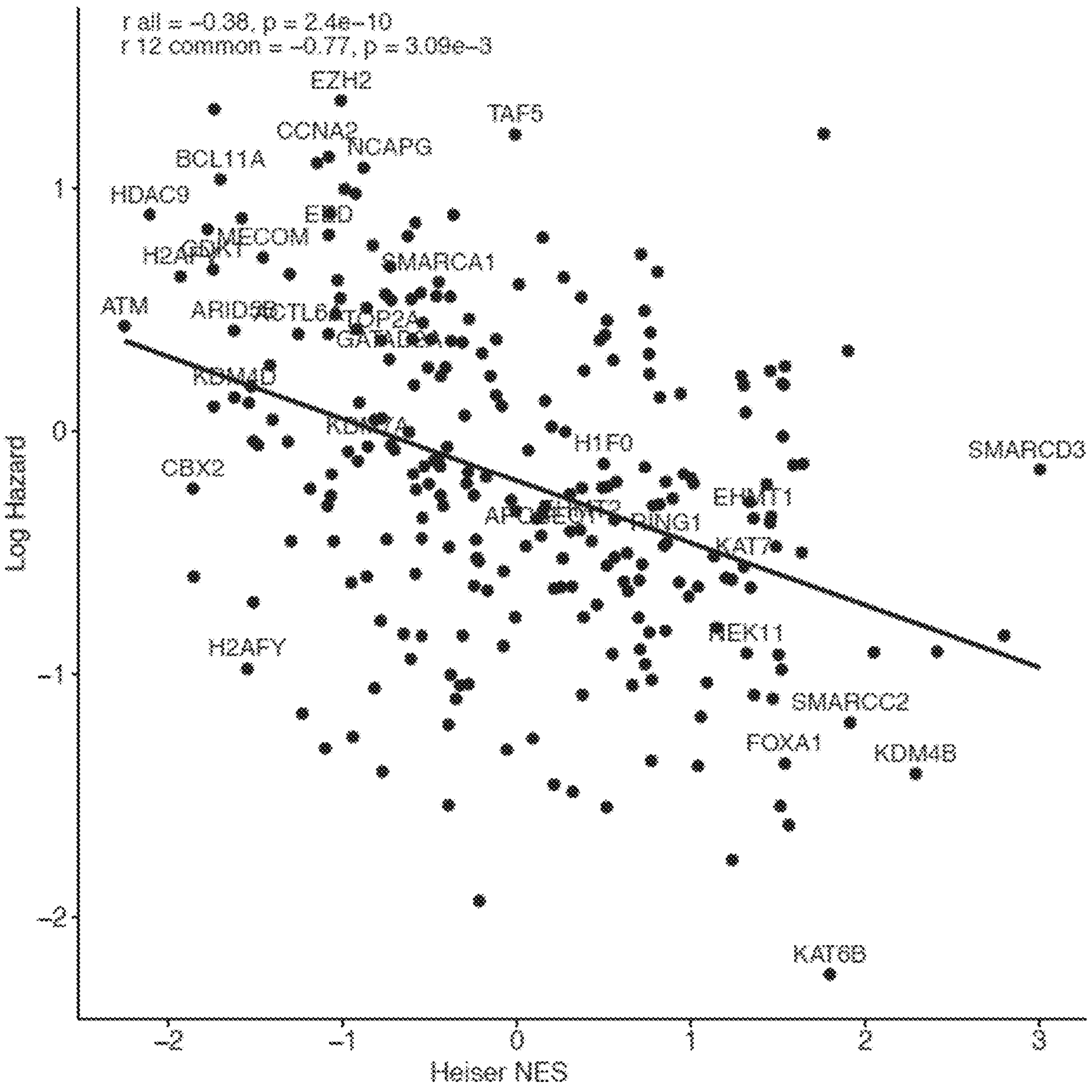
FIG. 17B provides a data chart showing the correlation between the enrichment of CRGs of the cell line analysis (specifically in the Heiser microarray dataset, Normalized Enriched Score, NES) and the hazard ratio of the anthracycline responsiveness derived from anthracycline vs non anthracycline treated patients, generated in accordance with various embodiments of the invention.
Figure 18:
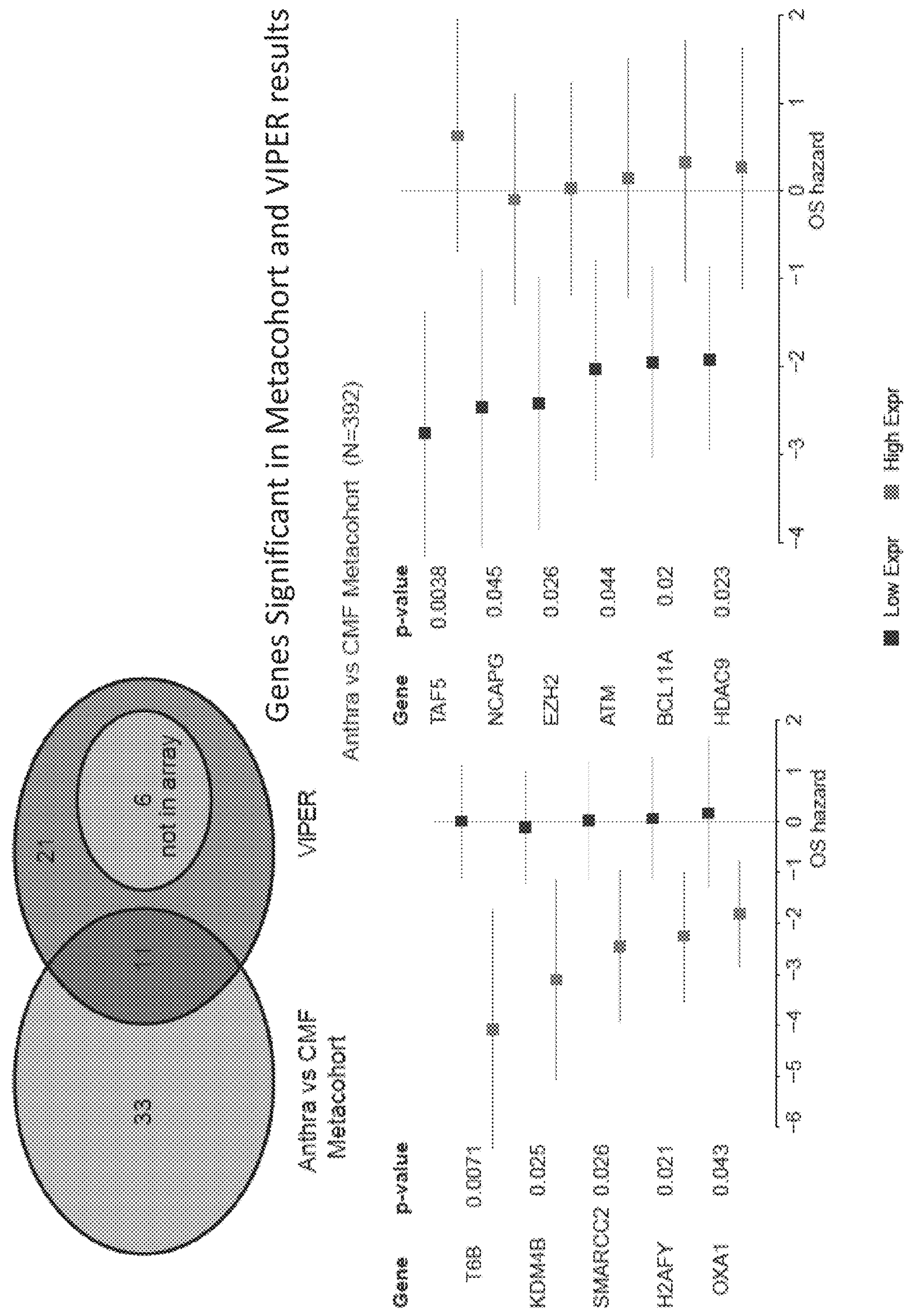
FIG. 18 provides data charts depicting expression levels of chromatin regulatory genes indicative of anthracycline responsiveness derived from anthracycline vs. CMF treated patients, generated in accordance with various embodiments of the invention.
Figure 19:
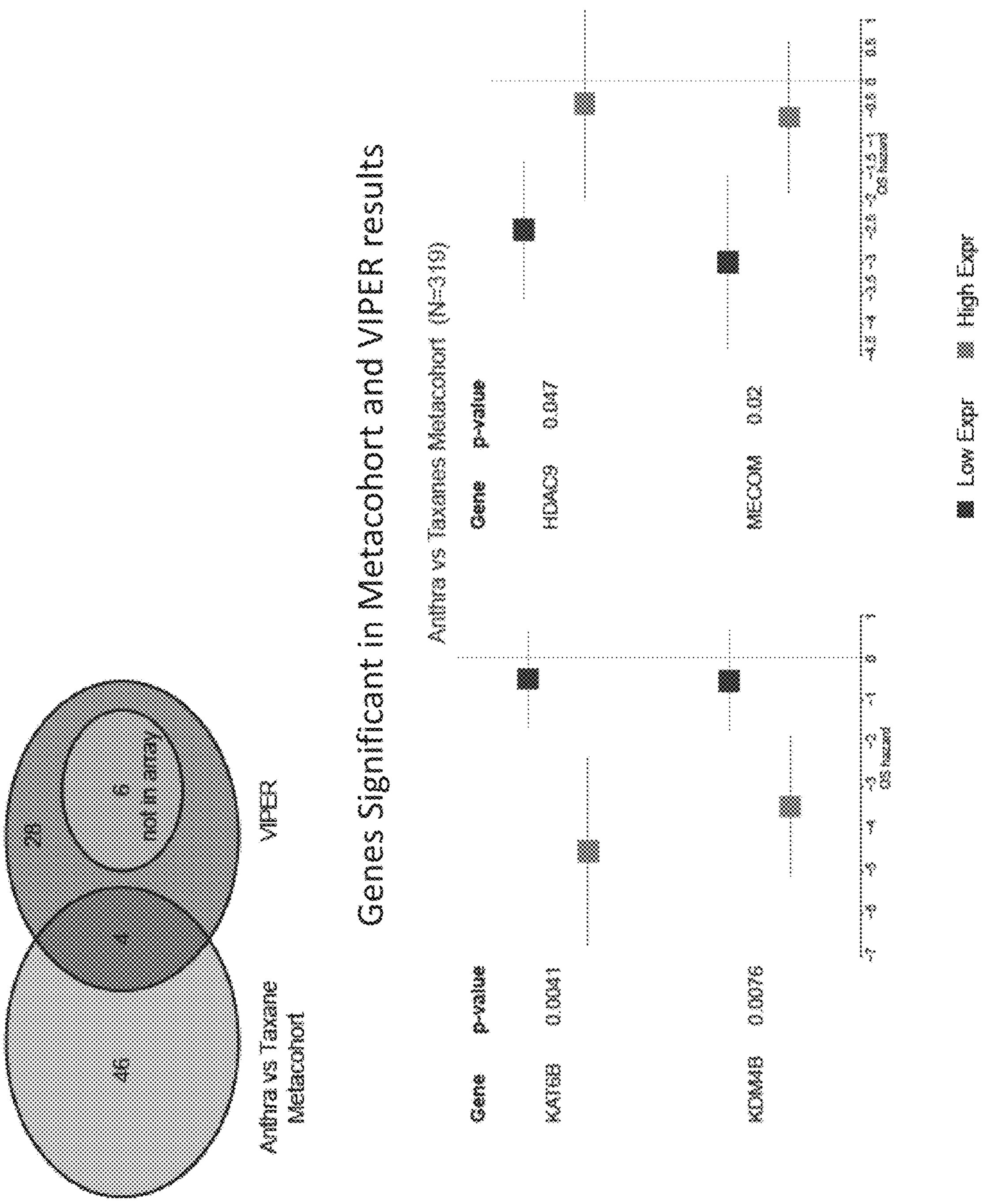
FIG. 19 provides data charts depicting expression levels of chromatin regulatory genes indicative of anthracycline responsiveness derived from anthracycline vs. taxane treated patients, generated in accordance with various embodiments of the invention.
Figure 20:
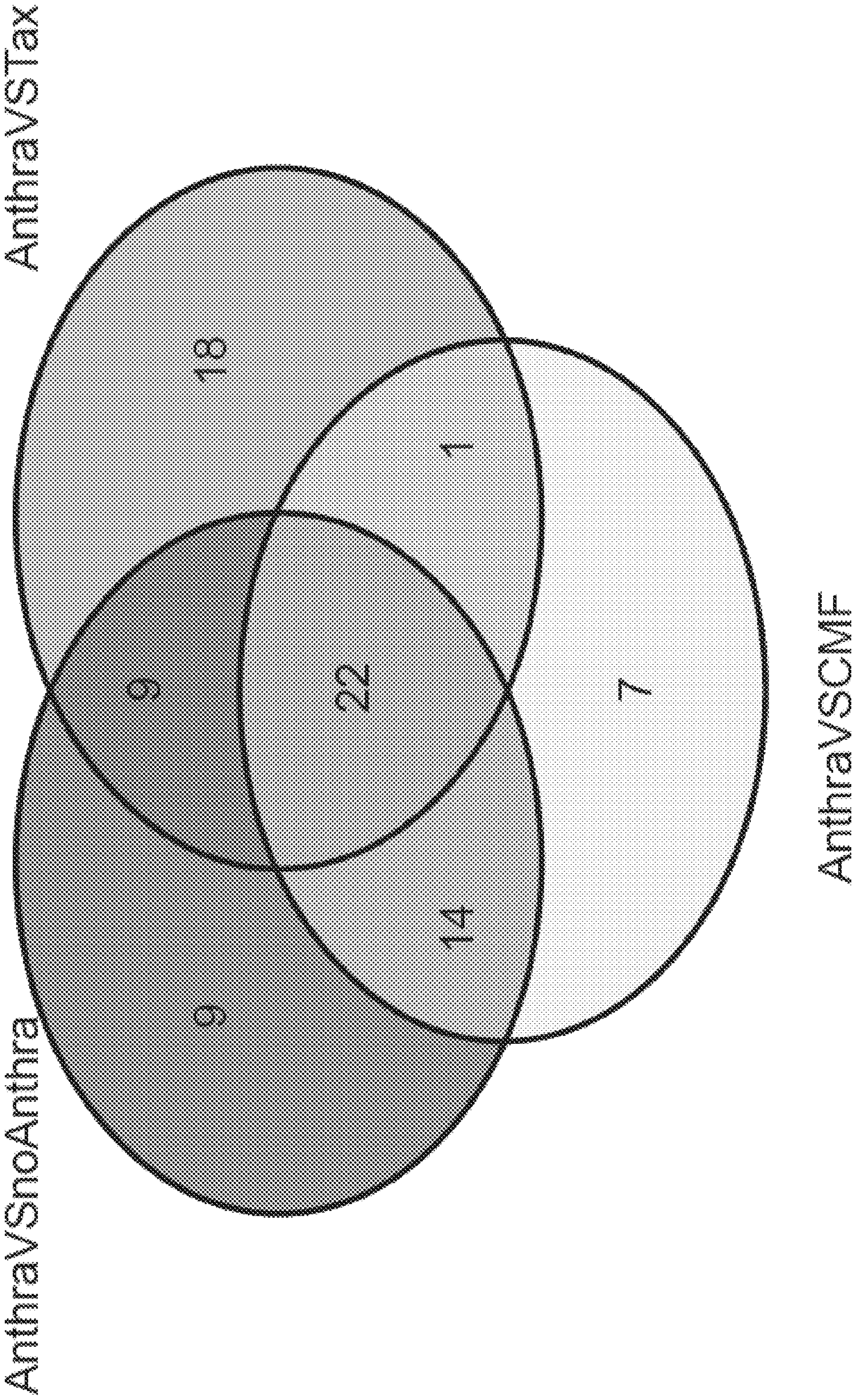
FIG. 20 provides an overview of the results of expression levels of chromatin regulatory genes indicative of anthracycline responsiveness in the various treatment comparisons, generated in accordance with various embodiments of the invention.

The intersection between CRGs associated with anthracycline response in the patient metacohort and the in vitro cell line analysis was examined. Of the 38 CRGs implicated in anthracycline response in vitro, 32 had available expression data in the metacohort and of these, 12 exhibited a significant interaction between expression and anthracycline usage in predicting overall survival when comparing anthracycline-treated versus non-anthracycline-treated patients (FIG. 17A). Enrichment in the in vitro analysis are highly correlated with negative hazard from the clinical outcome analysis (Pearson correlation −0.38, whilst if we select only the 12 genes that are significant both in vivo and in vitro, the Pearson correlation is −0.77 (FIG. 17B). To assess whether the identified CRGs that are important for anthracycline benefit were also more generally implicated in benefit to other chemotherapies, anthracycline was compared with two other standard chemotherapeutic regimes. In one set of experiment, patients treated with anthracyclines (N=218) were compared patients treated with the chemotherapy regimen CMF (cyclophosphamide/methotrexate/5-fluorouracil; that does not contain an anthracycline) (N=174) (Table 5). In another set of experiments, patients treated with anthracyclines and no taxanes (N=196) were compared to patients treated with taxanes and no anthracyclines (N=123) (Table 6). In the CMF comparison, 44 CRGs with a significant ($p<0.05$) interaction between expression and treatment in predicting overall survival were identified. Amongst the 44 CRGs that were significant when comparing anthracycline-treated versus CMF-treated patients, eleven genes were also significant in the in vitro analysis (KAT6B, KDM4B, SMARCC2, MACROH2A1, FOXA1, TAF5, NCAPG, EZH2, ATM, BCL11A and HDAC9) (FIG. 18). In the taxane comparison, 50 genes with a significant ($p<0.05$) interaction between their expression and treatment in predicting overall survival were identified. Of the 50 genes from the anthracycline-treated versus taxane-treated comparison, four genes were significant in the in vitro analysis (KAT6B, KDM4B, HDAC9, and MECOM) (FIG. 19). There were 22 CRGs shared among three comparisons (FIG. 20), three of which (KDM4B, KAT6B and HDAC9) were significant in all three comparisons in the patient metacohort, as well as in the in vitro network analysis. These results suggest that the CRGs identified in these analyses are specifically implicated in anthracycline sensitivity, rather than general chemosensitivity.

While the analyses described in the previous paragraphs adjusted for ER, PR, and HER2 status, it was sought to determine whether the gene expression associations were also significant within each of the clinical subgroups. To evaluate this, the metacohort was stratified into the three clinical subtypes: ER-positive/HER2-negative (N=204) (Table 7), HER2-positive (N=216) (Table 8), and triple-negative (TNBC) (N=113) (Table 9). For the ER-positive/HER2-negative group hormonal treatment was also included as a covariate. Notably, across these subgroups, the directionality of the hazard ratios for most of the 54 CRGs remained the same (3 changed direction in ER-positive/

Figure 21:
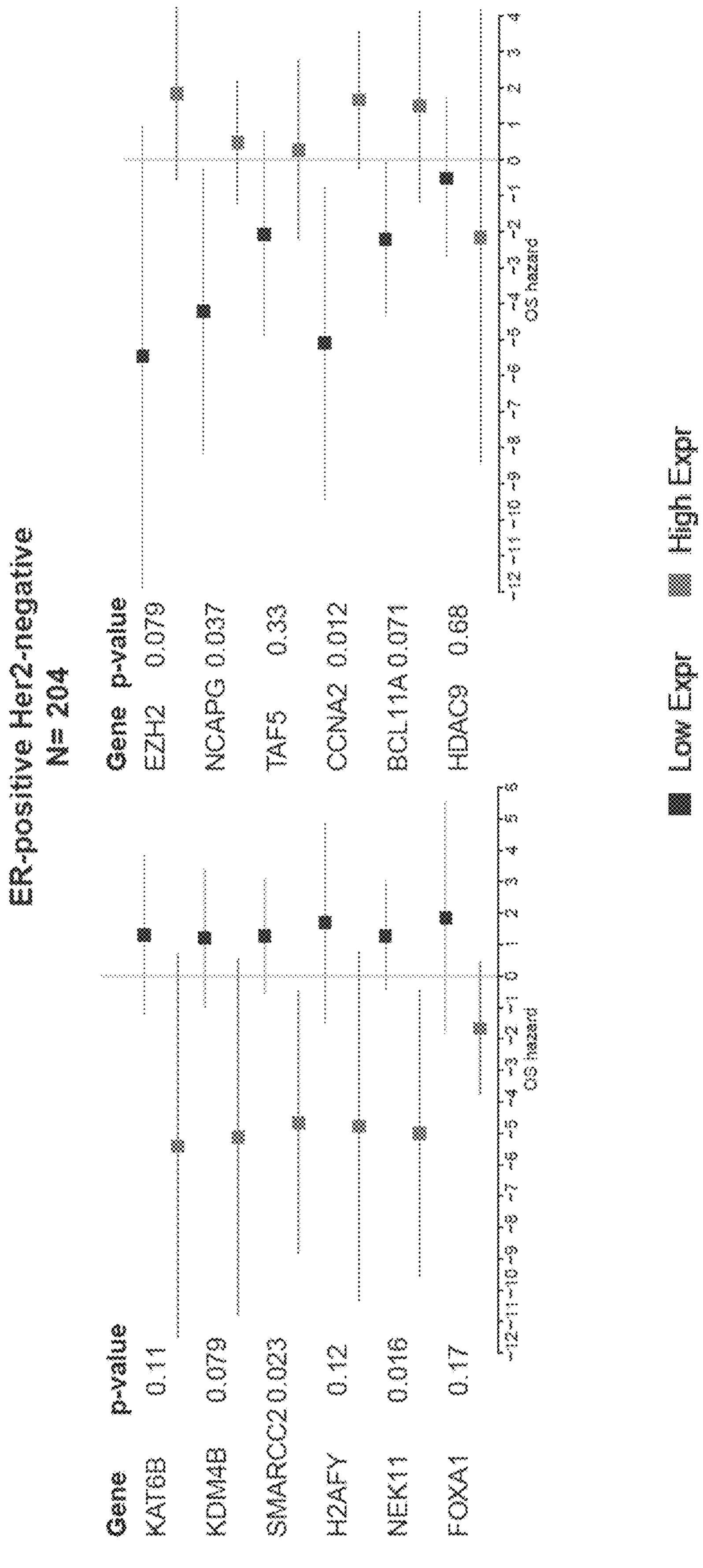
FIG. 21 provides data charts depicting expression levels of chromatin regulatory genes indicative of anthracycline responsiveness derived from ER-positive, HER2-negative patients, generated in accordance with various embodiments of the invention.
Figure 22:
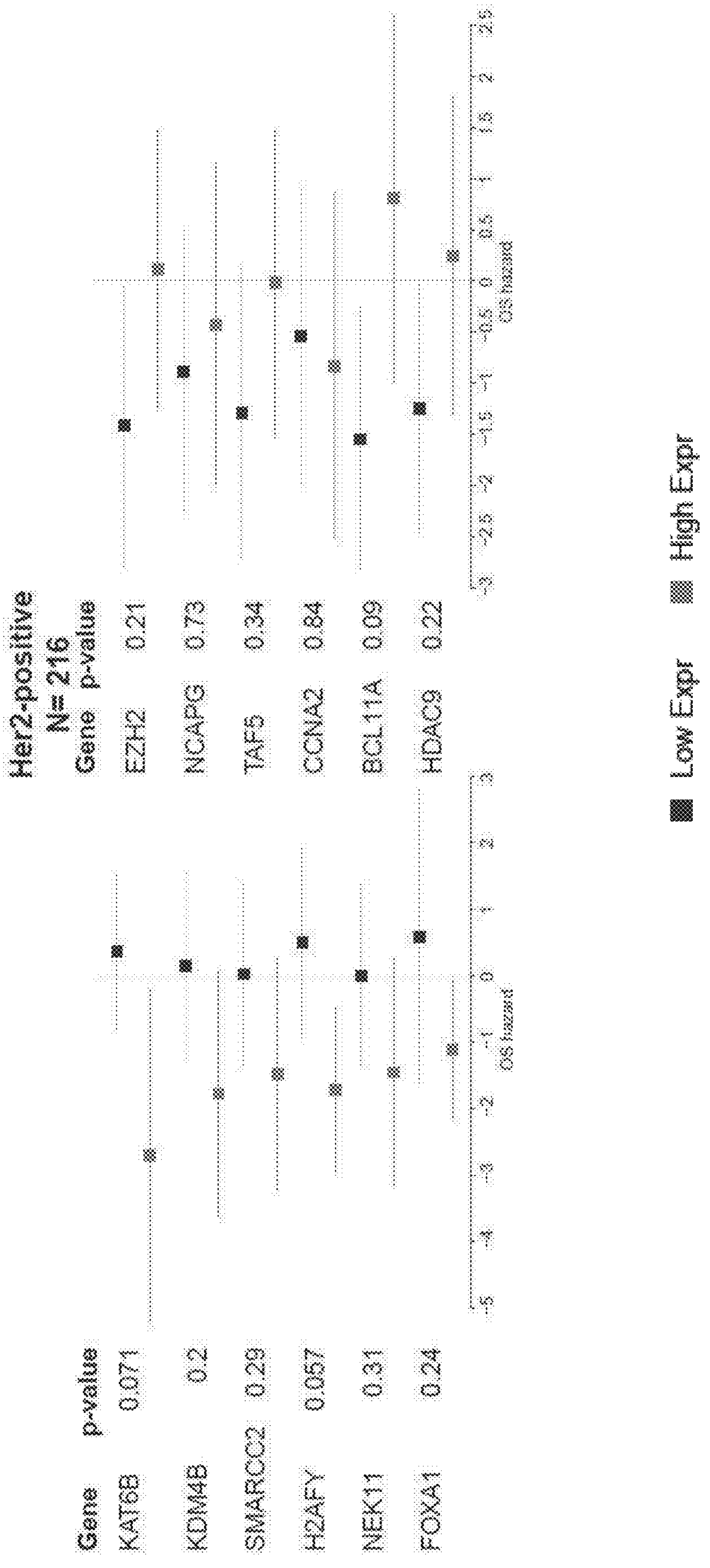
FIG. 22 provides data charts depicting expression levels of chromatin regulatory genes indicative of anthracycline responsiveness derived from HER2-positive patients, generated in accordance with various embodiments of the invention.
Figure 23:
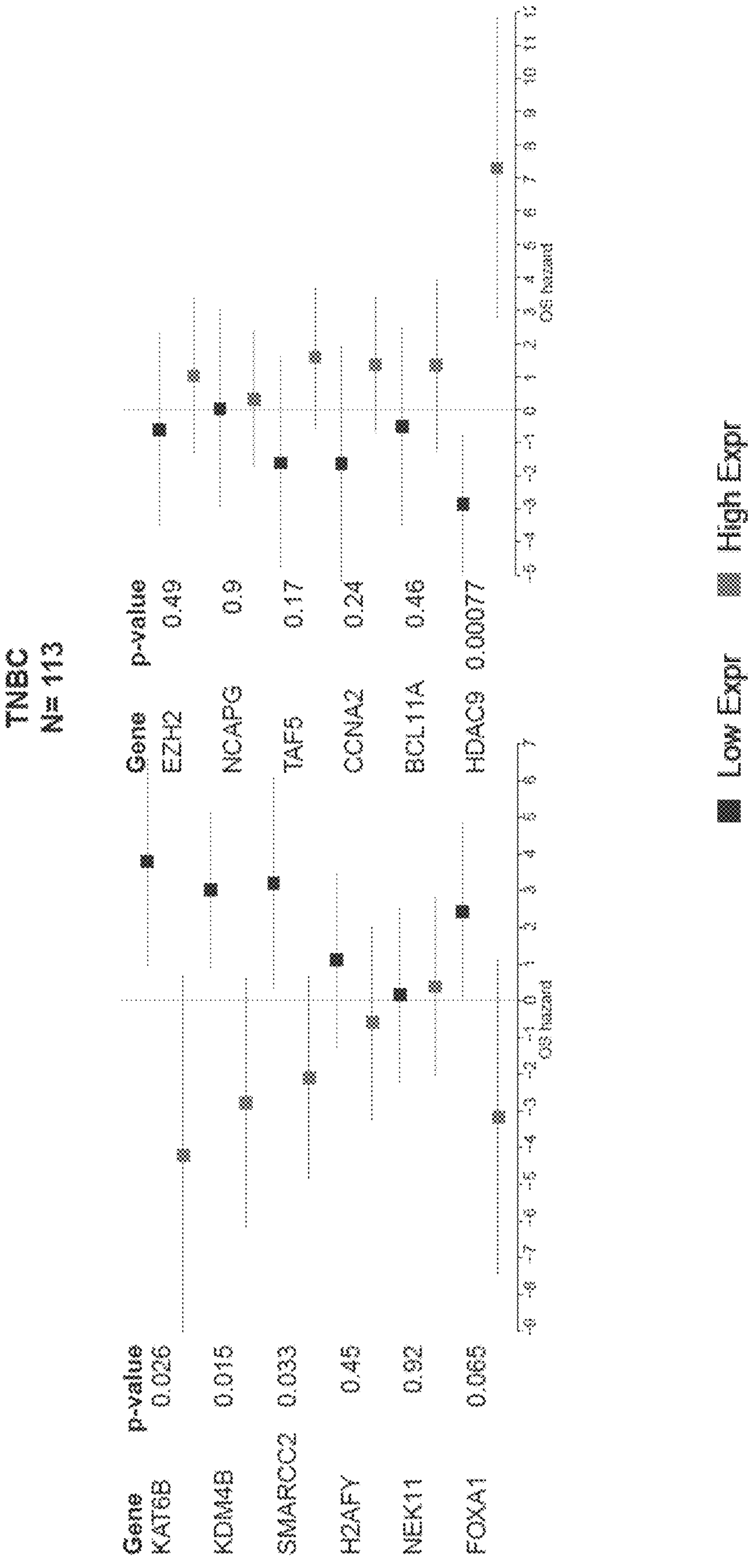
FIG. 23 provides data charts depicting expression levels of chromatin regulatory genes indicative of anthracycline responsiveness derived from triple-negative breast cancer patients, generated in accordance with various embodiments of the invention.

HER2-negative tumors, 9 changed direction in HER-positive tumors, and 7 changed direction in TNBC) (FIGS. 21 to 23). Even when some associations were not statistically significant ($p<0.05$), likely due to sample size, these findings suggest that CRGs are predictive of anthracycline benefit irrespective of subgroup and point to their more general regulatory function.

Example 3: Knockdown of KDM4B or KAT6B in Breast Cancer Cells Induces Anthracycline Resistance Across the analysis of both cell line and patient data, KDM4B expression emerged as a strong candidate CRG to determine the success of a course of anthracycline treatment for breast cancer. In particular, both in vitro and in vivo, higher KDM4B or KAT6B expression was associated with an ability to respond to anthracycline treatments.

KDM4B is a histone demethylase that recognizes H3K9me2/3 and converts the histone tail to H3K9me1, effectively changing the histone mark from one that is associated with an inaccessible, transcriptionally inactive chromatin state to one that is associated with a more accessible, transcriptionally active state. It is therefore plausible that lower levels of KDM4B expression could induce changes in histone methylation that render DNA inaccessible to TOP2, resulting in decreased anthracycline efficacy.

Figure 24:
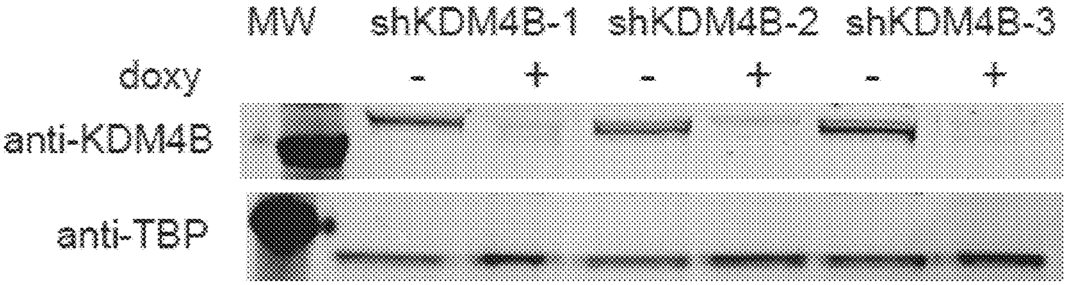
FIG. 24 provides an image of western blot depicting the knockdown of KDM4B by a short-hairpin RNA in a breast cancer cell line, generated in accordance with various embodiments of the invention.
Figure 25:
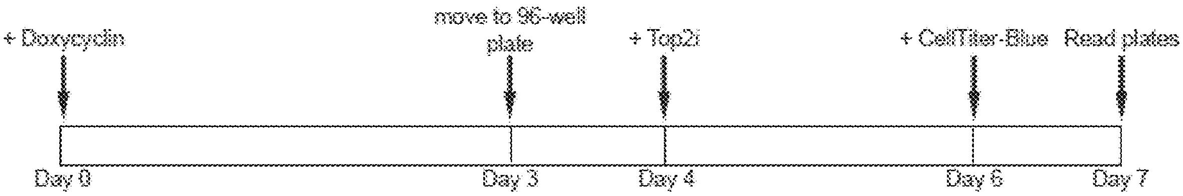
FIG. 25 provides a schematic for treatment of breast cancer cell lines modified to have reduced KDM4B expression with anthracyclines or other agents, used in accordance with various embodiments of the invention.
Figure 26:
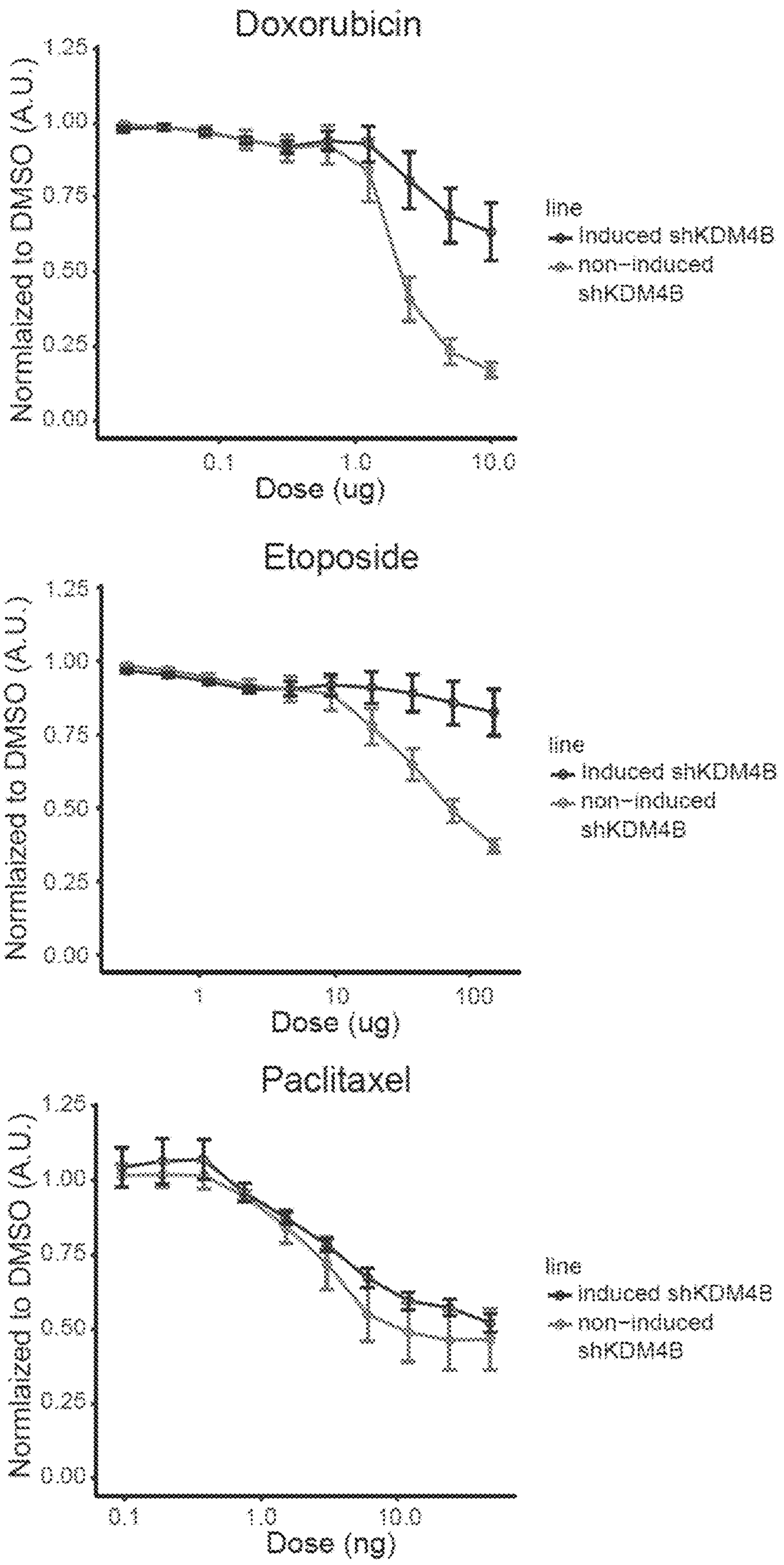
FIG. 26 provides data graphs depicting doxorubicin, etoposide, and paclitaxel treatment of a breast cancer cell line having reduced KDM4B expression, generated in accordance with various embodiments of the invention.
Figure 27:
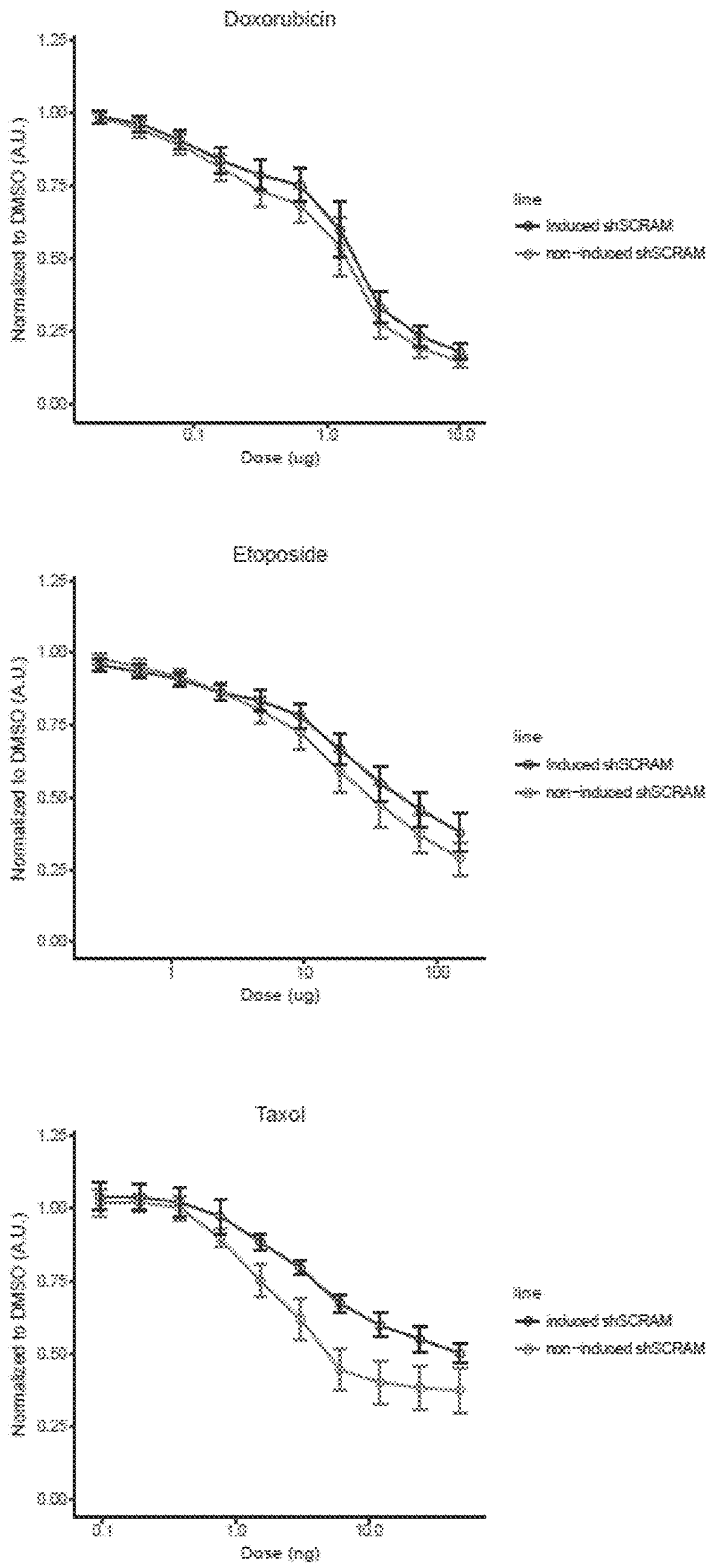
FIG. 27 provides data graphs depicting doxorubicin, etoposide, and paclitaxel treatment of a control breast cancer cell line, generated in accordance with various embodiments of the invention.
Figure 28:
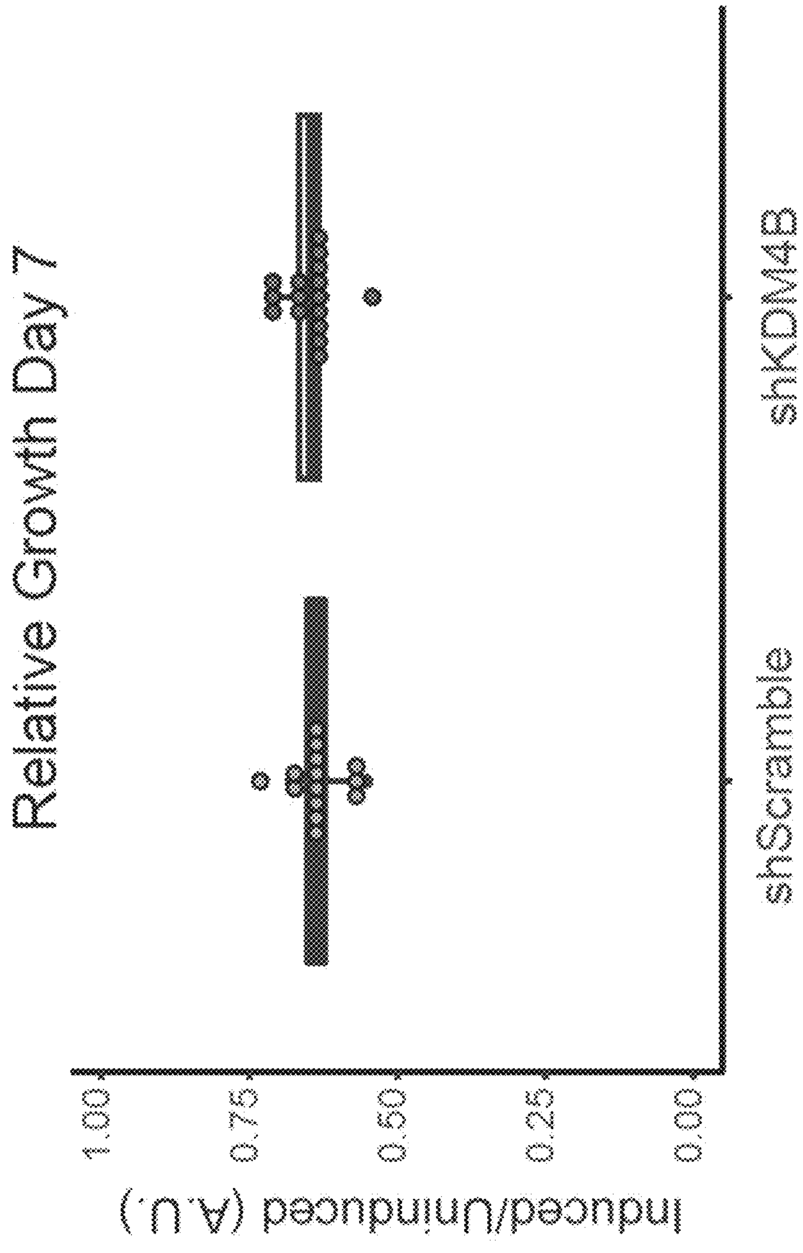
FIG. 28 provides a data graph depicting relative growth of a breast cancer cell line having reduced KDM4B expression and a control breast cancer cell line, generated in accordance with various embodiments of the invention.
Figure 29A:
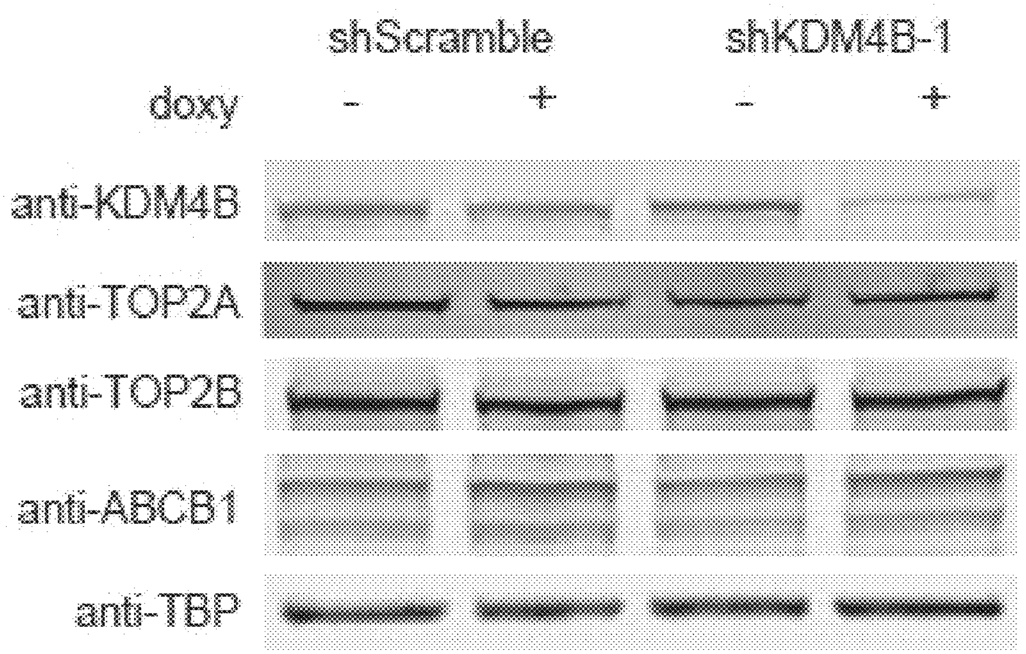
FIG. 29A provides an image of a western blot depicting expression of various chromatin regulatory genes in a breast cancer cell line having reduced KDM4B expression and a control breast cancer cell line (without knockdown of KDM4B), generated in accordance with various embodiments of the invention.
Figure 29B:
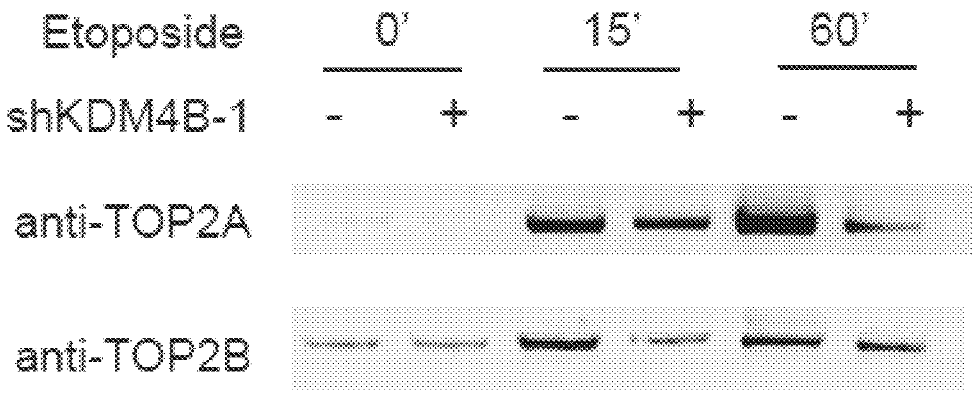
FIG. 29B provides an image of a western blot depicting the change of protein expression of TOP2A and TOP2B upon treatment with etoposide in KDM4B knockdown or in control lines, generated in accordance with various embodiments of the invention.
Figure 30:
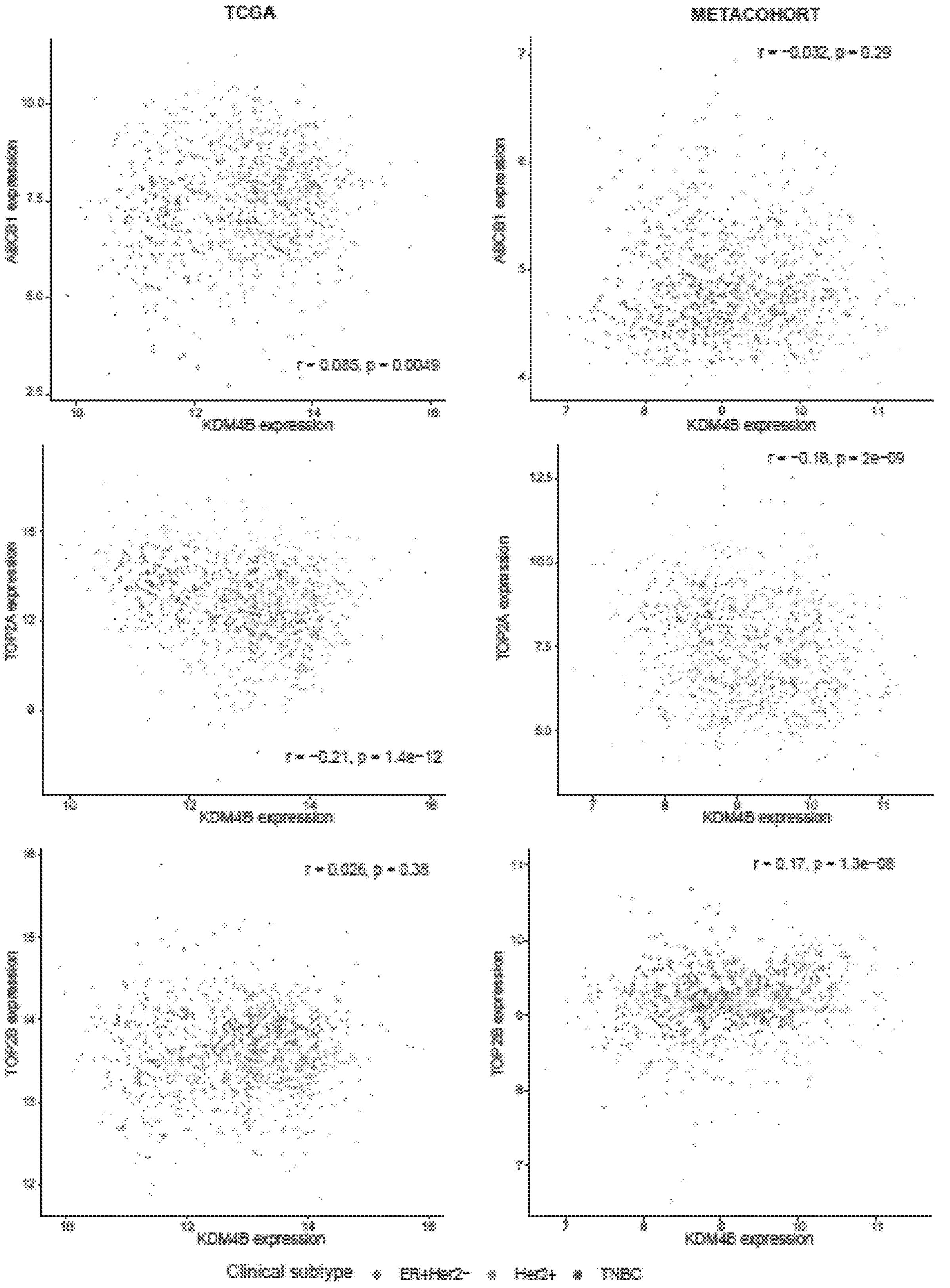
FIG. 30 provides data graphs depicting correlations between expression levels of various chromatin regulatory genes derived from a metacohort of breast cancer patients, generated in accordance with various embodiments of the invention.

To functionally evaluate the role of KDM4B expression in anthracycline sensitivity, three inducible shRNA knockdown constructs were used to lower the levels of KDM4B protein in the HCC1954 breast cancer cell line (FIG. 24). HCC1954 is ER−/HER2+, but not TOP2A amplified, and is doxorubicin-sensitive. The expression KDM4B was knocked down for four days, and then the cells were treated with either doxorubicin, etoposide (a non-anthracycline TOP2 inhibitor) or paclitaxel (a taxane commonly used to treat breast cancer that functions via tubulin inhibition) for three days, after which cell viability was measured (FIG. 25). All experiments were normalized to DMSO vehicle-only controls and were performed under both induced and non-induced conditions. Consistent with the patient data, where CRG expression levels, including KDM4B, predicted outcome with anthracycline but not taxane treatment, knockdown of KDM4B induced resistance to doxorubicin, as well as etoposide, but remained sensitive to paclitaxel (FIG. 26). An inducible scrambled shRNA did not show significant changes in sensitivity to drug treatment (FIG. 27). Furthermore, it was confirmed that the resistance induced by knockdown was not due to a decrease in cell proliferation, loss of the drug target (TOP2A or TOP2B), or upregulation of the ABCB1 multi-drug exporter protein (FIGS. 28, 29A & 29B). Similarly, in the patient metacohort, there was minimal ($R<\pm0.2$) correlation between KDM4B expression and TOP2A, TOP2B or ABCB1 expression (FIG. 30). In sum, the results from the cell line model suggest that the correlation between KDM4B expression and anthracycline response observed in patients is replicable in vitro and highlights the specificity of CRGs in mediating response to TOP2 inhibitors.

Figure 31:
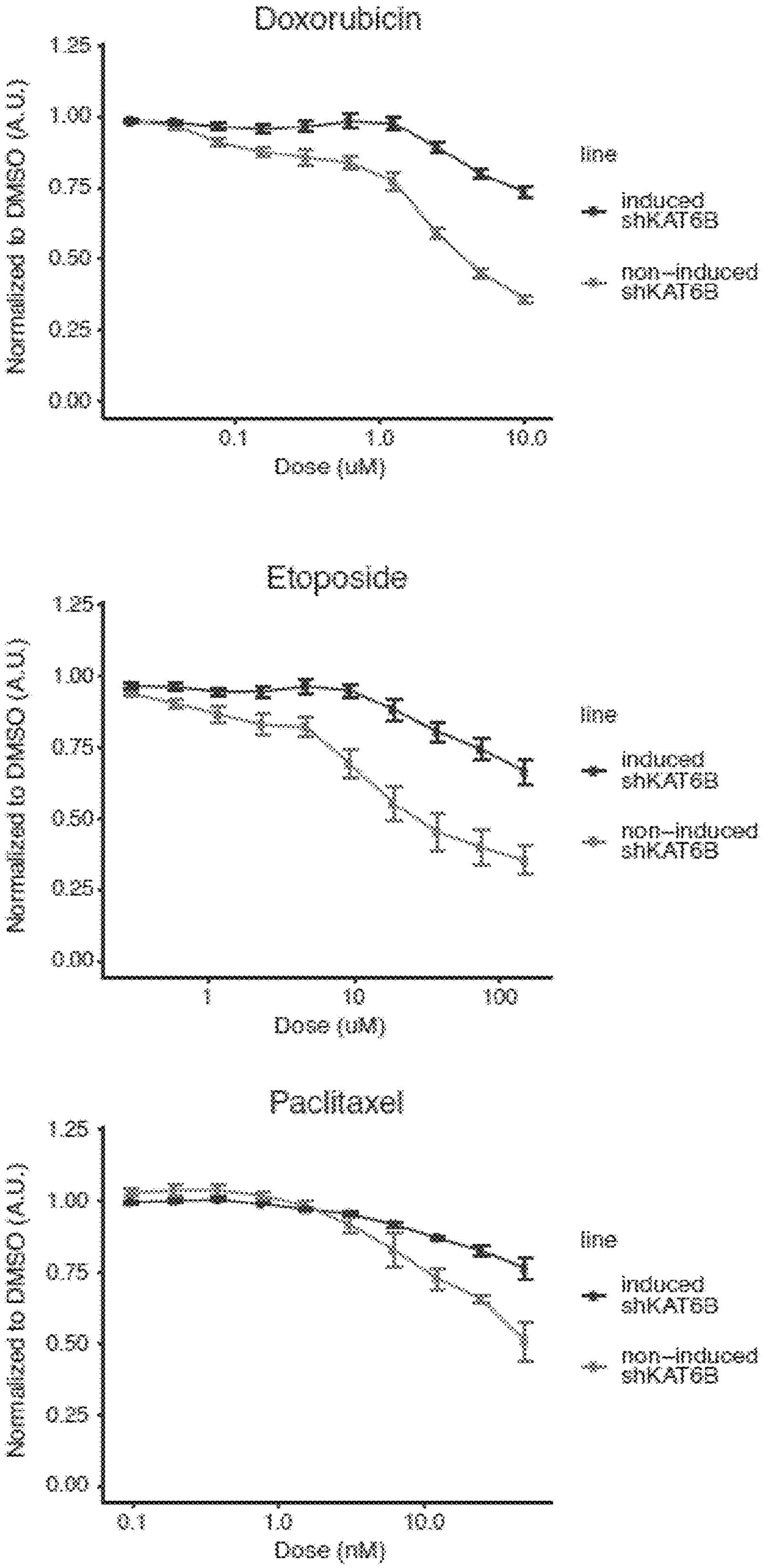
FIG. 31 provides data graphs depicting doxorubicin, etoposide, and paclitaxel treatment of a breast cancer cell line having reduced KAT6B expression, generated in accordance with various embodiments of the invention.
Figure 32:
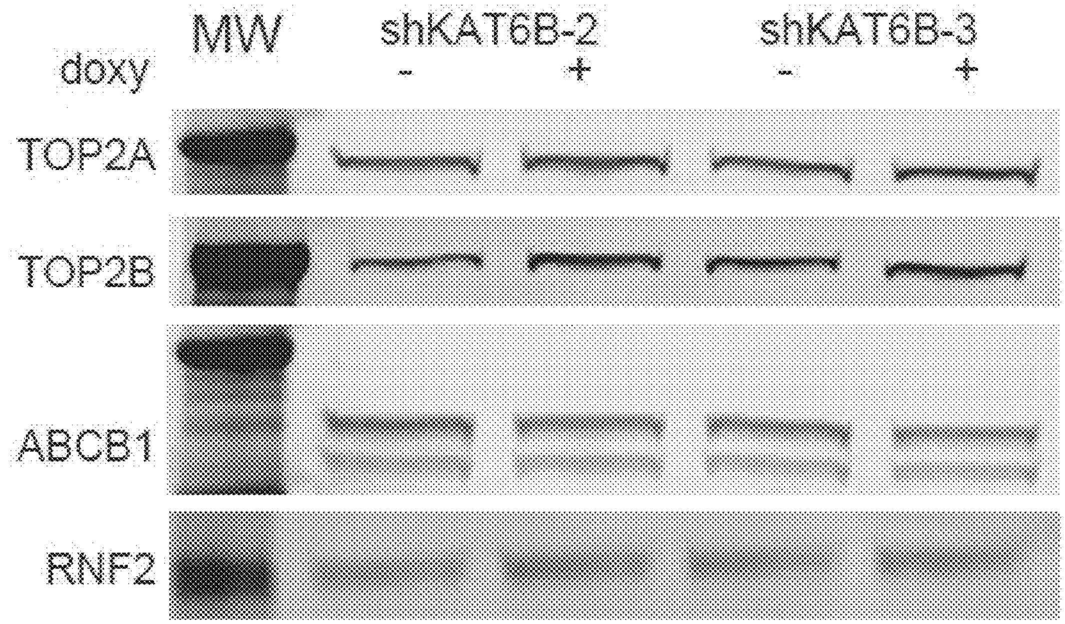
FIG. 32 provides an image of a western blot depicting expression of various chromatin regulatory genes of a breast cancer cell line having reduced KAT6B expression and a control breast cancer cell line, generated in accordance with various embodiments of the invention.

A similar experiment was performed by knocking down KAT6B expression to evaluate the role of KAT6B expression in anthracycline sensitivity. Three inducible shRNA knockdown constructs were used to lower the levels of KAT6B protein in the HCC1954 breast cancer cell line. Consistent with the KDM4B knockdown data knockdown of KAT6B induced resistance to doxorubicin, as well as etoposide, but remained sensitive to paclitaxel (FIG. 31). Likewise, it was confirmed that the resistance induced by knockdown was not due to loss of the drug target (TOP2A or TOP2B), or upregulation of the ABCB1 multi-drug exporter protein (FIG. 32).

Example 4: Predictive Modeling to Determine Anthracycline Benefit

The identified CRGs were evaluated to determine their predictive ability to determine whether a particular patient will benefit from anthracycline-based chemotherapy based on their CRG expression levels. The same clinical dataset was used to build various models based on principal component analysis.

In a first Cox Proportional Hazard model, CRGs were selected in an unsupervised way using principal component analysis or kernel principal component analysis with a Gaussian kernel (which captures non-linear relationships between the genes). The unsupervised selection resulted in thirty-two CRGs. The Cox model includes relevant clinical covariates (age, ER status, PR status, Her2 status, Lymph node positive/negative and tumor size) and the interaction between the first five PCA or KPCA with the anthracycline vs non anthracycline.

A 10 times 10 fold cross validation scheme to evaluate the predictive utility of the PCA and KPCA CPH models compared with a CPH without molecular information (using only drug or covariate information).

Figure 33:
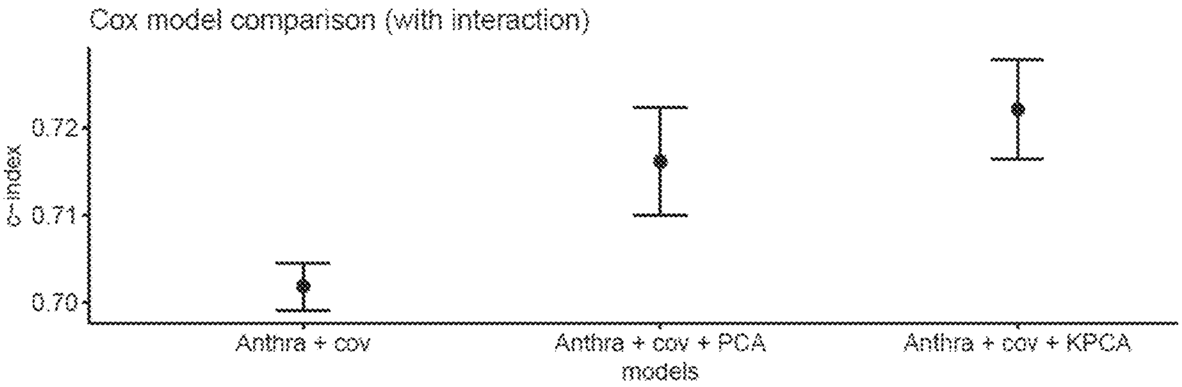
FIG. 33 provides a comparison of C-index scores between three Cox proportional hazard models, generated in accordance with various embodiments of the invention.
Figure 34:
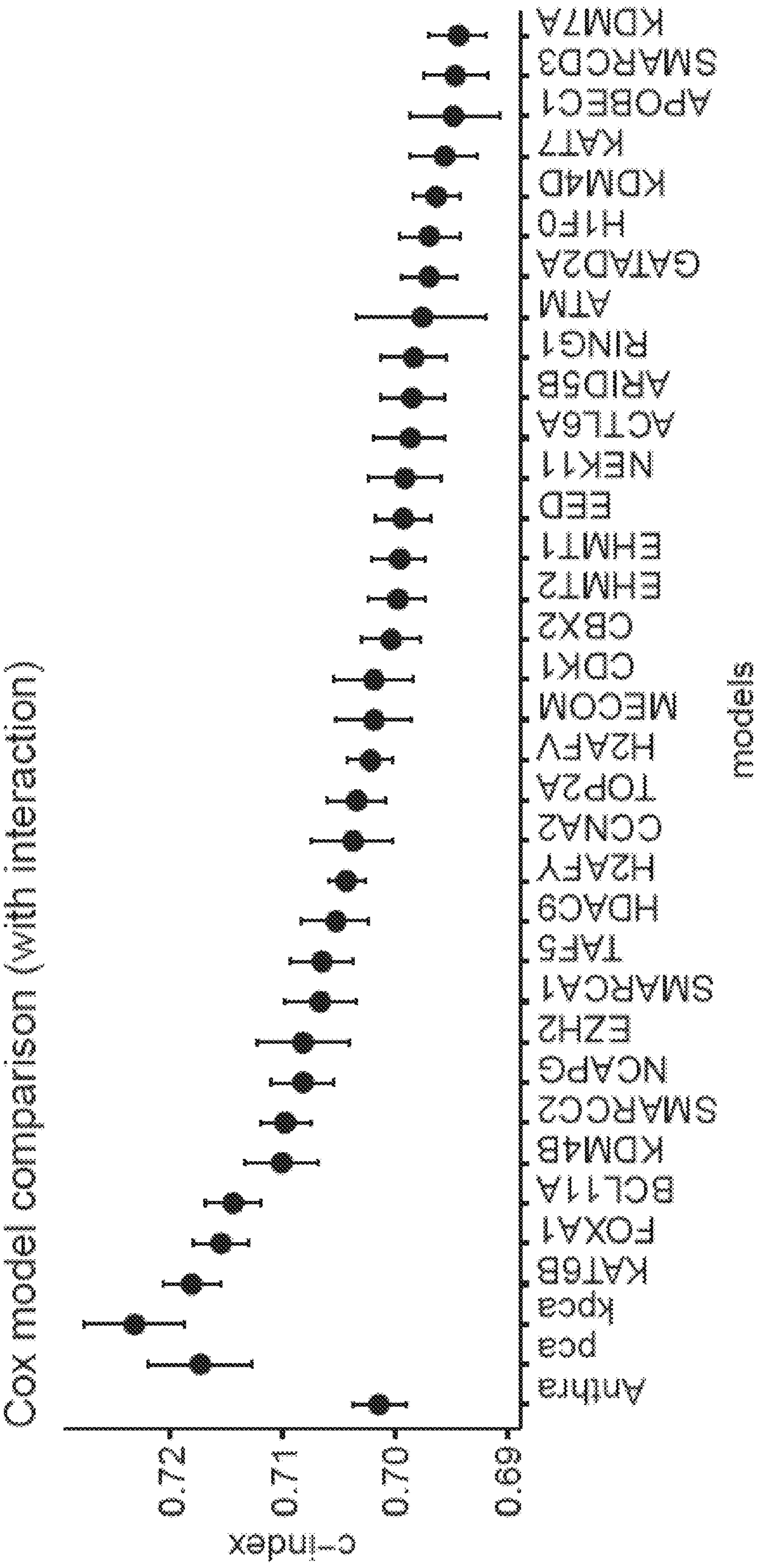
FIG. 34 provides a comparison of C-index scores between three Cox proportional hazard models of FIG. 33 and Cox proportional hazard models of individual chromatin regulatory genes, generated in accordance with various embodiments of the invention.
Figure 35:
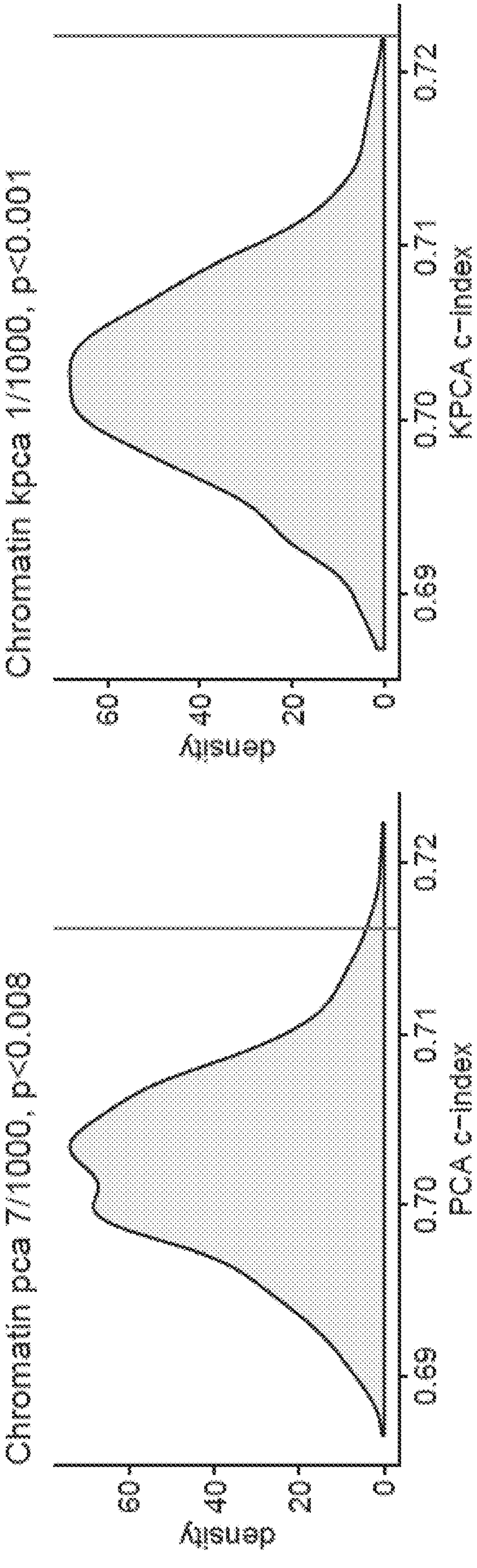
FIG. 35 provides a comparison C-index scores between randomly generated Cox proportional hazard models and the PCA and KPCA Cox proportional hazard models, generated in accordance with various embodiments of the invention.

Comparing the c-index for these Cox proportional hazard models, the KPCA model (KCPA+clinical covariates+anthracycline treatment) yields the best results with a mean c-index of 0.72 (sd 0.0056), followed by the PCA model (CPA+clinical covariates+anthracycline treatment) mean c-index of 0.716 (sd 0.0061) and the clinical model (clinical covariates+anthracycline treatment) with a mean c-index of 0.701 (sd 0.0027) (FIG. 33). In addition, individual CRG Cox proportional hazards models (gene X+clinical covariates+anthracycline treatment) were generated utilizing the selected genes to show the predictive power of each gene (FIG. 34).

The selected genes were also compared with randomly selected gene sets. Using the same 10 times 10 fold cross validation scheme to compare the PCA and KPCA models with the CRG genes with 1000 random sets of the same number of genes that were used in the original models. PCA model is ranked 7 of 1000 ($p<0.008$) whilst KPCA ranked 1 of 1000 ($p<0.001$) (Figure BC).

These analyses indicate that the 38 CRGs identified in the in vitro analysis have predictive power beyond clinical covariates alone and better predictive power than random selected genes.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

TABLE 1

| Chromatin Regulatory Genes | |
|---|---|
| Gene Name[1] | Entrez ID No.[2] |
| ACTB | 60 |
| ACTL6A | 86 |
| ACTL6B | 51412 |
| ACTR5 | 79913 |
| ACTR6 | 64431 |
| ACTR8 | 93973 |
| AEBP2 | 121536 |
| AICDA | 57379 |
| ALKBH1 | 8846 |
| ALKBH2 | 121642 |
| APEX1 | 328 |
| APOBEC1 | 339 |
| APOBEC2 | 10930 |
| APOBEC3A | 200315 |
| APOBEC3C | 27350 |
| APOBEC3F | 200316 |
| ARID1A | 8289 |
| ARID1B | 57492 |
| ARID4A | 5926 |
| ARID4B | 51742 |
| ARID5B | 84159 |
| ASH1L | 55870 |
| ASH2L | 9070 |
| ASXL1 | 171023 |
| ASXL2 | 55252 |
| ATF2 | 1386 |
| ATF7IP | 55729 |
| ATM | 472 |
| ATRX | 546 |
| BAP1 | 8314 |
| BARD1 | 580 |
| BAZ1A | 11177 |
| BAZ1B | 9031 |
| BAZ2A | 11176 |
| BAZ2B | 29994 |
| BCL11A | 53335 |
| BCL11B | 64919 |
| BCL7A | 605 |
| BCL7B | 9275 |
| BCL7C | 9274 |
| BEND3 | 57673 |
| BMI1 | 648 |
| BPTF | 2186 |
| BRCA1 | 672 |
| BRD9 | 65980 |
| BRMS1 | 25855 |
| BRMS1L | 84312 |
| C17orf49 | 124944 |
| CBX2 | 84733 |
| CBX4 | 8535 |
| CBX7 | 23492 |
| CBX8 | 57332 |
| CCNA2 | 890 |
| CDCA5 | 113130 |
| CDK1 | 983 |
| CDK2 | 1017 |
| CDY2A | 9426 |
| CDY2B | 203611 |
| CECR2 | 27443 |
| CHAF1A | 10036 |
| CHAF1B | 8208 |
| CHD1 | 1105 |
| CHD2 | 1106 |
| CHD3 | 1107 |
| CHD4 | 1108 |
| CHD5 | 26038 |
| CHD6 | 84181 |
| CHD7 | 55636 |
| CHD8 | 57680 |
| CHD9 | 80205 |
| CHRAC1 | 54108 |
| CLOCK | 9575 |
| CREBBP | 1387 |
| CTCF | 10664 |
| DMAP1 | 55929 |
| DNMT1 | 1786 |

TABLE 1-continued

| Chromatin Regulatory Genes | |
|---|---|
| Gene Name[1] | Entrez ID No.[2] |
| DNMT3A | 1788 |
| DNMT3B | 1789 |
| DNMT3L | 29947 |
| DOT1L | 84444 |
| DPF1 | 8193 |
| DPF2 | 5977 |
| DPF3 | 8110 |
| DPY30 | 84661 |
| EED | 8726 |
| EHMT1 | 79813 |
| EHMT2 | 10919 |
| ELP3 | 55140 |
| ELP4 | 26610 |
| EP300 | 2033 |
| EPC1 | 80314 |
| EPC2 | 26122 |
| EPOP | 100170841 |
| ERCC5 | 2073 |
| EZH1 | 2145 |
| EZH2 | 2146 |
| FOS | 2353 |
| FOXA1 | 3169 |
| FOXK1 | 221937 |
| FOXK2 | 3607 |
| FTO | 79068 |
| GATAD2A | 54815 |
| GATAD2B | 57459 |
| GCNA | 93953 |
| GNAS | 2778 |
| GTF3C4 | 9329 |
| H1-0 | 3005 |
| H1-7 | 341567 |
| H1-8 | 132243 |
| H1-10 | 8971 |
| H2AB1 | 474382 |
| H2AB2 | 474381 |
| H2AB3 | 83740 |
| H2AJ | 55766 |
| H2AZ2 | 94239 |
| H2AX | 3014 |
| MACROH2A1 | 9555 |
| MACROH2A2 | 55506 |
| H2AZ1 | 3015 |
| H2BW2 | 286436 |
| H2BS1 | 54145 |
| H2BW1 | 158983 |
| H3-3A | 3020 |
| H3-3B | 3021 |
| H3-5 | 440093 |
| HAT1 | 8520 |
| HCFC1 | 3054 |
| HDAC1 | 3065 |
| HDAC10 | 83933 |
| HDAC11 | 79885 |
| HDAC2 | 3066 |
| HDAC3 | 8841 |
| HDAC4 | 9759 |
| HDAC5 | 10014 |
| HDAC6 | 10013 |
| HDAC7 | 51564 |
| HDAC8 | 55869 |
| HDAC9 | 9734 |
| HELLS | 3070 |
| HEMK1 | 51409 |
| HIPK4 | 147746 |
| HIST1H1A | 3024 |
| HIST1H1B | 3009 |
| HIST1H1C | 3006 |
| HIST1H1D | 3007 |
| HIST1H1E | 3008 |
| HIST1H1T | 3010 |
| HIST1H2AA | 221613 |
| HIST1H2AB | 8335 |
| HIST1H2AC | 8334 |
| HIST1H2AD | 3013 |
| HIST1H2AE | 3012 |

TABLE 1-continued

| Chromatin Regulatory Genes | |
|---|---|
| Gene Name[1] | Entrez ID No.[2] |
| HIST1H2AG | 8969 |
| HIST1H2AH | 85235 |
| HIST1H2AI | 8329 |
| HIST1H2AJ | 8331 |
| HIST1H2AL | 8332 |
| HIST1H2AM | 8336 |
| HIST1H2BA | 255626 |
| HIST1H2BB | 3018 |
| HIST1H2BC | 8347 |
| HIST1H2BD | 3017 |
| HIST1H2BE | 8344 |
| HIST1H2BF | 8343 |
| HIST1H2BG | 8339 |
| HIST1H2BH | 8345 |
| HIST1H2BI | 8346 |
| HIST1H2BJ | 8970 |
| HIST1H2BK | 85236 |
| HIST1H2BL | 8340 |
| HIST1H2BM | 8342 |
| HIST1H2BN | 8341 |
| HIST1H2BO | 8348 |
| HIST1H3A | 8350 |
| HIST1H3B | 8358 |
| HIST1H3C | 8352 |
| HIST1H3D | 8351 |
| HIST1H3E | 8353 |
| HIST1H3F | 8968 |
| HIST1H3G | 8355 |
| HIST1H3H | 8357 |
| HIST1H3I | 8354 |
| HIST1H3J | 8356 |
| HIST1H4A | 8359 |
| HIST1H4B | 8366 |
| HIST1H4C | 8364 |
| HIST1H4D | 8360 |
| HIST1H4E | 8367 |
| HIST1H4F | 8361 |
| HIST1H4G | 8369 |
| HIST1H4H | 8365 |
| HIST1H4I | 8294 |
| HIST1H4J | 8363 |
| HIST1H4K | 8362 |
| HIST1H4L | 8368 |
| HIST2H2AA3 | 8337 |
| HIST2H2AA4 | 723790 |
| HIST2H2AB | 317772 |
| HIST2H2AC | 8338 |
| HIST2H2BE | 8349 |
| HIST2H2BF | 440689 |
| HIST2H3A | 333932 |
| HIST2H3C | 126961 |
| HIST2H3D | 653604 |
| HIST2H4A | 8370 |
| HIST2H4B | 554313 |
| HIST3H2A | 92815 |
| HIST3H2BB | 128312 |
| HIST3H3 | 8290 |
| HIST4H4 | 121504 |
| HMG20B | 10362 |
| HMGXB4 | 10042 |
| ING3 | 54556 |
| INO80 | 54617 |
| INO80B | 83444 |
| INO80C | 125476 |
| INO80E | 283899 |
| JARID2 | 3720 |
| JMJD6 | 23210 |
| KAT14 | 57325 |
| KAT2A | 2648 |
| KAT2B | 8850 |
| KAT5 | 10524 |
| KAT6A | 7994 |
| KAT6B | 23522 |
| KAT7 | 11143 |
| KAT8 | 84148 |
| KDM1A | 23028 |

TABLE 1-continued

| Chromatin Regulatory Genes | |
|---|---|
| Gene Name[1] | Entrez ID No.[2] |
| KDM1B | 221656 |
| KDM2A | 22992 |
| KDM2B | 84678 |
| KDM3A | 55818 |
| KDM3B | 51780 |
| KDM4A | 9682 |
| KDM4B | 23030 |
| KDM4C | 23081 |
| KDM4D | 55693 |
| KDM5A | 5927 |
| KDM5B | 10765 |
| KDM5C | 8242 |
| KDM5D | 8284 |
| KDM6A | 7403 |
| KDM6B | 23135 |
| KDM7A | 80853 |
| KDM8 | 79831 |
| KMT2A | 4297 |
| KMT2B | 9757 |
| KMT2C | 58508 |
| KMT2D | 8085 |
| KMT2E | 55904 |
| KMT5A | 387893 |
| KMT5B | 51111 |
| KMT5C | 84787 |
| MAP3K12 | 7786 |
| MBD2 | 8932 |
| MBD3 | 53615 |
| MCRS1 | 10445 |
| MECOM | 2122 |
| MED24 | 9862 |
| MEN1 | 4221 |
| METTL8 | 79828 |
| MGMT | 4255 |
| MIER1 | 57708 |
| MIER2 | 54531 |
| MTA1 | 9112 |
| MTA2 | 9219 |
| MTA3 | 57504 |
| MTF2 | 22823 |
| MTRR | 4552 |
| NAA60 | 79903 |
| NACC2 | 138151 |
| NCAPD2 | 9918 |
| NCAPD3 | 23310 |
| NCAPG | 64151 |
| NCAPG2 | 54892 |
| NCAPH | 23397 |
| NCAPH2 | 29781 |
| NCOA1 | 8648 |
| NCOA3 | 8202 |
| NCR1 | 9437 |
| NEK11 | 79858 |
| NFRKB | 4798 |
| NSD1 | 64324 |
| NSD2 | 7468 |
| NSD3 | 54904 |
| OGT | 8473 |
| PBRM1 | 55193 |
| PCGF2 | 7703 |
| PCGF6 | 84108 |
| PDS5A | 23244 |
| PDS5B | 23047 |
| PHC1 | 1911 |
| PHC2 | 1912 |
| PHC3 | 80012 |
| PHF1 | 5252 |
| PHF10 | 55274 |
| PHF19 | 26147 |
| PHF2 | 5253 |
| PHF21A | 51317 |
| PHF8 | 23133 |
| POLE3 | 54107 |
| PPM1D | 8493 |
| PRDM16 | 63976 |
| PRDM2 | 7799 |

TABLE 1-continued

| Chromatin Regulatory Genes | |
|---|---|
| Gene Name[1] | Entrez ID No.[2] |
| PRDM6 | 93166 |
| PRDM7 | 11105 |
| PRDM9 | 56979 |
| PRKCD | 5580 |
| RAD21 | 5885 |
| RAD21L1 | 642636 |
| RB1 | 5925 |
| RBBP4 | 5928 |
| RBBP5 | 5929 |
| RBBP7 | 5931 |
| RCOR1 | 23186 |
| REC8 | 9985 |
| REST | 5978 |
| RING1 | 6015 |
| RIOX2 | 84864 |
| RNF2 | 6045 |
| RPS6KA4 | 8986 |
| RPS6KA5 | 9252 |
| RSF1 | 51773 |
| RUVBL1 | 8607 |
| RUVBL2 | 10856 |
| SALL1 | 6299 |
| SAP18 | 10284 |
| SAP30 | 8819 |
| SAP30L | 79685 |
| SETD1A | 9739 |
| SETD1B | 23067 |
| SETD2 | 29072 |
| SETD3 | 84193 |
| SETD7 | 80854 |
| SETDB1 | 9869 |
| SETDB2 | 83852 |
| SETMAR | 6419 |
| SIN3A | 25942 |
| SIN3B | 23309 |
| SIRT1 | 23411 |
| SIRT2 | 22933 |
| SMARCA1 | 6594 |
| SMARCA2 | 6595 |
| SMARCA4 | 6597 |
| SMARCA5 | 8467 |
| SMARCB1 | 6598 |
| SMARCC1 | 6599 |
| SMARCC2 | 6601 |
| SMARCD1 | 6602 |
| SMARCD2 | 6603 |
| SMARCD3 | 6604 |
| SMARCE1 | 6605 |
| SMC1A | 8243 |
| SMC1B | 27127 |
| SMC2 | 10592 |
| SMC3 | 9126 |
| SMC4 | 10051 |
| SMYD1 | 150572 |
| SMYD2 | 56950 |
| SMYD3 | 64754 |
| SRCAP | 10847 |
| SS18 | 6760 |
| STAG1 | 10274 |
| STAG2 | 10735 |
| STAG3 | 10734 |
| SUDS3 | 64426 |
| SUPT3H | 8464 |
| SUPT7L | 9913 |
| SUV39H1 | 6839 |
| SUV39H2 | 79723 |
| SUZ12 | 23512 |
| TADA1 | 117143 |
| TADA2B | 93624 |
| TADA3 | 10474 |
| TAF1 | 6872 |
| TAF10 | 6881 |
| TAF12 | 6883 |
| TAF1L | 138474 |
| TAF5 | 6877 |
| TAF5L | 27097 |
| TAF6L | 10629 |
| TAF9 | 6880 |
| TAF9B | 51616 |
| TDG | 6996 |
| TET1 | 80312 |
| TET2 | 54790 |
| TET3 | 200424 |
| TFPT | 29844 |
| TOP1 | 7150 |
| TOP1MT | 116447 |
| TOP2A | 7153 |
| TOP2B | 7155 |
| TOP3A | 7156 |
| TOP3B | 8940 |
| TRIM37 | 4591 |
| UCHL5 | 51377 |
| USF1 | 7391 |
| UTY | 7404 |
| VPS72 | 6944 |
| WAPL | 23063 |
| WDR5 | 11091 |
| YEATS4 | 8089 |
| YY1 | 7528 |
| YY1AP1 | 55249 |

[1]Gene Names in accordance with HUGO Gene Nomenclature Committee (HGNC) (https://www.genenames.org/)
[2]Gene ID Nos. in accordance with Entrez Gene of National Institute of Health - National Center for Biotechnology Information, U.S. Nation Library of medicine (https://www.ncbi.nlm.nih.gov/gene)

TABLE 2

| Chromatin Regulatory Genes Found to Be Significant | | | |
|---|---|---|---|
| Gene Name[1] | Gene ID No.[2] | Evaluations to Find CRG To Be Significant[3] | Correlation |
| ACTL6A | 86 | IV | Negative |
| ACTR5 | 79913 | ANA, ACMF, AT | Positive |
| AEBP2 | 121536 | IV | |
| APOBEC1 | 339 | IV | Positive |
| APOBEC2 | 10930 | AT | Positive |
| APOBEC3C | 27350 | ANA, ACMF, AT | Negative |
| ARID1A | 8289 | ANA, ACMF, AT | Positive |
| ARID5B | 84159 | IV | Negative |
| ATF7IP | 55729 | AT | Positive |
| ATM | 472 | ACMF, IV | Negative |
| BAZ1B | 9031 | ANA, ACMF | Positive |
| BAZ2A | 11176 | ANA, ACMF, AT | Positive |
| BCL11A | 53335 | ANA, ACMF, IV | Negative |
| BCL7A | 605 | AT | Positive |
| CBX2 | 84733 | IV | Negative |
| CCNA2 | 890 | ANA, IV | Negative |
| CDK1 | 983 | IV | Negative |
| CECR2 | 27443 | IV | Positive |
| CHARC1 | 54108 | IV | Positive |
| CHD4 | 1108 | ANA, AT | Positive |
| CHD5 | 26038 | ANA | Positive |
| CHD8 | 57680 | ACMF | Positive |
| DNMT3A | 1788 | AT | Positive |
| DPF1 | 8193 | AT | Positive |
| DPF3 | 8110 | ANA, AT | Positive |
| EED | 8726 | IV | Negative |
| EHMT1 | 79813 | IV | Positive |
| EHMT2 | 10919 | IV | Positive |
| EZH2 | 2146 | ANA, ACMF, IV | Negative |
| FOXA1 | 3169 | ANA, ACMF, IV | Positive |
| GATAD2A | 54815 | IV | Negative |
| H1-0 | 3005 | IV | Positive |
| H2AZ2 | 94239 | IV | Negative |
| H2AFX | 3014 | AT | Positive |
| MACROH2A1 | 9555 | ANA, ACMF, IV | Positive/Negative |
| HCFC1 | 3054 | ANA, ACMF, AT | Positive |
| HDAC11 | 79885 | ANA, ACMF, AT | Positive |

TABLE 2-continued

Chromatin Regulatory Genes Found to Be Significant

| Gene Name[1] | Gene ID No.[2] | Evaluations to Find CRG To Be Significant[3] | Correlation |
|---|---|---|---|
| HDAC5 | 10014 | AT | Positive |
| HDAC6 | 10013 | AT | Positive |
| HDAC7 | 51564 | ANA | Positive |
| HDAC9 | 9734 | ANA, ACMF, AT, IV | Negative |
| HEMK1 | 51409 | ANA, ACMF | Positive |
| HIST1H2AJ | 8331 | ACMF | Positive |
| HIST1H4D | 8360 | ANA, AT | Positive |
| HMG20B | 10362 | ACMF | Positive |
| ING3 | 54556 | ANA, ACMF, AT | Negative |
| INO80B | 83444 | ANA, ACMF, AT | Positive |
| KAT14 | 57325 | IV | Positive |
| KAT2B | 8850 | AT | Negative |
| KAT6B | 23522 | ANA, ACMF, AT, IV | Positive |
| KAT7 | 11143 | IV | Positive |
| KDM2A | 22992 | AT | Positive |
| KDM3B | 51780 | ANA, ACMF | Positive |
| KDM4A | 9682 | AT | Positive |
| KDM4B | 23030 | ANA, ACMF, AT, IV | Positive |
| KDM4C | 23081 | ACMF, AT | Negative |
| KDM4D | 55693 | IV | Positive |
| KDM5C | 8242 | ANA, AT | Positive |
| KDM6B | 23135 | ANA, ACMF, AT | Positive |
| KDM7A | 80853 | IV | Negative |
| KMT2A | 4297 | ANA, ACMF, AT | Positive |
| MAP3K12 | 7786 | ANA, ACMF | Positive |
| MBD2 | 8932 | ACMF | Negative |
| MBD3 | 53615 | AT | Positive |
| MCRS1 | 10445 | ANA | Positive |
| MECOM | 2122 | AT, IV | Negative |
| MIER2 | 54531 | ANA, ACMF, AT | Positive |
| MTF2 | 22823 | ANA, ACMF | Negative |
| NCAPG | 64151 | ANA, ACMF, IV | Negative |
| NCAPH2 | 29781 | AT | Negative |
| NCOA3 | 8202 | ANA, AT | Positive |
| NEK11 | 79858 | ANA, IV | Positive |
| NSD1 | 64324 | ANA, AT | Positive |
| PCGF2 | 7703 | ACMF | Positive |
| PHF1 | 5252 | ACMF | Positive |
| PHF2 | 5253 | ANA, ACMF, AT | Positive |
| PRDM2 | 7799 | ANA | Positive |
| RING1 | 6015 | IV | Positive |
| RSF1 | 51773 | ANA, AT | Positive/Negative |
| RUVBL2 | 10856 | ANA, ACMF | Positive |
| SAP18 | 10284 | ANA, ACMF, AT | Positive |
| SAP30 | 8819 | ANA, ACMF, AT | Negative |
| SETD1A | 9739 | ANA, AT | Positive |
| SMARCA1 | 6594 | IV | Negative |
| SMARCA2 | 6595 | ANA, ACMF, AT | Positive |
| SMARCC2 | 6601 | ANA, ACMF, IV | Positive |
| SMARCD1 | 6602 | ANA, ACMF | Positive |
| SMARCD3 | 6604 | IV | Positive |
| SMC1B | 27127 | IV | Negative |
| SMC2 | 10592 | ANA | Negative |
| SMC3 | 9126 | ANA, ACMF, AT | Negative |
| SMYD1 | 150572 | IV | Negative |
| SRCAP | 10847 | ANA, ACMF, AT | Positive |
| SUPT3H | 8464 | AT | Negative |
| TAF1 | 6872 | ANA, ACMF, AT | Positive |
| TAF5 | 6877 | ANA, ACMF, IV | Negative |
| TAF5L | 27097 | ANA | Negative |
| TAF6L | 10629 | AT | Positive |
| TOP1 | 7150 | ANA, AT | Positive |
| TOP2A | 7153 | IV | Negative |
| TOP3A | 7156 | AT | Positive |
| TOP3B | 8940 | AT | Positive |
| UCHL5 | 51377 | ANA, ACMF | Negative |

TABLE 2-continued

Chromatin Regulatory Genes Found to Be Significant

| Gene Name[1] | Gene ID No.[2] | Evaluations to Find CRG To Be Significant[3] | Correlation |
|---|---|---|---|
| UTY | 7404 | ANA, AT | Positive |
| YY1 | 7528 | ANA, ACMF | Positive |

[1]Gene Names in accordance with HUGO Gene Nomenclature Committee (HGNC) (https://www.genenames.org/)

[2]Gene ID Nos. in accordance with the National Center for Biotechnology Information (NCBI) Gene Database of National Institute of Health - National Center for Biotechnology Information, U.S. National Library of Medicine (https://www.ncbi.nlm.nih.gov/gene) - the sequences (RefSeqs) of the transcripts of each Gene ID from the NCBI Gene Database are each incorporated herein by reference

[3]ANA = Clinical Evaluation: Anthracycline vs. Non-Anthracycline

ACMF = Clinical Evaluation: Anthracycline vs. CMF

AT = Clinical Evaluation: Anthracycline vs. Taxane

IV = In Vitro Breast Cancer Cell Line Evaluation

TABLE 3

Chromatin Regulatory Genes Found Significant in Breast Cancer Cell Lines

| Gene Name | Association | p-Value |
|---|---|---|
| ACTL6A | Negative | 0.0491 |
| AEBP2 | Positive | 0.0225 |
| APOBEC1 | Positive | 0.0329 |
| ARID5B | Negative | 0.0244 |
| ATM | Negative | 0.0183 |
| BCL11A | Negative | 0.0001 |
| CBX2 | Negative | 0.0062 |
| CCNA2 | Negative | 0.0227 |
| CDK1 | Negative | 0.0041 |
| CECR2 | Positive | 0.0249 |
| CHARC1 | Positive | 0.0412 |
| EED | Negative | 0.0069 |
| EHMT1 | Positive | 0.0127 |
| EHMT2 | Negative | 0.0451 |
| EZH2 | Negative | 0.0178 |
| FOXA1 | Positive | 0.0004 |
| GATAD2A | Positive | 0.0456 |
| H1-0 | Positive | 0.0177 |
| H2AZ2 | Negative | 0.0308 |
| MACROH2A1 | Negative | 0.0436 |
| HDAC9 | Negative | 0.0041 |
| KAT14 | Positive | 0.0342 |
| KAT6B | Positive | 0.0156 |
| KAT7 | Positive | 0.0031 |
| KDM4B | Positive | 0.0001 |
| KDM4D | Negative | 0.0253 |
| KDM7A | Negative | 0.0293 |
| MECOM | Negative | 0.0498 |
| NCAPG | Negative | 0.0477 |
| NEK11 | Positive | 0.0335 |
| RING1 | Negative | 0.0233 |
| SMARCA1 | Negative | 0.0492 |
| SMARCC2 | Positive | 0.0322 |
| SMARCD3 | Positive | 0.0198 |
| SMC1B | Negative | 0.0032 |
| SMYD1 | Negative | 0.0129 |
| TAF5 | Positive | 0.0217 |
| TOP2A | Negative | 0.0017 |

TABLE 4

Chromatin Regulatory Genes Found Significant in Clinical Evaluation of comparing Breast Cancer Patients: Anthracycline vs. Non-Anthracycline Treated

| Gene Name | Association | p-Value |
|---|---|---|
| ACTR5 | Positive | 0.0035 |
| APOBEC3C | Negative | 0.0122 |
| ARID1A | Positive | 0.0146 |

TABLE 4-continued

Chromatin Regulatory Genes Found Significant in Clinical Evaluation of comparing Breast Cancer Patients: Anthracycline vs. Non-Anthracycline Treated

| Gene Name | Association | p-Value |
|---|---|---|
| BAZ1B | Positive | 0.0354 |
| BAZ2A | Positive | 0.0005 |
| BCL11A | Negative | 0.0105 |
| CCNA2 | Negative | 0.0148 |
| CHD4 | Positive | 0.0128 |
| CHD5 | Positive | 0.0477 |
| DPF3 | Positive | 0.0183 |
| EZH2 | Negative | 0.0020 |
| MACROH2A1 | Positive | 0.0277 |
| HCFC1 | Positive | 0.0097 |
| HDAC11 | Positive | 0.0072 |
| HDAC7 | Positive | 0.0463 |
| HDAC9 | Negative | 0.0103 |
| HEMK1 | Positive | 0.0223 |
| HIST1H4D | Positive | 0.0300 |
| ING3 | Negative | 0.0281 |
| INO80B | Positive | 0.0112 |
| KAT6B | Positive | 0.0013 |
| KDM3B | Positive | 0.0039 |
| KDM4B | Positive | 0.0036 |
| KDM5C | Positive | 0.0048 |
| KDM6B | Positive | 0.0023 |
| KMT2A | Positive | 0.0015 |
| MAP3K12 | Positive | 0.0162 |
| MCRS1 | Positive | 0.0199 |
| MIER2 | Positive | 0.0279 |
| MTF2 | Negative | 0.0154 |
| NCAPG | Negative | 0.0455 |
| NCOA3 | Positive | 0.0490 |
| NEK11 | Positive | 0.0069 |
| NSD1 | Positive | 0.0093 |
| PHF2 | Positive | 0.0382 |
| PRDM2 | Positive | 0.0080 |
| RSF1 | Negative | 0.0499 |
| RUVBL2 | Positive | 0.0006 |
| SAP18 | Positive | 0.0007 |
| SAP30 | Negative | 0.0246 |
| SETD1A | Positive | 0.0268 |
| SMARCA2 | Positive | 0.0123 |
| SMARCC2 | Positive | 0.0446 |
| SMARCD1 | Positive | 0.0286 |
| SMC | Negative | 0.0096 |
| SMC2 | Negative | 0.0077 |
| SRCAP | Positive | 0.0044 |
| TAF1 | Positive | 0.0067 |
| TAF5 | Negative | 0.0238 |
| TAF5L | Negative | 0.0175 |
| TOP1 | Positive | 0.0373 |
| UCHL5 | Negative | 0.0078 |
| UTY | Positive | 0.0343 |
| YY1 | Positive | 0.034 |

TABLE 5

Chromatin Regulatory Genes Found Significant in Clinical Evaluation of comparing Breast Cancer Patients: Anthracycline vs. CMF Treated

| Gene Name | Association | p-Value |
|---|---|---|
| ACTR5 | Positive | 0.0360 |
| APOBEC3C | Negative | 0.0392 |
| ARID1A | Positive | 0.0248 |
| ATM | Negative | 0.0440 |
| BAZ1B | Positive | 0.0445 |
| BAZ2A | Positive | 0.0054 |
| BCL11A | Negative | 0.0197 |
| CHD8 | Positive | 0.0491 |
| EZH2 | Negative | 0.0262 |
| MACROH2A1 | Positive | 0.0207 |
| HCFC1 | Positive | 0.0272 |

TABLE 5-continued

Chromatin Regulatory Genes Found Significant in Clinical Evaluation of comparing Breast Cancer Patients: Anthracycline vs. CMF Treated

| Gene Name | Association | p-Value |
|---|---|---|
| HDAC11 | Positive | 0.0105 |
| HDAC9 | Negative | 0.0232 |
| HEMK1 | Positive | 0.0145 |
| HIST1H2AJ | Positive | 0.0420 |
| HMG20B | Positive | 0.0377 |
| ING3 | Negative | 0.0226 |
| INO80B | Positive | 0.0036 |
| KAT6B | Positive | 0.0071 |
| KDM3B | Positive | 0.0039 |
| KDM4C | Negative | 0.0025 |
| KDM6B | Positive | 0.0488 |
| KMT2A | Positive | 0.0443 |
| MAP3K12 | Positive | 0.0009 |
| MBD2 | Negative | 0.0191 |
| MIER2 | Positive | 0.0329 |
| MTF2 | Negative | 0.0140 |
| NCAPG | Negative | 0.0446 |
| PCGF2 | Positive | 0.0417 |
| PHF1 | Positive | 0.0393 |
| PHF2 | Positive | 0.0028 |
| RUVBL2 | Positive | 0.0192 |
| SAP18 | Positive | 0.0281 |
| SAP30 | Negative | 0.0310 |
| SMARCA2 | Negative | 0.0250 |
| SMARCC2 | Positive | 0.0262 |
| SMARCD1 | Positive | 0.0402 |
| SMC3 | Negative | 0.0208 |
| SRCAP | Positive | 0.0055 |
| TAF1 | Positive | 0.0110 |
| TAF5 | Negative | 0.0038 |
| UCHL5 | Negative | 0.0065 |
| UTY | Positive | 0.0044 |

TABLE 6

Chromatin Regulatory Genes Found Significant in Clinical Evaluation of comparing Breast Cancer Patients: Anthracycline vs. Taxane Treated

| Gene Name | Association | p-Value |
|---|---|---|
| ACTR5 | Positive | 0.0099 |
| APOBEC2 | Positive | 0.0134 |
| APOBEC3C | Negative | 0.0439 |
| ARID1A | Positive | 0.0018 |
| ATF7IP | Positive | 0.0329 |
| BAZ2A | Positive | 0.0034 |
| BCL7A | Positive | 0.0048 |
| CHD4 | Positive | 0.0092 |
| DNMT3A | Positive | 0.0229 |
| DPF1 | Positive | 0.0301 |
| DPF3 | Positive | 0.0066 |
| H2AX | Positive | 0.0001 |
| HCFC1 | Positive | 0.0038 |
| HDAC11 | Positive | 0.0112 |
| HDAC5 | Positive | 0.0195 |
| HDAC6 | Positive | 0.0280 |
| HDAC9 | Negative | 0.0466 |
| HIST1H4D | Positive | 0.0182 |
| ING3 | Negative | 0.0475 |
| INO80B | Positive | 0.0004 |
| KAT2B | Negative | 0.0080 |
| KAT6B | Positive | 0.0041 |
| KDM2A | Positive | 0.0100 |
| KDM4A | Positive | 0.0359 |
| KDM4B | Positive | 0.0076 |
| KDM4C | Negative | 0.0061 |

TABLE 6-continued

| Chromatin Regulatory Genes Found Significant in Clinical Evaluation of comparing Breast Cancer Patients: Anthracycline vs. Taxane Treated | | |
|---|---|---|
| Gene Name | Association | p-Value |
| KDM5C | Positive | 0.0007 |
| KDM6B | Positive | 0.0005 |
| KMT2A | Positive | 0.0152 |
| MBD3 | Positive | 0.0229 |
| MECOM | Negative | 0.0197 |
| MIER2 | Positive | 0.0034 |
| NCAPH2 | Positive | 0.0069 |
| NCOA3 | Positive | 0.0045 |
| NSD1 | Positive | 0.0162 |
| PHF2 | Positive | 0.0367 |
| SAP18 | Positive | 0.0030 |
| SAP30 | Negative | 0.0005 |
| SETD1A | Positive | 0.0269 |
| SMARCA2 | Negative | 0.0066 |
| SMC3 | Negative | 0.0097 |
| SRCAP | Positive | 0.0027 |
| SUPT3H | Negative | 0.0341 |
| TAF1 | Positive | 0.0004 |
| TAF6L | Positive | 0.0394 |
| TOP1 | Positive | 0.0395 |
| TOP3A | Positive | 0.0481 |
| TOP3B | Positive | 0.0185 |
| UTY | Positive | 0.0061 |
| YY1 | Positive | 0.0475 |

TABLE 7

| Chromatin Regulatory Genes Found Significant in Clinical Evaluation of comparing ER+/HER2− Breast Cancer Patients: Anthracycline vs. Non-Anthracycline Treated | | |
|---|---|---|
| Gene Name | Association | p-Value |
| ACTR5 | Positive | 0.0477 |
| BCL7A | Positive | 0.0194 |
| CCNA2 | Negative | 0.0119 |
| CHAF1B | Negative | 0.0237 |
| CHD9 | Negative | 0.0035 |
| DPF3 | Positive | 0.0174 |
| HEMK1 | Positive | 0.0282 |
| HIST1H1T | Positive | 0.0191 |
| HIST3H3 | Positive | 0.0302 |
| INO80B | Positive | 0.0475 |
| KDM6B | Positive | 0.0191 |
| KMT2B | Negative | 0.0218 |
| MECOM | Negative | 0.0007 |
| MGMT | Positive | 0.0156 |
| MTF2 | Negative | 0.0427 |
| NCAPG | Negative | 0.0375 |
| NEK11 | Positive | 0.0375 |
| PHC3 | Negative | 0.0448 |
| PHF1 | Positive | 0.0086 |
| PPM1D | Negative | 0.0048 |
| RING1 | Positive | 0.0409 |
| SAP18 | Positive | 0.0139 |
| SAP30 | Negative | 0.0047 |
| SMARCA2 | Positive | 0.0037 |
| SMARCA4 | Negative | 0.0398 |
| SMARCA5 | Negative | 0.0083 |
| SMARCC2 | Positive | 0.0234 |
| SMARCE1 | Positive | 0.0271 |
| SMC4 | Negative | 0.0351 |
| WAPAL | Positive | 0.0190 |

TABLE 8

| Chromatin Regulatory Genes Found Significant in Clinical Evaluation of comparing HER2+ Breast Cancer Patients: Anthracycline vs. Non-Anthracycline Treated | | |
|---|---|---|
| Gene Name | Association | p-Value |
| ARID5B | Negative | 0.0301 |
| ATF2 | Positive | 0.0180 |
| CDY1 | Negative | 0.0176 |
| CHAF1A | Positive | 0.0287 |
| CREBBP | Positive | 0.0441 |
| FOXK2 | Positive | 0.0133 |
| HDAC5 | Positive | 0.0389 |
| HIST1H3E | Positive | 0.0478 |
| HIST1H4D | Positive | 0.0117 |
| KDM3B | Positive | 0.0074 |
| KMT2B | Positive | 0.0410 |
| RBBP4 | Positive | 0.0372 |
| RBBP5 | Positive | 0.0148 |
| SMARCA1 | Negative | 0.0465 |
| UTY | Positive | 0.0061 |

TABLE 9

| Chromatin Regulatory Genes Found Significant in Clinical Evaluation of comparing ER−/PR−/HER2− Breast Cancer Patients: Anthracycline vs. Non-Anthracycline Treated | | |
|---|---|---|
| Gene Name | Association | p-Value |
| ACTR5 | Positive | 0.0095 |
| ACTR6 | Positive | 0.0109 |
| AICDA | Negative | 0.0096 |
| ASH2L | Negative | 0.0119 |
| ATRX | Positive | 0.0350 |
| BAZ1A | Positive | 0.0130 |
| BAZ2A | Positive | 0.0011 |
| CHD3 | Positive | 0.0138 |
| CHD4 | Positive | 0.0084 |
| CHD8 | Positive | 0.0422 |
| DNMT3B | Positive | 0.0240 |
| GNAS | Positive | 0.0039 |
| H2AX | Positive | 0.0218 |
| H2BS1 | Negative | 0.0465 |
| HCFC1 | Positive | 0.0101 |
| HDAC9 | Negative | 0.0008 |
| HIST1H2AC | Negative | 0.0104 |
| HIST1H2BD | Negative | 0.0163 |
| HIST1H2BK | Negative | 0.0434 |
| HIST1H3E | Negative | 0.0425 |
| HIST1H4H | Negative | 0.0213 |
| HIST3H2A | Positive | 0.0280 |
| KAT2B | Negative | 0.0330 |
| KAT6B | Positive | 0.0265 |
| KDM4A | Positive | 0.0411 |
| KDM4B | Positive | 0.0153 |
| KDM5B | Positive | 0.0098 |
| KDM5C | Positive | 0.0405 |
| KDM6B | Positive | 0.0126 |
| KMT2A | Positive | 0.0106 |
| KMT2B | Positive | 0.0210 |
| MAP3K12 | Positive | 0.0433 |
| MBD2 | Negative | 0.0408 |
| MCRS1 | Positive | 0.0165 |
| NCOA3 | Positive | 0.0273 |
| PHF2 | Negative | 0.0179 |
| RUVBL2 | Positive | 0.0029 |
| SALL1 | Negative | 0.0044 |
| SAP30 | Negative | 0.0292 |
| SETD1A | Positive | 0.0060 |
| SMARCA2 | Negative | 0.0034 |
| SMARCA4 | Positive | 0.0120 |
| SMARCA5 | Positive | 0.0430 |
| SMARCC1 | Positive | 0.0328 |
| SMARCC2 | Positive | 0.0326 |
| SMYD2 | Negative | 0.0439 |
| SRCAP | Positive | 0.0180 |

TABLE 9-continued

| Chromatin Regulatory Genes Found Significant in Clinical Evaluation of comparing ER−/PR−/HER2− Breast Cancer Patients: Anthracycline vs. Non-Anthracycline Treated | | |
|---|---|---|
| Gene Name | Association | p-Value |
| TAF1 | Positive | 0.0182 |
| TAF9B | Positive | 0.0366 |
| TDG | Positive | 0.0028 |
| TOP1 | Positive | 0.0044 |

TABLE 10

| SEQ. ID No. | Gene Name[1] | Gene ID No.[2] | RefSeq ID No.[3] |
|---|---|---|---|
| Sequence Listing | | | |
| 1 | ACTL6A | 86 | NM_004301.5 |
| 2 | AEBP2 | 121536 | NM_153207.5 |
| 3 | APOBEC1 | 339 | NM_001644.5 |
| 4 | ARID5B | 84159 | NM_032199.3 |
| 5 | ATM | 472 | NM_000051.3 |
| 6 | BCL11A | 53335 | NM_022893.4 |
| 7 | CBX2 | 84733 | NM_005189.3 |
| 8 | CCNA2 | 890 | NM_001237.5 |
| 9 | CDK1 | 983 | NM_001786.5 |
| 10 | CECR2 | 27443 | NM_001290047.2 |
| 11 | CHARC1 | 54108 | NM_017444.6 |
| 12 | EED | 8726 | NM_003797.5 |
| 13 | EHMT1 | 79813 | NM_024757.5 |
| 14 | EHMT2 | 10919 | NM_001363689.1 |
| 15 | EZH2 | 2146 | NM_004456.5 |
| 16 | FOXA1 | 3169 | NM_004496.5 |

TABLE 10-continued

| SEQ. ID No. | Gene Name[1] | Gene ID No.[2] | RefSeq ID No.[3] |
|---|---|---|---|
| Sequence Listing | | | |
| 17 | GATAD2A | 54815 | NM_001300946.2 |
| 18 | H1-0 | 3005 | NM_005318.4 |
| 19 | H2AZ2 | 94239 | NM_012412.5 |
| 20 | MACROH2A1 | 9555 | NM_001040158.1 |
| 21 | HDAC9 | 9734 | NM_178425.3 |
| 22 | KAT14 | 57325 | NM_020536.4 |
| 23 | KAT6B | 23522 | NM_012330.4 |
| 24 | KAT7 | 11143 | NM_007067.5 |
| 25 | KDM4B | 23030 | NM_015015.3 |
| 26 | KDM4D | 55693 | NM_018039.3 |
| 27 | KDM7A | 80853 | NM_030647.2 |
| 28 | MECOM | 2122 | NM_004991.4 |
| 29 | NCAPG | 64151 | NM_022346.5 |
| 30 | NEK11 | 79858 | NM_024800.5 |
| 31 | RING1 | 6015 | NM_002931.4 |
| 32 | SMARCA1 | 6594 | NM_001282874.2 |
| 33 | SMARCC2 | 6601 | NM_001330288.2 |
| 34 | SMARCD3 | 6604 | NM_001003801.2 |
| 35 | SMC1B | 27127 | NM_148674.5 |
| 36 | SMYD1 | 150572 | NM_198274.4 |
| 37 | TAF5 | 6877 | NM_006951.5 |
| 38 | TOP2A | 7153 | NM_001067.4 |

[1]Gene Names in accordance with HUGO Gene Nomenclature Committee (HGNC) (https://www.genenames.org/)
[2]Gene ID Nos. in accordance with the National Center for Biotechnology Information (NCBI) Gene Database of National Institute of Health - National Center for Biotechnology Information, U.S. National Library of Medicine (https://www.ncbi.nlm.nih.gov/gene) - a RefSeqs transcripts of each Gene ID was utilized to form the Sequence Listing
[3]RefSeq ID Nos. in accordance with the National Center for Biotechnology Information (NCBI) Nucleotide Database of National Institute of Health - National Center for Biotechnology Information, U.S. National Library of Medicine (https://www.ncbi.nlm-.nih.gov/gene) -

What is claimed is:

1. A method for assessing anthracycline treatment response of an individual having breast cancer, comprising:

obtaining an assessment of nucleic acid expression levels of a set of chromatin regulatory genes comprising HDAC9, KAT6B, and KDM4B in a breast cancer biopsy of the individual;

determining the likelihood of survival of the individual with anthracycline treatment utilizing a first survival model and the assessment of nucleic acid expression levels of the set of chromatin regulatory genes;

determining the likelihood of survival of the individual without anthracycline treatment utilizing a second survival model and the assessment of nucleic acid expression levels of the set of chromatin regulatory genes;

determining a treatment regimen for the individual based on a contrast between the likelihood of survival of the individual with anthracycline treatment and the likelihood of survival of the individual without anthracycline treatment; and administering a treatment regimen to the individual, wherein:

when the contrast between the likelihood of survival of the individual with anthracycline treatment and the likelihood of survival of the individual without anthracycline treatment is greater than a threshold, the treatment regimen includes anthracycline; and when the contrast between the likelihood of survival of the individual with anthracycline treatment and the likelihood of survival of the individual without anthracycline treatment is below the threshold, the treatment regimen includes non-anthracycline chemotherapy, radiotherapy, immunotherapy or hormone therapy and excludes anthracycline.

2. The method of claim 1, wherein the breast cancer biopsy biopsy is a liquid biopsy that includes cell-free nucleic acids derived from the breast cancer or a solid tissue biopsy extracted from a breast tumor or collection of cancerous breast cells.

3. The method of claim 1, wherein the breast cancer biopsy is an excision of a tumor performed during a surgical procedure.

4. The method of claim 1, wherein the assessment of nucleic acid expression levels of the set of chromatin regulatory genes is assessed by nucleic acid hybridization, RNA-seq, or RT-PCR, or immunodetection.

5. The method of claim 1, wherein the set of chromatin regulatory genes further comprises at least one of the following genes: ACTL6A, ACTR5, AEBP2, APOBEC1, APOBEC2, APOBEC3C, ARID1A, ARID5B, ATF7IP, ATM, BAZ1B, BAZ2A, BCL11A, BCL7A, CBX2, CCNA2, CDK1, CECR2, CHARC1, CHD4, CHD5, CHD8, DNMT3A, DPF1, DPF3, EED, EHMT1, EHMT2, EZH2, FOXA1, GATAD2A, H1-0, H2AZ2, H2AFX, MACROH2A1, HCFC1, HDAC11, HDAC5, HDAC6, HDAC7, HEMK1, HIST1H2AJ, HIST1H4D, HMG20B, ING3, INO80B, KAT14, KAT2B, KAT7, KDM2A, KDM3B, KDM4A, KDM4C, KDM4D, KDM5C, KDM6B, KDM7A, KMT2A, MAP3K12, MBD2, MBD3, MCRS1, MECOM, MIER2, MTF2, NCAPG, NCAPH2, NCOA3, NEK11, NSD1, PCGF2, PHF1, PHF2, PRDM2, RING1, RSF1, RUVBL2, SAP18, SAP30, SETD1A, SMARCA1, SMARCA2, SMARCC2, SMARCD1, SMARCD3, SMC1B, SMC2, SMC3, SMYD1, SRCAP, SUPT3H, TAF1, TAF5, TAF5L, TAF6L, TOP1, TOP2A, TOP3A, TOP3B, UCHL5, UTY, or YY1.

6. The method of claim 1, wherein the likelihood of survival with anthracycline treatment and the likelihood of survival without anthracycline treatment are each determined utilizing a survival model selected from the group consisting of: a Cox proportional hazard model, a Cox regularized regression, a LASSO Cox model, a ridge Cox model, an elastic net Cox model, a multi-state Cox model, a Bayesian survival model, an accelerated failure time model, survival trees, survival neural networks, bagging survival trees, a random survival forest, survival support vector machines, and survival deep learning models.

7. The method of claim 1, wherein the likelihood of survival with anthracycline treatment and the likelihood of survival without anthracycline treatment each incorporate at least one of: tumor grade, metastatic status, lymph node status, and treatment regimen.

8. The method of claim 1, wherein the breast cancer is a Stage I, II, IIIA, IIB, IIC, or IV breast cancer.

9. The method of claim 1, wherein the breast cancer is HER2-positive, ER-positive, or triple negative breast cancer.

10. The method of claim 1, wherein the anthracycline is daunorubicin, doxorubicin, epirubicin, idarubicin, valrubicin or mitoxantrone.

11. The method of claim 1, wherein the treatment regimen is an adjuvant treatment regimen or a neoadjuvant treatment regimen.

12. The method of claim 1, wherein when the contrast between the likelihood of survival of the individual with anthracycline treatment and the likelihood of survival of the individual without anthracycline treatment is greater than a threshold, the treatment regimen further includes non-anthracycline chemotherapy, radiotherapy, immunotherapy or hormone therapy.

13. The method of claim 12, wherein the non-anthracycline chemotherapy, the radiotherapy, the immunotherapy or the hormone therapy comprises one of: cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, denosumab, bevacizumab, cetuximab, trastuzumab, alemtuzumab, ipilimumab, nivolumab, ofatumumab, panitumumab, or rituximab.

* * * * *